United States Patent
Kano et al.

(10) Patent No.: US 6,825,187 B2
(45) Date of Patent: Nov. 30, 2004

(54) CARBAPENEM DERIVATIVES OF QUARTERNARY SALT TYPE

(75) Inventors: Yuko Kano, Yokohama (JP); Takahisa Maruyama, Yokohama (JP); Yasuo Yamamoto, Yokohama (JP); Eiki Shitara, Yokohama (JP); Toshiro Sasaki, Yokohama (JP); Kazuhiro Aihara, Yokohama (JP); Kunio Atsumi, Yokohama (JP); Katsuyoshi Iwamatsu, Yokohama (JP); Takashi Ida, Yokohama (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 0 days.

(21) Appl. No.: 10/182,180

(22) PCT Filed: Jan. 26, 2001

(86) PCT No.: PCT/JP01/00529

§ 371 (c)(1),
(2), (4) Date: Jul. 25, 2002

(87) PCT Pub. No.: WO01/55155

PCT Pub. Date: Aug. 2, 2001

(65) Prior Publication Data

US 2003/0022881 A1 Jan. 30, 2003

(30) Foreign Application Priority Data

Jan. 26, 2000 (JP) .......................... 2000-17418

(51) Int. Cl.$^7$ .................. C07D 519/06; A61K 31/429; A61P 31/04
(52) U.S. Cl. .................. 514/210.09; 540/302
(58) Field of Search ............ 540/302; 514/210.09

(56) References Cited

U.S. PATENT DOCUMENTS 6,310,056 B1 * 10/2001 Kano et al. ............. 540/302

FOREIGN PATENT DOCUMENTS

| WO | 96/28455 | 9/1996 |
|---|---|---|
| WO | 98/23623 | 6/1998 |
| WO | 98/32760 | 7/1998 |
| WO | 00/06581 | 2/2000 |

OTHER PUBLICATIONS

Heinzl, "Neue Antiinfektiva Bericht von der 40th Interscience Conference on Antimicrobial Agents and Chemotherapy, Toronto□□17. bis 20. Sep. 2000", Chemotherapie Journal vol. 2, pp. 64–71 (2001).*

* cited by examiner

*Primary Examiner*—Mark L. Berch
(74) *Attorney, Agent, or Firm*—Wenderoth, Lind & Ponack L.L.P.

(57) ABSTRACT

An objective of the present invention is to provide carbapenem derivatives which have potent antibiotic activity against MRSA, PRSP, Influenzavirus, and β-lactamase-producing bacteria and are stable against DHP-1. The compounds according to the present invention are compounds represented by formula (I) or pharmaceutically acceptable salts thereof:

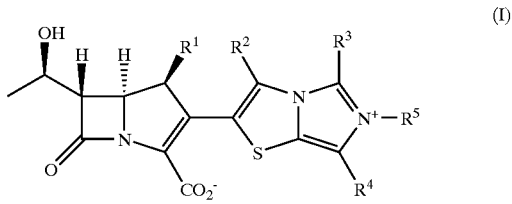

(I)

wherein $R^1$ represents H or methyl; $R^2$ and $R^3$ each independently represent H, halogen, lower alkyl or the like; $R^4$ represents optionally substituted lower alkylthio or the like; and $R^5$ represents optionally substituted lower alkyl or the like.

13 Claims, No Drawings

CARBAPENEM DERIVATIVES OF QUARTERNARY SALT TYPE

BACKGROUND OF THE INVENTION

1. Field of the Invention

The present invention relates to novel carbapenem derivatives which have excellent antibiotic activity against a wide spectrum of bacteria, and more particularly to novel carbapenem derivatives which have a substituted imidazo[5,1-b]thiazole group at the 2-position on the carbapenem ring.

2. Related Art

Carbapenem derivatives, by virtue of potent antibiotic activity against a wide-spectrum of bacteria, have been energetically studied as a highly useful β-lactam agent, and Imipenem, Panipenem, and Meropenem have already been clinically used.

At the present time, both Imipenem and Panipenem, however, are used as a mixture due to instability against renal dehydropeptidase-1 (hereinafter abbreviated to "DHP-1") in the case of Imipenem and in order to reduce nephrotoxicity in the case of Panipenem. Meropenem which has recently been marketed has a methyl group at the 1β-position, so that it has increased stability against DHP-1 and thus can be used alone. The stability against DHP-1, however, is still unsatisfactory. The antibiotic activity also is not necessarily satisfactory against methicillin resistant *Staphylococcus aureus* (hereinafter abbreviated to "MRSA"), penicillin resistant *Streptococcus pneumoneae* (hereinafter abbreviated to "PRSP"), resistant *Pseudomonas aeruginosa*, enterococci, and Influenzavirus which currently pose serious clinical problems. Therefore, drugs useful for these bacteria responsible for infectious diseases have been desired in the art.

WO 96/28455 describes carbapenem derivatives having a novel aromatic heterocyclic imidazo[5,1-b]thiazolium-6-ylmethyl group at the 2-position of the carbapenem ring, WO 98/23623 describes carbapenem derivatives having an imidazo[5,1-b]thiazole group through a pyrrolidinylthio group at the 2-position of the carbapenem ring, and WO 98/32760 describes derivatives with a carbon atom on an imidazo[5,1-b]thiazole group being attached to the 2-position of the carbapenem ring.

SUMMARY OF THE INVENTION

An object of the present invention is to provide carbapenem derivatives which have potent antibiotic activity against MRSA, PRSP, Influenzavirus, and β-lactamase-producing bacteria and are stable against DHP-1.

According to one aspect of the present invention, there is provided a compound represented by formula (I) or a pharmaceutically acceptable salt thereof:

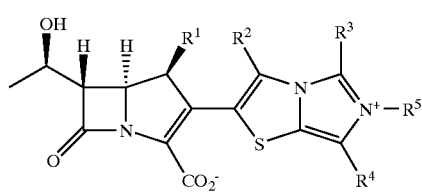

(I)

wherein
$R^1$ represents a hydrogen atom or methyl;
$R^2$ and $R^3$, which may be the same or different, each independently represent a hydrogen atom,
a halogen atom,
lower alkyl on which one or more hydrogen atoms are optionally substituted by hydroxyl or amino,
lower alkylcarbonyl,
carbamoyl,
aryl, or
lower alkylthio;
$R^4$ represents
lower alkylthio on which one or more hydrogen atoms are optionally substituted by a group selected from the group consisting of: a halogen atom; nitro; azido; cyano; lower cycloalkyl; lower alkylthio; hydroxyl; lower alkoxy; phosphonoxy; formyl; lower alkylcarbonyl; arylcarbonyl; carboxy; lower alkoxycarbonyl; carbamoyl; N-lower alkylcarbamoyl; N,N-di-lower alkylcarbamoyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)-sulfonylamino; formimidoylamino; acetimidoylamino; guanidino; aminosulfonyl; (N-lower alkylamino)sulfonyl; (N,N-di-lower alkylamino)sulfonyl; aryl; a monocyclic or bicyclic heterocyclic ring containing one or more hetero atoms which may be the same or different; pyridinium-1-yl; 1-azonia-4-azabicyclo[2,2,2]oct-1-yl; and 4-lower alkyl-1,4-diazoniabicyclo[2,2,2]oct-1-yl wherein one or more hydrogen atoms of the lower alkyl portion are optionally substituted by a group selected from the group consisting of a halogen atom, hydroxyl, carbamoyl, and amino, lower cycloalkylthio wherein one or more hydrogen atoms of the cycloalkyl portion are optionally substituted by a group selected from the group consisting of a halogen atom, nitro, cyano, hydroxyl, carbamoyl, and amino, $C_{2-4}$ alkenylthio,
$C_{2-4}$ alkynylthio,
arylthio,
thio substituted by a monocyclic or bicyclic heterocyclic ring containing one or more hetero atoms which may be the same or different,
lower alkylsulfinyl wherein one or more hydrogen atoms of the alkyl portion are optionally substituted by a group selected from the group consisting of halogen atom, hydroxyl, carbamoyl, and amino,
lower alkylsulfonyl wherein one or more hydrogen atoms of the alkyl portion are optionally substituted by a group selected from the group consisting of a halogen atom, hydroxyl, carbamoyl, and amino,
lower alkylcarbonyl, or
arylcarbonyl or
$R^4$ and $R^5$ together form —$R^4$—$R^5$— which represents —S—$(CH_2)_n$— wherein n is an integer of 2 to 4;
$R^5$ represents
lower alkyl on which one or more hydrogen atoms are optionally substituted by a group selected from the group consisting of: a halogen atom; nitro; azido; cyano; lower cycloalkyl; lower alkylthio wherein one or more hydrogen atoms of the alkyl portion are optionally substituted by a halogen atom, hydroxyl, carbamoyl, or amino; thio substituted by a monocyclic or bicyclic heterocyclic ring containing one or more hetero atoms which may be the same or different, wherein one or more hydrogen atoms of the ring are optionally substituted by carbamoyl, hydroxymethyl, aminosulfonylamino, or aminosulfonylaminomethyl; isothioureido; hydroxyl; lower alkoxy on which one or more hydrogen atoms are optionally substituted by a halogen atom, hydroxyl, carbamoyl, or amino; phosphonoxy; formyl; lower alkylcarbonyl; arylcarbonyl wherein one or more hydrogen atoms of the aryl portion are optionally substituted by a group selected from the group consisting of a halogen atom, nitro, cyano, lower alkyl on which one or more hydrogen atoms are optionally substituted by a halogen atom, hydroxyl, carbamoyl, or amino, hydroxyl, lower alkoxy, benzyloxy, carboxy, lower alkoxycarbonyl, carbamoyl, amino, and hydroxyamino; carboxy; lower alkoxycarbonyl; carbamoyl; N-aminocarbamoyl; N-lower alkylcarbamoyl wherein one or more hydrogen atoms of the alkyl portion are optionally substituted by amino, formimidoylamino, acetimidoylamino, or hydroxyl; N,N-di-lower alkylcarbamoyl wherein one or more hydrogen atoms of the alkyl portion are optionally substituted by amino, formimidoylamino, acetimidoylamino, or hydroxyl; alicyclic aminocarbonyl in which one or more hetero atoms may be contained as the member atom of the ring; N-arylcarbamoyl; N-hydroxycarbamoyl; N-benzyloxycarbamoyl; N-lower alkyl-N-lower alkoxycarbamoyl; hydrazinocarbonyl; amino; N-lower alkylamino wherein one or more hydrogen atoms of the alkyl portion are optionally substituted by amino, formimidoylamino, acetimidoylamino, or hydroxyl; N,N-di-lower alkylamino wherein one or more hydrogen atoms of the alkyl portion are optionally substituted by amino, formimidoylamino, acetimidoylamino, or hydroxyl; formylamino; lower alkylcarbonylamino; aminosulfonylamino; (N-lower alkylamino)sulfonylamino; (N,N-di-lower alkylamino)sulfonylamino; piperazinyl-carbonylamino; N-lower alkylpiperazinylcarbonylamino; N-arylpiperazinylcarbonylamino; formimidoylamino; acetimidoylamino; guanidino; lower alkylsulfonyl wherein one or more hydrogen atoms of the alkyl portion are optionally substituted by a halogen atom, amino, or hydroxyl; arylsulfonyl wherein one or more hydrogen atoms of the aryl portion are optionally substituted by a halogen atom, amino, or hydroxyl; aminosulfonyl; (N-lower alkylamino)sulfonyl; (N,N-di-lower alkylamino)sulfonyl; aryl on which one or more hydrogen atoms are optionally substituted by a group selected from the group consisting of a halogen atom, nitro, cyano, lower alkyl on which one or more hydrogen atoms are optionally substituted by a halogen atom, hydroxyl, carbamoyl, N,N-di-lower alkylcarbamoyl, amino, or amino-substituted lower alkyl, hydroxyl, lower alkoxy, benzyloxy, carboxy, lower alkoxycarbonyl, carbamoyl, N-lower alkylcarbamoyl N,N-di-lower alkylcarbamoyl, amino, and hydroxyamino; and a monocyclic or bicyclic aliphatic or heteroaromatic ring, containing one or more hetero atoms which may be the same or different, wherein one or more hydrogen atoms of the ring are optionally substituted by a halogen atom, hydroxyl, carbamoyl, or amino and, when the ring contains a nitrogen atom, lower alkyl optionally substituted by carbamoyl may be attached to the nitrogen atom and, in addition, the nitrogen atom may be in the form of a quaternary ammonium atom, lower cycloalkyl, $C_{2-4}$ alkenyl, $C_{2-4}$ alkynyl, a four- to seven-membered aliphatic heterocyclic ring containing one or more nitrogen atoms, wherein the heterocyclic ring may further comprise one or more oxygen or sulfur atoms as the ring member atom and one or more hydrogen atoms on the carbon atoms in the heterocyclic ring are optionally substituted by a group selected from the group consisting of: lower alkyl on which one or more hydrogen atoms are optionally substituted by hydroxyl or amino; carboxy; lower alkoxycarbonyl; carbamoyl; N-lower alkylcarbamoyl; and N,N-di-lower alkylcarbamoyl, and wherein a hydrogen atom on the nitrogen atom in the heterocyclic ring is optionally substituted by lower alkyl, $C_{2-4}$ alkenyl, formimidoyl, acetimidoyl, or amidino, or a group selected from the following groups:

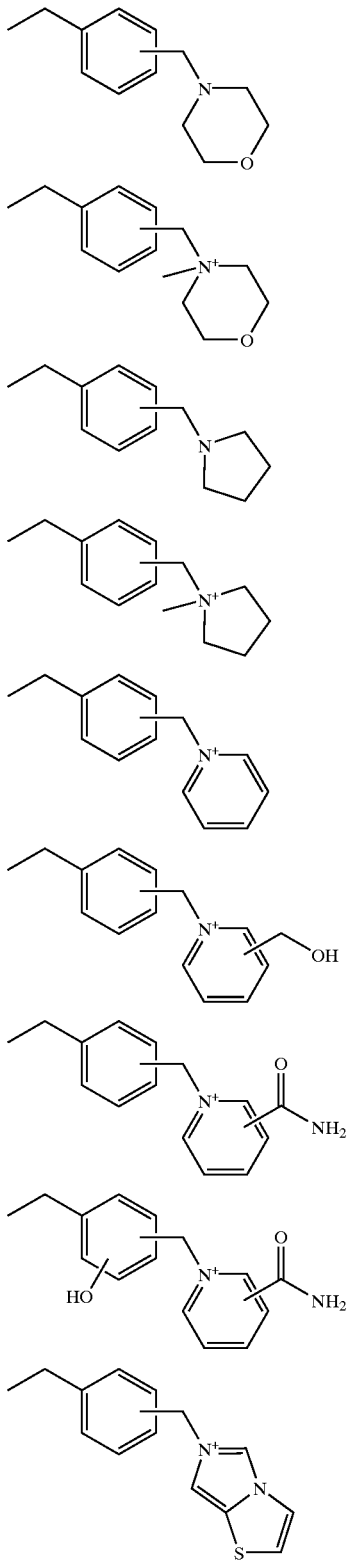

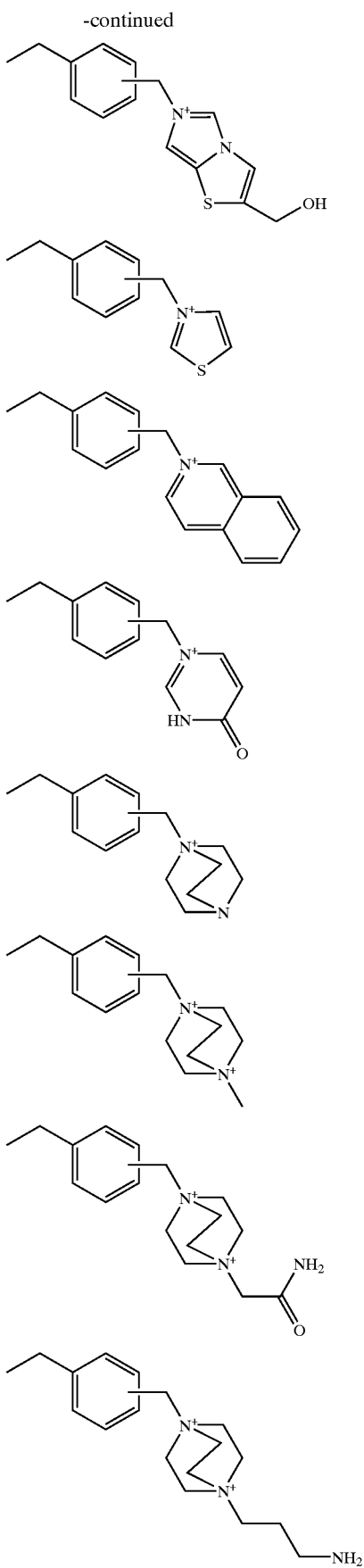

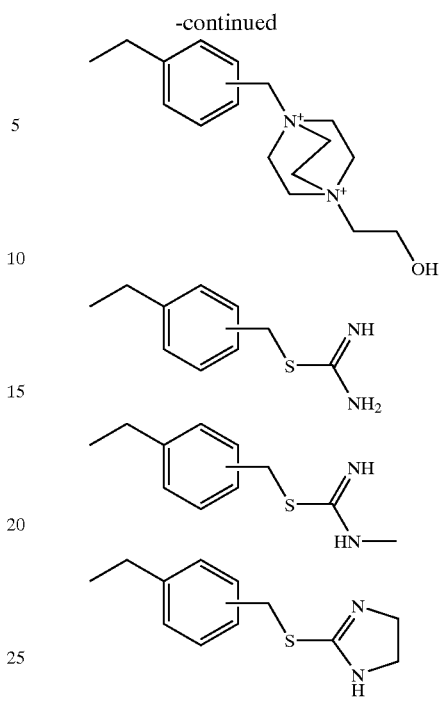

According to another aspect of the present invention, there is provided a pharmaceutical composition comprising as active ingredient a compound represented by formula (I) or a pharmaceutically acceptable salt thereof. This pharmaceutical composition is useful for the treatment and/or prevention of infectious diseases.

According to still another aspect of the present invention, there is provided use of a compound represented by formula (I) or a pharmaceutically acceptable salt thereof, for the manufacture of the medicament.

According to a further aspect of the present invention, there is provided a method for treating and/or preventing infectious diseases, comprising the step of administering a compound represented by formula (I) or a pharmaceutically acceptable salt thereof in an amount effective for the treatment and/or prevention of infectious diseases, to mammals including humans.

The carbapenem derivatives represented by formula (I) have potent antibiotic activities against a wide spectrum of Gram-positive bacteria and Gram-negative bacteria. The compounds represented by formula (I) have potent antibiotic activity particularly against MRSA, PRSP, Influenzavirus, and β-lactamase-producing bacteria. The carbapenem derivatives of the present invention advantageously have low toxicity and high safety.

DETAILED DESCRIPTION OF THE INVENTION

As used herein, the term "lower alkyl" or "lower alkoxy" as a group or a part of a group means straight-chain or branched $C_{1-6}$, preferably $C_{1-4}$, alkyl or alkyloxy. Examples of the lower alkyl include methyl, ethyl, n-propyl, i-propyl, n-butyl, i-butyl, s-butyl, t-butyl, n-pentyl, and n-hexyl. Examples of the lower alkoxy include methoxy, ethoxy, n-propoxy, i-propoxy, n-butoxy, s-butoxy, and t-butoxy.

The term "lower cycloalkyl", means $C_{3-6}$ monocyclic alkyl.

The term "halogen atom" means a fluorine, chlorine, bromine, or iodine atom.

The term "aryl" as a group or a part of a group means a monocyclic or bicyclic aromatic ring, and examples thereof include phenyl and naphthyl with phenyl being preferred.

The term "hetero atom" as used herein means an atom selected from a nitrogen atom, an oxygen atom, and a sulfur atom.

The "monocyclic or bicyclic heterocyclic ring containing one or more hetero atoms" preferably means a five- to twelve-membered monocyclic or bicyclic saturated or unsaturated heterocyclic ring containing 1 to 4 hetero atoms. The hetero atom constituting the heterocyclic ring is preferably one or two nitrogen atoms.

Examples of this heterocyclic ring include pyrrolidine, piperidine, pyridine, imidazole, thiazole, and thiophene.

The "four- to seven-membered aliphatic heterocyclic ring containing one or more nitrogen atoms" preferably means a four- to seven-membered aliphatic heterocyclic ring containing one or two nitrogen atoms. Examples of the aliphatic heterocyclic ring include pyrrolidine and piperidine.

The four- to seven-membered aliphatic heterocyclic ring containing one or more nitrogen atoms may further comprise an oxygen or sulfur atom as the ring member atom. Examples of the aliphatic heterocyclic ring containing an oxygen or sulfur atom as the ring member atom include morpholine.

The alicyclic amino in the alicyclic aminocarbonyl means a four- to seven-membered aliphatic heterocyclic ring, containing one or more nitrogen atoms, which may further contain an oxygen or sulfur atom as the ring member atom, and examples of the alicyclic aminocarbonyl include morpholinylcarbonyl and piperazinylcarbonyl.

$R^1$ preferably represents methyl.

$R^2$ and $R^3$, which may be the same or different, preferably represent a hydrogen atom, lower alkyl optionally substituted by hydroxyl, or lower alkylthio optionally substituted by hydroxyl, more preferably a hydrogen atom, methyl, hydroxymethyl, or methylthio, particularly preferably a hydrogen atom.

$R^4$ preferably represents lower alkylthio wherein one or more hydrogen atoms of the lower alkyl portion may be substituted and examples of preferred substituents include a halogen atom, carbamoyl, amino, formylamino, guanidino, aryl, pyridyl, pyridinium-1-yl, 1-azonia-4-azabicyclo[2,2,2]oct-1-yl, and 4-lower alkyl-1,4-diazoniabicyclo[2,2,2]oct-1-yl, thio substituted by a heterocyclic ring or heterocyclic rings, which may be the same or different, selected from the group consisting of pyrrolidine, piperidine, and pyridine, lower alkylsulfinyl, lower alkylsulfonyl, lower alkylcarbonyl, or arylcarbonyl or $R^4$ and $R^5$ together form —$R^4$—$R^5$— which represents —S—$(CH_2)_n$— wherein n is an integer of 2 to 4.

Examples of more preferred $R^4$ include methylthio, ethylthio, n-propylthio, isopropylthio, fluoromethylthio, trifluoromethylthio, 2-fluoroethylthio, 2-hydroxyethylthio, 3-hydroxypropylthio, carbamoylmethylthio, 2-aminoethylthio, 3-aminopropylthio, 2-formylaminoethylthio, 2-guanidinoethylthio, 3-guanidinopropylthio, benzylthio, (pyridin-2-yl)methylthio, 2-(4-methyl-1,4-diaoziabicyclo[2,2]oct-1-yl)ethylthio, (3S)-pyrrolidin-3-ylthio, piperidin-4-ylthio, (pyridin-2-yl)thio, methanesulfinyl, methanesulfonyl, acetyl, and benzoyl.

Alternatively, $R^4$ and $R^5$ may together form —$R^4$—$R^5$— which represents —S—$(CH_2)_2$— wherein n is an integer of 2 to 4. $R^4$ more preferably represents optionally substituted lower alkylthio, particularly preferably lower alkylthio optionally substituted by amino, most preferably methylthio or 3-aminopropylthio.

$R^5$ preferably represents lower alkyl on which one or more hydrogen atoms may be substituted and the substituent is preferably selected from the group consisting of: a halogen atom; nitro; lower alkylthio optionally substituted by amino; thio substituted by a heterocyclic ring selected from the group consisting of pyrrolidine, piperidine, and pyridine wherein one or more hydrogen atoms of the ring are optionally substituted by carbamoyl, hydroxymethyl, aminosulfonylamino, or aminosulfonylaminomethyl; isothioureido; hydroxyl; lower alkoxy optionally substituted by a halogen atom; arylcarbonyl optionally substituted by hydroxyamino; carboxy; lower alkoxycarbonyl; carbamoyl; N-aminocarbamoyl; N-lower alkylcarbamoyl wherein one or more hydrogen atoms of the alkyl portion are optionally substituted by amino, acetimidoylamino, or hydroxyl, N,N-di-lower alkylcarbamoyl; morpholinylcarbonyl; piperazinyl-carbonyl; N-arylcarbamoyl; N-hydroxycarbamoyl; N-benzyloxycarbamoyl; N-lower alkyl-N-lower alkoxycarbamoyl; amino; N-lower alkylamino optionally substituted by amino; lower alkylcarbonylamino; aminosulfonylamino; N-arylpiperazinylcarbonylamino; formimidoylamino; acetimidoylamino; lower alkylsulfonyl optionally substituted by amino; benzenesulfonyl optionally substituted by hydroxyl; aminosulfonyl; aryl on which one or more hydrogen atoms are optionally substituted by a group selected from the group consisting of a halogen atom, cyano, lower alkyl on which one or more hydrogen atoms are optionally substituted by hydroxyl, N,N-di-lower alkylcarbamoyl, or amino-substituted lower alkyl, hydroxyl, lower alkoxy, benzyloxy, carboxy, lower alkoxycarbonyl, carbamoyl, amino, and hydroxyamino; and a heterocyclic ring selected from the group consisting of pyrrolidine, imidazole, thiazole, piperidine, pyridine, and thiophene, wherein one or more hydrogen atoms of the ring are optionally substituted by amino and, when the ring contains a nitrogen atom, lower alkyl optionally substituted by carbamoyl may be attached to the nitrogen atom and the nitrogen atom may be in the form of a quaternary ammonium atom, a pyrrolidine or piperidine ring wherein one or more hydrogen atoms on carbon atoms of the heterocyclic ring are optionally substituted by a group selected from the group consisting of: lower alkyl optionally substituted by hydroxyl; carboxy; lower alkoxycarbonyl; and N,N-di-lower alkylcarbamoyl, and wherein one or more hydrogen atoms on the nitrogen atom of the heterocyclic ring are optionally substituted by acetimidoyl or amidino, or a group selected from the following groups:

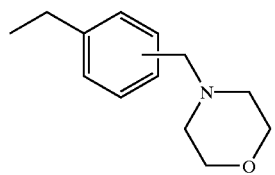

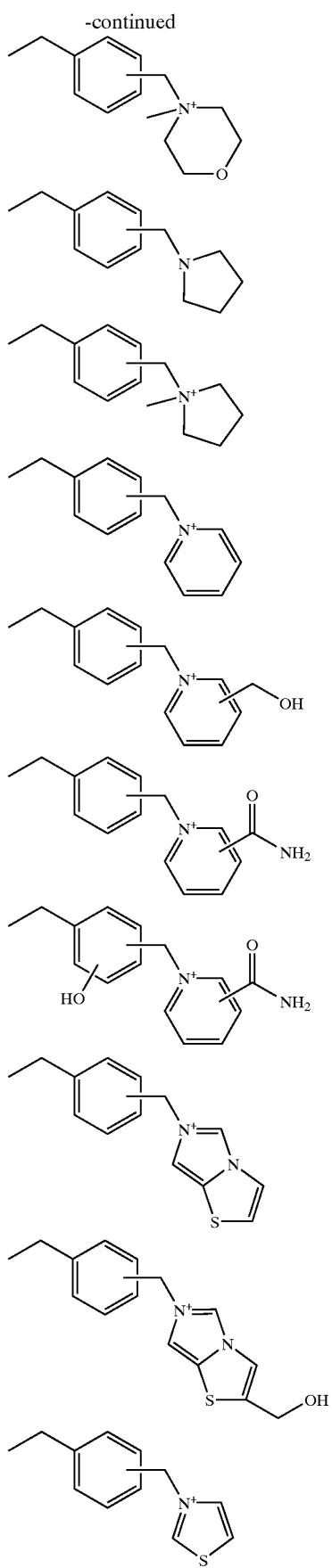
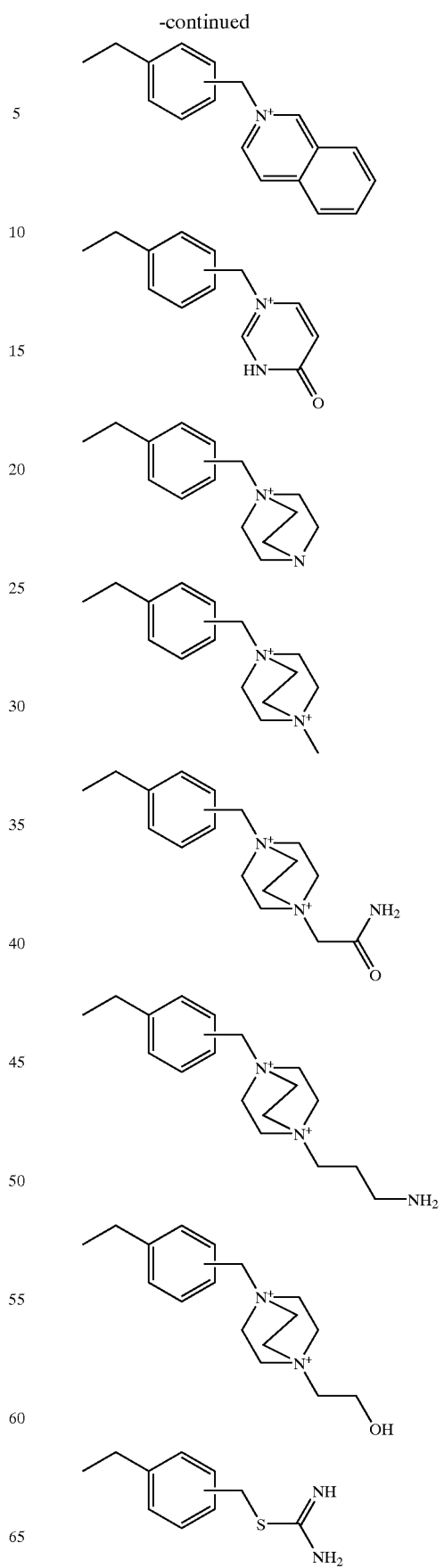

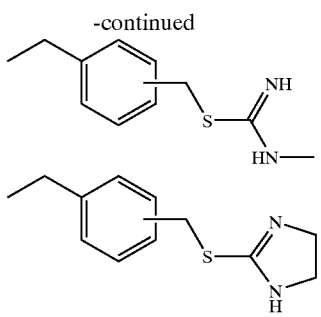

Examples of more preferred R⁵ include methyl, ethyl, n-propyl, 2-fluoroethyl, 2-bromoethyl, 2-nitroethyl, 2-(2-aminoethyl)thioethyl, 3-isothioureidopropyl, 3-(4,5-dihydro-1H-imidazol-2-yl)thiopropyl, 2-((3S)-pyrrolidin-3-yl)thioethyl, 2-((3S,5S)-5-carbamoylpyrrolidin-3-yl)thioethyl, 2-((3S,5S)-5-hydroxymethylpyrrolidin-3-yl)thioethyl, 2-[(3S,5S)-5-(aminosulfonylamino)methylpyrrolidin-3-yl]thioethyl, 2-hydroxyethyl, 3-hydroxypropyl, (2S)-2,3-dihydroxypropyl, (2R)-2,3-dihydroxypropyl, 2-oxo-2-phenylethyl, 2-(4-hydroxyaminophenyl)-2-oxoethyl, ethoxycarbonylmethyl, 2-ethoxycarbonylethyl, carbamoylmethyl, 2-carbamoylethyl, N-methylcarbamoylmethyl, N-(3-aminopropyl)carbamoyl-methyl, N-(3-acetimidoylamino-propyl)carbamoylmethyl, N-(3-hydroxypropyl)carbamoylmethyl, N,N-dimethylcarbamoylmethyl, N-(3-aminopropyl)-N-methylcarbamoylmethyl, 4-morpholinecarbonylmethyl, 2-oxo-2-(piperazin-1-yl)ethyl, N-phenylcarbamoylmethyl, N-hydroxycarbamoyl, N-benzyloxycarbamoylmethyl, (N-methoxy-N-methylcarbamoyl)methyl, hydrazinocarbonylmethyl, 2-aminoethyl, 3-aminopropyl, 4-aminobutyl, 5-aminopentyl, 6-aminohexyl, (2R)-3-amino-2-methylpropyl, (2R)-3-amino-2-hydroxypropyl, (2S)-3-amino-2-hydroxypropyl, (1S)-2-amino-1-hydroxymethylethyl, (2R)-3-amino-2-methoxypropyl, (2R)-3-amino-2-fluoromethoxypropyl, 3-amino-3-carbamoylpropyl, 2-(N-methylamino)ethyl, 2-[N-(2-aminoethyl)amino]ethyl, 2-(N-acetylamino)ethyl, 2-(aminosulfonylamino)ethyl, 3-(aminosulfonylamino)propyl, 3-(4-phenylpiperazin-1-yl)carbonylaminopropyl, 3-formimidoylaminopropyl, 2-acetimidoylaminoethyl, 3-acetimidoylaminopropyl, (2R)-3-acetimidoylamino-2-hydroxypropyl, 2-(2-aminoethyl)sulfonylethyl, 2-(3,4-dihydroxyphenyl)sulfonylethyl, 3-(aminosulfonyl)propyl, benzyl, phenethyl, 1-phenylethyl, carboxyphenylmethyl, 4-chlorobenzyl, 4-cyanobenzyl, 3-aminomethylbenzyl, 4-aminomethylbenzyl, 3-hydroxybenzyl, 3,5-dihydroxybenzyl, 3-methoxybenzyl, 4-(benzyloxybenzyl, 4-carboxybenzyl, 4-methoxycarbonylbenzyl, 2-(N,N-diethylcarbamoyl)benzyl, 4-(N,N-diethylcarbamoyl)benzyl, 3-aminobenzyl, 4-hydroxyaminobenzyl, (2R)-pyrrolidin-2-ylmethyl, pyridin-2-ylmethyl, 2-(pyridin-2-yl)ethyl, 2-(1-methylpyridinium-2-yl)ethyl, 4-thiazolylmethyl, (4-methylthiazol-5-yl)methyl, (2-aminothiazol-4-yl)methyl, 4-imidazolylmethyl, 2-thiophenylmethyl, 3-pyrrolidinyl, (3S)-3-pyrrolidinyl, 4-piperidinyl, (3R,5S)-5-hydroxymethylpyrrolidin-3-yl, (3S,5S)-5-carboxypyrrolidin-3-yl, (3S,5S)-5-methoxycarbonyl-pyrrolidin-3-yl, (3R,5S)-5-methoxycarbonylpyrrolidin-3-yl, (3S,5S)-5-(N,N-dimethylamino)carbonylpyrrolidin-3-yl, (3S)-1-acetimidoylpyrrolidin-3-yl, (3S)-1-amidinopyrrolidin-3-yl, (3-isothioureidomethyl)benzyl, (4-isothioureidomethyl)benzyl, [3-(N-methyl)isothioureidomethyl]benzyl, [3-(4,5-dihydro-1H-imidazol-2-yl)thiomethyl]benzyl, [3-(morpholin-4-yl)methyl]benzyl, [2-(4-methylmorpholinium-4-yl)methyl]benzyl, [3-(4-methylmorpholinium-4-yl)methyl]benzyl, [4-(4-methylmorpholinium-4-yl)methyl]benzyl, [3-(1-methylpyrrolidinium-1-yl)methyl]benzyl, [4-(1-methylpyrrolidinium-1-yl)methyl]benzyl, [3-(4-methyl-1,4-diazoniabicyclo[2,2,2]oct-1-yl)methyl]benzyl, [4-(4-methyl-1,4-diazoniabicyclo[2,2,2]oct-1-yl)methyl]benzyl, [3-[4-(3-aminopropyl)-1,4-diazoniabicyclo[2,2,2]oct-1-yl]methyl]benzyl, [3-(4-carbamoylmethyl-1,4-diazoniabicyclo[2,2,2]oct-1-yl)methyl]benzyl, [3-[4-(2-hydroxyethyl)-1,4-diazoniabicyclo[2,2,2]oct-1-yl]methyl]benzyl, [2-(pyridinium-1-yl)methyl]benzyl, (3-(pyridinium-1-yl)methyl]benzyl, [4-(pyridinium-1-yl)methyl]benzyl, [3-(2-hydroxymethylpyridinium-1-yl)methyl]benzyl, [3-(3-hydroxymethylpyridinium-1-yl)methyl]benzyl, [3-(4-hydroxymethylpyridinium-1-yl)methyl]benzyl, [3-(3-carbamoylpyridinium-1-yl)methyl]benzyl, [4-(4-carbamoylpyridinium-1-yl)methyl]benzyl, [5-(3-carbamoylpyridinium-1-yl)methyl-3-hydroxy)benzyl, [3-(imidazo[5,1-b]thiazolium-6-yl)methyl]benzyl, [4-(imidazo[5,1-b]thiazolium-6-yl)methyl]benzyl, [3-(2-hydroxymethylimidazo[5,1-b]thiazolium-6-yl)methyl]benzyl, [3-(thiazolium-3-yl)methyl]benzyl, [4-(thiazolium-3-yl)methyl]benzyl, [3-(isoquinolinium-2-yl)methyl]benzyl, [4-(isoquinolinium-2-yl)methyl]benzyl, and [3-(4-oxo-3,4-dihydropyridinium-1-yl)methyl]benzyl. More preferred are optionally substituted lower alkyl, optionally substituted monocyclic or bicyclic aliphatic and heteroaromatic rings such as pyrrolidine and piperidine. Particularly preferred are carbamoyl, amino, hydroxyl, or aryl-substituted lower alkyl, pyrrolidine ring, 3-(4-carbamoylmethyl-1,4-diazoniabicyclo[2,2,2]oct-1-yl)methylbenzyl, and 3-(pyridinium-1-yl)methylbenzyl. Most preferred are carbamoylmethyl, 3-aminopropyl, (3S)-pyrrolidin-3-yl, (2R)-3-amino-2-hydroxypropyl, benzyl, 3-(4-carbamoyl-methyl-1,4-diazoniabicyclo[2,2,2]oct-1-yl)methylbenzyl, and 3-(pyridinium-1-yl)methylbenzyl.

Among the compounds represented by formula (I), a group of preferred compounds include those wherein R⁴ represents optionally substituted lower alkylthio, thio substituted by a monocyclic or bicyclic heterocyclic ring containing one or more hetero atoms which may be the same or different, optionally substituted lower alkylsulfinyl, optionally substituted lower alkylsulfonyl, lower alkylcarbonyl, or arylcarbonyl or R⁴ and R⁵ together form —R⁴—R⁵— which represents —S—(CH₂)ₙ— wherein n is an integer of 2 to 4; and R⁵ represents optionally substituted lower alkyl or an optionally substituted four- to seven-membered aliphatic heterocyclic ring containing one or more nitrogen atoms.

Another group of preferred compounds include those wherein

R⁴ represents optionally substituted lower alkylthio, optionally substituted lower cycloalkylthio, C₂₋₄ alkenylthio, C₂₋₄ alkynylthio, arylthio, thio substituted by a monocyclic or bicyclic heterocyclic ring containing one or more hetero atoms which may be the same or different, optionally substituted lower alkylsulfinyl, optionally substituted lower alkylsulfonyl, lower alkylcarbonyl, or arylcarbonyl or R⁴ and R⁵ together form —R⁴—R⁵— which represents —S—(CH₂)ₙ— wherein n is an integer of 2 to 4, and R⁵ represents lower alkyl on which one or more hydrogen atoms are optionally substituted by a substituent selected from the group consisting of: a halogen atom; nitro; azido; cyano; lower cycloalkyl; lower alkylthio; hydroxyl; lower alkoxy; phosphonoxy; formyl; lower alkylcarbonyl; optionally substituted arylcarbonyl; carboxy; lower alkoxycarbonyl; carbamoyl; optionally substituted N-lower alkylcarbamoyl; optionally substituted N,N-di-lower alkylcarbamoyl; alicyclic aminocarbonyl wherein at least one hetero atom may be contained as the member atom of the ring; N-arylcarbamoyl; N-hydroxycarbamoyl; N-benzyloxy-carbamoyl; N-lower alkyl-N-lower alkoxycarbamoyl; amino; N-lower alkylamino wherein a hydrogen atom(s) of the alkyl portion is optionally substituted; N,N-di-lower alkylamino wherein a hydrogen atom(s) of the alkyl portion is optionally substituted; formylamino; lower alkylcarbonylamino; aminosulfonylamino; (N-lower alkylamino)sulfonylamino; (N,N-di-lower alkylamino)sulfonylamino; piperazinylcarbonylamino; N-lower alkylpiperazinylcarbonylamino; N-arylpiperazinylcarbonylamino; formimidoylamino; acetimidoylamino; guanidino; aminosulfonyl; (N-lower alkylamino)sulfonyl; (N,N-di-lower alkylamino)sulfonyl; aryl on which one or more hydrogen atoms are optionally substituted by a group selected from the group consisting of a halogen atom, nitro, cyano, optionally substituted lower alkyl, hydroxyl, lower alkoxy, benzyloxy, carboxy, lower alkoxycarbonyl, carbamoyl, amino, and hydroxyamino; and an optionally substituted monocyclic or bicyclic aliphatic or heteroaromatic ring which contains one or more hetero atoms which may be the same or different, lower cycloalkyl, C₂₋₄ alkenyl, C₂₋₄ alkynyl, or an optionally substituted four- to seven-membered aliphatic heterocyclic ring containing one or more nitrogen atoms.

A group of more preferred compounds include those wherein

R¹ represents a hydrogen atom or methyl,

R² and R³, which may be the same or different, represents a hydrogen atom, lower alkyl optionally substituted by hydroxyl, or lower alkylthio, R⁴ represents lower alkylthio wherein one or more hydrogen atoms of the alkyl portion are optionally substituted by a group selected from the group consisting of a halogen atom, hydroxyl, carbamoyl, amino, formylamino, guanidino, aryl, pyridyl, pyridinium-1-yl, 1-azonia-4-azabicyclo[2,2,2]oct-1-yl, and 4-lower alkyl-1,4-diazoniabicyclo[2,2,2]oct-1-yl, arylthio, thio substituted by a heterocyclic ring selected from the group consisting of pyrrolidine, piperidine, and pyridine, lower alkylsulfinyl, lower alkylsulfonyl, lower alkylcarbonyl, or arylcarbonyl or R⁴ and R⁵ together form —R⁴—R⁵— which represents —S—(CH₂)ₙ— wherein n is an integer of 2 to 4, and R⁵ represents lower alkyl on which one or more hydrogen atoms are optionally substituted by a group selected from the group consisting of: a halogen atom; nitro; lower alkylthio optionally substituted by amino; thio substituted by a heterocyclic ring selected from the group consisting of pyrrolidine, piperidine, and pyridine, wherein one or more hydrogen atoms of the ring are optionally substituted by carbamoyl, hydroxymethyl, aminosulfonylamino, or aminosulfonylaminomethyl; isothioureido; hydroxyl; lower alkoxy optionally substituted by a halogen atom; arylcarbonyl optionally substituted by hydroxyamino; carboxy; lower alkoxycarbonyl; carbamoyl; N-aminocarbamoyl; N-lower alkylcarbamoyl wherein one or more hydrogen atoms of the alkyl portion are optionally substituted by amino, acetimidoylamino, or hydroxyl; N,N-di-lower alkylcarbamoyl; morpholinylcarbonyl; piperazinylcarbonyl; N-arylcarbamoyl; N-hydroxycarbamoyl; N-benzyloxycarbamoyl; N-lower alkyl-N-lower alkoxycarbamoyl; amino; N-lower alkylamino optionally substituted by amino; lower alkylcarbonylamino; aminosulfonylamino; N-arylpiperazinylcarbonylamino; formimidoylamino; acetimidoylamino; lower alkylsulfonyl optionally substituted by amino; benzenesulfonyl optionally substituted by hydroxyl; aminosulfonyl; aryl on which one or more hydrogen atoms are optionally substituted by a group selected from the group consisting of a halogen atom, cyano, lower alkyl on which one or more hydrogen atoms are optionally substituted by hydroxyl, N,N-di-lower alkylcarbamoyl, or amino-substituted lower alkyl, hydroxyl, lower alkoxy, benzyloxy, carboxy, lower alkoxycarbonyl, carbamoyl, amino, and hydroxyamino; and a heterocyclic ring selected from the group consisting of pyrrolidine, imidazole, thiazole, piperidine, pyridine, and thiophene, wherein one or more hydrogen atoms of the ring are optionally substituted by amino and, when the ring contains a nitrogen atom, lower alkyl optionally substituted by carbamoyl may be attached to the nitrogen atom and the nitrogen atom may be in the form of a quaternary ammonium atom, a pyrrolidine or piperidine ring wherein one or more hydrogen atoms on carbon atoms of the heterocyclic ring are optionally substituted by a group selected from the group consisting of: lower alkyl optionally substituted by hydroxyl; carboxy; lower alkoxycarbonyl; and, N,N-di-lower alkylcarbamoyl, and wherein one or more hydrogen atoms on the nitrogen atom of the heterocyclic ring are optionally substituted by acetimidoyl or amidino, or a group selected from the following groups:

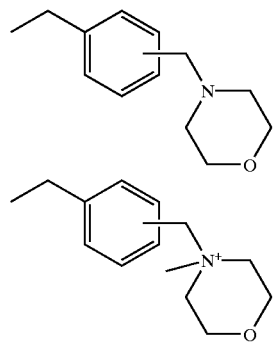

-continued
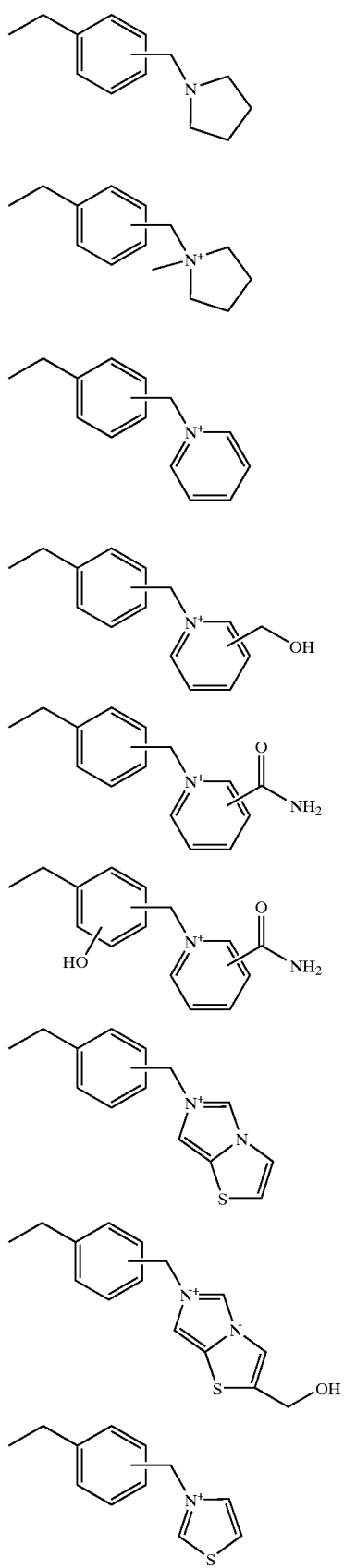
-continued
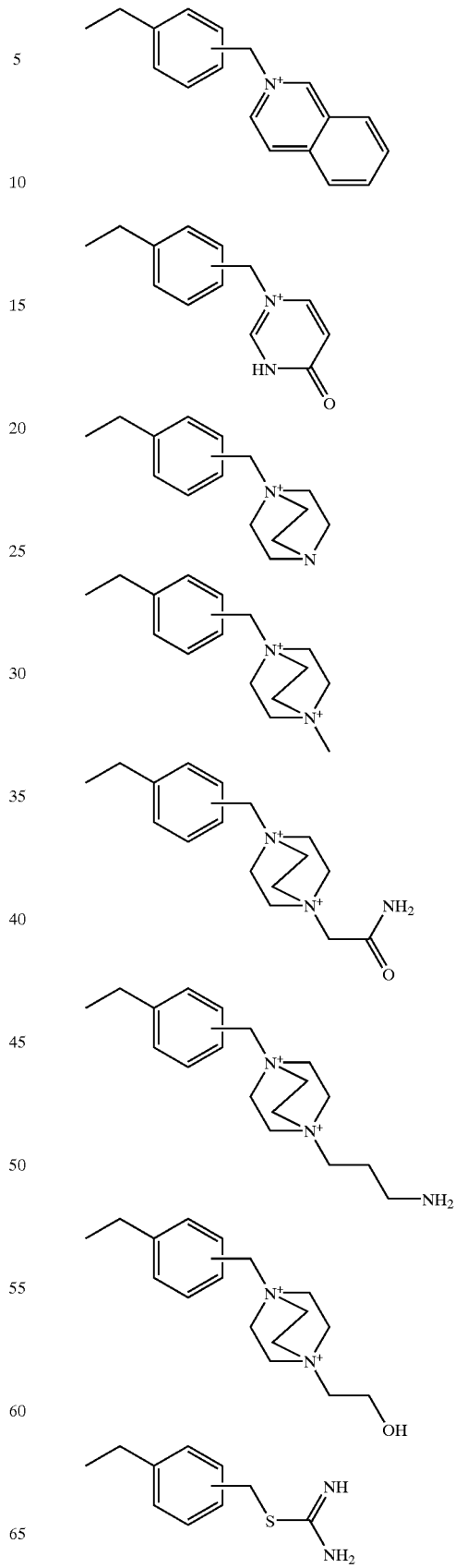

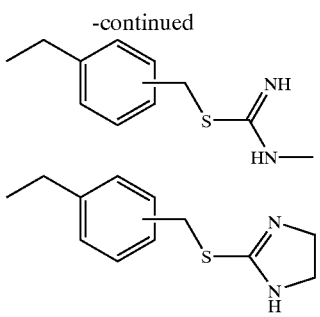

Another group of more preferred compounds include those wherein $R^1$ represents methyl; $R^2$ and $R^3$ each represent a hydrogen atom; $R^4$ represents optionally substituted lower alkylthio; and $R^5$ represents optionally substituted lower alkyl.

Still another group of more preferred compounds include those wherein $R^1$ represents methyl; $R^2$ and $R^3$ each represent a hydrogen atom; $R^4$ represents optionally substituted lower alkylthio; and $R^5$ represents an optionally substituted four- to seven-membered aliphatic heterocyclic ring containing one or more nitrogen atoms.

A group of further preferred compounds include those wherein $R^1$ represents methyl; $R^2$ and $R^3$ each represent a hydrogen atom; $R^4$ represents lower alkylthio; and $R^5$ represents lower alkyl substituted by carbamoyl, lower alkyl substituted by amino, pyrrolidinyl, lower alkyl substituted by amino and hydroxy, lower alkyl substituted by aryl, 3-(4-carbamoylmethyl-1,4-diazoniabicyclo[2,2,2]oct-1-yl)methylbenzyl, or 3-(pyridinium-1-yl)methylbenzyl.

Particularly preferred compounds include those wherein $R^1$ represents methyl; $R^2$ and $R^3$ each represent a hydrogen atom; $R^4$ represents methylthio; and $R^5$ represents carbamoylmethyl, 3-aminopropyl, (3S)-pyrrolidin-3-yl, (2R)-3-amino-2-hydroxypropyl, benzyl, 3-(4-carbamoylmethyl-1,4-diazoniabicyclo[2,2,2]oct-1-yl)methylbenzyl, or 3-(pyridinium-1-yl)methylbenzyl.

Other particularly preferred compound is one wherein $R^1$ represents methyl; $R^2$ and $R^3$ each represent a hydrogen atom; $R^4$ represents 3-aminopropylthio; and $R^5$ represents carbamoylmethyl.

Salts of the compounds represented by formula (I) are pharmaceutically acceptable salts, and include, for example, inorganic salts, such as lithium, sodium, potassium, calcium, and magnesium salts, ammonium salts, salts with organic bases, such as triethylamine and diisopropylethylamine, salts with mineral acids, such as hydrochloric acid, sulfuric acid, phosphoric acid, and nitric acid, or salts with organic acids, such as acetic acid, carbonic acid, citric acid, malic acid, oxalic acid, and methanesulfonic acid. Preferred are intramolecular salts, sodium salts, potassium salts, and hydrochlorides.

Specific examples of carbapenem derivatives according to the present invention include:

1. (1S,5R,6S)-6-((1R)-1-hydroxyethyl)-2-(7-methanesulfinyl-6-methylimidazo[5,1-b]thiazolium-2-yl)-1-methyl-1-carbapen-2-em-3-carboxylate (intramolecular salt) (a mixture of diastereomers);

2. (1S,5R,6S)-6-((1R)-1-hydroxyethyl)-1-methyl-2-(6-methyl-7-methylthioimidazo[5,1-b]thiazolium-2-yl)-1-carbapen-2-em-3-carboxylate (intramolecular salt);

3. (1S,5R,6S)-2-(6-carbamoylmethyl-7-methylthioimidazo[5,1-b]thiazolium-2-yl)-6-((1R)-1-hydroxyethyl)-1-methyl-1-carbapen-2-em-3-carboxylate (intramolecular salt);

4. (1S,5R,6S)-2-(6-carbamoylmethyl-7-carbamoylmethylthioimidazo[5,1-b]thiazolium-2-yl)-6-((1R)-1-hydroxyethyl)-1-methyl-1-carbapen-2-em-3-carboxylate (intramolecular salt);

5. (5R,6S)-6-((1R)-1-hydroxyethyl)-2-(6-methyl-7-methylthioimidazo[5,1-b]thiazolium-2-yl)-1-carbapen-2-em-3-carboxylate (intramolecular salt);

6. (5R,6S)-6-((1R)-1-hydroxyethyl)-2-(7-methanesulfinyl-6-methylimidazo[5,1-b]thiazolium-2-yl)-1-carbapen-2-em-3-carboxylate (intramolecular salt);

7. (5R,6S)-2-(5,6-dimethyl-7-methylthioimidazo[5,1-b]thiazolium-2-yl)-6-((1R)-1-hydroxyethyl)-1-carbapen-2-em-3-carboxylate (intramolecular salt);

8. (5R,6S)-2-[6-(3-aminopropyl)-5-methyl-7-methylthioimidazo[5,1-b]thiazolium-2-yl]-6-((1R)-1-hydroxyethyl)-1-carbapen-2-em-3-carboxylate (intramolecular 9. (1S,5R,6S)-6-((1R)-1-hydroxyethyl)-2-(7-methanesulfonyl-6-methylimidazo[5,1-b]thiazolium-2-yl)-1-methyl-1-carbapen-2-em-3-carboxylate (intramolecular salt);

10. (1S,5R,6S)-2-(5,6-dimethyl-7-methylthioimidazo[5,1-b]thiazolium-2-yl)-6-((1R)-1-hydroxyethyl)-1-methyl-1-carbapen-2-em-3-carboxylate (intramolecular salt);

11. (1S,5R,6S)-2-[6-(2-ethoxycarbonyl)ethyl-7-methylthioimidazo[5,1-b]thiazolium-2-yl]-6-((1R)-1-hydroxyethyl)-1-methyl-1-carbapen-2-em-3-carboxylate (intramolecular salt);

12. (1S,5R,6S)-6-((1R)-1-hydroxyethyl)-2-[7-(2-hydroxyethyl)thio-6-methylimidazo[5,1-b]thiazolium-2-yl]-1-methyl-1-carbapen-2-em-3-carboxylate (intramolecular salt);

13. (1S,5R,6S)-2-(7-acetyl-6-methylimidazo[5,1-b]thiazolium-2-yl)-6-((1R)-1-hydroxyethyl)-1-methyl-1-carbapen-2-em-3-carboxylate (intramolecular salt);

14. (1S,5R,6S)-2-[6-(3-aminopropyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

15. (1S,5R,6S)-6-((1R)-1-hydroxyethyl)-2-[6-(3-hydroxypropyl)-7-methylthioimidazo[5,1-b]thiazolium-2-yl]-1-methyl-1-carbapen-2-em-3-carboxylate (intramolecular salt) hydrochloride;

16. (1S,5R,6S)-2-(6-ethyl-7-methylthioimidazo[5,1-b]thiazolium-2-yl)-6-((1R)-1-hydroxyethyl)-1-methyl-1-carbapen-2-em-3-carboxylate (intramolecular salt);

17. (1S,5R,6S)-2-[5,7-bis(methylthio)-6-methylimidazo[5,1-b]thiazolium-2-yl]-6-((1R)-1-hydroxyethyl)-1-methyl-1-carbapen-2-em-3-carboxylate (intramolecular salt);

18. (5R,6S)-6-((1R)-1-hydroxyethyl)-2-[7-(2-hydroxyethyl)thio-6-methylimidazo[5,1b]thiazolium-2-yl]-1-carbapen-2-em-3-carboxylate (intramolecular salt);

19. (1S,5R,6S)-6-((1R)-1-hydroxyethyl)-1-methyl-2-(6-methyl-7-phenylthioimidazo[5,1-b]thiazolium-2-yl)-1-carbapen-2-em-3-carboxylate (intramolecular salt);

20. (1S,5R,6S)-6-((1R)-1-hydroxyethyl)-1-methyl-2-[7-methylthio-6-(piperidin-4-yl)imidazo[5,1-b]-thiazolium-2-yl]-1-carbapen-2-em-3-carboxylate; (intramolecular salt);

21. (1S,5R,6S)-2-[6-(2-fluoroethyl)-7-methylthioimidazo[5,1-b]thiazolium-2-yl]-6-((1R)-1-hydroxyethyl)-1-methyl-1-carbapen-2-em-3-carboxylate (intramolecular salt);

22. (1S,5R,6S)-6-((1R)-1-hydroxyethyl)-2-[6-(2-hydroxyethyl)-7-methylthioimidazo[5,1-b]thiazolium-2- yl]-1-methyl-1-carbapen-2-em-3-carboxylate (intramolecular salt);

23. (1S,5R,6S)-2-[6-(3-aminosulfonylpropyl)-7-methylthioimidazo[5,1-b]thiazolium-2-yl]-6-((1R)-1-hydroxyethyl)-1-methyl-1-carbapen-2-em-3-carboxylate (intramolecular salt);

24. (1S,5R,6S)-2-(7-ethylthio-6-methylimidazo[5,1-b]thiazolium-2-yl)-6-((1R)-1-hydroxyethyl)-1-methyl-1-carbapen-2-em-3-carboxylate (intramolecular salt);

25. (1S,5R,6S)-6-((1R)-1-hydroxyethyl)-1-methyl-2-(7-methylthio-6-propylimidazo[5,1-b]thiazolium-2-yl)-1-carbapen-2-em-3-carboxylate (intramolecular salt);

26. (5R,6S)-2-(7-ethylthio-6-methylimidazo[5,1-b]thiazolium-2-yl)-6-((1R)-1-hydroxyethyl)-1-carbapen-2-em-3-carboxylate (intramolecular salt);

27. (5R,6S)-2-(3,6-dimethyl-7-methylthioimidazo[5,1-b]thiazolium-2-yl)-6-((1R)-1-hydroxyethyl)-1-carbapen-2-em-3-carboxylate (intramolecular salt);

28. (5R,6S)-2-(6-carbamoylmethyl-7-methylthioimidazo[5,1-b]thiazolium-2-yl)-6-((1R)-1-hydroxyethyl)-1-carbapen-2-em-3-carboxylate (intramolecular salt);

29. (1S,5R,6S)-2-[7-(2-aminoethyl)thio-6-methylimidazo[5,1-b]thiazolium-2-yl]-6-((1R)-1-hydroxyethyl)-1-methyl-1-carbapen-2-em-3-carboxylate (intramolecular salt);

30. (5R,6S)-6-((1R)-1-hydroxyethyl)-2-(3-hydroxymethyl-6-methyl-7-methylthioimidazo[5,1-b]thiazolium-2-yl)-1-carbapen-2-em-3-carboxylate (intramolecular salt);

31. (1S,5R,6S)-2-[6-(2-bromoethyl)-7-methylthioimidazo[5,1-b]thiazolium-2-yl]-6-((1R)-1-hydroxyethyl)-1-methyl-1-carbapen-2-em-3-carboxylate (intramolecular salt);

32. (5R,6S)-2-[6-(3-aminopropyl)-3-methyl-7-methylthioimidazo[5,1-b]thiazolium-2-yl]-6-((1R)-1-hydroxyethyl)-1-carbapen-2-em-3-carboxylate (intramolecular salt);

33. (1S,5R,6S)-2-[6-(2-carbamoylethyl)-7-methylthioimidazo[5,1-b]thiazolium-2-yl]-6-((1R)-1-hydroxyethyl)-1-methyl-1-carbapen-2-em-3-carboxylate (intramolecular salt);

34. (5R,6S)-2-(6-carbamoylmethyl-3-methyl-7-methylthioimidazo[5,1-b]thiazolium-2-yl)-6-((1R)-1-hydroxyethyl)-1-carbapen-2-em-3-carboxylate (intramolecular salt);

35. (1S,5R,6S)-2-(6-carbamoylmethyl-7-ethylthioimidazo[5,1-b]thiazolium-2-yl)-6-((1R)-1-hydroxyethyl)-1-methyl-1-carbapen-2-em-3-carboxylate (intramolecular salt);

36. (5R,6S)-2-[7-(2-aminoethyl)thio-6-methylimidazo[5,1-b]thiazolium-2-yl]-6-((1R)-1-hydroxyethyl)-1-carbapen-2-em-3-carboxylate (intramolecular salt);

37. (5R,6S)-2-[5,7-bis(methylthio)-6-methylimidazo[5,1-b]thiazolium-2-yl]-6-((1R)-1-hydroxyethyl)-1-carbapen-2-em-3-carboxylate (intramolecular salt);

38. (1S,5R,6S)-2-[7-ethylthio-6-(2-hydroxyethyl)imidazo[5,1-b]thiazolium-2-yl]-6-((1R)-1-hydroxyethyl)-1-methyl-1-carbapen-2-em-3-carboxylate (intramolecular salt);

39. (1S,5R,6S)-2-[6-((3S,5S)-5-carboxypyrrolidin-3-yl)-7-methylthioimidazo[5,1-b]thiazolium-2-yl]-6-((1R)-1-hydroxyethyl)-1-methyl-1-carbapen-2-em-3-carboxylate (intramolecular salt);

40. (1S,5R,6S)-2-(7,8-dihydroimidazo[5,1-b:4,3-b']bisthiazol-2-yl)-6-((1R)-1-hydroxyethyl)-1-methyl-1-carbapen-2-em-3-carboxylic acid (intramolecular salt);

41. (1S,5R,6S)-2-[6-(N,N-dimethylcarbamoylmethyl)-7-methylthioimidazo[5,1-b]thiazolium-2-yl]-6-((1R)-1-hydroxyethyl)-1-methyl-1-carbapen-2-em-3-carboxylate (intramolecular salt);

42. (1S,5R,6S)-6-((1R)-1-hydroxyethyl)-1-methyl-2-[7-methylthio-6-(4-morpholinecarbonylmethyl)imidazo-[5,1-b]thiazolium-2-yl]-1-carbapen-2-em-3-carboxylate (intramolecular salt);

43. (1S,5R,6S)-2-(7-benzoyl-6-methylimidazo[5,1-b]-thiazolium-2-yl)-6-((1R)-1-hydroxyethyl)-1-methyl-1-carbapen-2-em-3-carboxylate (intramolecular salt);

44. (1S,5R,6S)-6-((1R)-1-hydroxyethyl)-1-methyl-2-[7-methylthio-6-(pyrrolidin-3-yl)imidazo[5,1-b]-thiazolium-2-yl]-1-carbapen-2-em-3-carboxylate (intramolecular salt) hydrochloride (a mixture of diastereomers);

45. (1S,5R,6S)-6-((1R)-1-hydroxyethyl)-1-methyl-2-[6-(N-methylcarbamoylmethyl)-7-methylthioimidazo[5,1-b]-thiazolium-2-yl]-1-carbapen-2-em-3-carboxylate (intramolecular salt);

46. (1S,5R,6S)-6-((1R)-1-hydroxyethyl)-2-[6-(4-hydroxyaminobenzyl)-7-methylthioimidazo[5,1-b]-thiazolium-2-yl]-1-methyl-1-carbapen-2-em-3-carboxylate (intramolecular salt);

47. (1S,5R,6S)-6-((1R)-1-hydroxyethyl)-1-methyl-2-(6-methyl-7-propylthioimidazo[5,1-b]thiazolium-2-yl)-1-carbapen-2-em-3-carboxylate (intramolecular salt);

48. (1S,5R,6S)-6-((1R)-1-hydroxyethyl)-1-methyl-2-[7-methylthio-6-(2-nitroethyl)imidazo[5,1-b]thiazolium-2-yl]-1-carbapen-2-em-3-carboxylate (intramolecular salt);

49. (1S,5R,6S)-6-((1R)-1-hydroxyethyl)-1-methyl-2-[6-[2-(N-methylamino)ethyl]-7-methylthioimidazo[5,1-b]thiazolium-2-yl]-1-carbapen-2-em-3-carboxylate (intramolecular salt);

50. (1S,5R,6S)-6-((1R)-1-hydroxyethyl)-1-methyl-2-[7-methylthio-6-((3S)-pyrrolidin-3-yl)imidazo[5,1-b]thiazolium-2-yl]-1-carbapen-2-em-3-carboxylate (intramolecular salt) hydrochloride;

51. (1S,5R,6S)-6-((1R)-1-hydroxyethyl)-1-methyl-2-[6-((3S,5S)-5-methoxycarbonylpyrrolidin-3-yl)-7-methylthioimidazo[5,1-b]thiazolium-2-yl]-1-carbapen-2-em-3-carboxylate (intramolecular salt) hydrochloride;

52. (1S,5R,6S)-6-((1R)-1-hydroxyethyl)-1-methyl-2-[6-((3R,5S)-5-methoxycarbonylpyrrolidin-3-yl)-7-methylthioimidazo[5,1-b]thiazolium-2-yl]-1-carbapen-2-em-3-carboxylate (intramolecular salt) hydrochloride;

53. (1S,5R,6S)-2-[6-(2-aminoethyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

54. (1S,5R,6S)-6-((1R)-1-Hydroxyethyl)-2-[6-((3R,5S)-5-hydroxymethylpyrrolidin-3-yl)-7-methylthioimidazo[5,1-b]thiazolium-2-yl]-1-methyl-1-carbapen-2-em-3-carboxylate (intramolecular salt) hydrochloride;

55. (1S,5R,6S)-2-[6-[2-[N-(2-aminoethyl)amino]ethyl]-7-methylthioimidazo[5,1-b]thiazolium-2-yl]-6-((1R)-1-hydroxyethyl)-1-methyl-1-carbapen-2-em-3-carboxylate (intramolecular salt) methanesulfonate;

56. (1S,5R,6S)-6-((1R)-1-hydroxyethyl)-2-(7-isopropylthio-6-methylimidazo[5,1-b]thiazolium-2-yl)-1-methyl-1-carbapen-2-em-3-carboxylate (intramolecular salt);

57. (1S,5R,6S)-2-[6-(4-aminobutyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

58. (1S,5R,6S)-2-[7-aminoethyl)thio-6-methyl-5-methylthioimidazo[5,1-b]thiazolium-2-yl]-6-((1R)-1-hydroxyethyl)-1-methyl-1-carbapen-2-em-3-carboxylate (intramolecular salt);

59. (1S,5R,6S)-2-[7-(2-aminoethyl)thio-6-(3-aminopropyl)imidazo[5,1-b]thiazolium-2-yl]-6-((1R)-1-hydroxyethyl)-1-methyl-1-carbapen-2-em-3-carboxylate (intramolecular salt) dihydrochloride;

60. (1S,5R,6S)-2-[6-(3-aminopropyl)-7-(2-hydroxyethyl)thioimidazo[5,1-b]thiazolium-2-yl]-6-((1R)-1-hydroxyethyl)-1-methyl-1-carbapen-2-em-3-carboxylate (intramolecular salt) hydrochloride;

61. (1S,5R,6S)-2-[7-(2-formylaminoethyl)thio-6-methylimidazo[5,1-b]thiazolium-2-yl]-6-((1R)-1-hydroxyethyl)-1-methyl-1-carbapen-2-em-3-carboxylate (intramolecular salt);

62. (1S,5R,6S)-6-((1R)-1-hydroxyethyl)-1-methyl-2-[7-methylthio-6-((2R)-pyrrolidin-2-yl)methylimidazo[5,1-b]thiazolium-2-yl]-1-carbapen-2-em-3-carboxylate (intramolecular salt) hydrochloride;

63. (1S,5R,6S)-2-[6-(6-aminohexyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

64. (1S,5R,6S)-2-(7-(3-aminopropyl)thio-6-methylimidazo[5,1-b]thiazolium-2-yl]-6-((1R)-1-hydroxyethyl)-1-methyl-1-carbapen-2-em-3-carboxylate (intramolecular salt) hydrochloride;

65. (1S,5R,6S)-6-((1R)-1-hydroxyethyl)-2-[7-methylthio-6-[2-oxo-2-(piperazin-1-yl)ethyl]imidazo[5,1-b]-thiazolium-2-yl]-1-methyl-1-carbapen-2-em-3-carboxylate (intramolecular salt) hydrochloride;

66. (1S,5R,6S)-2-[6-[N-(3-aminopropyl)carbamoylmethyl]-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

67. (1S,5R,6S)-6-((1R)-1-hydroxyethyl)-2-[6-[N-(3-hydroxypropyl)carbamoylmethyl]-7-methylthioimidazo[5,1-b]thiazolium-2-yl]-1-methyl-1-carbapen-2-em-3-carboxylate (intramolecular salt);

68. (1S,5R,6S)-2-[6-(3-acetimidoylaminopropyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

69. (1S,5R,6S)-2-[6-((3S)-1-acetimidoylpyrrolidin-3-yl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

70. (1S,5R,6S)-2-[6-((3S)-1-amidinopyrrolidin-3-yl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

71. (1S,5R,6S)-2-[6-carbamoylmethyl-7-(piperidin-4-yl)thioimidazo[5,1-b]thiazolium-2-yl]-6-((1R)-1-hydroxyethyl)-1-methyl-1-carbapen-2-em-3-carboxylate (intramolecular salt) hydrochloride;

72. (1S,5R,6S)-2-[6-(3-formimidoylaminopropyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

73. (1S,5R,6S)-2-[6-[N-(3-acetimidoylaminopropyl)carbamoylmethyl]-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

74. (1S,5R,6S)-2-[6-[N-(3-aminopropyl)-N-methylcarbamoylmethyl]-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

75. (1S,5R,6S)-2-[6-((3S,5S)-5-N,N-dimethylcarbamoylpyrrolidin-3-yl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

76. (1S,5R,6S)-2-[6-(2-acetimidoylaminoethyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

77. (1S,5R,6S)-6-((1R)-1-hydroxyethyl)-1-methyl-2-(6-methyl-7-trifluoromethylthioimidazo[5,1-b]-thiazolium-2-yl)-1-carbapen-2-em-3-carboxylate (intramolecular salt);

78. (1S,5R,6S)-2-[7-(2-guanidinoethyl)thio-6-methylimidazo[5,1-b]thiazolium-2-yl]-6-((1R)-1-hydroxyethyl)-1-methyl-1-carbapen-2-em-3-carboxylate (intramolecular salt) hydrochloride;

79. (1S,5R,6s)-2-(7-fluoromethylthio-6-methylimidazo[5,1-b]thiazolium-2-yl)-6-((1R)-1-hydroxyethyl)-1-methyl-1-carbapen-2-em-3-carboxylate (intramolecular salt);

80. (1S,5R,6S)-6-((1R)-1-hydroxyethyl)-1-methyl-2-[6-methyl-7-((3S)-pyrrolidin-3-yl)thioimidazo[5,1-b]-thiazolium-2-yl]-1carbapen-2-em-3-carboxylate (intramolecular salt) hydrochloride;

81. (1S,5R,6S)-2-[6-[2-(4-hydroxyaminophenyl)-2-oxoethyl]-7-methylthioimidazo[5,1-b]thiazolium-2-yl]-6-((1R)-1-hydroxyethyl)-1-methyl-1-carbapen-2-em-3-carboxylate (intramolecular salt);

82. (1S,5R,6S)-2-(6-benzyl-7-methylthioimidazo[5,1-b]thiazolium-2-yl)-6-((1R)-1-hydroxyethyl)-1-methyl-1-carbapen-2-em-3-carboxylate (intramolecular salt);

83. (1S,5R,6S)-6-((1R)-1-hydroxyethyl)-2-[6-(3-methoxybenzyl)-7-methylthioimidazo[5,1-b]thiazolium-2-yl]-1-methyl-1-carbapen-2-em-3-carboxylate (intramolecular salt);

84. (1S,5R,6S)-2-[6-(4-chlorobenzyl)-7-methylthioimidazo[5,1-b]thiazolium-2-yl]-6-((1R)-1-hydroxyethyl)-1-methyl-1-carbapen-2-em-3-carboxylate (intramolecular salt);

85. (1S,5R,6S)-2-(6-carbamoylmethyl-7-fluoromethylthioimidazo[5,1-b]thiazolium-2-yl)-6-((1R)-1-hydroxyethyl)-1-methyl-1-carbapen-2-em-3-carboxylate (intramolecular salt);

86. (1S,5R,6S)-6-((1R)-1-hydroxyethyl)-1-methyl-2-(7-methylthio-6-phenethylimidazo[5,1-b]thiazolium-2-yl)-1-carbapen-2-em-3-carboxylate (intramolecular salt);

87. (1S,5R,6S)-2-[6-((3RS)-3-amino-3-carbamoylpropyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

88. (1S,5R,6S)-6-((1R)-1-hydroxyethyl)-1-methyl-2-[7-methylthio-6-(2-oxo-2-phenylethyl)imidazo[5,1-b]-thiazolium-2-yl]-1-carbapen-2-em-3-carboxylate (intramolecular salt);

89. (1S,5R,6S)-2-[6-(4-cyanobenzyl)-7-methylthioimidazo[5,1-b]thiazolium-2-yl]-6-((1R)-1-hydroxyethyl)-1-methyl-1-carbapen-2-em-3-carboxylate (intramolecular salt);

90. (1S,5R,6S)-2-[6-(3-hydroxybenzyl)-7-methylthioimidazo[5,1-b]thiazolium-2-yl]-6-((1R)-1-hydroxyethyl)-1-methyl-1-carbapen-2-em-3-carboxylate (intramolecular salt);

91. (1S,5R,6S)-6-((1R)-1-hydroxyethyl)-1-methyl-2-[7-methylthio-6-(N-phenyl)carbamoylmethyl]imidazo[5,1-b]thiazolium-2-yl]-1-carbapen-2-em-3-carboxylate (intramolecular salt);

92. (1S,5R,6S)-6-((1R)-1-hydroxyethyl)-2-(6-N-methoxy-N-methylcarbamoylmethyl-7-methylthioimidazo[5,1-b]thiazolium-2-yl)-1-methyl-1-carbapen-2-em-3-carboxylate (intramolecular salt);

93. (1S,5R,6S)-2-[6-((1S)-2-amino-1-hydroxymethyl)ethyl-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

94. (1S,5R,6S)-2-[6-((2R)-3-amino-2-methylpropyl)-7-methylthioimidazo[5,1-b]thiazolium-2-yl-6-((1R)-1-hydroxyethyl)-1-methyl-1-carbapen-2-em-3-carboxylate (intramolecular salt) hydrochloride;

95. (1S, 5R,6S)-2-(6-ethoxycarbonylmethyl-7-methylthioimidazo[5,1-b]thiazolium-2-yl)-6-((1R)-1-hydroxyethyl)-1-methyl-1-carbapen-2-em-3-carboxylate (intramolecular salt);

96. (1S,5R,6S)-2-[6-(2-acetylamino)ethyl-7-methylthioimidazo[5,1-b]thiazolium-2-yl]-6-((1R)-1-hydroxyethyl)-1-methyl-1-carbapen-2-em-3-carboxylate (intramolecular salt);

97. (1S,5R,6S)-6-((1R)-1-hydroxyethyl)-2-[7-methylthio-6-(thiazol-4-yl)methylimidazo[5,1-b]thiazolium-2-yl]-1-methyl-1-carbapen-2-em-3-carboxylate (intramolecular salt);

98. (1S,5R,6S)-2-[6-(2-aminosulfonylaminoethyl)-7-methylthioimidazo[5,1-b]thiazolium-2-yl]-6-((1R)-1-hydroxyethyl)-1-methyl-1-carbapen-2-em-3-carboxylate (intramolecular salt);

99. (1S,5R,6S)-2-[6-((2R)-3-amino-2-hydroxy)propyl-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

100. (1S,5R,6S)-2-[6-((2S)-2,3-dihydroxy)propyl-7-methylthioimidazo[5,1-b]thiazolium-2-yl]-6-((1R)-1-hydroxyethyl)-1-methyl-1-carbapen-2-em-3-carboxylate (intramolecular salt);

101. (1S,5R, 6S)-6-((1R)-1-hydroxyethyl)-1-methyl-2-[6-[2-(pyridin-2-yl)ethyl]-7-methylthioimidazo[5,1-b]-thiazolium-2-yl]-1-carbapen-2-em-3-carboxylate (intramolecular salt);

102. (1S,5R,6S)-6-((1R)-1-hydroxyethyl)-1-methyl-2-[6-[2-(1-methylpyridinium-2-yl)ethyl]-7-methylthioimidazo[5,1-b]thiazolium-2-yl]-1-carbapen-2-em-3-carboxylate chloride (intramolecular salt);

103. (1S,5R,6S)-2-[6-((2R)-3-acetimidoylamino-2-hydroxypropyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

104. (1S,5R,6S)-2-[6-(3-aminosulfonylaminopropyl)-7-methylthioimidazo[5,1-b]thiazolium-2-yl]-6-((1R)-1-hydroxyethyl)-1-methyl-1-carbapen-2-em-3-carboxylate (intramolecular salt);

105. (1S,5R,6S)-6-((1R)-1-hydroxyethyl)-1-methyl-2-(7-methylthio-6-(pyridin-2-yl)methylimidazo[5,1-b]-thiazolium-2-yl]-1-carbapen-2-em-3-carboxylate (intramolecular salt);

106. (1S,5R,6S)-2-[6-(4-benzyloxy)benzyl-7-methylthioimidazo[5,1-b]thiazolium-2-yl]-6-((1R)-1-hydroxyethyl)-1-methyl-1-carbapen-2-em-3-carboxylate (intramolecular salt);

107. (1S,5R,6S)-6-((1R)-1-hydroxyethyl)-1-methyl-2-[7-methylthio-6-[3-(4-phenylpiperazin-1-yl)carbonylaminopropyl]imidazo[5,1-b]thiazolium-2-yl]-1-carbapen-2-em-3-carboxylate (intramolecular salt);

108. (1S,5R,6S)-2-(6-N-benzyloxycarbamoylmethyl-7-methylthioimidazo[5,1-b]thiazolium-2-yl)-6-((1R)-1-hydroxyethyl)-1-methyl-1-carbapen-2-em-3-carboxylate (intramolecular salt);

109. (1S,5R,6S)-6-((1R)-1-hydroxyethyl)-2-[6-(4-methylthiazol-5-yl)methyl-7-methylthioimidazo[5,1-b]thiazolium-2-yl]-1-methyl-1-carbapen-2-em-3-carboxylate (intramolecular salt);

110. (1S,5R,6S)-6-((1R)-1-hydroxyethyl)-2-[6-(imidazol-4-yl)methyl-7-methylthioimidazo[5,1-b]thiazolium-2-yl]-1-methyl-1-carbapen-2-em-3-carboxylate (intramolecular salt) hydrochloride;

111. (1S,5R,6S)-2-[7-(3-aminopropyl)thio-6-carbamoylmethylimidazo[5,1-b]thiazolium-2-yl]-6-((1R)-1-hydroxyethyl)-1-methyl-1-carbapen-2-em-3-carboxylate (intramolecular salt) hydrochloride;

112. (1S,5R,6S)-2-[7-(3-hydroxypropyl)thio-6-carbamoylmethylimidazo[5,1-b]thiazolium-2-yl]-6-((1R)-1-hydroxyethyl)-1-methyl-1-carbapen-2-em-3-carboxylate (intramolecular salt);

113. (1S,5R,6S)-2-[6-((2S)-3-amino-2-hydroxy)propyl-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

114. (1S,5R,6S)-2-[6-((2R-2,3-dihydroxy)propyl-7-methylthioimidazo[5,1-b]thiazolium-2-yl]-6-((1R)-1-hydroxyethyl)-1-methyl-1-carbapen-2-em-3-carboxylate (intramolecular salt);

115. (1S,5R,6S)-2-[6-((2R)-3-amino-2-hydroxy)propyl-7-methanesulfinylimidazo[5,1-b]thiazolium-2-yl]-6-((1R)-1-hydroxyethyl)-1-methyl-1-carbapen-2-em-3-carboxylate (intramolecular salt) hydrochloride (a mixture of diastereomers);

116. (1S,5R,6S)-6-((1R)-1-hydroxyethyl)-2-[6-(2-hydroxyethyl)-7-methanesulfinylimidazo[5,1-b]thiazolium-2-yl]-1-methyl-1-carbapen-2-em-3-carboxylate (intramolecular salt) (a mixture of diastereomers);

117. (1S,5R,6S)-2-[6-(2-aminothiazol-4-yl)methyl-7-methylthioimidazo[5,1-b]thiazolium-2-yl]-6-((1R)-1-hydroxyethyl)-1-methyl-1-carbapen-2-em-3-carboxylate (intramolecular salt);

118. (1S,5R,6S)-6-((1R)-1-hydroxyethyl)-1-methyl-2-[7-methylthio-6-(1-phenylethyl)imidazo[5,1-b]thiazolium-2-yl]-1-carbapen-2-em-3-carboxylate (intramolecular salt) (a mixture of diastereomers);

119. (1S,5R,6S)-6-((1R)-1-hydroxyethyl)-1-methyl-2-[7-methylthio-6-(carboxy)(phenyl)methylimidazo[5,1-b]-thiazolium]-2-yl-1-carbapen-2-em-3-carboxylate (intramolecular salt) (admixture of diastereomers);

120. (1S,5R,6S)-2-[6-(4-carboxybenzyl)-7-methylthioimidazo[5,1-b]thiazolium-2-yl]-6-((1R)-1-hydroxyethyl)-1-methyl-1-carbapen-2-em-3-carboxylate (intramolecular salt);

121. (1S,5R,6S)-2-(6-N-hydroxyaminocarbonylmethyl-7-methylthioimidazo[5,1-b]thiazolium-2-yl)-6-((1R)-1-hydroxyethyl)-1-methyl-1-carbapen-2-em-3-carboxylate (intramolecular salt);

122. (1S,5R,6S)-6-((1R)-1-hydroxyethyl)-1-methyl-2-[6-methyl-7-[2-(4-methyl-1,4-diazoniabicyclo[2,2,2]oct-1-yl)ethyl]thioimidazo[5,1-b]thiazolium-2-yl]-1-carbapen-2-em-3-carboxylate dichloride (intramolecular salt);

123. (1S,5R,6S)-6-((1R)-1-hydroxyethyl)-1-methyl-2-[7-methylthio-6-(thiophene-2-yl)methylimidazo[5,1-b]thiazolium-2-yl]-1-carbapen-2-em-3-carboxylate (intramolecular salt);

124. (1S,5R,6S)-6-((1R)-1-hydroxyethyl)-2-[6-(4-methoxycarbonylbenzyl)-7-methylthioimidazo[5,1-b]thiazolium-2-yl]-1-methyl-1-carbapen-2-em-3-carboxylate (intramolecular salt);

125. (1S,5R,6S)-2-(6-hydrazinocarbonylmethyl-7-methylthioimidazo[5,1-b]thiazolium-2-yl)-6-((1R)-1-hydroxyethyl)-1-methyl-1-carbapen-2-em-3-carboxylate (intramolecular salt);

126. (1S,5R,6S)-2-[6-(3-aminobenzyl)-7-methylthioimidazo[5,1-b]thiazolium-2-yl]-6-((1R)-1-hydroxyethyl)-1-methyl-1-carbapen-2-em-3-carboxylate (intramolecular salt) hydrobromide;

127. (1S,5R,6S)-6-((1R)-1-hydroxyethyl)-1-methyl-2-[6-[2-(4-methylmorpholinium-4-yl)methylbenzyl]-7-methylthioimidazo[5,1-b]thiazolium-2-yl]-1-carbapen-2-em-3-carboxylate bromide (intramolecular salt);

128. (1S,5R,6S)-6-((1R)-1-hydroxyethyl)-1-methyl-2-[6-[3-(4-methylmorpholinium-4-yl)methylbenzyl]-7-methylthioimidazo[5,1-b]thiazolium-2-yl]-1-carbapen-2-em-3-carboxylate bromide (intramolecular salt);

129. (1S,5R,6S)-6-((1R)-1-hydroxyethyl)-1-methyl-2-[6-[4-(4-methylmorpholinium-4-yl)methylbenzyl]-7-methylthioimidazo[5,1-b]thiazolium-2-yl]-1-carbapen-2-em-3-carboxylate bromide (intramolecular salt);

130. (1S,5R,6S)-6-((1R)-1-hydroxyethyl)-1-methyl-2-[7-methylthio-6-[2-(pyridinium-1-yl)methylbenzyl]-imidazo[5,1-b]thiazolium-2-yl]-1-carbapen-2-em-3-carboxylate bromide (intramolecular salt);

131. (1S,5R,6S)-6-((1R)-1-hydroxyethyl)-1-methyl-2-[7-methylthio-6-[3-(pyridinium-1-yl)methylbenzyl]-imidazo[5,1-b]thiazolium-2-yl]-1-carbapen-2-em-3-carboxylate bromide (intramolecular salt);

132. (1S,5R,6S)-6-((1R)-1-hydroxyethyl)-1-methyl-2-[7-methylthio-6-[4-(pyridinium-1-yl)methylbenzyl]imidazo[5,1-b]thiazolium-2-yl]-1-carbapen-2-em-3-carboxylate bromide (intramolecular salt);

133. (1S,5R,6S)-2-[6-carbamoylmethyl-7-(3-guanidinopropyl)thioimidazo[5,1-b]thiazolium-2-yl]-6-((1R)-1-hydroxyethyl)-1-methyl-1-carbapen-2-em-3-carboxylate (intramolecular salt) hydrochloride;

134. (1S,5R,6S)-6-((1R)-1-hydroxyethyl)-2-[6-(3-isothioureidomethylbenzyl)-7-methylthioimidazo[5,1-b]-thiazolium-2-yl]-1-methyl-1-carbapen-2-em-3-carboxylate (intramolecular salt) hydrochloride;

135. (1S,5R,6S)-6-((1R)-1-hydroxyethyl)-1-methyl-2-[6-[3-(4-methyl-1,4-diazoniabicyclo[2,2,2]oct-1-yl)methylbenzyl]-7-methylthioimidazo[5,1-b]thiazolium-2-yl]-1-carbapen-2-em-3-carboxylate dichloride (intramolecular salt);

136. (1S,5R,6S)-2-[6-(2-diethylcarbamoylbenzyl)-7-methylthioimidazo[5,1-b]thiazolium-2-yl]-6-((1R)-1-hydroxyethyl)-1-methyl-1-carbapen-2-em-3-carboxylate (intramolecular salt);

137. (1S,5R,6S)-2-[6-(4-diethylcarbamoylbenzyl)-7-methylthioimidazo[5,1-b]thiazolium-2-yl]-6-((1R)-1-hydroxyethyl)-1-methyl-1-carbapen-2-em-3-carboxylate (intramolecular salt);

138. (1S,5R,6S)-2-[7-acetyl-6-(3-aminopropyl)imidazo[5,1-b]thiazolium-2-yl]-6-((1R)-1-hydroxyethyl)-1-methyl-1-carbapen-2-em-3-carboxylate (intramolecular salt) hydrochloride;

139. (1S,5R,6S)-2-(7-benzylthio-6-carbamoylmethylimidazo[5,1-b]thiazolium-2-yl)-6-((1R)-1-hydroxyethyl)-1-methyl-1-carbapen-2-em-3-carboxylate (intramolecular salt);

140. (1S,5R,6S)-2-[6-((2R)-3-amino-2-methoxypropyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

141. (1S,5R,6S)-6-((1R)-1-hydroxyethyl)-2-[6-(3-isothioureidopropyl)-7-methylthioimidazo[5,1-b]-thiazolium-2-yl]-1-methyl-1-carbapen-2-em-3-carboxylate (intramolecular salt) hydrochloride;

142. (1S,5R,6S)-6-((1R)-1-hydroxyethyl)-2-[6-(4-isothioureidomethylbenzyl)-7-methylthioimidazo[5,1-b]thiazolium-2-yl]-1-methyl-1-carbapen-2-em-3-carboxylate (intramolecular salt) hydrochloride;

143. (1S,5R,6S)-6-((1R)-1-hydroxyethyl)-1-methyl-2-[6-[4-(4-methyl-1,4-diazoniabicyclo[2,2,2]oct-1-yl)methylbenzyl]-7-methylthioimidazo[5,1-b]thiazolium-2-yl]-1-carbapen-2-em-3-carboxylate dichloride (intramolecular salt);

144. (1S,5R,6S)-2-[7-(3-aminopropylthio)-6-benzylimidazo[5,1-b]thiazolium-2-yl]-6-((1R)-1-hydroxyethyl)-1-methyl-1-carbapen-2-em-3-carboxylate (intramolecular salt) hydrobromide;

145. (1S,5R,6S)-2-[6-(3,5-dihydroxybenzyl)-7-methylthioimidazo[5,1-b]thiazolium-2-yl]-6-((1R)-1-hydroxyethyl)-1-methyl-1-carbapen-2-em-3-carboxylate (intramolecular salt);

146. (1S,5R,6S)-6-((1R)-1-hydroxyethyl)-1-methyl-2-[6-[3-(1-methylpyrrolidinium-1-yl)methyl-benzyl]-7-methylthioimidazo[5,1-b]thiazolium-2-yl]-1-carbapen-2-em-3-carboxylate bromide (intramolecular salt);

147. (1S,5R,6S)-6-((1R)-1-hydroxyethyl)-2-[6-[3-(3-hydroxymethylpyridinium-1-yl)methylbenzyl]-7-methylthioimidazo[5,1-b]thiazolium-2-yl]-1-methyl-1-carbapen-2-em-3-carboxylate bromide (intramolecular salt);

148. (1S,5R,6S)-6-((1R)-1-hydroxyethyl)-2-[6-[3-(4-hydroxymethylpyridinium-1-yl)methylbenzyl]-7-methylthioimidazo[5,1-b]thiazolium-2-yl]-1-methyl-1-carbapen-2-em-3-carboxylate bromide (intramolecular salt);

149. (1S,5R,6S)-2-[6-[3-[4-(3-aminopropyl)-1,4-diazoniabicyclo[2,2,2]oct-1-yl]methylbenzyl3-7-methylthioimidazo[5,1-b]thiazolium-2-yl]-6-((1R)-1-hydroxyethyl)-1-methyl-1-carbapen-2-em-3-carboxylate dichloride (intramolecular salt) hydrochloride;

150. (1S,5R,6S)-2-[6-[3-(4-carbamoylmethyl-1,4-diazoniabicyclo[2,2,2]oct-1-yl)methylbenzyl]-7-methylthioimidazo[5,1-b]thiazolium-2-yl]-6-((1R)-1-hydroxyethyl)-1-methyl-1-carbapen-2-em-3-carboxylate dichloride (intramolecular salt);

151. (1S,5R,6S)-6-((1R)-1-hydroxyethyl)-1-methyl-2-[6-[3-(N-methylisothioureido)methylbenzyl]-7-methylthioimidazo[5,1-b]thiazolium-2-yl]-1-carbapen-2-em-3-carboxylate (intramolecular salt) hydrochloride;

152. (1S,5R,6S)-2-[6-carbamoylmethyl-7-(pyridin-2-yl)methylthioimidazo[5,1-b]thiazolium-2-yl]-6-((1R)-1-hydroxyethyl)-1-methyl-1-carbapen-2-em-3-carboxylate (intramolecular salt);

153. (1S,5R,6S)-6-((1R)-1-hydroxyethyl)-1-methyl-2-[7-methylthio-6-[3-(morpholin-4-yl)methylbenzyl]-imidazo[5,1-b]thiazolium-2-yl]-1-carbapen-2-em-3-carboxylate (intramolecular salt) hydrochloride;

154. (1S,5R,6S)-6-((1R)-1-hydroxyethyl)-1-methyl-2-[6-[4-(1-methylpyrrolidinium-1-yl)methylbenzyl]-7- methylthioimidazo[5,1-b]thiazolium-2-yl]-1-carbapen-2-em-3-carboxylate bromide (intramolecular salt);

155. (1S,5R,6S)-6-((1R)-1-hydroxyethyl)-2-[6-13-(2-hydroxymethylpyridinium-1-yl)methylbenzyl]-7-methylthioimidazo[5,1-b]thiazolium-2-yl]-1-methyl-1-carbapen-2-em-3-carboxylate bromide (intramolecular salt);

156. (1S,5R,6S)-6-((1R)-1-hydroxyethyl)-2-[6-[3-(2-hydroxymethylimidazo[5,1-b]thiazolium-6-yl)methylbenzyl]-7-methylthioimidazo[5,1-b]thiazolium-2-yl]-1-methyl-1-carbapen-2-em-3-carboxylate bromide (intramolecular salt);

157. (1S,5R,6S)-6-((1R)-1-hydroxyethyl)-2-[6-[3-(imidazo[5,1-b]thiazolium-6-yl)methylbenzyl]-7-methylthioimidazo[5,1-b]thiazolium-2-yl]-1-methyl-1-carbapen-2-em-3-carboxylate bromide (intramolecular salt);

158. (1S,5R,6S)-6-((1R)-1-hydroxyethyl)-2-[6-[4-(imidazo[5,1-b]thiazolium-6-yl)methylbenzyl]-7-methylthioimidazo[5,1-b]thiazolium-2-yl]-1-methyl-1-carbapen-2-em-3-carboxylate bromide (intramolecular salt);

159. (1S,5R,6S)-2-[6-[3-(4,5-dihydro-1H-imidazol-2-yl)thiomethylbenzyl]-7-methylthioimidazo[5,1-b]-thiazolium-2-yl]-6-((1R)-1-hydroxyethyl)-1-methyl-1-carbapen-2-em-3-carboxylate (intramolecular salt) hydrochloride;

160. (1S,5R,6S)-2-[6-[3-(4,5-dihydro-1H-imidazol-2-yl)thiopropyl]-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

161. (1S,5R,6S)-6-((1R)-1-hydroxyethyl)-2-[6-[3-[4-(2-hydroxyethyl)-1 4-diazoniabicyclo[2,2,2]oct-1-yl]-methylbenzyl]-7-methylthioimidazo[5,1-b]thiazolium-2-yl]-1-methyl-1-carbapen-2-em-3-carboxylate dichloride (intramolecular salt);

162. (1S,5R,6S)-6-((1R)-1-hydroxyethyl)-1-methyl-2-(7-methylthio-6-[3-(thiazolium-3-yl)methylbenzyl]imidazo[5,1-b]thiazolium-2-yl]-1-carbapen-2-em-3-carboxylate bromide (intramolecular salt);

163. (1S,5R,6S)-6-((1R)-1-hydroxyethyl)-1-methyl-2-(7-methylthio-6-[4-(thiazolium-3-yl)methylbenzyl]-imidazo[5,1-b]thiazolium-2-yl]-1-carbapen-2-em-3-carboxylate bromide (intramolecular salt);

164. (1S,5R,6S)-6-((1R)-1-hydroxyethyl)-2-[6-[3-(isoquinolinium-2-yl)methylbenzyl]-7-methylthioimidazo[5,1-b]thiazolium-2-yl]-1-methyl-1-carbapen-2-em-3-carboxylate bromide (intramolecular salt);

165. (1S,5R,6S)-6-((1R)-1-hydroxyethyl)-1-methyl-2-[7-methylthio-6-[3-(3H-pyrimidinium-4-one-1-yl)methylbenzyl]imidazo[5,1-b]thiazolium-2-yl]-1-carbapen-2-em-3-carboxylate bromide (intramolecular salt);

166. (1S,5R,6S)-6-((1R)-1-hydroxyethyl)-2-[6-[4-(isoquinolinium-2-yl)methylbenzyl]-7-methylthioimidazo[5,1-b]thiazolium-2-yl]-1-methyl-1-carbapen-2-em-3-carboxylate bromide (intramolecular salt);

167. (1S,5R,6S)-2-[7-(3-aminopropyl)thio-6-(3,5-dihydroxy)benzylimidazo[5,1-b]thiazolium-2-yl]-6-((1R)-1-hydroxyethyl)-1-methyl-1-carbapen-2-em-3-carboxylate (intramolecular salt) hydrochloride;

168. (1S,5R,6S)-2-[6-(3-aminomethylbenzyl)-7-methylthioimidazo[5,1-b]thiazolium-2-yl]-6-((1R)-1-hydroxyethyl)-1-methyl-1-carbapen-2-em-3-carboxylate (intramolecular salt) hydrobromide;

169. (1S,5R,6S)-2-[6-(4-aminomethylbenzyl)-7-methylthioimidazo[5,1-b]thiazolium-2-yl]-6-((1R)-1-hydroxyethyl)-1-methyl-1-carbapen-2-em-3-carboxylate (intramolecular salt) hydrobromide;

170. (1S,5R,6S)-2-[6-[3-(3-carbamoylpyridinium-1-yl)methylbenzyl]-7-methylthioimidazo[5,1-b]thiazolium-2-yl]-6-((1R)-1-hydroxyethyl)-1-methyl-1-carbapen-2-em-3-carboxylate bromide (intramolecular salt);

171. (1S,5R,6S)-2-[6-[2-[(3S,5S)-5-(aminosulfonyl-aminomethyl)pyrrolidin-3-yl]thioethyl]-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

172. (1S,5R,6S)-2-[6-carbamoylmethyl-7-(2-fluoroethyl)thioimidazo[5,1-b]thiazolium-2-yl]-6-((1R)-1-hydroxyethyl)-1-methyl-1-carbapen-2-em-3-carboxylate (intramolecular salt);

173. (1S,5R,6S)-2-[6-[2-(2-aminoethyl)thioethyl]-7-methylthioimidazo[5,1-b]thiazolium-2-yl]-6-((1R)-1-hydroxyethyl)-1-methyl-1-carbapen-2-em-3-carboxylate (intramolecular salt) methanesulfonate;

174. (1S,5R,6S)-2-[6-[2-(2-aminoethyl)sulfonylethyl]-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

175. (1S,5R,6S)-2-[6-[4-(4-carbamoylpyridinium-1-yl)methylbenzyl]-7-methylthioimidazo[5,1-b]thiazolium-2-yl]-6-((1R)-1-hydroxyethyl)-1-methyl-1-carbapen-2-em-3-carboxylate bromide (intramolecular salt);

176. (1S,5R,6S)-2-[6-((2R)-3-amino-2-fluoromethoxypropyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

177. (1S,5R,6S)-2-[6-(5-aminopentyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

178. (1S,5R,6S)-6-((1R)-1-hydroxyethyl)-1-methyl-2-[6-[2-((3S)-pyrrolidin-3-yl)thioethyl]-7-methylthioimidazo[5,1-b]thiazolium-2-yl]-1-carbapen-2-em-3-carboxylate (intramolecular salt) hydrochloride;

179. (1S,5R,6S)-2-[6-[2-(3,4-dihydroxybenzyl)sulfonylethyl]-7-methylthioimidazo[5,1-b]thiazolium-2-yl]-6-((1R)-1-hydroxyethyl)-1-methyl-1-carbapen-2-em-3-carboxylate (intramolecular salt);

180. (1S,5R,6S)-2-[6-carbamoylmethyl-7-(pyridin-2-yl)thioimidazo[5,1-b]thiazolium-2-yl]-6-((1R)-1-hydroxyethyl)-1-methyl-1-carbapen-2-em-3-carboxylate (intramolecular salt);

181. (1S,5R,6S)-2-[6-[2-((3S,5S)-5-carbamoylpyrrolidin-3-yl)thioethyl]-7-methylthioimidazo[5,1-b]thiazolium-2-yl]-6-((1R)-1-hydroxyethyl)-1-methyl-1-carbapen-2-em-3-carboxylate (intramolecular salt) hydrochloride;

182. (1S,5R,6S)-6-((1R)-1-hydroxyethyl)-2-[6-[2-((3S,5S)-5-hydroxymethylpyrrolidin-3-yl)thioethyl]-7-methylthioimidazo[5,1-b]thiazolium-2-yl]-1-methyl-1-carbapen-2-em-3-carboxylate (intramolecular salt) hydrochloride; and 183. (1S,5R,6S)-2-[6-[3-(3-carbamoylpyridinium-1-yl)methyl-5-hydroxybenzyl]-7-methylthioimidazo[5,1-b]-thiazolium-2-yl]-6-((1R)-1-hydroxyethyl)-1-methyl-1-carbapen-2-em-3-carboxylate bromide (intramolecular salt).

The compounds represented by formula (I) according to the present invention are preferably produced according to the following scheme:

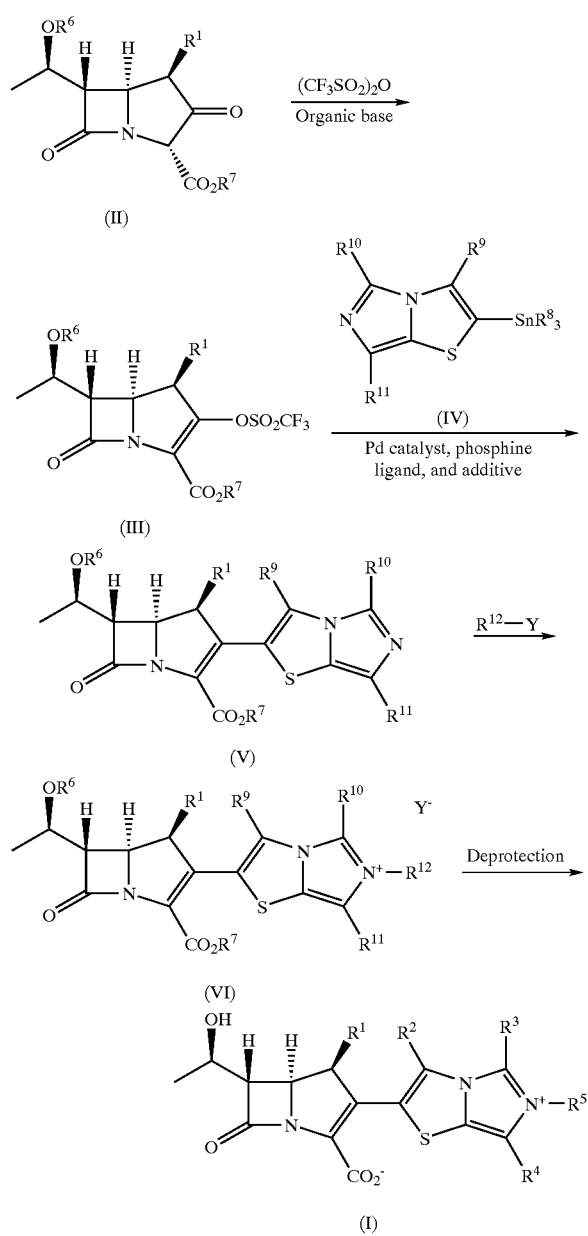

wherein $R^1$, $R^2$, $R^3$, $R^4$ and $R^5$ each have the same meaning as defined in formula (I), $R^6$ represents a hydrogen atom or a protective group of hydroxyl, for example, t-butyldimethylsilyl, trimethylsilyl, triethylsilyl, 4-nitrobenzyloxycarbonyl, 4-methoxybenzyloxycarbonyl, or allyloxycarbonyl; $R^7$ represents a protective group of carboxyl, for example, 4-nitrobenzyl, 4-methoxybenzyl, diphenylmethyl, t-butyldimethylsilyl, or allyl; $R^8$ represents lower alkyl, preferably n-butyl or methyl; $R^9$ and $R^{10}$ have the same meaning as $R^2$ and $R^3$ or represent a group in which a functional group, for example, hydroxyl, amino, or carboxyl, contained in $R^2$ and $R^3$ has been protected by a conventional protective group; $R^{11}$ has the same meaning as $R^4$ or represents a group in which a functional group, for example, hydroxyl, amino, or carboxyl, contained in $R^4$ has been protected by a conventional protective group; $R^{12}$ has the same meaning as $R^5$ or represents a group in which a functional group, for example, hydroxyl, amino, or carboxyl, contained in $R^5$ has been protected by a conventional protective group; and Y represents a suitable elimination group, for example, Cl, Br, I, —$OSO_2CF_3$, —$OSO_2CH_3$, or —$OSO_2PhCH_3$. The term "conventional protective group" as used herein refers to a protective group described in Protective Groups in Organic Synthesis, Theodora W. Greene and Peter G. M. Wuts, published by John Wiley & Sons, Inc.

The compound of formula (II) indicated in the scheme in the first step can be synthesized by the conventional process, and the tin compound of formula (IV) indicated in the scheme in the second step can be synthesized by a process described in WO 98/32760.

In the first step, the compound of formula (II) can be converted to the compound of formula (III) by the following method. Specifically, the compound of formula (II) is reacted with one equivalent or an excessive amount of trifluoromethanesulfonic anhydride in the presence of an organic base, preferably diisopropylethylamine, in an amount of one equivalent or an excessive amount relative to trifluoromethanesulfonic anhydride in an inert solvent, such as acetonitrile, tetrahydrofuran, dichloromethane, or toluene or a mixed solvent composed of the above inert solvents, at a temperature of −50° C. to +50° C. for 10 min to 24 hr, followed by conventional separation and purification to give the compound of formula (III).

Next, in the second step, the compound of formula (III) can be converted to the compound of formula (V) by the following method. Specifically, the compound of formula (III) is reacted with one equivalent or an excessive amount of the compound of formula (IV) in the presence of 0.001 to 1 equivalent of a palladium catalyst, for example, tetrakis(triphenylphosphine)palladium(0), tris(dibenzylideneacetone)dipalladium(0), or tris(dibenzylideneacetone)dipalladium(0)-chloroform adduct, 0.01 to 1 equivalent of a phosphine ligand, for example, triphenylphosphine, tri-2-furylphosphine, tri-2-thienylphosphine, or tris(2,4,6-trimethoxyphenyl)phosphine, and 1 to 10 equivalents of an additive, for example, zinc chloride, lithium chloride, or cesium fluoride alone or in combination thereof, in an inert solvent, for example, tetrahydrofuran, dimethoxyethane, dioxane, acetonitrile, acetone, ethanol, dimethylsulfoxide, sulfolane, N,N-dimethylformamide, N,N-dimethylacetamide, N-methylpyrrolidinone, or hexamethylphosphoric triamide or a mixed solvent composed of the above inert solvents, at 0° C. to 100° C. for 10 min to 7 days, followed by conventional post-treatment to give the compound of formula (V).

In the third step, the compound of formula (V) can be converted to the compound of formula (VI) by the following method. Specifically, one equivalent or an excessive amount of $R^{12}$—Y, for example, methyl iodide, carbamoylmethyl iodide, methyltrifluoromethane sulfonate, [1-(4-nitrobenzyloxycarbonyl)pyrrolidin-3-yl]trifluoromethane sulfonate, 3-azidopropyltrifluoromethane sulfonate, is added to the compound of formula (V) in the absence or presence of a single or mixed inert solvent, for example, acetonitrile, acetone, tetrahydrofuran, dichloromethane, toluene, N,N-dimethylformamide, N,N-dimethylacetamide, or dimethyl sulfoxide, and a reaction is allowed to proceed at −80° C. to +60° C. for 15 min to one week, followed by conventional post-treatment to give the compound of formula (VI).

Finally, in the fourth step, the protective group in the compound of formula (VI) may be removed by a deprotection reaction in one stage or plural stages depending on the kinds of the protective groups to give the compound of formula (I) according to the present invention.

In this case, the deprotection reaction for removing the protective group may be carried out by conventional methods commonly known in the art, although it varies depending upon the kinds of protective groups used. When any one of or all the protective groups can be removed under acidic conditions, a mineral acid such as hydrochloric acid, an organic acid such as formic acid, acetic acid or citric acid, or a Lewis acid such as aluminum chloride may be used. On the other hand, when the protective groups are removed under reducing conditions, a catalytic reduction in the presence of a variety of catalysts, or a metallic reducing agent such as zinc or iron may be used. When $R^6$ is a silyl-type protective group such as t-butyldimethylsilyl, trimethylsilyl, or triethylsilyl, it can be easily removed with a fluorine ion reagent such as tetrabutylammonium fluoride. When $R^6$ is allyloxycarbonyl and $R^7$ is allyl, the protective groups can be easily removed with a variety of palladium complexes, for example, tetrakis(triphenylphosphine)palladium(0).

The compounds: of formula (I) thus obtained can be isolated and purified, for example, by crystallization, chromatography with nonionic macro-high porous resin, gel filtration with Sephadex or the like, or reverse phase column chromatography on silica gel.

Alternatively, the compound of formula (V) may be produced by a process shown in the following scheme:

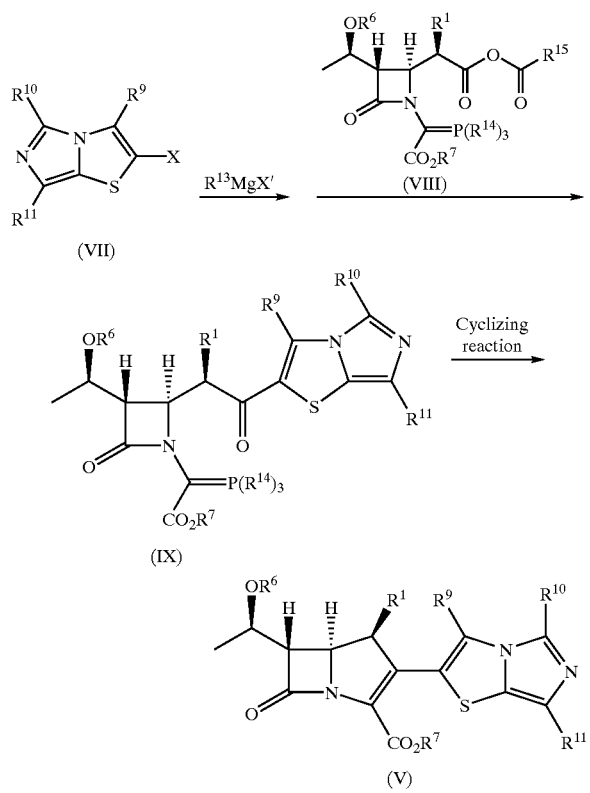

wherein $R^1$ is as defined in formula (I); $R^6$, $R^7$, $R^9$, $R^{10}$, and $R^{11}$ are as defined above; $R^{13}$ represents lower alkyl or aryl; $R^{14}$ represents lower alkyl optionally substituted by a halogen atom, lower alkyl, or aryl optionally substituted by a halogen atom; $R^{15}$ represents lower alkyl optionally substituted by a halogen atom, or phenyl, one or more hydrogen atoms on which ring are optionally substituted by a group or groups, which may be the same or different, selected from the group consisting of a halogen atom, optionally substituted lower alkyl, lower alkoxy, and —NR$^5$R$^6$ wherein $R^5$ and $R^6$, which may be the same or different, represent lower alkyl, or $R^5$ and $R^6$ together represent group —(CH$_2$)$_n$— wherein n is an integer of 2 to 6; and X and X' each represent a halogen atom, preferably a bromine or iodine atom.

In the step of reacting a reaction mixture which has been obtained by treating the compound of formula (VII) with a Grignard reagent, with the compound of formula (VIII) to give the compound of formula (IX), the compound of formula (VII) may be used in an amount of one equivalent or an excessive amount relative to the compound of formula (VIII). The compound of formula (VII) is dissolved or suspended in an inert solvent, such as tetrahydrofuran, diethyl ether, dioxane, dimethoxyethane, toluene, benzene, dichloromethane, or hexamethylphosphoric triamide. A Grignard reagent, such as alkylmagnesium chloride, alkylmagnesium bromide, alkylmagnesium iodide, or arylmagnesium bromide, preferably methylmagnesium iodide or ethylmagnesium bromide, is added to the solution or suspension at −100° C. to +70° C., preferably at −80° C. to −20° C. The mixture is then stirred for 10 min to 24 hr. A solution of the compound of formula (VIII) in an inert solvent, such as tetrahydrofuran, diethyl ether, dioxane, dimethoxyethane, toluene, benzene, dichloromethane, or hexamethylphosphoric triamide, is then added thereto. Alternatively, a solution or suspension of the compound of formula (VII), which has been treated with a Grignard reagent such as alkylmagnesium chloride, alkylmagnesium bromide, alkylmagnesium iodide, or arylmagnesium bromide, preferably methylmagnesium iodide or ethylmagnesium bromide, is added to a solution of the compound of formula (VIII) in an inert solvent such as tetrahydrofuran, diethyl ether, dioxane, dimethoxyethane, toluene, benzene, dichloromethane, or hexamethylphosphoric triamide. A reaction is then allowed to proceed at −100° C. to +70° C., preferably at −80° C. to 0° C., for 10 min to 24 hr. Conventional post-treatment is then carried out to give the compound of formula (IX).

If necessary, before the next step, the compound of formula (IX) thus obtained may be purified, for example, by precipitation, crystallization, gel filtration with Sephadex or the like, or column chromatography on silica gel.

Next, the compound of formula (IX) can be converted to the compound of formula (V) under Wittig ring-forming conditions well known in the art, that is, by reacting the compound of formula (IX) dissolved in an inert solvent, such as benzene, toluene, xylene, tetrahydrofuran, or dioxane, optionally in the presence of a catalytic amount of an additive (preferably hydroquinone), at a temperature in the range of room temperature to reflux temperature for 10 min to 24 hr.

The compound of formula (VII) used in the reaction may be synthesized by the following process:

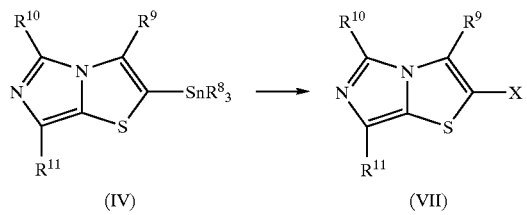

wherein $R^8$, $R^9$, $R^{10}$, $R^{11}$, and X are as defined above.

A compound represented by formula (IV) is dissolved in an inert solvent such as tetrahydrofuran, diethyl ether, dioxane, dimethoxyethane, toluene, benzene, or hexamethylphosphoric triamide. The solution is treated with a base, such as n-butyllithium, methyllithium, lithiumbis (trimethylsilyl)amide, or sodiumbis(trimethylsilyl)amide, at −100° C. to +50° C. A halogenating agent such as bromine, iodine, 1,2-dibromoethane, 1,2-dibromotetrafluoroethane, 1,1,2,2-tetrabromoethane, N-bromosuccinimide, N-iodosuccinimide, or 2-bromothiazole is then added thereto, and a reaction is allowed to proceed for additional 10 min to 24 hr, followed by conventional post-treatment to give the compound of formula (VII). The compound of formula (VII) thus obtained can be isolated and purified, for example, by precipitation, crystallization, gel filtration with Sephadex or the like, or column chromatography on silica gel.

The compound of formula (VIII) used in the reaction can be synthesized by the following process.

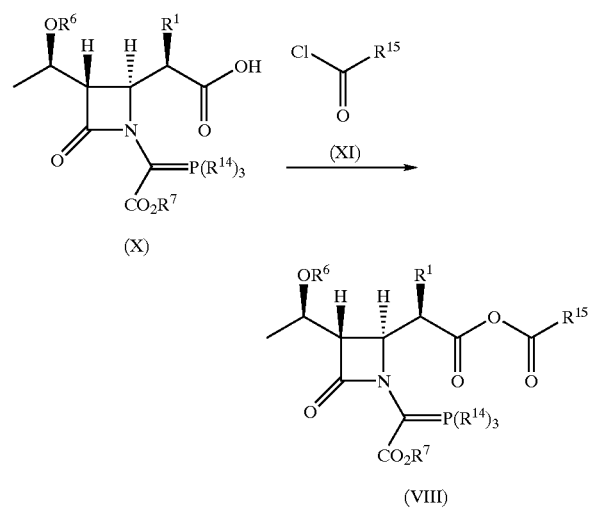

wherein $R^1$ is as defined in formula (I); and $R^6$, $R^7$, $R^{14}$, and $R^{15}$ are as defined above.

A compound of formula (X) is reacted with one equivalent or an excessive amount of a compound of formula (XI), which is commercially available or can be easily prepared from a corresponding carboxylic acid using thionyl chloride, oxalic acid chloride or the like, in the presence of one equivalent or an excessive amount of a base, for example, triethylamine, diisopropylethylamine, diazabicyclo[2,2,2]undecene, pyridine, 4-dimethylaminopyridine, or 2,6-lutidine, in an inert solvent, for example, dichloromethane, 1,2-dichloroethane, chloroform, acetonitrile, tetrahydrofuran, N,N-dimethylformamide, toluene, or benzene, at −20° C. to reflux temperature for 10 min to 24 hr, followed by conventional separation and purification to give the compound of formula (VIII). Examples of compounds represented by formula (XI) include pivaloyl chloride, chloropivaloyl chloride, 4-methoxybenzoyl chloride, 4-isopropyloxybenzoyl chloride, 4-(N,N-dimethylamino)benzoyl chloride, and 4-(N,N-diethylamino)benzoyl chloride. The compound of formula (VIII) thus obtained can, if necessary, be isolated and purified for example, by precipitation, crystallization, gel filtration with Sephadex or the like, or column chromatography on silica gel.

The compounds according to the present invention have potent antibiotic activity against a wide spectrum of Gram-positive and Gram-negative bacteria, and, in addition, have potent antibiotic activity against MRSA, PRSP, Influenzavirus, and β-lactamase-producing bacteria. Further, they have no significant toxicity and are stable against DHP-1.

Thus, the compounds according to the present invention can be used for the treatment of infectious diseases caused by various pathogenic bacteria in animals including humans. A pharmaceutical composition comprising as active ingredient the compound according to the present invention or a pharmacologically acceptable salt thereof can be administered orally or parenterally by administration routes, for example, intravenous injection, intramuscular injection, or subcutaneous, rectal, or percutaneous administration, to a human and a non-human animal.

The pharmaceutical composition comprising as active ingredient the compound according to the present invention can be formulated into appropriate dosage forms, primarily into any one of the preparation forms including: injections such as intravenous injection or intramuscular injection; preparations for oral administration such as capsules, tablets, granules, powders, pills, particulates, or troches; preparations for rectal administration; and fatty suppositories, depending on its administration routes. These preparations can be prepared by the usual methods with pharmaceutically acceptable additives for preparations commonly used in the art, for example, excipients, fillers, binders, humidifiers, disintegrants, surface active agents, lubricants, dispersants, buffers, preservatives, dissolution aids, antiseptics, flavoring agents, analgesic agents, and stabilizers.

Such non-toxic additives usable herein include, for example, lactose, fructose, glucose, starch, gelatin, magnesium carbonate, synthetic magnesium silicate, talc, magnesium stearate, methylcellulose or a salt thereof, gum arabic, polyethylene glycol, syrup, petrolatum, glycerin, ethanol, propylene glycol, citric acid, sodium chloride, sodium sulfite, and sodium phosphate. The dosage may be appropriately determined, for example, in consideration of the dosage route and the age, sex and condition of patients, and the preparation may be administered for the treatment of infectious diseases usually in an amount of about 25 mg to 2000 mg, preferably 50 mg to 1000 mg, per day per adult in one or several portions.

EXAMPLES

Synthesis Example 1

7-Methylthio-2-(tri-n-butylstannyl)imidazo[5,1-b]thiazole a) 7-Methylthioimidazo[5,1-b]thiazole A 0.95 M ethylmagnesium bromide/THF solution (1.4 ml) was added to a solution of 310 mg of 7-iodoimidazo[5,1-b]thiazole in 3 ml of dry THF under an argon atmosphere with cooling in ice. The mixture was stirred at that temperature for one hr. Methyl methanethiolsulfonate (0.15 ml) was added thereto, and the mixture was stirred at room temperature for 12 hr. A saturated aqueous ammonium chloride solution was added to the reaction mixture, and the mixture was then extracted with ethyl acetate, followed by washing with a dilute aqueous sodium thiosulfate solution and saturated brine in that order. The organic layer was dried over anhydrous magnesium sulfate. The solvent was removed by distillation, and the residue was purified by column chromatography on silica gel (ethyl acetate) to prepare 150 mg of 7-methylthioimidazo[5,1-b]thiazole.

NMR (CDCl$_3$) δ: 2.41 (3H, s), 6.86 (1H, d, J=4.2 Hz), 7.39 (1H, d, J=4.2 Hz), 8.00 (1H, s)

b) 7-Methylthio-2-(tri-n-butylstannyl)imidazo[5,1-b]thiazole

The procedure of Synthesis Example 2c) was repeated, except that 790 mg of 7-methylthioimidazo[5,1-b]thiazole was used as the starting compound. Thus, 1.50 g of the title compound was prepared.

NMR (CDCl$_3$) δ: 0.92 (9H, t, J=7.2 Hz), 1.1–1.2 (6H, m), 1.3–1.40 (6H, m), 1.55–1.65 (6H, m), 2.40 (3H, s), 7.13 (1H, s), 7.94 (1H, s)

Synthesis Example 2
5-Methyl-7-methylthio-2-(tri-n-butylstannyl)imidazo[5,1-b]thiazole a) 7-Iodo-5-methylimidazo[5,1-b]thiazole 5-Methylimidazo[5,1-b]thiazole (6.90 g) was dissolved in 500 ml of dichloromethane. N-Iodosuccinimide (10.6 g) was added to the solution. The mixture was stirred at room temperature for 24 hr. N-Iodosuccinimide (1.06 g) was then added thereto, and the mixture was stirred for additional one hr. The reaction solution was washed with an aqueous sodium thiosulfate solution and brine in that order, was dried over anhydrous magnesium sulfate, and was then filtered. The solvent was removed by distillation under the reduced pressure. The residue was dissolved in 200 ml of dichloromethane and 100 ml of ethyl acetate. Silica gel (30 g) was added to the solution, and the mixture was stirred. The silica gel was removed by filtration. The filtrate was washed with 200 ml of a mixed solution composed of dichloromethane:ethyl acetate=2:1, and was concentrated under the reduced pressure. Thus, 13.08 g of 7-iodo-5-methylimidazo[5,1-b]thiazole was prepared.

NMR (CDCl$_3$) δ: 2.58 (3H, s), 6.83 (1H, d, J=4.2 Hz), 7.29 (1H, d, J=4.2 Hz)

b) 5-Methyl-7-methylthioimidazo[5,1-b]thiazole

A 0.95 M ethylmagnesium bromide/THF solution (25.7 ml) was added to a solution of 5.28 g of 7-iodo-5-methylimidazo[5,1-b]thiazole in 100 ml of dry THF under an argon atmosphere with cooling in ice. The mixture was stirred at that temperature for one hr. Methyl methanethiolsulfonate (2.26 ml) was added thereto, and the mixture was stirred at room temperature for 1.5 hr. A saturated aqueous ammonium chloride solution was added to the reaction mixture. Ethyl acetate was then added thereto, followed by washing with a dilute aqueous sodium thiosulfate solution and saturated brine in that order. The organic layer was dried over anhydrous magnesium sulfate. The solvent was removed by distillation, and the residue was purified by column chromatography on silica gel (dichloromethane:ethyl acetate=1:1) to prepare 3.56 g of 5-methyl-7-methylthioimidazo[5,1-b]thiazole.

NMR (CDCl$_3$) δ: 2.40 (3H, s), 2.56 (3H, s), 6.81 (1H, d, J=4.2 Hz), 7.20 (1H, d, J=4.2 Hz)

c) 5-Methyl-7-methylthio-2-(tri-n-butylstannyl)imadazo[5,1-b]thiazole

5-Methyl-7-methylthioimidazo[5,1-b]thiazole (3.34 g) was dissolved in 150 ml of THF. A 1.59 N n-butyllithium/n-hexane solution (22.8 ml) was added dropwise to the solution at −73° C. under an argon atmosphere. The mixture was stirred at that temperature for 40 min. Tri-n-butylstannyl chloride (6.39 ml) was then added thereto, and the mixture was stirred at that temperature for one hr. An ammonium chloride solution was then added to the reaction solution, and the mixture was extracted with ethyl acetate. The extract was dried over anhydrous magnesium sulfate, and was filtered. The solvent was removed by distillation under the reduced pressure. The residue was purified by column chromatography on silica gel (hexane:ethyl:acetate 2:1 to 1:1) to prepare 6.04 g of the title compound.

NMR (CDCl$_3$) δ: 0.92 (9H, t, J=7.3 Hz), 1.1–1.2 s), 2.56 (3H, s), 6.92 (1H, s)

Synthesis Example 3
7-(2-t-Butyldimethylsilyloxyethyl)thio-2-(tri-n-butylstannyl)imidazo[5,1-b]thiazole 7-(2-t-Butyldimethylsilyloxyethyl)thioimidazo[5,1-b]thiazole A solution of 250 mg of 7-iodoimidazo[5,1-b]thiazole in 5 ml of dry THF was cooled in ice. A 0.93 M methylmagnesium bromide/THF solution (1.08 ml) was added to the cooled solution under an argon atmosphere. The mixture was stirred at that temperature for 25 min. The solvent was then removed by distillation under the reduced pressure. The residue was suspended in 5 ml of THF. Sulfur (34 mg) was added to the suspension, and the mixture was heated under reflux for 40 min. Separately, 2-t-butyldimethylsilyloxy ethanol (246 mg) was dissolved in 5 ml of dichloromethane. 2,6-Lutidine (0.179 ml) and 0.247 ml of trifluoromethanesulfonic anhydride were added to the solution at −30° C. under an argon atmosphere. The mixture was stirred at that temperature for 40 min. The reaction solution was then diluted with dichloromethane, and washed with an aqueous dilute hydrochloric acid solution. The organic layer was dried over anhydrous magnesium sulfate, and was concentrated under the reduced pressure. The residue was dissolved in 3 ml of THF. The solution was added at room temperature to the above reaction solution with sulfur added thereto. The mixture was stirred for 2 hr. A saturated aqueous ammonium chloride solution was added to the reaction mixture. Ethyl acetate was then added thereto, and the mixture was washed with a dilute aqueous sodium thiosulfate solution and saturated brine in that order. The organic layer was dried over anhydrous magnesium sulfate. The solvent was removed by distillation, and the residue was purified by column chromatography on silica gel (hexane:ethyl acetate=1:1) to prepare 146 mg of 7-(2-t-butyldimethylsilyloxyethyl)thioimidazo[5,1-b]thiazole.

NMR (CDCl$_3$) δ: 0.02 (6H, s), 0.85 (9H, s), 2.85–2.95 (2H, m), 3.75–3.85 (2H, m), 6.87 (1H, d, J=4.2 Hz), 7.39 (1H, d, J=4.2 Hz), 7.99 (1H, s)

b) 7-(2-t-Butyldimethylsilyloxyethyl)thio-2-(tri-n-butylstannyl)imidazo[5,1-h]thiazole Tri-n-butylstannyl chloride (1.79 ml) and 13.2 ml of a 1.0 N lithiumbis(trimethylsilyl)amide/THF solution were added to a solution of 1.734 g of 7-(2-t-butyldimethylsilyloxyethyl)thioimidazo[5,1-b]thiazole in 60 ml of THF at −40° C. under an argon atmosphere. The mixture was stirred at that temperature for one hr. An aqueous ammonium chloride solution was added to the reaction solution, and the mixture was extracted with ethyl acetate, followed by washing with brine. The organic layer was dried over anhydrous magnesium sulfate. The solvent was then removed by distillation, and the residue was purified by column chromatography on silica gel (hexane:ethyl acetate=3:1) to prepare 2.784 g of the title compound.

NMR (CDCl$_3$) δ: 0.01 (6H, s), 0.84 (9H, s), 0.91 (9H, t, J=7.4 Hz), 1.1–1.2 (6H, m), 1.3–1.45 (6H, m), 1.5–1.65 (6H, m), 2.85–2.95 (2H, m), 3.75–3.85 (2H, m), 7.12 (1H, s), 7.91 (1H, s)

Synthesis Example 4
7-Acetyl-2-(tri-n-butylstannyl)imidazo[5,1-b]thiazole

A 1.0 N lithiumbis(trimethylsilyl)amide/THF solution (69.7 ml) was added dropwise to a solution of 10.5 g of 7-acetylimidazo[5,1-b]thiazole in 500 ml of THF at −73° C. under an argon atmosphere. The mixture was stirred at that temperature for 50 min. A 1.59 N n-butyllithium/n-hexane solution (87.5 ml) was then added dropwise thereto. The mixture was stirred at that temperature for 50 min. Tri-n-butylstannyl chloride (21.5 ml) was then added dropwise thereto. The mixture was stirred at that temperature for additional 40 min. Ammonium chloride solution was added to the reaction solution, and the mixture was extracted with ethyl acetate, followed by washing with brine. The extract was dried over anhydrous magnesium sulfate, and was filtered. The solvent was removed by distillation under the reduced pressure. The residue was purified by column chromatography on silica gel (hexane:ethyl acetate=1:1) to prepare 19.5 g of the title compound.

NMR (CDCl$_3$) δ: 0.91 (9H, t, J=7.2 Hz), 1.19 (6H, m), 1.35 (6H, m), 1.58 (6H, m), 2.61 (3H, s), 7.28 (1H, s), 7.94 (1H, s)

Synthesis Example 5

5,7-Bis(methylthio)-2-(tri-n-butylstannyl)imidazo[5,1-b]thiazole a) 5,7-Bis(methylthio)imidazo[5,1-b]thiazole The procedure of Synthesis Example 2b) was repeated, except that 5.50 g of 5,7-diiodoimidazo[5,1-b]thiazole was used as the starting compound. Thus, 1.40 g of 5,7-bis(methylthio)imidazo[5,1-b]thiazole was prepared.

NMR (CDCl$_3$) δ: 2.43 (3H, s), 2.55 (3H, s), 6.86 (1H, d, J=4.1 Hz), 7.38 (1H, d, J=4.1 Hz)

b) 5,7-Bis(methylthio)-2-(tri-n-butylstannyl)imidazo[5,1-b]thiazole 5,7-Bis(methylthio)imidazo[5,1-b]thiazole (1.66 g) was dissolved in 50 ml of THF under an argon atmosphere, and the solution was cooled to −60° C. A 1.6 N n-butyllithium/n-hexane solution (5.76 ml) and 2.29 ml of tri-n-butylstannyl chloride were added dropwise in that order to the cooled solution. The temperature of the mixture was raised to −40° C. over one hr. Ethyl acetate (100 ml) was added to the reaction solution, and the mixture was washed with 100 ml of brine. The organic layer was dried over anhydrous magnesium sulfate, and was filtered. The solvent was removed by distillation under the reduced pressure. The residue was purified by column chromatography on silica gel (hexane:ethyl acetate=4:1) to prepare 2.31 g of the title compound.

NMR (CDCl$_3$) δ: 0.92 (9H, t, J=7.3 Hz), 1.15–1.20 (6H, m), 1.30–1.41 (6H, m), 1.56–1.62 (6H, m), 2.42 (1H, s), 2.54 (1H, s), 7.12 (1H, s)

Synthesis Example 6

7-Phenylthio-2-(tri-n-butylstannyl)imidazo[5,1-b]thiazole a) 7-Phenylthioimidazo[5,1-b]thiazole A 1 M ethylmagnesium bromide/THF solution (3.46 ml) was added to a solution of 840 mg of 7-iodoimidazo[5,1-b]thiazole in 20 ml of dry THF with cooling in ice under an argon atmosphere. The mixture was stirred at that temperature for one hr. Phenylbenzenethiol sulfonate (939 mg) was added thereto, and the mixture was stirred at that temperature for one hr. A saturated aqueous ammonium chloride solution was added to the reaction mixture. Ethyl acetate was then added thereto, and the mixture was washed with a dilute aqueous sodium thiosulfate solution and saturated brine in that order. The organic layer was dried over anhydrous magnesium sulfate. The solvent was removed by distillation, and the residue was purified by column chromatography on silica gel (hexane:ethyl acetate=1:1) to prepare 385 mg of 7-phenylthioimidazo[5,1-b]thiazole.

NMR (CDCl$_3$) δ: 6.90 (1H, d, J=4.3 Hz), 7.1–7.2 (1H, m), 7.2–7.25 (5H, m), 7.45 (1H, d, J=4.3 Hz), 8.09 (1H, s)

b) 7-Phenylthio-2-(tri-n-butylstannyl)imidazo[5,1-b]thiazole

A 1.59 N n-butyllithium/n-hexane solution (0.189 ml) was added dropwise to a solution of 66.5 mg of 7-phenylthioimidazo[5,1-b]thiazole in 3 ml of THF at −73° C. under an argon atmosphere, and 0.098 ml of tri-n-butylstannyl chloride was then added thereto. The mixture was stirred at that temperature for 15 min. The temperature of the mixture was raised to −40° C. A 1.0 N lithiumbis(trimethylsilyl)amide/THF solution (0.11 ml) was added thereto, and the mixture was stirred for one hr. Ammonium chloride solution was added to the reaction solution, and the mixture was extracted with ethyl acetate. The extract was dried over anhydrous magnesium sulfate, and was filtered. The solvent was removed by distillation under the reduced pressure. The residue was purified by column chromatography on silica gel (hexane:ethyl acetate=5:1) to prepare 115 mg of the title compound.

NMR (CDCl$_3$) δ: 0.91 (9H, t, J=7.2 Hz), 1.1–1.2 (6H, m), 1.3–1.4 (6H, m), 1.5–1.7 (6H, m), 7.05–7.15 (1H, m), 7.15–7.25 (6H, m), 8.03 (1H, s)

Synthesis Example 7

7-Ethylthio-2-(tri-n-butylstannyl)imidazo[5,1-b]thiazole a) Ethylethanethiol sulfonate Diethyl disulfide (3.69 ml) was dissolved in 450 ml of dichloromethane. 3-Chloroperbenzoic acid (19.43 g) was added to the solution under ice cooling. The mixture was stirred at room temperature for 3 hr. The insolubles were removed by filtration. The filtrate was washed with an aqueous sodium thiosulfate solution, an aqueous sodium hydrogencarbonate solution, and brine in that order, was dried over anhydrous magnesium sulfate, and was then filtered. The solvent was removed by distillation under the reduced pressure. The residue was purified by column chromatography on silica gel (hexane:ethyl acetate=5:1) to prepare 2.05 g of ethylethanethiol sulfonate.

NMR (CDCl$_3$) δ: 1.44 (3H, t, J=7.4 Hz), 1.48 (3H, t, J=7.4 Hz), 3.16 (2H, q, J=7.4 Hz), 3.33 (2H, q, J=7.4 Hz)

b) 7-Ethylthioimidazo[5,1-b]thiazole

A 1 M ethylmagnesium bromide/THF solution (8.52 ml) was added to a solution of 2.07 g of 7-iodoimidazo[5,1-b]thiazole in 40 ml of dry THF with cooling in ice under an argon atmosphere. The mixture was stirred at that temperature for one hr. Ethylethanethiol sulfonate (1.527 g) was added thereto, and the mixture was stirred at room temperature for 30 min. A saturated aqueous ammonium chloride solution was added to the reaction mixture. Ethyl acetate was then added thereto, and the mixture was washed with a dilute aqueous sodium thiosulfate solution and saturated brine in that order. The organic layer was dried over anhydrous magnesium sulfate. The solvent was removed by distillation, and the residue was purified by column chromatography on silica gel (dichloromethane:ethyl acetate=1:1) to prepare 1.064 g of 7-ethylthioimidazo[5,1-b]thiazole.

NMR (CDCl$_3$) δ: 1.26 (3H, t, J=7.4 Hz), 2.83 (2H, q, J=7.4 Hz), 6.87 (1H, d, J=4.2 Hz), 7.40 (1H, d, J=4.2 Hz), 8.01 (1H, s)

c) 7-Ethylthio-2-(tri-n-butylstannyl)imidazo[5,1-b]thiazole

The procedure of Synthesis Example 6b) was repeated, except that 1.10 g of 7-ethylthioimidazo[5,1-b]thiazole was used as the starting compound. Thus, 2.34 g of the title compound was prepared.

NMR (CDCl$_3$) δ: 0.92 (9H, t, J=7.4 Hz), 1.1–1.2 (6H, m), 1.27 (3H, t, J=7.3 Hz), 1.3–1.4 (6H, m), 1.5–1.65 (6H, m), 2.82 (2H, q, J=7.3 Hz), 7.14 (1H, s), 7.95 (1H, s)

Synthesis Example 8

3-Methyl-7-methylthio-2-(tri-n-butylstannyl)imidazo[5,1-b]thiazole a) 7-Iodo-3-methylimidazo[5,1-b]thiazole The procedure of Synthesis Example 2a) was repeated, except that 505 mg of 3-methylimidazo[5,1-b]thiazole was used as the starting compound. Thus, 525 mg of 7-iodo-3-methylimidazo[5,1-b]thiazole was prepared.

NMR (CDCl$_3$) δ: 2.40 (3H, s), 6.46 (1H, s), 7.84 (1H, s)

b) 3-Methyl-7-methylthioimidazo[5,1-b]thiazole

The procedure of Synthesis Example 2b) was repeated, except that 3.0 g of 7-iodo-3-methylimidazo[5,1-b]thiazole was used as the starting compound. Thus, 1.88 g of 3-methyl-7-methylthioimidazo[5,1-b]thiazole was prepared.

NMR (CDCl$_3$) δ: 2.40 (3H, s), 2.43 (3H, s), 6.44 (1H, s), 7.89 (1H, s)

c) 3-Methyl-7-methylthio-2-(tri-n-butylstannyl)imadazo[5,1-b]thiazole

The procedure of Synthesis Example 2c) was repeated, except that 2.15 g of 3-methyl-7-methylthioimidazo[5,1-b]thiazole was used as the starting compound. Thus, 4.70 g of the title compound was prepared.

NMR (CDCl$_3$) δ: 0.91 (9H, t, J=7.3 Hz), 1.1–1.2 (6H, m), 1.25–1.4 (6H, m), 1.5–1.65 (6H, m), 2.36 (3H, s), 2.42 (3H, s), 7.81 (1H, s)

Synthesis Example 9

7-2-(4-Nitrobenzyloxycarbonyl)aminoethyl]thio-2-(tri-n-butylstannyl)imidazo[5,1-b]-thiazole a) 7-Acetylthioimidazo[5,1-b]thiazole The procedure of Synthesis Example 15a) was repeated, except that 5.0 g of 7-iodoimidazo[5,1-b]thiazole and 1.71 ml of acetyl chloride were used as the starting compounds. Thus, 2.02 g of 7-acetylthioimidazo[5,1-b]thiazole was prepared.

NMR (CDCl$_3$) δ: 2.41 (3H, s), 6.92 (1H, d, J=4.2 Hz), 7.46 (1H, d, J=4.2 Hz), 8.08 (1H, s)

b) 7-[2-(4-Nitrobenzyloxycarbonyl)aminoethyl]thioimidazo[5,1-b]thiazole

A solution of 396 mg of 7-acetylthioimidazo[5,1-b]thiazole in 2 ml of methanol was cooled in ice. A 1.018 M sodium methoxide/methanol solution (2.16 ml) was added to the cooled solution, and the mixture was stirred for 10 min. A solution of 700 mg of 2-(4-nitrobenzyloxycarbonyl)aminoethyl methanesulfonate in 2 ml of dichloromethane was added thereto, and the mixture was stirred at room temperature for 3 hr. An aqueous ammonium chloride solution was added to the reaction solution, and the mixture was extracted with ethyl acetate twice. The organic layer was washed with brine, and was dried over anhydrous magnesium sulfate. The solvent was removed by distillation, and the residue was purified by column chromatography on silica gel (dichloromethane:ethyl acetate=1:1 to ethyl acetate only) to prepare 376 mg of 7-[2-(-4-nitrobenzyloxycarbonyl)aminoethyl]thioimidazo[5,1-b]-thiazole.

NMR (CDCl$_3$) δ: 2.85–2.95 (2H, m), 3.4–3.5 (2H, m), 5.19 (2H, s), 6.2–6.3 (1H, m), 6.90 (1H, d, J=4.2 Hz), 7.42 (1H, d, J=4.2 Hz), 7.50 (2H, d, J=8.5 Hz), 8.01 (1H, s), 8.20 (2H, d, J=8.5 Hz)

c) 7-[2-(4-Nitrobenzyloxycarbonyl)aminoethyl]thio-2-(tri-n-butylstannyl)imidazo[5,1-b]thiazole Tri-n-butylstannyl chloride (0.07 ml) and 0.494 ml of a 1.0 N lithiumbis(trimethylsilyl)amide/THF solution were added to a solution of 62.3 mg of 7-[2-(4-nitrobenzyloxycarbonyl)aminoethyl]thioimidazo[5,1-b]-thiazole in 2 ml of THF at −40° C. under an argon atmosphere. The mixture was stirred for 30 min. An aqueous ammonium chloride solution was added to the reaction solution, and the mixture was extracted with ethyl acetate, followed by washing with brine. The organic layer was dried over anhydrous magnesium sulfate. The solvent was then removed by distillation, and the residue was purified by column chromatography on silica gel (hexane:ethyl acetate=1:1) to prepare 60.3 mg of the title compound.

NMR (CDCl$_3$,) δ: 0.92 (9H, t, J=7.3 Hz), 1.1–1.2 (6H, m), 1.3–1.4 (6H, m), 1.5–1.65 (6H, m), 2.85–2.95 (2H, m), 3.4–3.5 (2H, m), 5.20 (2H, s), 6.3–6.4 (1H, m), 7.15 (1H, s), 7.51 (2H, d, J=8.6 Hz), 7.94 (1H, s), 8.20 (2H, d, J=8.6 Hz)

Synthesis Example 10

3-t-Butyldimethylsilyloxymethyl-7-methylthio-2-(tri-n-butylstannyl)imidazo[5,1-b]-thiazole a) 3-t-Butyldimethylsilyloxymethyl-7-iodoimidazo-[5,1-b]thiazole The procedure of Synthesis Example 2a) was repeated, except that 3.26 g of 3-t-butyldimethylsilyloxymethylimidazo[5,1-b]thiazole was used as the starting compound. Thus, 3.21 g of 3-t-butyldimethylsilyloxymethyl-7-iodoimidazo[5,1-b]thiazole was prepared.

NMR (CDCl$_3$) δ: 0.10 (6H, s), 0.90 (9H, s), 4.75 (2H, s), 6.66 (1H, s), 7.98 (1H, s)

b) 3-t-Butyldimethylsilyloxymethyl-7-methylthioimidazo[5,1-b]thiazole

The procedure of Synthesis Example 2b) was repeated, except that 1.70 g of 3-t-butyldimethylsilyloxymethyl-7-iodoimidazo[5,1-b]thiazole was used as the starting compound. Thus, 1.06 g of 3-t-butyldimethylsilyloxymethyl-7-methylthioimidazo[5,1-b]thiazole was prepared.

NMR (CDCl$_3$) δ: 0.11 (6H, s), 0.91 (9H, s), 2.44 (3H, s), 4.76 (2H, s), 6.64 (1H, s), 8.02 (1H, s)

c) 3-t-Butyldimethylsilyloxymethyl-7-methylthio-2-(tri-n-butylstannyl)imidazo[5,1-b]thiazole The procedure of Synthesis Example 2c) was repeated, except that 1.06 g of 3-t-butyldimethylsilyloxymethyl-7-methylthioimidazo[5,1-b]thiazole was used as the starting compound. Thus, 1.77 g of the title compound was prepared.

NMR (CDCl$_3$) δ: 0.14 (6H, s), 0.91 (9H, t, J=7.4 Hz), 0.92 (9H, s), 1.1–1.2 (6H, m), 1.3–1.4 (6H, m), 1.5–1.65 (6H, m), 2.43 (3H, s), 4.66 (2H, s), 7.99 (1H, s)

Synthesis Example 11

7-Benzoyl-2-(tri-n-butylstannyl)imidazo[5,1-b]thiazole

Aluminum chloride (5.33 g) was added to a solution of 4.64 ml of benzoyl chloride in 50 ml of carbon disulfide. A solution of 1.24 g of imidazo[5,1-b]thiazole in 50 ml of dichloromethane was then added dropwise to the mixture. The mixture was stirred at room temperature for 2 hr. The reaction solution was then poured into 50 g of ice. Dichloromethane (100 ml) was added thereto. Sodium carbonate (16.7 g) and 16.7 g of sodium sulfate were added in that order to the mixture with stirring. The insolubles were removed by filtration on Celite, followed by washing with dichloromethane. The filtrate was concentrated under the reduced pressure. The residue was purified by column chromatography on silica gel (hexane:ethyl acetate=5:1 to dichloromethane:ethyl acetate=2:1) to prepare 1.39 g of 7-benzoylimidazo[5,1-b]thiazole.

NMR (CDCl$_3$) δ: 7.16 (1H, d, J=4.1 Hz), 7.54 (3H, m), 7.60 (1H, d, J=4.1 Hz), 8.09 (1H, s), 8.54 (2H, m)

b) 7-Benzoyl-2-(tri-n-butylstannyl)imidazo[5,1-b]thiazole

The procedure of Synthesis Example 3b) was repeated, except that 1.39 g of 7-benzoylimidazo[5,1-b]thiazole was used as the starting compound. Thus, 2.59 g of the title compound was prepared.

NMR (CDCl$_3$) δ: 0.92 (9H, t, J=7.2 Hz), 1.21 (6H, m), 1.36 (6H, m), 1.60 (6H, m), 7.34 (1H, s), 7.53 (3H, m), 8.03 (1H, s), 8.51 (2H, m)

Synthesis Example 12

7Propylthio)-2-(tri-n-butylstannyl)imidazo[5,1b]thiazole a) Propyl-1-propanethiol sulfonate The procedure of Synthesis Example 7a) was repeated, except that 1.57 ml of dipropyl disulfide was used as the starting compound. Thus, 666 mg of propyl-1-propanethiol sulfonate was prepared.

NMR (CDCl$_3$) δ: 1.04 (3H, t, J=7.4 Hz), 1.09 (3H, t, J=7.4 Hz), 1.7–1.85 (2H, m), 1.9–2.05 (2H, m), 3.05–3.15 (2H, m), 3.25–3.35 (2H, m)

b) 7-Propylthioimidazo[5,1-b]thiazole

The procedure of Synthesis Example 7b) was repeated, except that 3.33 g of 7-iodoimidazo[5,1-b]thiazole and 3.03 g of propyl-1-propanethiol sulfonate were used as the starting compounds. Thus, 1.74 g of 7-propylthioimidazo[5,1-b]thiazole was prepared.

NMR (CDCl$_3$) δ: 0.99 (3H, t, J=7.4 Hz), 1.55–1.7 (2H, m), 2.75–2.85 (2H, m), 6.86 (1H, d, J=4.2 Hz), 7.39 (1H, d, J=4.2 Hz), 8.00 (1H, s)

c) 7-Propylthio-2-(tri-n-butylstannyl)imidazo[5,1-b]thiazole

The procedure of Synthesis Example 3b) was repeated, except that 882 mg of 7-propylthioimidazo[-5,1-b]thiazole was used as the starting compound. Thus, 1.84 g of the title compound was prepared.

NMR (CDCl$_3$) δ: 0.92 (9H, t, J=7.4 Hz), 0.99 (3H, t, J=7.4 Hz), 1.1–1.2 (6H, m), 1.3–1.4 (6H, m), 1.5–1.7 (8H, m), 2.7–2.8 (2H, m), 7.13 (1H, s), 7.94 (1H, s)

Synthesis Example 13
7-Isopropylthio-2-(tri-n-butylstannyl)imidazo[5,1b]thiazole a) 7-Isopropylthioimidazo[5,1-b]thiazole A 0.69 M isopropylmagnesium bromide/THF solution (9.13 ml) was added to a solution of 1.50 g of 7-iodoimidazo[5,1-b]thiazole in 30 ml of dry THF under an argon atmosphere with cooling in ice. The mixture was stirred at that temperature for 20 min. Sulfur (211 mg) was then added thereto, and the mixture was heated under reflux for one hr. A saturated aqueous ammonium chloride solution was added to the reaction mixture, and the mixture was extracted with ethyl acetate twice, followed by washing with an aqueous sodium thiosulfate solution and saturated brine in that order. The organic layer was dried over anhydrous magnesium sulfate. The solvent was removed by distillation, and the residue was purified by column chromatography on silica gel (hexane:ethyl acetate 1:2) to prepare 833 mg of 7-isopropylthioimidazo[5,1-b]thiazole.

NMR (CDCl$_3$) δ: 1.28 (6H, d, J=6.7 Hz), 3.28 (1H, sept, J=6.7 Hz), 6.87 (1H, d, J=4.2 Hz), 7.40 (1H, d, J=4.2 Hz), 8.02 (1H, s)

b) 7-Isopropylthio-2-(tri-n-butylstannyl)imidazo[5 1-b]thiazole

The procedure of Synthesis Example 3b) was repeated, except that 1.02 g of 7-isopropylthioimidazo[5,1-b]thiazole was used as the starting compound. Thus, 1.38 g of the title compound was prepared.

NMR (CDCl$_3$) δ: 0.92 (9H, t, J=7.3 Hz), 1.1–1.2 (6H, m), 1.28 (6H, d, J=6.8 Hz), 1.3–1.4 (6H, m), 1.5–1.65 (6H, m), 3.26 (1H, sept, J=6.8 Hz), 7.14 (1H, s), 7.95 (1H, s)

Synthesis Example 14
7-(2-Azidoethyl)thio-5-methylthio-2-(tri-n-butylstannyl)imidazo[5,1-b]thiazole a) 2-Methanesulfonyloxyethyl disulfide N,N-Diisopropylethylamine (4.35 ml) and 1.70 ml of methanesulfonyl chloride were added to a suspension of 1.22 ml of 2-hydroxyethyl disulfide in 30 ml of dichloromethane at −40° C. under an argon atmosphere. The mixture was stirred at that temperature for 30 min. The reaction solution was then diluted with dichloromethane, and the diluted solution was washed with an aqueous dilute hydrochloric acid solution, an aqueous sodium hydrogencarbonate solution, and water in that order, and was dried over anhydrous magnesium sulfate. The solvent was removed by distillation under the reduced pressure. Thus, 3.08 g of 2-methanesulfonyloxyethyl disulfide was prepared.

NMR (CDCl$_3$) δ: 3.0–3.1 (4H, m), 3.07 (6H, s), 4.4–4.5 (4H, m)

b) 2-Azidoethyl disulfide

Sodium azide (572 mg) was added to a solution of 910 mg of 2-methanesulfonyloxyethyl disulfide in 20 ml of DMF. The mixture was stirred at 50° C. for 2.5 hr. Brine was added to the reaction solution, and the mixture was extracted with ethyl acetate twice. The organic layers were, combined, were washed with brine twice, and were dried over anhydrous magnesium sulfate. The solvent was removed by distillation under the reduced pressure. The residue was purified by column chromatography on silica gel (hexane:ethyl acetate 10:1) to prepare 50.9 mg of 2-azidoethyl disulfide.

NMR (CDCl$_3$) δ: 2.85–2.95 (4H, m), 3.55–3.65 (4H, m)

c) 2-Azidoethyl (2-azidoethane)thiolsulfonate

A solution of 509 mg of 2-azidoethyl disulfide in 30 ml of dichloromethane was cooled in ice. 3-Chloroperbenzoic acid (1.661 g) was added to the cooled solution. The mixture was stirred at that temperature for one hr. The reaction solution was diluted with dichloromethane, and the diluted solution was washed with an aqueous sodium thiosulfate solution, an aqueous sodium hydrogencarbonate solution, and water in that order, and was dried over anhydrous magnesium sulfate. The solvent was removed by distillation, and the residue was purified by column chromatography on silica gel (hexane:ethyl acetate=2:1) to prepare 212 mg of 2-azidoethyl (2-azidoethane)thiolsulfonate.

NMR (CDCl$_3$) δ: 3.3–3.4 (2H, m), 3.6–3.75 (4H, m), 3.8–3.9 (2H, m)

d) 7-Iodo-5-methylthioimidazo[5,1-b]thiazole

The procedure of Synthesis Example 1a) was repeated, except that 7.77 g of 5,7-diiodoimidazo[5,1-b]thiazole was used as the starting compound. Thus, 3.96 g of 7-iodo-5-methylthioimidazo[5,1-b]thiazole was prepared.

NMR (CDCl$_3$) δ: 2.53 (3H, s), 6.90 (1H, d, J=4.1 Hz), 7.50 (1H, d, J=4.1 Hz)

e) 7-(2-Azidoethyl)thio-5-methylthioimidazo[5,1-b]thiazole

A solution of 395 mg of 7-iodo-5-methylthioimidazo[5,1-b]thiazole in 7 ml of THF was cooled in ice. A 0.96 M ethylmagnesium bromide/THF solution (1.39 ml) was added to the solution under an argon atmosphere. The mixture was stirred at that temperature for 15 min. A solution of 355 mg of 2-azidoethyl (2-azidoethane)thiolsulfonate in 2 ml of THF was then added thereto, and the mixture was stirred at that temperature for 25 min. An aqueous ammonium chloride solution was added to the reaction solution, and the mixture was extracted with ethyl acetate twice. The extract was washed with an aqueous sodium thiosulfate solution and brine in that order, and was then dried over anhydrous magnesium sulfate. The solvent was removed by distillation, and the residue was purified by column chromatography on silica gel (hexane:ethyl acetate=5:1) to prepare 292 mg of 7-(2-azidoethyl)thio-5-methylthioimidazo[5,1-b]thiazole.

NMR (CDCl$_3$) δ: 2.58 (3H, S), 2.9–3.0 (2H, m), 3.4–3.55 (2H, m), 6.9(1H, d, J=4.2 Hz), 7.40 (1H, d, J=4.2 Hz)

f) 7-(2-Azidoethyl)thio-5-methylthio-2-(tri-n-butylstannyl)imidazo[5,1-b]thiazole The procedure of Synthesis Example 15c) was repeated, except that 292 mg of 7-(2-azidoethyl)thio-5-methylthioimidazo[5,1-b]thiazole was used as the starting compound. Thus, 485 mg of the title compound was prepared.

NMR (CDCl$_3$) δ: 0.92 (9H, t, J=7.4 Hz), 1.15–1.25 (6H, m), 1.3–1.45 (6H, m), 1.5–1.65 (6H, m), 2.56 (3H, s), 2.9–3.0 (2H, m), 3.45–3.55 (2H, m), 7.12 (1H, s)

Synthesis Example 15

7-(2-Azidoethyl)thio-2-(tri-n-butylstannyl)imidazo[5,1-b]thiazole a) 7-(2-Hydroxyethyl)thioimidazo[5,1-b]thiazole

A solution of 5.0 g of 7-iodoimidazo[5,1-b]thiazole in 100 ml of dry THF was cooled in ice. A 0.95 M methylmagnesium bromide/THF solution (23.15 ml) was added dropwise to the cooled solution under an argon atmosphere. The mixture was stirred at that temperature for 30 min. The solvent was then removed by distillation under the reduced pressure. The residue was suspended in 100 ml of THF. Sulfur (672 mg) was added, and the mixture was heated under reflux for 30 min. The reaction solution was cooled to room temperature. 2-Iodoethanol (1.87 ml) was added to the cooled solution, and the mixture was stirred; for 4 hr. A saturated aqueous ammonium chloride solution and a dilute aqueous sodium thiosulfate solution were added to the reaction mixture. The mixture was extracted with ethyl acetate once and then with dichloromethane twice. The organic layer was dried over anhydrous magnesium sulfate. The solvent was removed by distillation and the residue was purified by column chromatography on silica gel (dichloromethane:methanol=20:1) to prepare 2.96 g of 7-(2-hydroxyethyl)thioimidazo[5,1-b]thiazole.

NMR (CDCl$_3$) δ: 2.9–3.0 (2H, m), 3.8–3.9 (2H, m), 6.90 (1H, d, J=4.3 Hz), 7.41 (1H, d, J=4.3 Hz), 8.01 (1H, s)

b) 7-(2-Azidoethyl)thioimidazo[5,1-b]thiazole 7-(2-Hydroxyethyl)thioimidazo[5,1-b]thiazole (1.67 g) was suspended in a mixed solvent composed of 70 ml of dichloromethane and 7 ml of DMF. N,N-Diisopropylethylamine (1.89 ml) and 0.774 ml of methanesulfonyl chloride were added to the suspension at −20° C. under an argon atmosphere. The mixture was stirred at that temperature for one hr. The reaction solution was then diluted with dichloromethane. The mixture was adjusted to pH 3.3 by the addition of a dilute aqueous hydrochloric acid solution. The organic layer was separated, and the aqueous layer was extracted with dichloromethane twice. The combined organic layer was washed with an aqueous sodium hydrogencarbonate solution, and was dried over anhydrous magnesium sulfate. DMF (25 ml) was added thereto. Dichloromethane was removed by distillation under the reduced pressure. Sodium azide (1.63 g) was added to the residue, and the mixture was stirred at 50° C. for 7 hr. Brine was added to the reaction solution, and the mixture was extracted with ethyl acetate three times. The organic layers were combined, were washed with brine three times, and were purified by column chromatography on silica gel (hexane:ethyl acetate=1:2 to only ethyl acetate) to prepare 1.496 g of 7-(2-azidoethyl)thioimidazo[5,1-b]thiazole.

NMR (CDCl$_3$) δ: 2.9–3.0 (2H, m), 3.4–3.5 (2H, m), 6.90 (1H, d, J=4.2 Hz), 7.42 (1H, d, J=4.2 Hz), 8.02 (1H, s)

c) 7-(2-Azidoethyl)thio-2-(tri-n-butylstannyl)imidozo[5,1-b]thiazole

Tri-n-butylstannyl chloride (3.53 ml) and 12.34 ml of a 1.0 N lithiumbis(trimethylsilyl)amide/THF solution were added to a solution of 2.32 g of 7-(2-azidoethyl)thioimidazo[5,1-b]thiazole in 75 ml of THF at −65° C. under an argon atmosphere. While raising the temperature to −30° C. over a period of 2 hr, 1.0 ml of a 1.0 N lithiumbis(trimethylsilyl)amide/THF solution was added thereto four times. An aqueous ammonium chloride solution was added to the reaction solution, and the mixture was extracted with ethyl acetate, followed by washing with brine. The organic layer was dried over anhydrous magnesium sulfate. The solvent was then removed by distillation, and the residue was purified by column chromatography on silica gel (hexane:ethyl acetate=2:1) to prepare 4.62 g of the title compound.

NMR (CDCl$_3$) δ: 0.92 (9H, t, J=7.2 Hz), 1.1–1.2 (6H, m), 1.3–1.4 (6H, m), 1.5–1.65 (6H, m), 2.9–3.0 (2H, m), 3.45–3.55 (2H, m), 7.16 (1H, s), 7.95 (1H, s)

Synthesis Example 16

7-(2-Formylaminoethyl)thio-2-(tri-n-butylstannyl)imidazo[5,1-b]thiazole

7-(2-Azidoethyl)thioimidazo[5,1-b]thiazole (397 mg) was dissolved in a mixed solvent composed of 10 ml of THF and 10 ml of water. A 1 N aqueous hydrochloric acid solution (5.3 ml) and 200 mg of 10% Pd—C were added to the solution. The air in the reaction vessel was replaced by hydrogen, and the contents of the reaction vessel were stirred at room temperature for 6 hr. The catalyst was removed by filtration on Celite, and washed with water. The filtrate was concentrated under the reduced pressure until the volume was substantially halved. Dichloromethane (20 ml) was added to the residue. The mixture was adjusted to pH 7.0 by the addition of an aqueous sodium hydrogencarbonate solution. Formic acid (0.90 ml) and 0.50 ml of acetic anhydride, which had been stirred at 50° C. for 5 min, were added thereto under cooling in ice. While maintaining the mixture at a pH value around 7.0, the mixture was stirred at that temperature for 20 min. The reaction solution was adjusted to pH 8.3 by the addition of an aqueous sodium hydrogencarbonate solution, and was extracted with dichloromethane three times. The organic layer was dried over anhydrous magnesium sulfate. The solvent was then removed by distillation, and the residue was purified by column chromatography on silica gel (dichloromethane:methanol=20:1) to prepare 250 mg of 7-(2-formylaminoethyl)thioimidazo[5,1-b]thiazole.

NMR (CDCl$_3$) δ: 2.85–2.95 (2H, m), 3.5–3.6 (2H, m), 6.92 (1H, d, J=4.3 Hz), 7.2–7.4 (1H, m), 7.43 (1H, d, J=4.3 Hz), 8.02 (1H, s), 8.22 (1H, s)

b) 7-(2-Formylaminoethyl)thio-2-(tri-n-butylstannyl)imidaza[5,1-b]thiazole

A 1.6 N n-butyllithium/n-hexane solution (11.7 ml) was added to a solution of 1.19 g of 7-(2-formylaminoethyl)thioimidazo[5,1-b]thiazole in 50 ml of THF at −55° C. under an argon atmosphere. The mixture was stirred at that temperature for 10 min. Tri-n-butylstannyl chloride (2.24 ml) was added thereto, and the mixture was stirred for 20 min. While raising the temperature to −30° C., 3.34 ml of a 1.6 N n-butyllithium/n-hexane solution and 2.4 ml of tri-n-butylstannyl chloride were additionally added thereto during a one hr period. An aqueous ammonium chloride solution was added to the reaction solution, and the mixture was extracted with ethyl acetate, followed by washing with brine. The organic layer was dried over anhydrous magnesium sulfate. The solvent was then removed by distillation, and the residue was purified by column chromatography on silica gel (only ethyl acetate to dichloromethane:methanol=20:1) to prepare 1.615 g of the title compound.

NMR (CDCl$_3$) δ: 0.92 (9H, t, J=7.3 Hz), 1.1–1.2 (6H, m), 1.3–1.45 (6H, m), 1.5–1.65 (6H, m), 2.75–2.85(2H, m), 3.5–3.6 (2H, m), 7.16 (1H, s), 7.6–7.7 (1H, m), 7.94 (1H, s), 8.21 (1H, s)

Synthesis Example 17

7-[3-(4-Nitrobenzyloxycarbonyl)aminopropyl]thio-2-(tri-n-butylstannyl)imidazo[5,1b]-thiazole a) 7-[3-(4-Nitrobenzyloxycarbonyl)aminopropyl]thioimidazo[5,1-b]thiazole

The procedure of Synthesis Example 15a) was repeated, except that 1.25 g of 7-iodoimidazo[5,1-b]thiazole and 1.82 g of 1-iodo-3-(4-nitrobenzyloxycarbonyl)aminopropane were used as the starting compounds. Thus, 810 mg of 7-[3-(4-nitrobenzyloxycarbonyl)aminopropyl]thioimidazo[5,1-b]thiazole was prepared.

NMR (CDCl$_3$) δ: 1.75–1.9 (2H, m), 2.8–2.9 (2H, m), 3.3–3.45 (2H, m), 5.18 (2H, s), 5.50 (1H, br s), 6.88 (1H, d, J=4.3 Hz), 7.41 (1H, d, J=4.3 Hz), 7.50 (2H, d, J=8.6 Hz), 8.01 (1H, s), 8.20 (2H, d, J=8.6 Hz)

b) 7-[3-(4-Nitrobenzyloxycarbonyl)aminopropyl]thio-2-(tri-n-butylstannyl)imidazo[5,1-b]thiazole Tri-n-butylstannyl chloride (1.21 ml) and 9.47 ml of a 1.0 N-lithiumbis(trimethylsilyl)amide/THF solution were added to a solution of 1.11 g of 7-[3-(4-nitrobenzyloxycarbonyl)aminopropyl]thioimidazo[5,1-b]-thiazole in 28 ml of THF at −45° C. under an argon atmosphere. The mixture was stirred for one hr. An aqueous ammonium chloride solution was added to the reaction solution, and the mixture was extracted with ethyl acetate, followed by washing with brine. The organic layer was dried over anhydrous magnesium sulfate. The solvent was then removed by distillation, and the residue was purified by column chromatography on silica gel (hexane:ethyl acetate=1:1) to prepare 1.24 g of the title compound.

NMR (CDCl$_3$) δ: 0.91 (9H, t, J=7.3 Hz), 1.1–1.2 (6H, m), 1.3–1.4 (6H, m), 1.5–1.6 (6H, m), 1.8–1.9 (2H, m), 2.8–2.9 (2H, m), 3.35–3.45 (2H, m), 5.18 (2H, s), 5.58 (1H, br s), 7.15 (1H, s), 7.50 (2H, d, J=8.7 Hz), 7.94 (1H, s), 8.20 (2H, d, J=8.7 Hz)

Synthesis Example 18

2-(Tri-n-butylstannyl)-7-trifluoromethylthioimidazo[5,1-b]thiazole a) 7-Trifluoromethylthioimidazo[5,1-b]thiazole The procedure of Synthesis Example 15a) was repeated, except that 2.91 g of 7-iodoimidazo[5,1-b]thiazole and 4.91 g of S-(trifluoromethyl)dibenzothiophenium trifluoromethanesulfonate were used as the starting compounds. Thus, 590 mg of 7-trifluoromethylthioimidazo[5,1-b]thiazole was prepared.

NMR (CDCl$_3$) δ: 6.99 (1H, d, J=4.4 Hz), 7.49 (1H, d, J=4.4 Hz), 8.09 (1H, s)

b) 2-(Tri-n-butylstannyl)-7-trifluoromethylthioimidazo[5,1-b]thiazole

7-Trifluoromethylthioimidazo[5,1-b]thiazole (590 mg) was dissolved in 10 ml of THF under an argon atmosphere. The solution was then cooled to −65° C. Tri-n-butylstannyl chloride (2.07 ml) and 7.2 ml of a 1.0 N lithiumbis(trimethylsilyl)amide/THF solution were added dropwise in that order to the cooled solution, and the temperature of the mixture was raised to −40° C. over a period of 30 min. Ethyl acetate (40 ml) was added to the reaction solution, and the mixture was washed with 40 ml of brine. The organic layer was dried over anhydrous magnesium sulfate, and then filtered. The solvent was removed by distillation under the reduced pressure. The residue was purified by column chromatography on silica gel (hexane:ethyl acetate=4:1) to prepare 951 mg of the title compound.

NMR (CDCl$_3$) δ: 0.92 (9H, t, J=7.3 Hz), 1.16–1.20 (6H, m), 1.30–1.41 (6H, m), 1.54–1.62 (6H, m), 7.21 (1H, s), 8.01 (1H, s)

Synthesis Example 19

7-Fluoromethylthio-2-(tri-n-butylstannyl)imidazo[5,1-b]thiazole a) 7-Fluoromethylthioimidazo[5,1-b]thiazole 7-Acetylthioimidazo[5,1b]thiazole was dissolved in 5 ml of methanol. A 1.02 N sodium methoxide/methanol solution and 2.5 g of bromofluoromethane were added in that order to the solution under cooling in ice. Dichloromethane (15 ml) was added to the reaction solution, and the mixture was washed with 15 ml of brine. The organic layer was dried over anhydrous magnesium sulfate, and was then filtered. The solvent was removed by distillation under the reduced pressure. The residue was purified by column chromatography on silica gel (hexane:ethyl acetate=4:1) to prepare 460 mg of 7-fluoromethylthioimidazo[5,1-b]thiazole.

NMR (CDCl$_3$) δ: 5.56 (1H, s), 5.69 (1H, s), 6.91 (1H, d, J=4.2 Hz), 7.16 (1H, d, J=4.2 Hz), 7.96 (1H, s) imidazo[5,1-b]thiazole 7-Fluoromethylthioimidazo[5,1-b]thiazole (578 mg) was dissolved in 12 ml of THF under an argon atmosphere. The solution was cooled to −45° C. Tri-n-butylstannyl chloride (0.916 ml) and 5.3 ml of a 1.0 N lithiumbis(trimethylsilyl)amide/THF solution were added dropwise in that order to the cooled solution. The mixture was stirred for 30 min. Ethyl acetate (40 ml) was added to the reaction solution, and the mixture was washed with 40 ml of brine. The organic layer was dried over anhydrous magnesium sulfate, and was then filtered. The solvent was removed by distillation under the reduced pressure. The residue was purified by column chromatography on silica gel (hexane:ethyl acetate=3:1) to prepare 951 mg of the title compound.

NMR (CDCl$_3$) δ: 0.92 (9H, t, J=7.2 Hz), 1.12–1.18 (6H, m), 1.30–1.40 (6H, m), 1.53–1.60 (6H, m), 5.56 (1H, 6), 5.69 (1H, s), 7.16 (1H, s), 7.96 (1H, s)

Synthesis Example 20

7-[(3S)-1-(4-Nitrobenzyloxycarbonyl)pyrrolidin-3-yl]thio-2-(tri-n-butylstannyl)imidazo[5,1-b]thiazole a) 7-[(3S)-1-(4-Nitrobenzyloxycarbonyl)pyrrolidin-3-yl]thioimidazo[5,1-b]thiazole The procedure of Synthesis Example 3a) was repeated, except that 1.00 g of 7-iodoimidazo[5,1-b]thiazole and 1.49 g of (3R)-3-hydroxy-1-(4-nitrobenzyloxycarbonyl)pyrrolidine were used as the starting compounds. Thus, 814 mg of 7-[(3S)-1-(4-nitrobenzyloxycarbonyl)pyrrolidin-3-yl)thioimidazo[5,1-b]thiazole was prepared.

NMR (DMSO-d$_6$) δ: 1.8–2.0 (1H, m), 2.1–2.3 (1H, m), 3.25–3.7 (5H, m), 5.20 (2H, s), 7.29, 7.31 (total 1H, s each), 7.58–7.66 (2H, m), 7.91, 7.92 (total 1H, s each), 8.20–8.30 (3H, m)

b) 7-[(3S)-1-(4-Nitrobenzyloxycarbonyl)pyrrolidin-3yl]thio-2-(tri-n-butylstannyl)imidazo[5,1-b]thiazole The procedure of Synthesis Example 15c) was repeated, except that 450 mg of 7-[(3S)-1-(4-nitrobenzyloxycarbonyl)pyrrolidin-3-yl]thioimidazo[5,1-b]thiazole was used as the starting compound. Thus, 203 mg of the title compound was prepared.

NMR (CDCl$_3$) δ: 0.8–1.0 (9H, m), 1.0–1.2 (6H, m), 1.3–1.5 (6H, m), 1.5–1.7 (6H, m), 1.9–2.3 (2H, m), 3.4–3.8 (5H, m), 5.22 (2H, s), 7.15, 7.16 (total 1H, s each), 7.45–7.55 (2H, m), 7.95, 7.96 (total 1H, s each), 8.15–8.25 (2H, m)

Synthesis Example 21

7-(3-Azidopropyl)thio-2-(tri-n-butylstannyl)imidazo[5,1-b]thiazole a) 7-(3-Azidopropyl)thioimidazo[5,1-b]thiazole The procedure of Synthesis Example 3a) was repeated, except that 12.5 g of 7-iodoimidazo[5,1-b]thiazole and 6.06 g of 3-azido-1-propanol were used as the starting compounds. Thus, 8.56 g of 7-(3-azidopropyl)thioimidazo[5,1-b]thiazole was prepared.

NMR (CDCl$_3$) δ: 1.75–1.9 (2H, m), 2.8–2.9 (2H, m), 3.4–3.5 (2H, m), 6.88 (1H, d, J=4.2 Hz), 7.41 (1H, d, J=4.2 Hz), 8.01 (1H, s)

b) 7-(3-Azidopropyl)thio-2-(tri-n-butylstannyl)imidazo[5,1-b]thiazole

The procedure of Synthesis Example 15c) was repeated, except that 2.01 g of 7-(3-azidopropyl)thioimidazo[5,1-b]thiazole was used as the starting compound. Thus, 3.70 g of the title compound was prepared.

NMR (CDCl$_3$) δ: 0.92 (9H, t, J=7.2 Hz), 1.1–1.2 (6H, m), 1.3–1.4 (6H, m), 1.5–1.6 (6H, m), 1.8–1.9 (2H, m), 2.8–2.9 (2H, m), 3.4–3.5 (2H, m), 7.14 (1H, s), 7.94 (1H, s)

Synthesis Example 22

7-[1-(4-Nitrobenzyloxycarbonyl)piperidin-4-yl]thio-2-(tri-n-butylstannyl)imidazo[5,1-b]thiazole a) 7-1-(4-Nitrobenzyloxycarbonyl)piperidin-4yl]-thioimidazo[5,1-b]thiazole 4-Hydroxy-1-(4-nitrobenzyloxycarbonyl)piperidine (336 mg) was dissolved in 5 ml of dichloromethane. 2,6-Lutidine (0.154 ml) and 0.212 ml of trifluoromethanesulfonic anhydride were added to the solution at −50° C. under an argon atmosphere. The mixture was stirred at that temperature for 25 min. The reaction solution was then diluted with dichloromethane, and the diluted solution was washed with a dilute aqueous hydrochloric acid solution. The organic layer was dried over anhydrous magnesium sulfate, and was concentrated under the reduced pressure until the volume of the organic layer was brought to about 2 ml. Separately, a solution of 198 mg of 7-acetylthioimidazo[5,1-b]thiazole in 1 ml of methanol was cooled in ice. A 1.018 M sodium methoxide/methanol solution (1.08 ml) was added to the cooled solution, and the mixture was stirred for 10 min. The above extract was added to this reaction mixture, and the mixture was stirred at room temperature for 2.5 hr. A saturated aqueous ammonium chloride solution was added to the reaction mixture, and the mixture was extracted with ethyl, acetate twice. The organic layer was washed with saturated brine, and was dried over anhydrous magnesium sulfate. The solvent was removed by distillation, and the residue was purified by column chromatography on silica gel (dichloromethane:ethyl acetate=1:1 to only ethyl acetate) to prepare 276 mg of 7-[1-(4-nitrobenzyloxycarbonyl)piperidin-4-yl]thioimidazo[5,1-b]thiazole.

NMR (CDCl$_3$) δ: 1.5–2.05 (4H, m), 2.9–3.2 (3H, m), 4.0–4.2 (2H, m), 5.20 (2H, s), 6.90 (1H, d, J=3.9 Hz), 7.43 (1H, d, J=3.9 Hz), 7.48 (2H, d, J=8.7 Hz), 8.05 (1H, s), 8.21 (2H, d, J=8.7 Hz)

b) 7-[1-(4-Nitrobenzyloxycarbonyl)piperidin-4-yl]-thio-2-(tri-n-butylstannyl)imidazo[5,1-b]thiazole The procedure of Synthesis Example 15c) was repeated, except that 276 mg of 7-[1-(4-nitrobenzyloxycarbonyl)piperidin-4-yl]thioimidazo[5,1-b]thiazole was used as the starting compound. Thus, 55.8 mg of the title compound was prepared.

NMR (CDCl$_3$) δ: 0.93 (9H, t, J=7.5 Hz), 1.1–1.2 (6H, m), 1.3–1.4 (6H, m), 1.4–1.75 (8H, m), 1.9–2.05 (2H, m), 2.9–3.2 (3H, m), 4.0–4.2 (2H, m), 5.20 (2H, s), 7.16 (1H, s), 7.49 (2H, d, J=8.7 Hz), 7.97 (1H, s), 8.21 (2H, d, J=8.7 Hz)

Synthesis Example 23

2-Iodo-7-methylthioimidazo[5,1-b]-thiazole

A solution of 0.23 g of 7-methylthio-2-(tri-n-butylstannyl)imidazo[5,1-b]thiazole in 2.5 ml of THF was cooled to −50° C. N-Iodosuccinimide (0.11 g) was added to the cooled solution. The mixture was stirred at that temperature for 4 hr. Ethyl acetate (50 ml) was then added to the reaction mixture. The mixture was washed with a dilute aqueous sodium hydrogencarbonate solution, a dilute aqueous sodium thiosulfate solution, and a saturated aqueous sodium chloride solution in that order. The organic layer was dried over anhydrous magnesium sulfate. The solvent was removed by distillation. A mixed solvent (3 ml) composed of hexane-:ethyl acetate=2:1 was added to the residue. The resultant precipitate was collected by filtration to prepare 0.13 g of the title compound.

NMR(CDCl$_3$) δ: 2.42 (3H, s), 7.50 (1H, s) 7.93 (1H, s)

Synthesis Example 24

7-(2-Bromoethyl)thio-2-(tri-n-butylstannyl)imidazo[5,1-b]thiazole a) 7-(2-Bromoethyl)thioimidazo[5,1-b]thiazole The procedure of Synthesis Example 22a) was repeated, except that 990 mg of 7-acetylthioimidazo[5,1-b]thiazole and 0.461 ml of 2-bromoethanol were used as the starting compounds. Thus, 1.06 g of 7-(2-bromoethyl)thioimidazo[5,1-b]thiazole was prepared.

NMR (CDCl$_3$) δ: 3.1–3.2 (2H, m), 3.5–3.6 (2H, m), 6.90 (1H, d, J=3.9 Hz), 7.42 (1H, d, J=3.9 Hz), 8.01 (1H, s)

b) 7-(2-Bromoethyl)thio-2-(tri-n-butylstannyl)imidazo[5,1-b]thiazole

The procedure of Synthesis Example 15c) was repeated, except that 1.06 g of 7-(2-bromoethyl)thioimidazo[5,1-b]thiazole was used as the starting compound. Thus, 1.62 g of the title compound was prepared.

NMR (CDCl$_3$) δ: 0.92 (9H, t, J=7.2 Hz), 1.1–1.2 (6H, m), 1.3–1.4 (6H, m), 1.5–1.65 (6H, m), 3.1–3.2 (2H, m), 3.5–3.6 (2H, m), 7.15 (1H, s), 7.94 (1H, s)

Synthesis Example 25

7-[3-N,N'-Bis(4-nitrobenzyloxycarbonyl)guanidinopropyl]thio-2-(tri-n-butylstannyl)imidazo[5,1-b]thiazole a) 7-(3-Azidopropyl)thioimidazo[5,1-b]thiazole The procedure of Synthesis Example 3a) was repeated, except that 12.5 g of 7-iodoimidazo[5,1-b]thiazole and 6.06 g of 3-azidopropanol were used as the starting compounds. Thus, 8.56 g of 7-(3-azidopropyl)thioimidazo[5,1-b]thiazole was prepared.

NMR (CDCl$_3$) δ: 1.8–1.9 (2H, m), 2.8–2.9 (2H, m), 3.4–3.5 (2H, m), 6.88 (1H, d, J=4.5 Hz), 7.41 (1H, d, J=4.5 Hz), 8.01 (1H, s)

b) 7-(3-Aminopropyl)thioimidazo[5,1-b]thiazole 7-(-3-Aminopropyl)thioimidazo[5,1-b]thiazole (1.46 g) was dissolved in 30 ml of ethanol and 6 ml of water. A 1 N aqueous hydrochloric acid solution (6.1 ml) and 1.46 g of 10%Pd—C were added to the solution. The air in the reaction vessel was replaced by hydrogen, and the contents of the reaction vessel were stirred at room temperature for 24 hr. The catalyst was removed by filtration through Celite, and was then washed with water. The filtrate was concentrated under the reduced pressure. A 1 N aqueous sodium hydroxide solution (20 ml) was added to the residue. The mixture was extracted with dichloromethane five times. The extract was dried over anhydrous magnesium sulfate. The solvent was removed by distillation. Thus, 1.15 g of 7-(3-aminopropyl)thioimidazo[5,1-b]thiazole was prepared.

NMR (CDCl$_3$) δ: 1.7–1.8 (2H, m), 2.8–2.9 (4H, m), 6.88 (1H, d, J=4.2 Hz), 7.40 (1H, d, J=4.2 Hz), 8.01 (1H, s)

c) 7-[3-N,N'-Bis(4-nitrobenzyloxycarbonyl)guanidinopropyl]thioimidazo[5,1-b]thiazole 7-(3-Aminopropyl)thioimidazo[5,1-b]thiazole (629 mg) was dissolved in 12 ml of DMF. 1H-Pyrazole-1-[N,N'-bis(4-nitrobenzyloxycarbonyl)]carboxamidine (1.66 g) was added to the solution. The mixture was stirred at room temperature for 19 hr. Brine was added to the reaction solution, and the mixture was extracted with ethyl acetate twice. The organic layer was washed with brine three times, and was dried over anhydrous magnesium sulfate. The solvent was removed by distillation. The residue was purified by column chromatography on silica gel (dichloromethane:ethyl acetate=1:1) to prepare 1.12 g of 7-[3-N,N'-bis(4-nitrobenzyloxycarbonyl)guanidinopropyl]thioimidazo[5,1-b]thiazole NMR (CDCl$_3$) δ: 1.85–1.95 (2H, m), 2.8–2.9 (2H, m), 3.6–3.7 (2H, m), 5.22 (2H, s), 5.27 (2H, s), 6.87 (1H, d, J=4.2 Hz), 7.39 (1H, d, J=4.2 Hz), 7.5–7.6 (4H, m), 8.00 (1H, s), 8.2–8.3 (4H, m), 8.35–8.5 (1H, m), 11.78 (1H, s)

d) 7-[3-N,N'-Bis(4-nitrobenzyloxycarbonyl)guanidinopropyl]thio2-(tri-n-butylstannyl)imidazo[5,1-b]thiazole The procedure of Synthesis Example 15c) was repeated, except that 992 mg of 7-[3-N,N'-bis(4-nitrobenzyloxycarbonyl)guanidinopropyl]thioimidazo[5,1-b]thiazole was used as the starting compound. Thus, 710 mg of the title compound was prepared.

NMR (CDCl$_3$) δ: 0.91 (9H, t, J=7.2 Hz), 1.1–1.2 (6H, m), 1.3–1.4 (6H, m), 1.5–1.6 (6H, m), 1.85–1.95 (2H, m), 2.8–2.9 (2H, m), 3.6–3.7 (2H, m), 5.22 (2H, 8), 5.27 (2H, s), 7.15 (1H, s), 7.5–7.6 (4H, m), 7.94 (1H, s), 8.15–8.25 (4H, m), 8.4–8.5 (1H, m), 11.78 (1H, s)

synthesis Example 26
7-Benzylthio-2-(tri-n-butylstannyl)imidazo[5,1-b]thiazole a) 7-Benzylthio[5,1-b]thiazoleimidazo A solution of 396 mg of 7-acetylthioimidazo[5,1-b]thiazole in 2 ml of methanol was cooled in ice. A 1.018 M sodium methoxide/methanol solution (2.16 ml) was added to the cooled solution. The mixture was stirred for 30 min. Benzyl bromide (0.262 ml) was added thereto, and the mixture was stirred at that temperature for 2 hr. An aqueous ammonium chloride solution was added to the reaction solution, and the mixture was extracted with ethyl acetate twice. The organic layer was washed with brine twice, and was dried over anhydrous magnesium sulfate. The solvent was removed by distillation. The residue was purified by column chromatography on silica gel (dichloromethane:methanol=30:1) to prepare 419 mg of 7-benzylthioimidazo[5,1-b]thiazole.

NMR (CDCl$_3$) δ: 3.99 (2H, s), 6.76 (1H, d, J=4.2 Hz), 7.1–7.25 (5H, m), 7.32 (1H, d, J=4.2 Hz), 7.99 (1H, s)

b) 7-Benzylthio-2-(tri-n-butylstannyl)imidazo[5,1-b]thiazole

The procedure of Synthesis Example 3b) was repeated, except that 330 mg of 7-benzylthioimidazo[5,1-b]thiazole was used as the starting compound. Thus, 602 mg of the title compound was prepared.

NMR (CDCl$_3$) δ: 0.92 (9H, t, J=7.2 Hz), 1.1–1.2 (6H, m), 1.3–1.4 (6H, m), 1.5–1.6 (6H, m), 3.99 (2H, s), 7.08 (1H, s), 7.15–7.2 (5H, m), 7.93 (1H, s)

Synthesis Example 27
7-(Pyridin-2-yl)methylthio-9-(tri-n-butylstannyl)imidazo[5,1-b]thiazole a) 7-(Pyridin-2-yl)methylthioimidazo[5,1b]thiazole Triphenylphosphine (2.95 g) and 3.73 g of carbon tetrabromide were added to a solution of 0.724 ml of (pyridin-2-yl)methanol in 40 ml of dichloromethane under cooling in ice. The mixture was stirred at that temperature for 1.5 hr. The reaction solution was purified by column chromatography on silica gel (dichloromethane:methanol=30:1) to prepare 2-bromomethylpyridine. Separately, a solution of 990 mg of 7-acetylthioimidazo[5,1-b]thiazole in 5 ml of methanol was cooled in ice. A 1.018 M sodium methoxide/methanol solution (5.4 ml) was added to the cooled solution. The mixture was stirred for 30 min. A solution of the above 2-bromomethylpyridine in 5 ml of dichloromethane was added to the mixture, followed by stirring at room temperature for 20 hr. A saturated aqueous ammonium chloride solution was added to the reaction mixture. The mixture was extracted with ethyl acetate three times. The organic layer was washed with saturated brine, and was dried over anhydrous magnesium sulfate. The solvent was removed by distillation. The residue was purified by column chromatography on silica gel (dichloromethane:methanol=20:1) to prepare 776 mg of 7-(pyridin-2-yl)methylthioimidazo[5,1-b]thiazole.

NMR (CDCl$_3$) δ: 4.12 (2H, s), 6.78 (1H, d, J=4.2 Hz), 7.05–7.15 (2H, m), 7.33 (1H, d, J=4.2 Hz), 7.45–7.55 (1H, m), 7.99 (1H, s), 8.45–8.5 (1H, m)

b) 7-(Pyridin-2-yl)methylthio-2-(tri-n-butylstannyl)imidazo[5,1-b]thiazole

The procedure of Synthesis Example 3b) was repeated, except that 776 mg of 7-(pyridin-2-yl)methylthioimidazo[5,1-b]thiazole was used as the starting compound. Thus, 1.18 g of the title compound was prepared.

NMR (CDCl$_3$) δ: 0.92 (9H, t, J=7.2 Hz), 1.1–1.2 (6H, m), 1.3–1.4 (6H, m), 1.5–1.6 (6H, m), 4.11 (2H, s), 7.05–7.2 (3H, m), 7.45–7.55 (1H, m), 7.92 (1H, s), 8.45–8.5.(1H, m)

Synthesis Example 28
7-(2-Fluoroethyl)thio-2-(tri-n-butylstannyl)imidazo[5.1-b]thiazole a) 7-(2-Fluoroethyl)thioimidazo[5,1-b]thiazole The procedure of Synthesis Example 3a) was repeated, except that 400 mg of 7-iodoimidazo[5,1-b]thiazole and 218 mg of 2-fluoroethanol were used as the starting compounds. Thus, 204 mg of 7-(2-fluoroethyl)thioimidazo[5,1-b]thiazole was prepared.

NMR (CDCl$_3$) δ: 3.02–3.12 (2H, m), 4.45–4.67 (2H, m), 6.89 (1H, d, J=4.2 Hz), 7.41 (1H, d, J=4.2 Hz), 8.01 (1H, s)

b) 7-(2-Fluoroethyl)thio-2-(tri-n-butylstannyl)imidazo[5,1-b]thiazole

The procedure of Synthesis Example 18b) was repeated, except that 202 mg of 7-(2-fluoroethyl)thioimidazo[5,1-b]thiazole was used as the starting compound. Thus, 951 mg of the title compound was prepared.

NMR (CDCl$_3$) δ: 0.92 (9H, t, J=7.3 Hz), 1.14–1.19 (6H, m), 1.31–1.41 (6H, m), 1.54–1.62 (6H, m), 3.01–3.09 (2H, m), 4.50 (1H, t, J=7.1 Hz), 4.62 (1H, t, J=7.1 Hz), 7.14 (1H, s), 7.94 (1H, s)

Synthesis Example 29
7-(Pyridin-2-yl)thio-2-(tri-n-butylstannyl)imidazo[5.1-b]thiazole a) 7-(Pyridin-2-yl)thioimidazo[5,1-b]thiazole A solution of 661 mg of 7-iodoimidazo[5,1-b]thiazole in 15 ml of dry THF was cooled in ice. A 0.95 M ethylmagnesium bromide/THF solution (2.89 ml) was added to the cooled solution in an argon atmosphere. The mixture was stirred at that temperature for 15 min. A solution of 798 mg of S-(pyridin-2-yl)pyridine-2-thiosulfonate in 10 ml of THF was added thereto, and the mixture was stirred at room temperature for 3 hr. A saturated aqueous ammonium chloride solution was added to the reaction mixture, and the mixture was then extracted with ethyl acetate twice. The extract was washed with brine. The organic layer was dried over anhydrous magnesium sulfate. The solvent was removed by distillation. The residue was purified by column chromatography on silica gel (ethyl acetate) to prepare 456 mg of 7-(pyridin-2-yl)thioimidazo[5,1-b]thiazole.

NMR (CDCl$_3$) δ: 6.9–7.0 (3H, m), 7.4–7.5 (1H, m), 7.50 (1H, d, J=3.9 Hz), 8.16 (1H, s), 8.35–8.45 (1H, m)

b) 7-(Pyridin-2-yl)thio-2-(tri-n-butylstannyl)imidazo[5,1-b]thiazole

The procedure of Synthesis Example 15c) was repeated, except that 456 mg of 7-(pyridin-2-yl)thioimidazo[5,1-b]

thiazole was used as the starting compound. Thus, 760 mg of the title compound was prepared.

NMR (CDCl$_3$) δ: 0.91 (9H, t, J=7.2 Hz), 1.1–1.2 (6H, m), 1.3–1.4 (6H, m), 1.5–1.65 (6H, m), 6.9–7.0 (2H, m), 7.23 (1H, s), 7.35–7.45 (1H, m), 8.09 (1H, 8), 8.35–8.45 (1H, m)

Example 1

(1S,5R,6S)-6-((1R)-1-Hydroxyethyl)-2-(7-methanesulfinyl-6-methylimidazo[5,1-b]thiazolium-2-yl)-1-methyl-1-carbapen-2-em-3-carboxylate (intramolecular salt) (a mixture of diastereomers)

a) 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate N,N-Diisopropylethylamine (8.49 ml) and 5.43 ml of trifluoromethanesulfonic anhydride were added dropwise in that order to a solution of 11.7 g of 4-nitrobenzyl (1R,3R,5R,6S)-6-((1R)-1-hydroxyethyl)-1-methyl-2-oxo-1-carbapenam-3-carboxylate in 300 ml of dry acetonitrile at −30° C. under an argon atmosphere. The mixture was stirred at that temperature for 30 min. Ethyl acetate (600 ml) was then added thereto. The mixture was washed with semi-saturated brine, a mixed solution (pH 1.1) composed of semi-saturated brine and a 1 N aqueous hydrochloric acid solution, a mixed solution (pH 8.9) composed of semi-saturated brine and a saturated aqueous sodium hydrogencarbonate solution, and semi-saturated brine in that order, was dried over anhydrous magnesium sulfate, and was then filtered. The solvent was removed by distillation under the reduced pressure. The residue was dissolved in 150 ml of dry N-methylpyrrolidinone. Tri-2-furylphosphine (163 mg), 1.54 g of zinc chloride, 163 mg of tris(dibenzylideneacetone)dipalladium (0), and 14.0 g of 7-methylthio-2-(tri-n-butylstannyl)imidazo[5,1-b]-thiazole were added to the solution. The mixture was stirred at 50° C. under an argon atmosphere for 1.5 hr. Ethyl acetate (400 ml) and 200 ml of semi-saturated aqueous sodium hydrogencarbonate solution were added to the reaction solution, and the mixture was stirred. The insolubles were removed by filtration. The organic layer of the filtrate was separated, was washed with 300 ml of semi-saturated brine three times, and was dried over anhydrous magnesium sulfate. The solvent was removed by distillation under the reduced pressure. The residue was purified by column chromatography on silica gel (dichloromethane:methanol=20:1) to prepare 14.0 g of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate.

NMR (CDCl$_3$) δ: 1.31 (3H, d, J=7.3 Hz), 1.40 (3H, d, J=6.3 Hz), 2.43 (3H, s), 3.35–3.40 (1H, m), 3.41–3.52 (1H, m), 4.30–4.42 (2H, m) 5.29 (1H, d, J=13.7 Hz), 5.53 (1H, d, J=13.7 Hz), 7.67 (2H, d, J=8.9 Hz), 8.02 (1H, s), 8.23 (2H, d, J=8.9 Hz), 8.29 (1H, S)

b) 4-Nitrobenzyl (1S,5R,6S)-6-((1R)-1-hydroxyethyl)-2-(7-methanesulfinylimidazo[5,1-b]thiazol-2-yl)-1-methyl-1-carbapen-2-em-3-carboxylate (a mixture of diastereomers)

A solution of 1.46 g of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate in 28 ml of THF and 28 ml of water was cooled in an ice-cold water bath. OXONE (manufactured by E.I. du Pont de Nemours & Co.) (1.75 g) was added to the cooled solution. The mixture was stirred at that temperature for 20 min. Dichloromethane (100 ml) and 100 ml of a dilute aqueous sodium hydrogencarbonate solution were then added thereto. The organic layer was separated, was washed with water and a saturated aqueous sodium chloride solution in that order, and was dried over anhydrous magnesium sulfate. The solvent was removed by distillation, and the residue was purified by column chromatography on silica gel (ethyl acetate containing 5 to 20% methanol) to prepare 0.75 g of 4-nitrobenzyl (1S,5R,6S)-6-((1R)-1-hydroxyethyl)-2-(7-methanesulfinylimidazo[5,1-b]thiazol-2-yl)-1-methyl-1-carbapen-2-em-3-carboxylate (a mixture of diastereomers).

NMR (CDCl$_3$) δ: 1.18 (3H, d, J=6.3 Hz), 1.22 (3H, d, J=7.1 Hz), 3.10, 3.12 (total 3H, s each), 3.40–3.45 (1H, m), 3.65–3.75 (1H, m), 3.90–4.05 (1H, m), 4.30–4.35 (1H, m), 7.73 (2H, d, J=8.8 Hz), 8.22 (2H, d, J=8.8 Hz), 8.40 (1H, s), 8.50 (1H, 8)

c) 4-Nitrobenzyl (1S,5R,6S)-6-((1R)-1-hydroxyethyl )-2-(7-methanesulfinyl-6-methylimidazo[5,1-b]thiazolium-2-yl)-1-methyl-1-carbapen-2-em-3-carboxylate trifluoromethanesulfonate (a mixture of diastereomers)

Methyl trifluoromethanesulfonate (0.07 ml) was added to a solution of 0.28 g of 4-nitrobenzyl (1S,5R,6S)-6-((1R)-1-hydroxyethyl)-2-(7-methanesulfinylimidazo[5,1-b]thiazol-2-yl)-1-methyl-1-carbapen-2-em-3-carboxylate (a mixture of diastereomers) in 5 ml of dichloromethane. The mixture was stirred at room temperature for 2 hr. The reaction mixture was concentrated to dryness to prepare 0.49 g of 4-nitrobenzyl (1S,5R,6S)-6-((1R)-1-hydroxyethyl)-2-(7-methanesulfinyl-6-methylimidazo[5,1-b]thiazolium-2-yl)-1-methyl-1-carbapen-2-em-3-carboxylate trifluoromethanesulfonate (a mixture of diastereomers).

NMR (CDCl$_3$) δ: 1.02, 1.19 (total 3H, d each, J=6.1 Hz), 1.07, 1.22 (total 3H, d each, J=7.4 Hz), 3.11, 3.15 (total 3H, s each), 3.45–3.50 (1H, m), 3.75–3.85 (1H, m), 4.00–4.15 (1H, m), 4.13 (3H, s), 4.35–4.45 (1H, m), 5.40–5.60 (2H, m), 7.75 (2H, d, J=8.8 Hz), 8.25 (2H, d, J=8.8 Hz), 8.78 (1H, s), 9.76 (1H, s)

d) (1S,5,R6s)-6-((1R)-1-Hydroxyethyl)-2-(7-methanesulfinyl-6-methylimidazo[5,1-b]thiazolium-2-yl)-1-methyl-1-carbapen-2-em-3-carboxylate (intramolecular salt (a mixture of diastereomers).

10% Pd—C (0.15 g) was added to a solution of 0.49 g of 4-nitrobenzyl (1S,5R,6S)-6-((1R)-1-hydroxyethyl)-2-(7-methanesulfinyl-6-methylimidazo[5,1-b]thiazolium-2-yl)-1-methyl-1-carbapen-2-em-3-carboxylate trifluoromethanesulfonate (a mixture of diastereomers) in 20 ml of a 0.1 N phosphate buffer (pH 6.8) and 20 ml of THF. The mixture was stirred in a hydrogen atmosphere for 1.5 hr. The 10% Pd—C was removed by filtration, and was washed with a mixed solvent composed of 5 ml of a 0.1 N phosphate buffer (pH 6.8) and 5 ml of THF. The mother liquid and the wash liquid were combined, and were washed with 25 ml of ethyl acetate. The aqueous layer was concentrated, and the residue was purified by column chromatography on Cosmosil 40C$_{18}$-PREP (15 to 20% aqueous methanol solution) to prepare 54 mg of the title compound.

NMR (D$_2$O) δ (HOD=4.80 ppm): 1.24–1.30 (3H, m), 1.32 (3H, d, J=6.3 Hz), 3.26, 3.30 (total 3H, s each), 3.58 (1H, dd, J$_1$=5.8 Hz, J$_2$=2.8 Hz), 3.63–3.73 (1H, m), 4.20, 4.22 (3H, s), 4.25–4.40 (2H, m), 8.27, 8.30 (1H, s)

Example 2

(1S,5R,6S)-6-((1R)-1-Hydroxyethyl)-1-methyl-2-(6-methyl-7-methylthioimidazo[5,1-b]thiazolium-2yl)-1-carbapen-2-em-3-carboxylate (intramolecular salt)

a) 4-Nitrobenzyl (1S,5R,6S)-6-((1R)-1-hydroxyethyl)-1-methyl-2-(6-methyl-7-methylthioimidazo[5,1-b]thiazolium-2-yl)-1-carbapen-2-em-3-carboxylate trifluoromethanesulfonate A solution of 0.1 g of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate in 2 ml of dichloromethane was cooled in an ice-cold water bath.

Methyl trifluoromethanesulfonate (0.022 ml) was added to the cooled solution. The mixture was stirred at that temperature for 30 min. The reaction mixture was concentrated to dryness to prepare 4-nitrobenzyl (1S,5R,6S)-6-((1R)-1-hydroxyethyl)-1-methyl-2-(6-methyl-7-methylthioimidazo[5,1-b]thiazolium-2-yl)-1-carbapen-2-em-3-carboxylate trifluoromethanesulfonate.

NMR (CDCl$_3$) δ: 1.33 (3H, d, J=7.0 Hz), 1.39 (3H, d, J=6.1 Hz), 2.42, (3H, s), 3.41 (1H, dd, J,=6.6 Hz, J$_2$=2.9 Hz), 3.78–3.87 (1H, m), 4.11 (3H, s), 4.24–4.31 (1H, m), 4.22 (1H, dd, J$_1$=9.5 Hz, J$_2$=2.8 Hz), 5.32 (1H, d, J=13.9 Hz), 5.54 (1H, d, J=13.9 Hz), 7.69 (2H, d, J=8.8 Hz), 8.24 (2H, d, J=8.8 Hz), 8.72 (1H, s), 9.81 (1H, s)

b) (1S,5R,6S)-6-((1R)-1-Hydroxyethyl)-1-methyl-2-(6-methyl-7-methylthioimidazo[5,1-b]thiazolium-2yl)-1-carbapen-2-em-3-carboxylate (intramolecular salt)

The procedure of Example 1d) was repeated, except that the whole quantity of 4-nitrobenzyl (1S,5R,6S)-6-((1R)-1-hydroxyethyl)-1-methyl-2-(6-methyl-7-methylthioimidazo[5,1-b]thiazolium-2-yl)-1-carbapen-2-em-3-carboxylate trifluoromethanesulfonate prepared in step a) was used as the starting compound. Thus, 44 mg of the title compound was prepared.

NMR (D$_2$O) δ (HOD=4.80 ppm): 1.26 (3H, d, J=7.2 Hz), 1.33 (3H, d, J=6.4 Hz), 2.40 (3H, s), 3.50–3.55 (1H, m), 3.60–3.70 (1H, m), 4.06 (3H, s), 4.25–4.35 (1H, m), 4.35–4.40 (1H, m), 8.13 (1H, s)

Example 3

(1R,5R,6S)-2-(6-Carbamoylmethyl-7-methylthioimidazo[5,1-b]thiazolium-2-yl)-6-((1R)-1-hydroxyethyl)-1-methyl-1-carbapen-2-em-3-carboxylate (intramolecular salt)

a) 4-Nitrobenzyl (1S,5R,6S)-2-(6-carbamoylmethyl-7-methylthioimidazo[5,1-b]thiazolium-2-yl)-6-((1R)-1-hydroxyethyl)-1-methyl-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (2.31 g) was dissolved in 30 ml of acetone. 2-Iodoacetamide (8.32 g) was added to the solution, and the mixture was stirred at room temperature for 2 days. The solvent was removed by distillation under the reduced pressure. The residue was purified by column chromatography on Sephadex LH-20 (chloroform:methanol=1:1) to prepare 2.805 g of 4-nitrobenzyl(1S,5R,6S)-2-(6-carbamoylmethyl-7-methylthioimidazo[5,1-b]thiazolium-2-yl)-6-((1R)-1-hydroxyethyl)-1-methyl-1-carbapen-2-em-3-carboxylate iodide.

NMR (DMSO-d$_6$) δ: 1.18 (3H, d, J=6.7 Hz), 1.25 (3H, d, J=7.1 Hz), 2.36 (3H, s), 3.51 (1H, dd, J$_1$=5.6 Hz, J$_2$=3.2 Hz), 3.65–3.8 (1H, m), 4.0–4.15 (1H, m), 4.40 (1H, dd, J$_1$=9.9 Hz, J$_2$=3.2 Hz), 5.21 (2H, s), 5.42 (1H, d, J=13.7 Hz), 5.55 (1H, d, J=13.7 Hz), 7.70 (1H, s), 7.75 (2H, d, J=8.5 Hz), 7.96 (1H, s), 8.24 (2H, d, J=8.5 Hz), 8.74 (1H, s), 9.73 (1H, s)

b) (1S,5R,6S)-2-(6-Carbamoylmethyl-7-methylthioimidazo[5,1-b]thiazolium-2-yl)-6-((1R)-1-hydroxyethyl)-1-methyl-1-carbapen-2-em-3-carboxylate (intramolecular salt)

4-Nitrobenzyl (1S,5R,6S)-2-(6-carbamoylmethyl-7-methylthioimidazo[5,1-b]thiazolium-2-yl)-6-((1R)-1-hydroxyethyl)-1-methyl-1-carbapen-2-em-3-carboxylate iodide (2.805 g) was dissolved in 130 ml of THF and 130 ml of a 1/15 M sodium phosphate buffer (pH 6.6). 10% Pd—C (3.0 g) was added to the solution. The air in the reaction vessel was replaced by hydrogen, and the contents of the reaction vessel were stirred at room temperature for 2 hr. The catalyst was removed by filtration on Celite, and washed with water. The filtrate was washed with ethyl acetate, and was then concentrated under the reduced pressure until the volume of the filtrate became about 10 ml. The residue was purified by column chromatography on Cosmosil 40C$_{18}$-PREP (a 20% aqueous methanol solution) to prepare 955 mg of the title compound.

NMR (D$_2$O) δ (HOD=4.80 ppm): 1.27 (3H, d, J=7.1 Hz), 1.32 (3H, d, J=6.3 Hz), 2.36 (3H, s), 3.57 (1H, dd, J$_1$=6.2 Hz, J$_2$=2.9 Hz), 3.6–3.7 (1H, m), 4.2–4.3 (1H, m), 4.36 (1H, dd, J$_1$=9.6 Hz, J$_2$=2.9 Hz), 5.33 (2H, s), 8.19 (1H, s)

Example 4

1S,5R,6S)-2-(6-Carbamoylmethyl-7-carbamoylmethylthioimidazo[5,1-b]-thiazolium-2-yl)-6-((1R)-1-hydroxyethyl)-1-methyl-1-carbapen-2-em-3-carboxylate a) 4-Nitrobenzyl(1S,5R,6S)-2-6-carbamoylmethyl-7-carbamoylmethylthioimidazo[5,1-b]thiazolium-2-yl)-6-((1R)-1-hydroxyethyl)-1-methyl-1-carbapen-2-em-3-carboxylate iodide A fraction was collected which had been eluted as the latter fraction in the column chromatography on Sephadex LH-20 in Example 3a) to obtain 283 mg of 4-nitrobenzyl (1S,5R,6S)-2-(6-carbamoylmethyl-7-carbamoylmethylthioimidazo[5,1-b]thiazolium-2-yl)-6-((1R)-1-hydroxyethyl)-1-methyl-1-carbapen-2-em-3-carboxylate iodide.

NMR (DMSO-d$_6$) δ: 1.18 (3H, d, J=6.5 Hz), 1.25 (3H, d, J=6.9 Hz), 3.35–3.53 (1H, m), 3.48 (2H, s), 3.70–3.80 (1H, m), 4.00–4.10 (1H, m), 4.36–4.44 (1H, m), 5.27 (2H, s), 5.42 (1H, d, J=13.5 Hz), 5.55 (1H, d, J=13.5 Hz), 7.19 (1H, br s), 7.53 (1H, br s), 7.65 (1H, br s), 7.75 (2H, d, J=8.7 Hz), 7.98 (1H, br s), 8.24 (2H, d, J=8.7 Hz), 8.72 (1H, s), 9.73 (1H, s)

b) (1S,5R,6S )-2-(6-Carbamoylmethyl-7-carbamoylmethylthioimidazo[5,1-b]thiazolium-2-yl)-6-((1R)-1-hydroxyethyl)-1-methyl-1-carbapen-2-em-3-carboxylate (intramolecular salt)

The procedure of Example 3b) was repeated, except that 283 mg of 4-nitrobenzyl (1S,5R,6S)-2-(6-carbamoylmethyl-7-carbamoylmethylthioimidazo[5,1-b]thiazolium-2-yl)-6-((1R)-1-hydroxyethyl)-1-methyl-1-carbapen-2-em-3-carboxylate iodide was used as the starting compound. Thus, 149 mg of the title compound was prepared.

NMR (D$_2$O) δ (HOD=4.80 ppm): 1.27 (3H, d, J=7.1 Hz), 1.32 (3H, d, J=6.4 Hz), 3.50 (2H, s), 3.57 (1H, dd, J$_1$=6.0 Hz, J$_2$=2.8 Hz), 3.61–3.73 (1H, m), 4.23–4.33 (1H, m), 4.36 (1H, dd, J$_1$=9.3 Hz, J$_2$=2.8 Hz), 5.36 (2H, s), 8.20 (1H, s)

Example 5

(5R,6S)-6-((1R)-1-Hydroxyethyl)-2-(6-methyl-7-methylthioimidazo[5,1-b]thiazolium-2-yl)-1-carbapen-2-em-3-carboxylate (intramolecular salt)

a) 4-Nitrobenzyl (5R,6S)-6-((1R)-1-hydroxyethyl)-2-(6-methyl-7-methylthioimidazo[5,1-b]thiazolium-2-yl)-1-carbapen-2-em-3-carboxylate trifluoromethanesulfonate 4-Nitrobenzyl (5R,6S)-6-((1R)-1-hydroxyethyl)-2-(7-methylthioimidazo[5,1-b]thiazol-2-yl)-1-carpen-2-em-3-carboxylate (322 mg) was dissolved in 5 ml of dichloromethane. Methyl trifluoromethanesulfonate (0.073 ml) was added to the solution. The mixture was stirred at room temperature for 30 min. The reaction solution was added dropwise to 30 ml of hexane. The precipitated solid was collected by filtration to prepare 417 mg of 4-nitrobenzyl (5R,6S)-6-((1R)-1-hydroxyethyl)-2-(6-methyl-7-methylthioimidazo[5,1-b]thiazolium-2-yl)-1-carbapen-2-em-3-carboxylate trifluoromethanesulfonate.

NMR (DMSO-d$_6$) δ: 1.16 (3H, d, J=6.4 Hz), 2.42 (3H, s), 3.39–3.54 (2H, m), 3.57–3.60 (1H, m), 4.00–4.03 (4H, m), 4.28–4.32 (1H, m), 5.18 (1H, d, J=4.9 Hz), 5.44 (1H, d, J=13.7 Hz), 5.57 (1H, d, J=13.7 Hz), 7.76 (2H, d, J=8.5 Hz), 8.25 (2H, d, J=8.5 Hz), 8.63 (1H, s), 9.71 (1H, s)

b) (5R,6S)-6-((1R)-1-Hydroxymethyl)-2-(6-methyl-7-methylthioimidazo[5,1-b]thiazolium-2-yl)-1-carbapen-2-em-3-carboxylate (intramolecular salt)

4-Nitrobenzyl (5R,6S)-2-(6-methyl-7-methylthioimidazo[5,1-b]thiazolium-2-yl)-6-((1R)-1-hydroxyethyl)-1-carbapen-2-em-3-carboxylate trifluoromethanesulfonate (417 mg) was dissolved in 18 ml of THF and 18 ml of a 1/15 M sodium phosphate buffer (pH 6.6). 10% Pd—C (312 mg) was added to the solution. The air in the reaction vessel was replaced by hydrogen, and the contents of the reaction vessel were stirred at room temperature for 2 hr. The catalyst was removed by filtration on Celite, and washed with water. The filtrate was washed with ethyl acetate, and was then concentrated under the reduced pressure until the volume of the filtrate was brought to about 10 ml. The residue was purified by column chromatography on Cosmosil 40C$_{18}$-PREP (a 20% aqueous methanol solution) to prepare 130 mg of the title compound.

NMR (D$_2$O) δ (HOD=4.65 ppm): 1.17 (3H, d, J=6.3 Hz), 2.25 (3H, s), 3.15–3.29 (2H, m), 3.41 (1H, dd, J$_1$=5.9 Hz, J$_2$=2.9 Hz), 3.91 (3H, s), 4.09–4.21 (2H, m), 7.83 (1H, s)

Example 6

(5R,6S)-6-((1R)-1-Hydroxyethyl)-2-(7-methanesulfinyl-6-methylimidazo[5,1-b]thiazolium-2-yl)-1-carbapen-2-em-3-carboxylate (intramolecular salt)

a) 4-Nitrobenzyl (5R,6S)-6-C((1R)-1-hydroxyethyl)-2-(7-methanesulfinyl-6-methylimidazo[5,1-b]thiazolium-2-yl)-1-carbapen-2-em-3-carboxylate trifluoromethane sulfonate 4-Nitrobenzyl (5R,6S)-6-((1R)-1-hydroxyethyl)-2-(6-methyl-7-methylthioimidazo[5,1-b]thiazolium-2-yl)-1-carbapen-2-em-3-carboxylate trifluoromethanesulfonate (104 mg) was dissolved in 10 ml of dichloromethane. 3-Chloroperbenzoic acid (67 mg) was added to the solution, and the mixture was stirred at room temperature for 30 min. Methanol (10 ml) was added to the reaction solution, and the mixture was purified by column chromatography on Sephadex LH-20 (chloroform:methanol=1:1) to prepare 93 mg of 4-nitrobenzyl (5R,6S)-6-((1R)-1-hydroxyethyl)-2-(7-methanesulfinyl-6-methylimidazo[5,1-b]thiazolium-2-yl)-1-carbapen-2-em-3-carboxylate trifluoromethanesulfonate.

NMR (DMSO-d$_6$) δ: 1.16 (3H, d, J=6.3 Hz), 3.13 (3H, s), 3.41–3.61 (3H, m), 4.01–4.09 (4H, m), 4.28–4.35 (1H, m), 5.45 (1H, d, J=13.7 Hz), 5.57 (1H, d, J=13.7 Hz), 7.76 (2H, d, J=8.5 Hz), 8.25 (2H, d, J=8.5 Hz), 8.69 (1H, s), 9.75 (1H, s)

b) (5R,6S)-6-((1R)-1-Hydroxyethyl)-2-(7-methanesulfinyl-6-methylimidazo[5,1-b]thiazolium-2-yl)-1-carbapen-2-em-3-carboxylate (intramolecular salt)

The procedure of Example 5b) was repeated, except that 93 mg of 4-nitrobenzyl (5R,6S)-6-((1R)-1-hydroxyethyl)-2-(7-methanesulfinyl-6-methylimidazo[5,1-b]-thiazolium-2-yl)-1-carbapen-2-em-3-carboxylate trifluoromethanesulfonate was used as the starting compound. Thus, 37 mg of the title compound was prepared.

NMR (D$_2$O) δ (HOD=4.65 ppm): 1.18 (3H, d, J=6.3 Hz), 3.17 (3H, s), 3.20–3.33 (2H, m), 3.43–3.46 (1H, m), 4.08 (3H, s), 4.11–4.23 (21H, m), 8.00 (1H, s)

Example 7

(5R,6S)-2-(5,6-Dimethyl-7-methylthioimidazo[5,1-b]thiazolium-2-yl)-6-((1R)-1-hydroxyethyl)-1-carbapen-2-em-3-carboxylate (intramolecular salt)

a) 4-Nitrobenzyl (5R,6S )-2-(5,6-dimethyl-7-methylthioimidazo[5,1-b]thiazolium-2-yl)-6-((1R)-1-hydroxyethyl)-1-carbapen-2-em-3-carboxylate trifluoromethanesulfonate 4-Nitrobenzyl (5R,6S)-6-((1R)-1-hydroxyethyl)-2-(5-methyl-7-methylthioimidazo[5,1-b]thiazol-2-yl)-1-carbapen-2-em-3-carboxylate (102 mg) was dissolved in 2 ml of dichloromethane. Methyl trifluoromethanesulfonate (0.024 ml) was added to the solution. The mixture was stirred at room temperature for 15 min. The precipitated solid was collected by filtration to prepare 92 mg of 4-nitrobenzyl (5R,6S)-2-(5,6-dimethyl-7-methylthioimidazo[5,1-b]thiazolium-2-yl)-6-((1R)-1-hydroxyethyl)-1-carbapen-2-em-3-carboxylate trifluoromethanesulfonate.

NMR (DMSO-d$_6$) δ: 1.17 (3H, d, J=6.4 Hz), 2.39 (3H, s), 2.88 (3H, s), 3.43–3.55 (2H, m), 3.61 (1H, dd, J$_1$=5.6 Hz, J$_2$=3.2 Hz), 3.90 (3H, s), 4.00–4.08 (1H, m), 4.30–4.37 (1H, m), 5.45 (1H, d, J=13.7 Hz), 5.57 (1H, d, J=13.7 Hz), 7.77 (2H, d, J=8.5 Hz), 8.26 (2H, d, J=8.5 Hz), 8.68 (1H, s)

b) (5R,6S)-2-(5,6-Dimethyl-7-methylthioimidazo[5,1-b]thiazolium-2-yl)-6-((1R)-1-hydroxyethyl)-1-carbapen-2-em-3-carboxylate (intramolecular salt)

The procedure of Example 5b) was repeated, except that 92 mg of 4-nitrobenzyl (5R,6S)-2-(5,6-dimethyl-7-methylthioimidazo[5,1-b]thiazolium-2-yl)-6-((1R)-1-hydroxyethyl)-1-carbapen-2-em-3-carboxylate trifluoromethanesulfonate was used as the starting compound. Thus, 38 mg of the title compound was prepared.

NMR (D$_2$O) δ(HOD=4.65 ppm): 1.18 (3H, d, J=6.6 Hz), 2.22 (3H, s), 2.70 (3H, s), 3.16–3.30 (2H, m), 3.42 (1H, dd, J$_1$=5.6 Hz, J$_2$=2.9 Hz), 3.79 (3H, s), 4.10–4.21 (2H, m), 7.78 (1H, s)

Example 8

(5R,6S)-2-[6-(3-Aminopropyl)-5-methyl-7-methylthioimidazo[5,1-b]thiazolium-2-yl]-6-((1R)-1-hydroxyethyl)-1-carbapen-2-em-3-carboxylate (intramolecular salt)

a) 4-Nitrobenzyl (5R,6S)-6-((1R)-1-hydroxyethyl)-2-[5-Methyl-7-methylthio-6-[3-(4-nitrobenzyloxycarbonyl)aminopropyl]imadazo[5,1-b]thiazolium-2-yl]-1-carbapen-2-em-3-carboxylate trifluoromethanesulfonate The procedure of Example 32b) was repeated, except that 198 mg of 4-nitrobenzyl (5R,6S)-6-((1R)-1-hydroxyethyl)-2-(5-methyl-7-methylthioimidazo[5,1-b]thiazol-2-yl)-1-carbapen-2-em-3-carboxylate was used as the starting compound. Thus, 111 mg of 4-nitrobenzyl (5R,6S)-6-((1R)-1-hydroxyethyl)-2-[5-methyl-7-methylthio-6-[3-(4-nitrobenzyloxycarbonyl)aminopropyl]imidazo[5,1-b]thiazolium-2-yl]-1-carbapen-2-em-3-carboxylate trifluoromethanesulfonate was prepared as a crude product.

b) (5R,6S)-2-[6-(3-Aminopropyl)-5-methyl-7-methylthioimidazo[5,1-b]thiazolium-2-yl]-6-((1R)-1-hydroxyethyl)-1-carbapen-2-em-3-carboxylate (intramolecular salt)

The procedure of Example 5b) was repeated, except that 111 mg of 4-nitrobenzyl (5R,6S)-6-((1R)-1-hydroxyethyl)-2-[5-methyl-7-methylthio-6-[3-(4-nitrobenzyloxycarbonyl)aminopropyl]imidazo[5,1-b]thiazolium-2-yl]-1-carbapen-2-em-3-carboxylate trifluoromethanesulfonate as the crude product was used as the starting compound. Thus, 2 mg of the title compound was prepared.

NMR (D$_2$O) δ (HOD=4.65 ppm): 1.17 (3H, d, J=6.3 Hz), 2.05–2.12 (2H, m), 2.26 (3H, s), 2.73 (3H, s), 3.02 (2H, t, J=8.3 Hz), 3.13–3.27 (2H, m), 3.40–3.44 (1H, m), 4.09–4.21 (2H, m), 4.31–4.38 (2H, m), 7.78 (1H, s)

Example 9

(1S,5R,6S)-6-((1R)-1-Hydroxyethyl)-2-(7-methanesulfonyl-6-methylimidazo[5,1-b]thiazolium-2-yl)-1-methyl-1-carbapen-3-carboxylate (intramolecular salt)

a) 4-Nitrobenzyl (1S,5R,6S)-6-((1R)-1-hydroxyethyl)-2-(7-methanesulfonyl-6-methylimidazo[5,1-b]thiazolium-2-yl)-1-methyl-1-carbapen-2-em-3-carboxylate trifluoromethanesulfonate 4-Nitrobenzyl (1S,5R,6S)-6-((1R)-1-hydroxyethyl)-2-(6-methyl-7-methylthioimidazo[-5,1-b]thiazolium-2-yl)-1-methyl-1-carbapen-2-em-3-carboxylate (112 mg) was dissolved in 2 ml of THF and 2 ml of water. OXONE (manufactured by E.I. du Pont de Nemours & Co.) (208 mg) was added to the solution. The mixture was stirred at room temperature for 4 hr. The reaction solution was extracted with 20 ml of dichloromethane five times. The solvent was then removed by distillation under the reduced pressure to prepare 63 mg of (1S,5R,6S)-6-((1R)-1-hydroxyethyl)-2-(7-4-nitrobenzylmethanesulfonyl-6-methylimidazo[5,1-b]thiazolium-2-yl)-1-methyl-1-carbapen-2-em-3-carboxylate trifluoromethanesulfonate as a crude product.

b) (1S,5R,6S)-6-((1R)-1-Hydroxyethyl)-2-(7-methanesulfonyl-6-methylimidazo[5,1-b]thiazolium-2-yl)-1-methyl-1-carbapen-2-em-3-carboxylate (intramolecular salt)

The procedure of Example 5b) was repeated, except that 63 mg of 4-nitrobenzyl (1S,5R,6S)-6-((1R)-1-hydroxyethyl)-2-(7-methanesulfonyl-6-methylimidazo[5,1-b]thiazolium-2-yl)-1-methyl-1-carbapen-2-em-3-carboxylate trifluoromethanesulfonate as the crude product was used as the starting compound. Thus, 10 mg of the title compound was prepared.

NMR (D$_2$O) δ (HOD=4.65 ppm): 1.11 (3H, d, J=7.4 Hz), 1.19 (3H, d, J=6.6 Hz), 3.38 (3H, s), 3.43 (1H, dd, J$_1$=6.1 Hz, J$_2$=2.7 Hz), 3.49–3.57 (1H, m), 4.11–4.17 (4H, m), 4.21 (1H, dd, J$_1$=9.5 Hz, J$_2$=2.7 Hz), 8.14 (1H, s)

Example 10

(1S,5R,6S)-2-(5,6-Dimethyl-7-methylthioimidazo[5,1-b]thiazolium-2-yl)-6-((1R)-1-hydroxyethyl)-1-methyl-1-carbapen-2-em-3-carboxylate (intramolecular salt)

a) 4-Nitrobenzyl (1S,5R,6S)-2-(5,6-dimethyl-7-methylthioimidazo[5,1-b]thiazolium-2-yl)-6-((1R)-1-hydroxyethyl)-1-methyl-1-carbapen-2em-3-carboxylate trifluoromethanesulfonate 4-Nitrobenzyl (1S,5R,6S)-6-((1R)-1-hydroxyethyl)-1-methyl-2-(5-methyl-7-methylthioimidazo[5,1-b]thiazol-2-yl)-1-carbapen-2-em-3-carboxylate (91 mg) was dissolved in 2 ml of dichloromethane. Methyl trifluoromethanesulfonate (0.020 ml) was added to the solution. The mixture was stirred at room temperature for 10 min. The solvent was removed by distillation under the reduced pressure. Thus, 121 mg of 4-nitrobenzyl (1S,5R,6S)-2-(5,6-dimethyl-7-methylthioimidazo[5,1-b]thiazolium-2-yl)-6-((1R)-1-hydroxyethyl)- 1-methyl-1-carbapen-2-em-3-carboxylate trifluoromethanesulfonate as a crude product was prepared.

b) (1S,5R,6S)-2-(5,6-Dimethyl-7-methylthioimidazo[5,1-b]thiazolium-2-yl)-6-((1R)-1-hydroxyethyl)-1-methyl-1-carbapen-2-em-3-carboxylate (intramolecular salt)

The procedure of Example 5b) was repeated, except that 121 mg of 4-nitrobenzyl (1S,5R,6S)-2-(5,6-dimethyl-7-methylthioimidazo[5,1-b]thiazolium-2-yl)-6-((1R)-1-hydroxyethyl)-1-methyl-1-carbapen-2-em-3-carboxylate trifluoromethanesulfonate as the crude product was used as the starting compound. Thus, 20 mg of the title compound was prepared.

NMR (D$_2$O) δ (HOD=4.65 ppm): 1.12 (3H, d, J=7.0 Hz), 1.17 (3H, d, J=6.3 Hz), 2.21 (3H, s), 2.70 (3H, s), 3.41 (1H, dd, J$_1$=6.1 Hz, J$_2$=2.9 Hz), 3.47–3.55 (1H, m), 3.80 (3H, s), 4.11–4.17 (1H, m), 4.20 (1H, dd, J$_1$=9.2 Hz, J$_2$=2.7 Hz), 7.91 (1H, s)

Example 11

(1S,5R,6S)-2-[6-(2-Ethoxycarbonyl)ethyl-7-methylthioimidazo[5,1-b]thiazolium-2-yl]-6-((1R)-1-hydroxyethyl)-1-methyl-1-carbapen-2-em-3-carboxylate (intramolecular salt)

The procedure of Example 82a) was repeated, except that 104 mg of 4-nitrobenzyl (1S,5R,6S)-6-((1R)-1-hydroxyethyl)-1-methyl-2-(7-methylthioimidazo[5,1-b]-thiazol-2-yl)-1-carbapen-2-em-3-carboxylate, 315 mg of ethyl 3-bromopropionate, and 150 mg of sodium iodide were used as the starting compounds. Thus a quaternary salt (30 mg) as a crude product was prepared. The procedure of Example 82b) was repeated, except that 30 mg of this quaternary salt as the crude product was used as the starting compound and THF-1/15 M sodium phosphate buffer (pH 6.8) (1:1) was used as the solvent for the reaction. Thus, 13 mg of the title compound was prepared.

NMR (DMSO-d$_6$) δ: 1.12–1.19 (6H, m), 2.42 (3H, s), 3.03 (2H, t, J=6.8 Hz), 3.15 (1H, dd, J$_2$=6.7 Hz, J$_2$=2.7 Hz), 3.44 (1H, m), 3.91 (1H, m), 4.05–4.10 (3H, m), 4.60 (2H, t, J=6.6 Hz), 5.06 (1H, d, J=5.1 Hz), 8.31 (1H, s), 9.54 (1H, s); MS (m/z) 480 (M+H)$^+$

Example 12

(1S,5R,6S)-6-((1R)-1-Hydroxyethyl)-2-[7-(2-hydroxyethyl)thio-6-methylimidazo[5,1-b]thiazolium-2-yl]-1-methyl-1-carbapen-2-em-3-carboxylate (intramolecular salt)

a) 4-Nitrobenzyl (1S,5R,6S)-2-[7-2-t-butyldimethylsilyloxyethyl)thioimidazo[5,1-b]thiazol-2-yl]-6-((1R)-1-hydroxyethyl)-1-methyl-1-carbapen-2-em-3-carboxylate The procedure of Example 1a) was repeated, except that 791 mg of 4-nitrobenzyl (1R,3R,5R,6S)-6-((1R)-1-hydroxyethyl)-1-methyl-2-oxo-1-carbapenam-3-carboxylate and 1.433 g of 7-(2-t-butyldimethylsilyloxyethyl)thio-2-(tri-n-butylstannyl)imidazo[5,1-b]thiazole were used as the starting compounds. Thus, 573 mg of 4-nitrobenzyl (1S,5R,6S)-2-[7-(2-t-butyldimethylsilyloxyethyl)thioimidazo[5,1-b]thiazol-2-yl]-6-((1R)-1-hydroxyethyl)-1-methyl-1-carbapen-2-em-3-carboxylate was prepared.

NMR (CDCl$_3$) δ: 0.02 (6H, s), 0.86 (9H, s), 1.31 (3H, d, J=7.3 Hz), 1.40 (3H, d, J=6.3 Hz), 2.9–3.0 (2H, m), 3.37 (1H, dd, J$_1$=6.6 Hz, J$_2$=2.8 Hz), 3.4–3.5 (1H, m), 3.75–3.85 (2H, m), 4.25–4.35 (1H, m), 4.38 (1H, dd, J$_1$=9.6 Hz, J$_2$=2.8 Hz), 5.28 (1H, d, J=13.7 Hz), 5.53 (1H, d, J=13.7 Hz), 7.68 (2H, d, J=8.9 Hz), 8.00 (1H, s), 8.25 (2H, d, J=8.9 Hz), 8.32 (1H, s)

b) 4-Nitrobenzyl (1S,5R,6S)-6-((1R)-1-hydroxyethyl)-2-[7(-2-hydroxyethyl)thioimidazo[5,1-b]thiazol-2-yl]-1-methyl-1-carbapen-2-em-3-carboxylate Acetic acid (0.207 ml) and 1.21 ml of a 1 M tetra-n-butylammonium fluoride/THF solution were added to a solution of 265 mg of 4-nitrobenzyl (1S,5R,6S)-2-[7-(2-t-butyldimethylsilyloxyethyl)thioimidazo[5,1-b]-thiazol-2-yl]-6-((1R)-1-hydroxyethyl)-1-methyl-1-carbapen-2-em-3-carboxylate in 5 ml of THF. The mixture was stirred at room temperature for 6 hr. Brine was added to the reaction solution. The mixture was adjusted to pH 8.2 by the addition of a saturated sodium hydrogencarbonate solution, and was extracted with ethyl acetate twice. The organic layers were combined, were washed with brine, and were dried over anhydrous magnesium sulfate. The solvent was then removed by distillation under the reduced pressure. The residue was purified by column chromatography on silica gel (dichloromethane:methanol=20:1) to prepare 208 mg of 4-nitrobenzyl (1S,5R,6S)-6-((1R)-1-hydroxyethyl)-2-[7-(2-hydroxyethyl)thioimidazo[5,1-b]thiazol-2-yl]-1-methyl-1-carbapen-2-em-3-carboxylate.

NMR (CDCl$_3$) δ: 1.31 (3H, d, J=7.4 Hz), 1.40 (3H, d, J=6.3 Hz), 2.9–3.0 (2H, m), 3.37 (1H, dd, J$_1$=6.4 Hz, J$_2$=2.7 Hz), 3.4–3.5 (1H, m), 3.8–3.9 (2H, m), 4.0 (1H, br s), 4.3–4.4 (1H, m), 4.38 (1H, dd, J$_1$=9.7 Hz, J$_2$=2.7 Hz), 5.28 (1H, d, J=13.7 Hz), 5.53 (1H, d, J=13.7 Hz), 7.68 (2H, d, J=8.4 Hz), 8.02 (1H, s), 8.25 (2H, d, J=8.4 Hz), 8.29 (1H, 8)

c) 4-Nitrobenzyl (1S,5R,6S)-6-((1R)-1-hydroxyethyl)-2-[7-(2-hydroxyethyl)thio-6-methylimidazo[5,1-b]-thiazolium-2-yl]-1-methyl-1-carbapen-2-em-3-carboxylate iodide 4-Nitrobenzyl (1S,5R,6S)-6-((1R)-1-hydroxyethyl)-2-[7-(2-hydroxyethyl)thioimidazo[5,1-b]thiazol-2-yl]-1-methyl-1-carbapen-2-em-3-carboxylate (64.4 mg) was dissolved in 2 ml of dichloromethane. Methyl iodide (4 ml) was added to the solution, and the mixture was stirred from temperature for 16 hr. The solvent was removed by distillation under the reduced pressure to prepare 4-nitrobenzyl (1S,5R,6S)-6-((1R)-1-hydroxyethyl)-2-[7-(2-hydroxyethyl)thio-6-methylimidazo[5,1-b]thiazolium-2-yl]-1-methyl-1-carbapen-2-em-3-carboxylate iodide.

NMR (CD$_3$OD) δ: 1.33 (3H, d, J=6.2 Hz), 1.34 (3H, d, J=7.2 Hz), 2.95–3.05 (2H, m), 3.50 (1H, dd, J$_1$=6.4 Hz, J$_2$=3.0 Hz), 3.69–3.76 (2H, m), 3.75–3.84 (1H, m), 4.14 (3H, s), 4.15–4.23 (1H, m), 4.43 (1H, dd, J$_2$=9.7 Hz, J$_2$=3.0 Hz), 5.37 (1H, d, J=13.7 Hz), 5.54 (1H, d, J=13.7 Hz), 7.74 (2H, d, J=8.8 Hz), 8.21 (2H, d, J=8.8 Hz), 8.26 (1H, s)

d) (1S,5R,6S)-6-((1R)-1-Hydroxyethyl)-2-[7-(2-hydroxyethyl)thio-6methylimidazo[5,1-b]thiazolium-2-yl]-1-methyl-1-carbapen-2-em-3-carboxylate (intramolecular salt)

The procedure of Example 3b) was repeated, except that the whole quantity of 4-nitrobenzyl (1S,5R,6S)-6-((1R)-1-hydroxyethyl)-2-[7-(2-hydroxyethyl)thio-6-methylimidazo[5,1-b]thiazolium-2-yl]-1-methyl-1-carbapen-2-em-3-carboxylate iodide prepared in step c) was used as the starting compound. Thus, 27.4 mg of the title compound was prepared.

NMR (D$_2$O) δ (HOD=4.80 ppm): 1.24 (3H, d, J=7.1 Hz), 1.31 (3H, d, J=6.3 Hz), 2.93–3.03 (2H, m), 3.54 (1H, dd, J$_1$=5.8 Hz, J$_2$=2.6 Hz), 3.58–3.72 (3H, m), 4.07 (3H, s), 4.23–4.36 (2H, m), 8.12 (1H, s)

Example 13

(1S,5R,6S)-2-(7-Acetyl-6-methylimidazo[5,1-b]thiazolium-2-yl)-6-((1R)-1-hydroxyethyl)-1-methyl-1-carbapen-2-em-3-carboxylate (intramolecular salt)

a) 4-Nitrobenzyl (1S,5R,6S)-2-(7-acetylimidazo[5,1-b]thiazol-2-yl)-6-((1R)-1-hydroxyethyl)-1-methyl-1-carbapen-2-em-3-carboxylate The procedure of Example 1a) was repeated, except that 5.80 g of 4-nitrobenzyl (1R,3R,5R,6S)-6-((1R)-1-hydroxyethyl)-1-methyl-2-oxo-1-carbapenam-3-carboxylate and 8.80 g of 7 acetyl-2-(tri-n-butylstannyl) imidazo[5,1-b]thiazole were used as the starting compounds. Thus, 5.93 g of 4-nitrobenzyl (1S,5R,6S)-2-(7-acetylimidazo[5,1-b]thiazol-2-yl)-6-((1R)-1-hydroxyethyl)-1-methyl-1-carbapen-2-em-3-carboxylate was prepared.

NMR (CDCl$_3$) δ: 1.31 (3H, d, J=7.4 Hz), 1.40 (3H, d, J=6.2 Hz), 2.61 (3H, s), 3.40 (1H, dd, J$_1$=6.6 Hz, J$_2$=2.9 Hz), 3.52 (1H, m), 4.32 (1H, m), 4.42 (1H, dd, J$_1$=9.7 Hz, J$_2$=2.9 Hz), 5.27 (1H, d, J=13.5 Hz), 5.52 (1H, d, J=13.5 Hz), 7.67 (2H, d, J=8.5 Hz), 8.01 (1H, s), 8.22 (2H, d, J=8.5 Hz), 8.50 (1H, s)

b) 4-Nitrobenzyl (1S,5R,6S)-2-(7-acetyl-6-methylimidazo[5,1-b]thiazolium-2-yl )-6-((1R)-1-hydroxyethyl 1-methyl-1-carbapen-2-em-1-carboxylate hydrogencarbonate 4-Nitrobenzyl (1S,5R,6S)-2-(7-acetylimidazo[5,1-b] thiazol-2-yl)-6-((1R)-1-hydroxyethyl)-1-methyl-1-carbapen-2-em-3-carboxylate (46.6 mg) was dissolved in 4 ml of dichloromethane. Methyl trifluoromethanesulfonate (0.036 ml) was added thereto, and the mixture was stirred at room temperature for 1.5 hr. The reaction solution was adjusted to pH 9.6 by the addition of water and an aqueous sodium hydrogencarbonate solution, and was then extracted with dichloromethane twice. The organic layer was dried over anhydrous magnesium sulfate. The solvent was then removed by distillation under the reduced pressure to prepare 4-nitrobenzyl (1S,5R,6S)-2-(7-acetyl-6methylimidazo [5,1-b]thiazolium-2-yl)-6-((1R)-1-hydroxyethyl)-1-methyl-1-carbapen-2-em-3-carboxylate hydrogencarbonate.

NMR (CD$_3$OD) δ: 1.30–1.38 (6H, m), 2.62 (3H, s), 3.51 (1H, dd, J$_1$=6.3 Hz, J$_2$=2.8 Hz), 3.75–3.87 (1H, m), 4.12–4.23 (1H, m), 4.32 (3H, s), 4.44 (1H, dd, J$_1$=9.8 Hz, J$_2$=2.8 Hz), 5.38 (1H, d, J=13.7 Hz), 5.56 (1H, d, J=13.7 Hz), 7.75 (2H, d, J=8.5 Hz), 8.22 (2H, d, J=8.5 Hz), 8.68 (1H, s), 9.58 (1H, s)

c) (1S,5R,6S)-2-(7-Acetyl-6-methylimidazo[5,1-b]-thiazolium-2-yl)-6-((1R)-1-hydroxyethyl)-1-methyl-1-carbapen-2-em-3-carboxylate (intramolecular salt)

The procedure of Example 3b) was repeated, except that the whole quantity of 4-nitrobenzyl (1S,5R,6S)-2-(7-acetyl-6-methylimidazo[5,1-b]thiazolium-2-yl)-6-((1R)-1-hydroxyethyl)-1-methyl-1-carbapen-2-em-3-carboxylate hydrogencarbonate prepared in step b) was used as the starting compound. Thus, 14.5 mg of the title compound was prepared.

NMR (D$_2$O) δ (HOD=4.80 ppm): 1.27 (3H, d, J=7.1 Hz), 1.32 (3H, d, J=6.1 Hz), 2.61 (3H, s), 3.53–3.60 (1H, m), 3.61–3.77 (1H, m), 4.28 (3H, s), 4.28–4.38 (2H, m), 8.31 (1H, s)

Example 14

(1S,5R,6S)-2-[6-(3-Aminopropyl)-7-methylthiomidazo[5,1-b]thiazolium-2-yl]-6-((1R)-1-hydroxyethyl)-1-methyl-1-carbapen-2-em-3-carboxylate (intramolecular salt) hydrochloride a) 4-Nitrobenzyl (1S,5R,6S)-2-[6-(3-azidopropyl)-7-methylthioimidazo[5,1-b]thiazolium-2-yl]-6-((1R)-1-hydroxyethyl)-1-methyl-1-carbapen-2-em-3-carboxylate chloride 3-Azidopropanol (1.21 g) was dissolved in 36 ml of dichloromethane. 2,6-Lutidine (1.54 ml) was added to the solution. Trifluoromethanesulfonic anhydride (2.12 ml) was added dropwise thereto at −60° C. The mixture was allowed to react at that temperature for 30 min. The reaction solution was diluted with 100 ml of dichloromethane. The diluted solution was washed with 15% brine, 15% brine+a 1 N aqueous hydrochloric acid solution, and 15% brine in that order, and was dried over anhydrous magnesium sulfate. The solvent was then removed by concentration under the reduced pressure until the volume of the solution is approximately halved. Thus, a solution of 3-azidopropyl trifluoromethanesulfonate in dichloromethane was prepared. 4-Nitrobenzyl (1S,5R,6S)-6-((1R)-1-hydroxyethyl)-1-methyl-2-(7-methylthioimidazo-[5,1-b]thiazol-2-yl)-1-carbapen-2em-3-carboxylate (5.14 g) was added to this solution under cooling in ice. A reaction was allowed to proceed at 10° C. for 6.5 hr. The solvent was removed by distillation under the reduced pressure. The residue was washed with ether, and was dissolved in a minor amount of ethyl acetate. The solution was added dropwise to 100 ml of diisopropyl ether. The resultant precipitate was collected by filtration, and was dried to prepare 6.78 g of 4-nitrobenzyl (1S,5R,6S)-2-[6-(3-azidopropyl)-7-methylthioimidazo[5,1-b]thiazolium-2-yl]-6-((1R)-1-hydroxyethyl)-1-methyl-1-carbapen-2-em-3-carboxylate trifluoromethanesulfonate. A part (1.05 g) of this product was dissolved in 30 ml of methanol. The solution was subjected to column chromatography (methanol) on Amberlyst A-26 as an ion-exchange resin (chloro form) to prepare 940 mg of 4-nitrobenzyl (1S,5R,6S)-2-[6-(3-azidopropyl)-7-methylthioimidazo[5,1-b]thiazolium-2-yl]-6-((1R)-1-hydroxyethyl)-1-methyl-1-carbapen-2-em-3-carboxylate chloride.

NMR (CDCl$_3$) δ: 1.34 (3H, d, J=7.1 Hz), 1.38 (3H, d, J=6.1 Hz), 2.28 (2H, t, J=6.5 Hz), 2.39 (3H, s), 3.35 (1H, dd, J$_1$=7.2 Hz, J$_2$=2.5 Hz), 3.56 (2H, t, J=6.4 Hz), 4.18 (2H, m), 4.57 (1H, dd, J$_1$=9.6 Hz, J$_2$=2.7 Hz), 4.66 (2H, t, J=7.4 Hz), 5.30 (1H, d, J=13.7 Hz), 5.54 (1H, d, J=13.7 Hz), 7.70 (2H, d, J=8.8 Hz), 8.28 (2H, d, J=8.8 Hz), 9.41 (1H, s), 10.87 (1H, s)

b) (1S,5R,6S)-2-[6-(3-Aminopropyl)-7-methylthiomidazo[5,1-b]thiazolium-2-yl]-6-((1R)-1-hydroxyethyl)-1-methyl-1-carbapen-2-em-3-carboxylate (intramolecular salt) hydrochloride 4-Nitrobenzyl (1S,5R,6S)-2-[6-(3-azidopropyl)-7-methylthioimidazo[5,1-b]thiazolium-2-yl]-6-((1R)-1-hydroxyethyl)-1-methyl-1-carbapen-2-em-3-carboxylate chloride (930 mg) was dissolved in 30 ml of THF and 30 ml of water. 10% Pd—C (900 mg) was added to the solution. The air in the reaction vessel was replaced by hydrogen, and the contents of the reaction vessel were stirred at room temperature for 1.5 hr. The catalyst was removed by filtration on Celite, and was washed with a 50% aqueous THF solution. The filtrate was washed with ethyl acetate, and was then concentrated under the reduced pressure until the volume of the filtrate was brought to about 10 ml. The residue was purified by column chromatography on Cosmosil 40C$_{18}$-PREP (a 20% aqueous methanol solution) to prepare 291 mg of the title compound.

NMR (D$_2$O) δ (HOD=4.65 ppm): 1.13 (3H, d, J=7.3 Hz), 1.18 (3H, d, J=6.3 Hz), 2.25 (2H, m), 2.29 (3H, s), 3.02 (2H, t, J=7.7 Hz), 3.43 (1H, dd, J$_1$=5.8 Hz, J$_2$=2.7 Hz), 3.52 (1H, m), 4.15 (1H, m), 4.21 (1H, dd, J$_1$=9.5 Hz, J$_2$=2.7 Hz), 8.04 (1H, s), 9.25 (1H, s)

Example 15
(1S,5R,6S)-6-((1R)-1-Hydroxyethyl)-2-[6-(3-hydroxypropyl)-7-methylthioimidazo[5,1-b]thiazolium-2-yl]-1-methyl-1-carbapen-2-em-3-carboxylate (intramolecular salt) hydrochloride The title compound (51 mg) was obtained from a fraction eluted with a 30% aqueous methanol solution in the column chromatography on Cosmosil 40C$_{18}$-PREP in the step of purification of Example 14b).

NMR (D$_2$O) δ (HOD=4.80 ppm): 1.26 (3H, d, J=7.1 Hz), 1.31 (3H, d, J=6.5 Hz), 2.18 (2H, m), 2.41 (3H, s), 3.57 (1H, dd, J$_1$=6.1 Hz, J$_2$=2.8 Hz), 3.6–3.72 (3H, m), 4.28 (1H, m), 4.35 (1H, dd, J$_1$=9.2 Hz, J$_2$=2.8 Hz), 4.55 (2H, t, J=7.4 Hz), 8.14 (1H, s), 9.34 (1H, s)

Example 16
(1S,5R,6S)-2-(6-Ethyl-7-methylthioimidazo-[5,1-b]thiazolium-2-yl)-6-((1R)-1-hydroxyethyl)-1-methyl-1-carbapen-2-em-3-carboxylate (intramolecular salt)

a) 4-Nitrobenzyl (1S,5R,6S)-2-(6-ethyl-7-methylthioimidazo[5,1-b]thiazolium-2-yl)-6-((1R)-1-hydroxyethyl)-1-methyl-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (103 mg) was dissolved in 2 ml of dichloromethane. Ethyl iodide (1.6 ml) was added to the solution. The mixture was stirred at room temperature for 3 days. The solvent was removed by distillation under the reduced pressure to prepare 131 mg of 4-nitrobenzyl (1S,5R,6S)-2-(6-ethyl-7-methylthioimidazo[5,1-b]thiazolium-2-yl)-6-((1R)-1-hydroxyethyl)-1-methyl-1-carbapen-2-em-3-carboxylate iodide as a crude product.

(1S,5R,6S)-2-(6-Ethyl-7-methylthioimidazo[5,1-b] thiazolium-2-yl)-6-((1R)-1-hydroxyethyl)-1-methyl-1-carbapen-2-em-3-carboxylate (intramolecular salt)

The procedure of Example 5b) was repeated, except that 131 mg of 4-Nitrobenzyl (1S,5R,6S)-2-(6-ethyl-7-methylthioimidazo[5,1-b]thiazolium-2-yl)-6-((1R)-1-hydroxyethyl)-1-methyl-1-carbapen-2-em-3-carboxylate iodide as the crude product was used as the starting compound. Thus, 24 mg of the title compound was prepared.

NMR (D$_2$O) δ (HOD=4.65 ppm): 1.13 (3H, d, J=7.0 Hz), 1.19 (3H, d, J=6.3 Hz), 1.43 (3H, t, J=7.4 Hz), 2.28 (3H, s), 3.44 (1H, dd, J$_1$=6.1 Hz, J$_2$=2.7 Hz), 3.47–3.56 (1H, m), 4.12–4.19 (1H, m), 4.22 (1H, dd, J$_1$=9.5 Hz, J$_2$=2.9 Hz), 4.34 (2H, q, J=7.4 Hz), 8.00 (1H, s)

Example 17
(1S,5R,6S)-2-[5,7-Bis(methylthio)-6-methylthioimidazo[5,1-b]thiazolium-2-yl]-6-((1R)-1-hydroxyethyl)-1-methyl-1-carbapen-2-em-3-carboxylate (intramolecular salt)

a) 4-Nitrobenzyl (1S,5R,6S)-2-[5,7-bis(methylthio) imidazo[5,1-b]thiazol-2-yl]-6-((1R)-1-hydroxyethyl)-1-methyl-1-carbapen-2-em-3-carboxylate The procedure of Example 1a) was repeated, except that 762 mg of 4-nitrobenzyl (1R,3R,5R,6S)-6-((1R)-1-hydroxyethyl)-1-methyl-2-oxo-1-carbapenam-3-carboxylate and 1.10 g of 5,7-bis(methylthio)-2-(tri-n-butylstannyl)imidazo[5,1-b]thiazole were used as the starting compounds. Thus, 720 mg of 4-nitrobenzyl (1S,5R,6S)-2-[5,7-bis(methylthio)imidazo[5,1-b]thiazol-2-yl]-6-((1R)-1-hydroxyethyl)-1-methyl-1-carbapen-2-em-3-carboxylate was prepared.

NMR (CDCl$_3$) δ: 1.31 (3H, d, J=7.3 Hz), 1.39 (3H, d, J=6.3 Hz), 2.43 (3H, s), 2.58 (3H, s), 3.34–3.38 (1H, m), 3.47–3.52 (1H, m), 4.28–4.35 (2H, m), 5.28 (1H, d, J=13.7 Hz), 5.53 (1H, d, J=13.4 Hz), 7.67 (2H, d, J=9.0 Hz), 8.13 (1H, s), 8.23 (2H, d, J=9.0 Hz)

b) 4-Nitrobenzyl (1S,5R,6S)-2-[5,7-bis(methylthio)-6-methylimidazo[5,1-b]thiazolium-2-yl]-6-((1R)-1-hydroxyethyl)-1-methyl-1-carbapen-2-em-3-carboxylate trifluoromethanesulfonate 4-Nitrobenzyl (1S,5R,6S)-2-[5,7-bis(methylthio)imidazo [5,1-b]thiazol-2-yl]-6-((1R)-1-hydroxyethyl)-1-methyl-1-carbapen-2-em-3-carboxylate (120 mg) was dissolved in 3 ml of dichloromethane. Methyl trifluoromethanesulfonate (0.025 ml) was added to the solution. The mixture was stirred at room temperature for 20 min. The solvent was removed by distillation under the reduced pressure. Thus, 150 mg of 4-nitrobenzyl (1S,5R,6S)-2-[5,7-bis(methylthio)-6-methylimidazo[5,1-b]thiazolium-2-yl]-6-((1R)-1-hydroxyethyl)-1-methyl-1-carbapen-2-em-3-carboxylate trifluoromethanesulfonate as a crude product was prepared.

c) (1S,5R,6S)-2-[5,7-Bis(methylthio)-6-methylimidazo [5,1-b]thiazolium-2-yl]-6-((1R)-1-hydroxyethyl)-1-methyl-1-carbapen-2-em-3-carboxylate (intramolecular salt The procedure of Example 5b) was repeated, except that 150 mg of 4-nitrobenzyl (1S,5R,6S)-2-[5,7-bis(methylthio)-6-methylimidazo[5,1-b]thiazolium-2-yl]-6-((1R)-1-hydroxyethyl)-1-methyl-1-carbapen-2-em-3-carboxylate trifluoromethanesulfonate as the crude product was used as the starting compound. Thus, 42 mg of the title compound was prepared.

NMR (D$_2$O) δ (HOD=4.65 ppm): 1.12 (3H, d, J=7.1 Hz), 1.18 (3H, d, J=6.4 Hz), 2.27 (3H, s), 2.42 (3H, s), 3.40–3.44 (1H, m), 3.52–3.61 (1H, m), 3.98 (3H, s), 4.10–4.18 (1H, m), 4.20–4.24 (1H, m), 8.07 (1H, s)

Example 18

(5R,6S)-6-((1R)-1-Hydroxyethyl)-2-[7-(2-hydroxyethyl)thio-6-methylimidazo[5,1-b]thiazolium-2-yl]-1-carbapen-2-em-3-carboxylate (intramolecular salt)

a) 4-Nitrobenzyl (5R,6S)-2-[7-(2-t-butyldimethylsilyloxyethyl)thioimidazo[5,1-b]thiazol-2-yl]-6-((1R)-1-hydroxyethyl)-1-carbapen-2-em-3-carboxylate The procedure of Example 1a) was repeated, except that 752 mg of 4-nitrobenzyl (3R,5R,6S)-6-((1R)-1-hydroxyethyl)-2-oxo-1-carbapenam-3-carboxylate and 1.433 g of 7-(2-t-butyldimethylsilyloxyethyl)thio-2-(tri-n-butylstannyl)imidazo[5,1-b]thiazole were used as the starting compounds. Thus, 703 mg of 4-nitrobenzyl (5R,6S)-2-[7-(2-t-butyldimethylsilyloxyethyl)thioimidazo[5,1-b]thiazol-2-yl]-6-((1R)-1-hydroxyethyl)-1-carbapen-2-em-3-carboxylate was prepared.

NMR (CDCl$_3$) δ: 0.02 (6H, s), 0.86 (9H, s), 1.40 (3H, d, J=6.3 Hz), 2.9–3.0 (2H, m), 3.3–3.4 (3H, m), 3.75–3.85 (2H, m), 4.3–4.4 (2H, m), 5.31 (1H, d, J=13.6 Hz), 5.55 (1H, d, J=13.6 Hz), 7.69 (2H, d, J=8.8 Hz), 7.99 (1H, s), 8.21 (1H, s), 8.25 (2H, d, J=8.9 Hz)

b) 4-Nitrobenzyl (5R,6S)-6-((1R)-1-hydroxyethyl)-2-[7-(2-hydroxyethyl)thioimidazo[5,1-b]thiazol-2-yl]-1-carbapen-2-em-3-carboxylate The procedure of Example 12b) was repeated, except that 238 mg of 4-nitrobenzyl (5R,6S)-2-[7-(2-t-butyldimethylsilyloxyethyl)thioimidazo[5,1-b]thiazol-2-yl]-6-((1R)-1-hydroxyethyl)-1-carbapen-2-em-3-carboxylate was used as the starting compound. Thus, 152 mg of 4-nitrobenzyl (5R,6S)-6-((1R)-1-hydroxyethyl)-2-[7-(2-hydroxyethyl)thioimidazo[5,1-b]thiazol-2-yl]-1-carbapen-2-em-3-carboxylate was prepared.

NMR (CDCl$_3$) δ: 1.40 (3H, d, J=6.3 Hz), 2.90–2.96 (2H, m), 3.28–3.37 (2H, m), 4.26–4.40 (2H, m), 5.32 (1H, d, J=13.5 Hz), 5.55 (1H, d, J=13.5 Hz), 7.70 (2H, d, J=8.7 Hz), 8.01 (1H, s), 8.17 (1H, s), 8.25 (2H, d, J=8.9 Hz)

c) 4-Nitrobenzyl (5R,6S)-6-((1R)-1-hydroxyethyl)-2-[7-(2-hydroxyethyl)thio-6-methylimidazo[5,1-b]-thiazolium-2-yl]-1-carbapen-2-em-3-carboxylate iodide The procedure of Example 12c) was repeated, except that 82.6 mg of 4-nitrobenzyl (5R,6S)-6-((1R)-1-hydroxyethyl)-2-[7-(2-hydroxyethyl)thioimidazo[5,1-b]thiazol-2-yl]-1-carbapen-2-em-3-carboxylate was used as the starting compound. Thus, 4-nitrobenzyl (5R,6S)-6-((1R)-1-hydroxyethyl)-2-[7-(2-hydroxyethyl)thio-6-methylimidazo[5,1-b]thiazolium-2-yl]-1-carbapen-2-em-3-carboxylate iodide was prepared.

NMR (DMSO-d$_6$) δ: 1.18 (3H, d, J=6.2 Hz), 2.87–2.96 (2H, m), 3.44–3.62 (5H, m), 3.98–4.08 (1H, m), 4.04 (3H, s), 4.27–4.36 (1H, m), 5.46 (1H, d, J=13.7 Hz), 5.58 (1H, d, J=13.7 Hz), 7.77 (2H, d, J=8.3 Hz), 8.26 (2H, d, J=8.3 Hz), 8.65 (1H, s), 9.72 (1H, s)

d) (5R,6S)-6-((1R)-1-Hydroxyethyl)-2-[7-(2-hydroxyethyl)thio-6-methylimidazo[5,1-b]thiazolium-2-yl]-1-carbapen-2-em-3-carboxylate (intramolecular salt)

The procedure of Example 3b) was repeated, except that the whole quantity of 4-nitrobenzyl (5R,6S)-6-((1R)-1-hydroxyethyl)-2-[7-(2-hydroxyethyl)thio-6-methylimidazo[5,1-b]thiazolium-2-yl]-1-carbapen-2-em-3-carboxylate iodide prepared in step c) was used as the starting compound. Thus, 31.7 mg of the title compound was prepared.

NMR (D$_2$O) δ (HOD=4.80 ppm): 1.31 (3H, d, J=6.3 Hz), 2.95–3.02 (2H, m), 3.26–3.45 (2H, m), 3.54 (1H, dd, J$_1$=5.7 Hz, J$_2$=2.9 Hz), 3.65–3.73 (2H, m), 4.05 (3H, s), 4.21–4.34 (2H, m), 7.98 (1H, s), 9.30 (1H, s)

Example 19

(1S,5R,6S)-6-((1R)-1-Hydroxyethyl)-1-methyl-2-(6-methyl-7-phenylthioimidazo[5,1-b]thiazolium-2-yl)-1-carbapen-2-em-3-carboxylate (intramolecular salt)

a) 4-Nitrobenzyl (1S,5R,6S)-6-((1R)-1-hydroxyethyl)-1-methyl-2-(7-phenylthioimidazo[5,1-b]thiazol-2-yl)-1-carbapen-2-em-3-carboxylate The procedure of Example 1a) was repeated, except that 146 mg of 4-nitrobenzyl (1R,3R,5R,6S)-6-((1R)-1-hydroxyethyl)-1-methyl-2-oxo-1-carbapenam-3-carboxylate and 231 mg of 7-phenylthio-2-(tri-n-butylstannyl)imidazo[5,1-b]thiazole were used as the starting compounds. Thus, 92.5 mg of 4-nitrobenzyl (1S,5R,6S)-6-((1R)-1-hydroxyethyl)-1-methyl-2-(7-phenylthioimidazo[5,1-b]thiazol-2-yl)-1-carbapen-2-em-3-carboxylate was prepared.

NMR (CDCl$_3$) δ: 1.30 (3H, d, J=7.3 Hz), 1.39 (3H, d, J=6.2 Hz), 3.36 (1H, dd, J$_1$=6.5 Hz, J$_2$=2.8 Hz), 3.4–3.5 (1H, m), 4.25–4.35 (1H, m), 4.36 (1H, dd, J$_1$=9.7 Hz, J$_2$=2.8 Hz), 5.27 (1H, d, J=13.5 Hz), 5.52 (1H, d, J=13.5 Hz), 7.1–7.25 (5H, m), 7.67 (2H, d, J=8.7 Hz), 8.10 (1H, s), 8.24 (2H, d, J=8.7 Hz), 8.35 (1H, s)

b) 4-Nitrobenzyl (1S,5R,6S)-6-((1R)-1-hydroxyethyl)-1-methyl-2-(6-methyl-7-phenylthioimidzo[5,1-b]-thiazolium-2-yl)-1-carbapen-2-em-3-carboxylate iodide The procedure of Example 12c) was repeated, except that 49.7 mg of 4-nitrobenzyl (1S,5R,6S)-6-((1R)-1-hydroxyethyl)-1-methyl-2-(7-phenylthioimidazo[5,1-b]thiazol-2-yl)-1-carbapen-2-em-3-carboxylate was used as the starting compound. Thus, 4-nitrobenzyl (1S,5R,6S)-6-((1R)-1-hydroxyethyl)-1-methyl-2-(6-methyl-7-phenylthioimidazo[5,1-b]thiazolium-2-yl)-1-carbapen-2-em-3-carboxylate iodide was prepared.

NMR (CDCl$_3$) δ: 1.39 (3H, d, J=6.4 Hz), 1.43 (3H, d, J=7.1 Hz), 3.43 (1H, dd, J$_1$=6.2 Hz, J$_2$=2.6 Hz), 3.85–4.0 (1H, m), 4.05 (3H, s), 4.26–4.38 (1H, m), 4.47 (1H, dd, J$_1$=9.8 Hz, J$_2$=2.6 Hz), 5.32 (1H, d, J=13.7 Hz), 5.54 (1H, d, J=13.7 Hz), 7.19–7.26 (2H, m), 7.30–7.40 (3H, m), 7.69 (2H, d, J=8.4 Hz), 8.24 (2H, d, J=8.4 Hz), 9.58 (1H, s)

c) (1S,5R,6S)-6-((1R)-1-Hydroxyethyl)-1-methyl-2-(6-methyl-7-phenylthioimidazo[5,1b]thiazolium-2-yl)-1-carbapen-2-em-3-carboxylate (intramolecular salt)

The procedure of Example 3b) was repeated, except that the whole quantity of 4-nitrobenzyl (1S,5R,6S)-6-((1R)-1-hydroxyethyl)-1-methyl-2-(6-methyl-7-phenylthioimidazo[5,1-b]thiazolium-2-yl)-1-carbapen-2-em-3-carboxylate iodide prepared in step b) was used as the starting compound. Thus, 8.3 mg of the title compound was prepared.

NMR (D$_2$O) δ (HOD=4.80 ppm): 1.26 (3H, d, J=7.2 Hz), 1.32 (3H, d, J=6.5 Hz), 3.50–3.70 (2H, m), 3.97 (3H, s), 4.22–4.36 (2H, m), 7.23–7.40 (5H, m), 8.17 (1H, s)

Example 20

(1S,5R,6S)-6-((1R)-1-Hydroxyethyl)-1-methyl-2-[7-methylthio-6-(piperidin-4-yl)imidazo[5,1-b]-thiazolium-2-yl]-1-carbapen-2-em-3-carboxylate (intramolecular salt)

a) 4-Nitrobenzyl (1S,5R,6S)-6-((1R)-1-hydroxyethyl)-1-methyl-2-[7-methylthio-6-[1-(4-nitrobenzyloxycarbonyl)piperidin-4-yl]imidazo[5,1-b]thiazolium-2-yl]-1-carbapen-2-em-3-carboxylate trifluoromethanesulfonate 4-Hydroxy-1-(4-nitrobenzyloxycarbonyl)piperidine (150 mg) was dissolved in 3 ml of dichloromethane. The solution was cooled to −60° C. 2,6-Lutidine (0.068 ml) and 0.094 ml of trifluoromethanesulfonic anhydride were then added to the cooled solution. The mixture was stirred for 15 min. Water (10 ml) was added to the reaction solution, and the mixture was extracted with 10 ml of dichloromethane. The extract was dried over anhydrous magnesium sulfate. 4-Nitrobenzyl (1S,5R,6S)-6-((1R)-1-hydroxyethyl)-1-methyl-2-(7-methylthioimidazo-[5,1-b]thiazol-2-yl)-1-carbapen-2-em-3-carboxylate (213 mg) was then added thereto. The solvent was removed by concentration until the volume of the solution was brought to 4 ml. The residue was stirred at room temperature for 24 hr. The solvent was then removed by distillation under the reduced pressure. The residue was purified by column chromatography on Sephadex LH-20 (chloroform:methanol=1:1) to prepare 53 mg of 4-nitrobenzyl (1S,5R,6S)-6-((1R)-1-hydroxyethyl)-1-methyl-2-[7-methylthio-6-[1-(4-nitro-benzyloxycarbonyl)piperidin-4-yl]imidazo[5,1-b]thiazolium-2-yl]-1-carbapen-2-em-3-carboxylate trifluoromethanesulfonate as a crude product.

b) (1S,5R,6S)-6-((1R)-1-Hydroxyethyl)-1-methyl-2-[7-methylthio-6-(piperidin-4-yl)imidazo[5,1-b]thiazolium-2-yl]-1-carbapen-2-em-3-carboxylate (intramolecular salt)

The procedure of Example 5b) was repeated, except that 113 mg of 4-nitrobenzyl (1S,5R,6S)-6-((1R)-1-hydroxyethyl)-1-methyl-2-[7-methylthio-6-[1-(4-nitro-benzyloxycarbonyl)piperidin-4-yl]imidazo[5,1-b]-thiazolium-2-yl]-1-carbapen-2-em-3-carboxylate trifluoromethanesulfonate as the crude product was used as the starting compound. Thus, 5 mg of the title compound was prepared.

NMR ($D_2O$) δ (HOD=4.65 ppm): 1.17 (3H, d, J=7.3 Hz), 1.24 (3H, d, J=6.3 Hz), 2.04–2.11 (2H, m), 2.31–2.35 (5H, m), 2.98–3.08 (2H, m), 3.37–3.60 (4H, m), 4.17–4.30 (2H, m), 4.85–4.96 (1H, m), 8.07 (1H, s)

Example 21
(1S,5,R,6S)-2-[6-(2-Fluoroethyl)-7-methylthioimidazo[5,1-b]thiazolium-2-yl]-6-((1R)-1-hydroxyethyl)-1-methyl-1-carbapen-2-em-3-carboxylate (intramolecular salt)

a) 4-Nitrobenzyl (1S,5R,6S)-2-[6-(2-fluoroethyl)-7-methylthioimidazo[5,1-b]thiazolium-2-yl]-6-((1R)-1-hydroxyethyl)-1-methyl-1-carbapen-2-em-3-carboxylate trifluoromethanesulfonate 2-Fluoroethanol (0.019 ml) was dissolved in 1 ml of dichloromethane. The solution was cooled to −60° C. 2,6-Lutidine (0.042 ml) and 0.058 ml of trifluoromethane-sulfonic anhydride were then added to the cooled solution. The mixture was stirred for 30 min. Water (5 ml) was added to the reaction solution, and the mixture was extracted with 5 ml of dichloromethane. The extract was dried over anhydrous magnesium sulfate. 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (154 mg) was then added thereto. The solvent was removed by concentration until the volume of the solution was brought to 3 ml. The residue was stirred at room temperature for 2 hr. The solvent was then removed by distillation under the reduced pressure. Thus, 180 mg of 4-nitrobenzyl (1S,5R,6S)-2-[6-(2-fluoroethyl)-7-methylthioimidazo[5,1-b]thiazolium-2-yl]-6-((1R)-1-hydroxyethyl)-1-methyl-1-carbapen-2-em-3-carboxylate trifluoromethanesulfonate as a crude product was prepared.

b) (1S,5R,6S)-2-[6-(2-Fluoroethyl)-7-methylthioimidazo[5,1-b]thiazolium-2-yl]-6-((1R)-1-hydroxyethyl)-1-methyl-1-carbapen-2-em-3-carboxylate (intramolecular salt)

The procedure of Example 5b) was repeated, except that 180 mg of 4-nitrobenzyl (1S,5R,6S)-2-[6-(2-fluoroethyl)-7-methylthioimidazo[5,1-b]thiazolium-2-yl]-6-((1R)-1-hydroxyethyl)-1-methyl-1-carbapen-2-em-3-carboxylate trifluoromethanesulfonate as the crude product was used as the starting compound. Thus, 70 mg of the title compound was prepared.

NMR ($D_2O$) δ (HOD=4.65 ppm): 1.11 (3H, d, J=7.1 Hz), 1.17 (3H, d, J=6.1 Hz), 2.25 (3H, s), 3.42 (1H, dd, $J_1$=6.1 Hz, $J_2$=2.9 Hz), 3.47–3.56 (1H, m), 4.10–4.17 (1H, m), 4.21 (1H, dd, $J_1$=9.5 Hz, $J_2$=2.7 Hz), 4.64–4.81 (4H, m), 8.01 (1H, s)

Example 22
(1S,5R,6S)-6-((1R)-1-Hydroxyethyl)-2-6-(2-hydroxyethyl)-7-methylthioimidazo[5,1-b]thiazolium-2-yl]-1-methyl-1-carbapen-2-em-3-carboxylate (intramolecular salt)

a) 4-Nitrobenzyl (1S,5R,6S)-2-[7-methylthio-6-(2-t-butyldimethylsilyloxyethyl)imidazo[5,1-b]thiazolium-2-yl]-6-((1R)-1-hydroxyethyl)-1-methyl-1-carbapen-2-em-3-carboxylate trifluoromethanesulfonate 2-t-Butyldimethylsilyloxy ethanol (226 mg) was dissolved in 5 ml of dichloromethane. The solution was cooled to −20° C. 2,6-Lutidine (0.163 ml) and 0.224 ml of trifluoromethanesulfonic anhydride were then added to the cooled solution. The mixture was stirred for 15 min. Water (10 ml) was added to the reaction solution, and the mixture was extracted with 10 ml of dichloromethane. The extract was dried over anhydrous magnesium sulfate. 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (560 mg) was then added thereto. The solvent was removed by concentration until the volume of the solution was brought to 10 ml. The residue was stirred at room temperature for 20 hr. The solvent was then removed by distillation under the reduced pressure. Thus, 786 mg of 4-nitrobenzyl (1S,5R,6S)-2-[7-methylthio-6-(2-t-butyldimethylsilyloxyethyl)imidazo[5,1-b]thiazolium-2-yl]-6-((1R)-1-hydroxyethyl)-1-methyl-1-carbapen-2-em-3-carboxylate trifluoromethane-sulfonate as a crude product was prepared.

b) (1S,5R,6S)-6-((1R)-1-Hydroxyethyl]-2-[6-(2-hydroxyethyl)-7-methylthioimidazo[5,1-b]thiazolium-2-yl]-1-methyl-1-carbapen-2-em-3-carboxylate (intramolecular salt)

4-Nitrobenzyl (1S,5R,6S)-2-[7-methylthio-6-(2-t-butyldimethylsilyloxyethyl)imidazo[5,1-b]thiazolium-2-yl]-6-((1R)-1-hydroxyethyl)-1-methyl-1-carbapen-2-em-3-carboxylate trifluoromethanesulfonate as the crude product (196 mg) was dissolved in 2 ml of THF under cooling in ice. Acetic acid (0.028 ml) and 0.285 ml of a 1 M tetra-n-butylammonium fluoride/THF solution were added to the solution. The mixture was stirred for one hr. THF (6 ml) and 10 ml of a 1/15 M sodium phosphate buffer (pH 6.6) were added to the reaction solution. Thereafter, the procedure of Example 5b) was repeated, except that this mixture was used. Thus, 31 mg of the title compound was prepared.

NMR ($D_2O$) δ (HOD=4.65 ppm): 1.14 (3H, d, J=7.3 Hz), 1.19 (3H, d, J=6.6 Hz), 2.29 (3H, s), 3.44 (1H, dd, $J_1$=5.9 Hz, $J_2$=2.8 Hz), 3.49–3.57 (1H, m), 3.88 (2H, t, J=5.7 Hz), 4.13–4.19 (1H, m), 4.23 (1H, dd, $J_1$=9.2 Hz, $J_2$=2.6 Hz), 4.25 (2H, t, J=7.3 Hz), 8.04 (1H, s), 9.23 (1H, s)

Example 23
(1S,5R,6S)-2-[6-(3-Aminosulfonylpropyl-7-methylthioimidazo[5,1-b]thiazolium-2-yl]-6-((1R)-1-hydroxyethyl)-1-methyl-1-carbapen-2-em-3-carboxylate (intramolecular salt)

a) 4-Nitrobenzyl (1S,5R,6S)-2-[6-(3-aminosulfonylpropyl)-7-methylthioimidazo[5,1-b]

thiazolium-2-yl]-6-((1R)-1-hydroxyethyl)-1-methyl-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (100 mg) was dissolved in 3 ml of acetone. 3-Iodopropanesulfonamide (498 mg) was added to the solution. The mixture was stirred at 60° C. for 6 days. The solvent was removed by distillation under the reduced pressure. The residue was purified by column chromatography on Sephadex LH-20 (chloroform:methanol=1:1) to prepare 28 mg of 4-nitrobenzyl (1S,5R,6S)-2-[6-(3-aminosulfonylpropyl)-7-methylthioimidazo[5,1-b]thiazolium-2-yl]-6-((1R)-1-hydroxyethyl)-1-methyl-1-carbapen-2-em-3-carboxylate iodide.

NMR (acetone-$d_6$) δ: 1.33 (3H, d, J=7.1 Hz), 1.42 (3H, d, J=6.6 Hz), 2.30–2.40 (2H, m), 2.60 (3H, s), 3.41 (2H, t, J=7.4 Hz), 3.59 (1H, dd, $J_1$=6.3 Hz, $J_2$=3.0 Hz), 3.86–3.93 (1H1, m), 4.10–4.20 (1H, m), 4.56 (1H, dd, $J_1$=10.2 Hz, $J_2$=3.2 Hz), 4.92 (2H, t, J=7.4 Hz), 5.48 (1H, d, J=13.6 Hz), 5.67 (1H, d, J=13.6 Hz), 6.42 (1H, br s), 7.88 (2H, d, J=8.8 Hz), 8.29 (2H, d, J=8.8 Hz), 9.03 (1H, s), 10.2 (1H, s)

b) (1S,5R,6S)-2-[6-(3-Aminosulfonylpropyl)-7-methylthioimidazo[5,1-b]thiazolium-2-yl]-6-((1R )-1-hydroxyethyl)-1-methyl-1-carbapen-2-em-3-carboxylate (intramolecular salt)

The procedure of Example 3b) was repeated, except that 25 mg of 4-nitrobenzyl (1S,5R,6S)-2-[6-(3-aminosulfonylpropyl)-7-methylthioimidazo[5,1-b]-thiazolium-2-yl]-6-((1R)-1-hydroxyethyl)-1-methyl-1-carbapen-2-em-3-carboxylate iodide was used as the starting compound. Thus, 3.4 mg of the title compound was prepared.

NMR ($D_2O$) δ (HOD=4.80 ppm): 1.26 (3H, d, J=7.1 Hz), 1.31 (3H, d, J=6.6 Hz), 2.42 (3H, s), 2.44–2.56 (2H, m), 3.37 (2H, t, J=7.4 Hz), 3.57 (1H, dd, $J_1$=6.3 Hz, $J_2$=3.0 Hz), 3.63–3.72 (1H, m), 4.24–4.32 (1H, m), 4.35 (1H, dd, $J_1$=9.3 Hz, $J_2$=2.7 Hz), 4.64 (2H, t, J=7.4 Hz), 8.15 (1H, s)

Example 24

(1S,5R,6S)-2-(7-Ethylthio-6-methylimidazo[5,1-b]-thiazolium-2-yl)-6-((1R)-1-hydroxyethyl)-1-methyl-1methyl-1-carbapen-2-em-3-carboxylate (intramolecular salt)

a) 4-Nitrobenzyl (1S,5R,6S)-2-7-ethylthioimidazo5,1-b]thiazol-2-yl)-6-((1R)-1-hydroxyethyl)-1-methyl-1-carbapen-2-em-3-carboxylate The procedure of Example 1a) was repeated, except that 724 mg of 4-nitrobenzyl (1R,3R,5R,6S)-6-((1R)-1-hydroxyethyl)-1-methyl-2-oxo-1-carbapenam-3-carboxylate and 1.04 g of 7-ethylthio-2-(tri-n-butylstannyl)imidazo[5,1-b]thiazole were used as the starting compounds. Thus, 731 mg of 4-nitrobenzyl (1S,5R,6S)-2-(7-ethylthioimidazo[5,1-b]thiazol-2-yl)-6-((1R)-1-hydroxyethyl)-1-methyl-1-carbapen-2-em-3-carboxylate was prepared.

NMR ($CDCl_3$) δ: 1.26 (3H, t, J=7.3 Hz), 1.31 (3H, d, J=7.2 Hz), 1.40 (3H, d, J=6.1 Hz), 2.84 (2H, q, J=7.3 Hz), 3.37 (1H, dd, $J_1$=6.5 Hz, $J_2$=2.8 Hz), 3.4–3.5 (1H, m), 4.25–4.35 (1H, m), 4.38 (1H, dd, $J_1$=9.4 Hz, $J_2$=2.8 Hz), 5.28 (1H, d, J=13.7 Hz), 5.53 (1H, d, J=13.7 Hz), 7.68 (2H, d, J=8.4 Hz), 8.03 (1H, s), 8.24 (2H, d, J=8.4 Hz), 8.30 (1H, s)

b) 4-Nitrobenzyl (1S,5R,6S)-2-(7-ethylthio-6-methylimidazo[5,1-b]thiazolium-2-yl)-6-((1R)-1-hydroxyethyl)-1-methyl-1-carbapen-2-em-3-carboxylate iodide The procedure of Example 12c) was repeated, except that 140 mg of 4-nitrobenzyl (1S,5R,6S)-2-(7-ethylthioimidazo[5,1-b]thiazol-2-yl)-6-((1R)-1-hydroxyethyl)-1-methyl-1-carbapen-2-em-3-carboxylate was used as the starting compound. Thus, 4-nitrobenzyl (1S,5R,6S)-2-(7-ethylthio-6-methylimidazo[5,1-b]-thiazolium-2-yl)-6-((1R)-1-hydroxyethyl)-1-methyl-1-carbapen-2-em-3-carboxylate iodide was prepared.

NMR (DMSO-$d_6$) δ: 1.16–1.21 (6H, m), 1.24 (3H, d, J=7.3 Hz), 2.88 (2H, q, J=7.3 Hz), 3.48–3.51 (1H, m), 3.72–3.82 (1H, m), 4.03 (3H, s), 4.37–4.43 (1H, m), 5.20 (1H, d, J=5.1 Hz), 5.42 (1H, d, J=13.9 Hz), 5.55 (1H, d, J=13.9 Hz), 7.75 (2H, d, J=8.3 Hz), 8.24 (2H, d, J=8.3 Hz), 8.73 (1H, s), 9.74 (1H, s)

c) (1S,5R,6S)-2-(7-Ethylthio-6-methylimidazo[5,1-b]thiazolium-2-yl)-6-((1R)-1-hydroxyethyl)-1-methyl-1-carbapen-2-em-3-carboxylate (intramolecular salt)

The procedure of Example 3b) was repeated, except that the whole quantity of 4-nitrobenzyl (1S,5R,6S)-2-(7-ethylthio-6-methylimidazo[5,1-b]thiazolium-2-yl)-6-((1R)-1-hydroxyethyl)-1-methyl-1-carbapen-2-em-3-carboxylate iodide prepared in step b) was used as the starting compound. Thus, 70.6 mg of the title compound was prepared.

NMR ($D_2O$) δ (HOD=4.80 ppm): 1.24 (3H, t, J=7.3 Hz), 1.29 (3H, d, J=7.1 Hz), 1.36 (3H, d, J=6.3 Hz), 2.89 (2H, q, J=7.3 Hz), 3.59 (1H, dd, $J_1$=5.8 Hz, $J_2$=2.7 Hz), 3.64–3.72 (1H, m), 4.09 (3H, s), 4.29–4.36 (1H, m), 4.37 (1H, dd, $J_1$=9.0 Hz, $J_2$=2.7 Hz), 8.16 (1H, s)

Example 25

(1S,5R,6S)-6-((1R)-1-Hydroxyethyl)-1-methyl-2-(7-methylthio-6-propylimidazo[5,1-b]thiazolium-2-yl)-1-carbapen-2-em-3-carboxylate (intramolecular salt)

a) 4-Nitrobenzyl (1S,5R,6S)-2-(6-allyl-7-methylthioimidazo[5,1-b]thiazolium-2-yl)-6-((1R)-1-hydroxyethyl)-1-methyl-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (70 mg) was dissolved in 2 ml of dichloromethane. Allyl iodide (1.2 ml) was added to the solution. The mixture was stirred at room temperature for 2 days. The solvent was removed by distillation under the reduced pressure. The residue was purified by column chromatography on Sephadex LH-20 (chloroform:methanol=1:1) to prepare 96 mg of 4-nitrobenzyl (1S,5R,6S)-2-(6-allyl-7-methylthioimidazo-[5,1-b]thiazolium-2-yl)-6-((1R)-1-hydroxyethyl)-1-methyl-1-carbapen-2-em-3-carboxylate iodide as a crude product.

b) (1S,5R,6S)-6-((1R)-1-Hydroxyethyl)-1-methyl-2-(7-methylthio-6-propylimidazo[5,1-b]thiazolium-2-yl)-1-carbapen-2-em-3-carboxylate (intramolecular salt)

The procedure of Example 5b) was repeated, except that 96 mg of 4-Nitrobenzyl (1S,5R,6S)-2-(6-allyl-7-methylthioimidazo[5,1-b]thiazolium-2-yl)-6-((1R)-1-hydroxyethyl)-1-methyl-1-carbapen-2-em-3-carboxylate iodide as the crude product was used as the starting compound. Thus, 16 mg of the title compound was prepared.

NMR ($D_2O$) δ (HOD=4.65 ppm): 0.82 (3H, t, J=7.3 Hz), 1.10 (3H, d, J=7.3 Hz), 1.16 (3H, d, J=6.3 Hz), 1.76–1.86 (2H, m), 2.25 (3H, s), 3.41 (1H, dd, $J_1$=6.1 Hz, $J_2$=2.7 Hz), 3.45–3.53 (1H, m), 4.09–4.16 (1H, m), 4.20 (1H, dd, $J_1$=9.5 Hz, $J_2$=2.9 Hz), 4.25 (2H, t, J=7.3 Hz), 7.97 (1H, s)

Example 26

(5R,6S)-2-(7-Ethylthio-6-methylimidazo[5,1-b]thiazolium-2-yl)-6-((1R)-1-hydroxyethyl)-1-carbapen-2-em-3-carboxylate (intramolecular salt)

a) 4-Nitrobenzyl (5R,6S)-2-(7-ethylthioimidazo[5,1-b]thiazol-2-yl)-6-((1R)-1-hydroxyethyl)-1-carbapen-2-em-3-carboxylate The procedure of Example 1a) was repeated, except that 869 mg of 4-nitrobenzyl (3R,5R,6S)-6-((1R)-1- hydroxyethyl)-2-oxo-1-carbapenam-3-carboxylate and 1.30 g of 7-ethylthio-2-(tri-n-butylstannyl)imidazo[5,1-b]thiazole were used as the starting compounds. Thus, 691 mg of 4-nitrobenzyl (5R,6S)-2-(7-ethylthioimidazo[5,1-b]thiazol-2-yl)-6-((1R)-1-hydroxyethyl)-1-carbapen-2-em-3-carboxylate was prepared.

NMR (CDCl$_3$) δ: 1.25 (3H, t, J=7.3 Hz), 1.40 (3H, d, J=6.4 Hz), 2.83 (2H, q, J=7.3 Hz), 3.3–3.4 (3H, m), 4.25–4.4 (2H, m), 5.32 (1H, d, J=13.6 Hz), 5.55 (1H, d, J=13.6 Hz), 7.69 (2H, d, J=9.0 Hz), 8.02 (1H, s), 8.20 (1H, s), 8.25 (2H, d, J=9.0 Hz)

b) 4-Nitrobenzyl (5R,6S)-2-(7-ethylthio-6-methylimidazo[5,1-b]thiazolium-2-yl)-6-((1R)-1-hydroxyethyl)-1-carbapen-2-em-3-carboxylate iodide The procedure of Example 12c) was repeated, except that 126 mg of 4-nitrobenzyl (5R,6S)-2-(7-ethylthioimidazo[5,1-b]thiazol-2-yl)-6-((1R)-1-hydroxyethyl)-1-carbapen-2-em-3-carboxylate was used as the starting compound. Thus, 4-nitrobenzyl (5R,6S)-2-(7-ethylthio-6-methylimidazo[5,1-b]thiazolium-2-yl)-6-((1R)-1-hydroxyethyl)-1-carbapen-2-em-3-carboxylate iodide was prepared.

NMR (DMSO-d$_6$) δ: 1.18 (3H, t, J=7.3 Hz), 1.18 (3H, d, J=5.9 Hz), 2.88 (2H, q, J=7.3 Hz), 3.43–3.56 (2H, m), 3.60 (1H, dd, J$_1$=6.1 Hz, J$_2$=2.9 Hz), 3.98–4.08 (1H, m), 4.03 (3H, s), 4.26–4.37 (1H, m), 5.46 (1H, d, J=14.1 Hz), 5.58 (1H, d, J=14.1 Hz), 7.77 (2H, d, J=8.7 Hz), 8.26 (2H, d, J=8.7 Hz), 8.66 (1H, s), 9.75 (1H, s)

c) (5R,6S)-2-(7-Ethylthio-6-methylimidazo[5,1-b]-thiazolium-2-yl)-6-((1R)-1-hydroxyethyl)-1-carbapen-2-em-3-carboxylate (intramolecular salt)

The procedure of Example 3b) was repeated, except that the whole quantity of 4-nitrobenzyl (5R,6S)-2-(7-ethylthio-6-methylimidazo[5,1-b]thiazolium-2-yl)-6-((1R)-1-hydroxyethyl)-1-carbapen-2-em-3-carboxylate iodide prepared in step b) was used as the starting compound. Thus, 57.9 mg of the title compound was prepared.

NMR (D$_2$O) δ (HOD=4.80 ppm): 1.20 (3H, t, J=7.3 Hz), 1.31 (3H, d, J=6.3 Hz), 2.85 (2H, q, J=7.3 Hz), 3.28–3.45 (2H, m), 3.55 (1H, dd, J$_1$=5.8 Hz, J$_2$=3.0 Hz), 4.03 (3H, s), 4.23–4.37 (2H, m), 7.98 (1H, s), 9.29 (1H, s)

Example 27

(5R,6S)-2-(3,6-Dimethyl-7-methylthioimidazo[5,1-b]thiazolium-2-yl)-6-((1R)-1-hydroxyethyl)-1-carbapen-2-em-3-carboxylate (intramolecular salt)

a) 4-Nitrobenzyl (5R,6S)-6-((1R)-1-hydroxyethyl)-2-(3-methyl-7-methylthioimidazo[5,1-b]thiazol-2-yl)-1-carbapen-2-em-3-carboxylate The procedure of Example 1a) was repeated, except that 1.044 g of 4-nitrobenzyl (3R,5R,6S)-6-((1R)-1-hydroxyethyl)-2-oxo-1-carbapenam-3-carboxylate and 1.56 g of 3-methyl-7-methylthio-2-(tri-n-butylstannyl)imidazo[5,1-b]thiazole were used as the starting compounds. Thus, 927 mg of 4-nitrobenzyl (5R,6S)-6-((1R)-1-hydroxyethyl)-2-(3-methyl-7-methylthioimidazo-[5,1-b]thiazol-2-yl)-1-carbapen-2-em-3-carboxylate was prepared.

NMR (CDCl$_3$) δ: 1.40 (3H, d, J=6.3 Hz), 2.19 (3H, s), 2.43 (3H, 8), 3.1–3.3 (2H, m), 3.36 (1H, dd, J$_1$=6.4 Hz, J$_2$=3.1 Hz), 4.25–4.45 (2H, m), 5.24 (1H, d, J=13.7 Hz), 5.43 (1H, d, J=13.7 Hz), 7.57 (2H, d, J=8.7 Hz), 7.85 (1H, s), 8.18 (2H, d, J=8.7 Hz)

b) 4-Nitrobenzyl (5R,6S)-2-(3,6-dimethyl-7-methylthioimidazo-[5,1-b]thiazolium-2-yl)-6-((1R)-1-hydroxyethyl)-1-carbapen-2-em-3-carboxylate iodide The procedure of Example 12c) was repeated, except that 426 mg of 4-nitrobenzyl (5R,6S)-6-((1R)-1-hydroxyethyl)-2-(3-methyl-7-methylthioimidazo[5,1-b]-thiazol-2-yl)-1-carbapen-2-em-3-carboxylate was used as the starting compound. Thus, 561 mg of 4-nitrobenzyl (5R,6S)-2-(3,6-dimethyl-7-methylthioimidazo-[5,1-b]-thiazolium-2-yl)-6-((1R)-1-hydroxyethyl)-1-carbapen-2-em-3-carboxylate iodide was prepared.

NMR (DMSO-d$_6$) δ: 1.16 (3H, d, J=6.3 Hz), 2.35 (3H, s) 2.42 (3H, s), 3.07–3.44 (2H, m), 3.58–3.63 (1H, m), 3.95–4.08 (1H, m), 4.01 (3H, s) 4.28–4.38 (1H, m), 5.27 (1H, d, J=13.2 Hz), 5.37 (1H, d, J=13.2 Hz), 7.57 (2H, d, J=8.8 Hz), 8.12 (2H, d, J=8.8 Hz), 9.88 (1H, s)

c) (5R,6S)-2-(3,6-Dimethyl-7-methylthioimindazo[5,1-b]thiazolium-2-yl)-6-((1R)-1-hydroxyethyl)-1-carbapen-2-em-3-carboxylate (intramolecular salt)

The procedure of Example 3b) was repeated, except that 130 mg of 4-nitrobenzyl (5R,6S)-2-(3,6-dimethyl-7-methylthioimidazo[5,1-b]thiazolium-2-yl)-6-((1R)-1-hydroxyethyl)-1-carbapen-2-em-3-carboxylate iodide was used as the starting compound. Thus, 38.5 mg of the title compound was prepared.

NMR (D$_2$O) δ (HOD=4.80 ppm): 1.29 (3H, d, J=6.3 Hz), 2.35 (3H, s), 2.40 (3H, s), 3.15 (1H, dd, J$_1$=17.3 Hz, J$_2$=10.1 Hz), 3.32 (1H, dd, J$_1$=17.3 Hz, J$_2$=8.3 Hz), 3.59 (1H, dd, J$_1$=5.8 Hz, J$_2$=3.0 Hz), 4.07 (3H, s), 4.21–4.32 (1H, m), 4.32–4.42 (1H, m), 9.35 (1H, s)

Example 28

(5R,6S)-2-(6-Carbamoylmethyl-7-methylthioimidazo[5,1-b]thiazolium-2-yl)-6-((1R)-1-hydroxyethyl)-1-carbapen-2-em-3-carboxylate (intramolecular salt)

a) 4-Nitrobenzyl (5R,6S)-2-(6-carbamoylmethyl-7-methylthioimidazo[5,1-b]thiazolium-2-yl)-6-((1R)-1-hydroxyethyl)-1-carbapen-2-em-3-carboxylate iodide 4-Nitrobenzyl (5R,6S)-6-((1R)-1-hydroxyethyl)-2-(7-methylthioimidazo[5,1-b]thiazol-2-yl)-1-carbapen-2-em-3-carboxylate (158 mg) was dissolved in 2 ml of acetone and 1 ml of DMF. 2-Iodoacetamide (584 mg) was added to the solution. The mixture was stirred at room temperature for 3 days. The solvent was removed by distillation under the reduced pressure. The residue was purified by column chromatography in Sephadex LH-20 (chloroform:methanol=1:1) to prepare 203 mg of 4-nitrobenzyl (5R,6S)-2-(6-carbamoylmethyl-7-methylthioimidazo[5,1-b]thiazolium-2-yl)-6-((1R)-1-hydroxyethyl)-1-carbapen-2-em-3-carboxylate iodide as a crude product.

b) (5R,6S)-2-(6-Carbamoylmethyl-7-methylthioimidazo [5,1-b]thiazolium-2-yl)-6-((1R)-1-hydroxyethyl)-1-carbapen-2-em-3-carboxylate (intramolecular salt)

The procedure of Example 5b) was repeated, except that 203 mg of 4-nitrobenzyl (5R,6S)-2-(6-carbamoylmethyl-7-methylthioimidazo[5,1-b]thiazolium-2-yl)-6-((1R)-1-hydroxyethyl)-1-carbapen-2-em-3-carboxylate iodide as the crude product was used as the starting compound. Thus, 30 mg of the title compound was prepared.

NMR (D$_2$O) δ (HOD=4.65 ppm): 1.21 (3H, d, J=6.3 Hz), 2.26 (3H, s), 3.20–3.35 (2H, m), 3.42 (1H, dd, J$_1$=5.9 Hz, J$_2$=3.1 Hz), 4.14–4.26 (2H, m), 5.21 (2H, s), 7.94 (1H, s), 9.29 (1H, s)

Example 29

(1S,5R,6S)-2-[7-(2-Aminoethyl)thio-6-methylimidazo[5,1-b]thiazolium-2-yl]-6-((1R)-1-hydroxyethyl)-1-methyl-1-carbapen-2-em-3-carboxylate (intramolecular salt)

a) 4-Nitrobenzyl (1S,5R,6S)-6-((1R)-1-hydroxyethyl)-1-methyl-2-[7-[2-(4-nitrobenzyloxycarbonyl)aminoethyl]thioimidazo[5,1-b]thiazol-2-yl]-1-carbapen-2-em-3-carboxylate The procedure of Example 1a) was repeated, except that 181 mg of 4-nitrobenzyl (1R,3R,5R,6S)-6-((1R)-1- hydroxyethyl)-1-methyl-2-oxo-1-carbapenam-3-carboxylate and 355 mg of 7-[2-(4-nitrobenzyloxycarbonyl)aminoethyl]thio-2-(tri-n-butylstannyl)imidazo[5,1-b]thiazole were used as the starting compounds. Thus, 194 mg of 4-nitrobenzyl (1S,5R,6S)-6-((1R)-1-hydroxyethyl)-1-methyl-2-[7-[2-(4-nitrobenzyloxycarbonyl)aminoethyl]thioimidazo[5,1-b]thiazol-2-yl]-1-carbapen-2-em-3-carboxylate was prepared.

NMR (CDCl$_3$) δ: 1.30 (3H, d, J=7.4 Hz), 1.40 (3H, d, J=6.3 Hz), 2.85–2.95 (2H, m), 3.37 (1H, dd, J$_1$=6.6 Hz, J$_2$=2.7 Hz), 3.4–3.5 (3H, m), 4.25–4.35 (1H, m), 4.38 (1H, dd, J$_1$=9.7 Hz, J$_2$=2.7 Hz), 5.19 (2H, s), 5.27 (1H, d, J=13.5 Hz), 5.52 (1H, d, J=13.5 Hz), 6.05–6.15 (1H, m), 7.50 (2H, d, J=8.7 Hz), 7.68 (2H, d, J=8.7 Hz), 8.01 (1H, s), 8.20 (2H, d, J=8.7 Hz), 8.24 (2H, d, J=8.7 Hz), 8.29 (1H, s)

b) 4-Nitrobenzyl (1S,5R,6S )-6-((1R)-1-hydroxyethyl)-1-methyl-2-[6-methyl-7-[2-(4-nitrobenzyloxycarbonyl)aminoethyl]thioimidazo[5,1-b]thiazolium-2-yl]-1-carbapen-2-em-3-carboxylate iodide The procedure of Example 12c) was repeated, except that the reaction was carried out in a mixed solvent composed of dichloromethane and DMF and 109 mg of 4-nitrobenzyl (1S,5R,6S)-6-((1R)-1-hydroxyethyl)-1-methyl-2-[7-[2-(4-nitrobenzyloxycarbonyl)aminoethyl]thioimidazo[5,1-b]thiazol-2-yl]-1-carbapen-2-em-3-carboxylate was used as the starting compound. Thus, 4-nitrobenzyl (1S,5R,6S)-6-((1R)-1-hydroxyethyl)-1-methyl-2-[6-methyl-7-[2-(4-nitrobenzyloxycarbonyl)aminoethyl]thioimidazo[5,1-b]thiazolium-2-yl]-1-carbapen-2-em-3-carboxylate iodide was prepared.

NMR (DMSO-d$_6$) δ: 1.19 (3H, d, J=6.3 Hz), 1.22 (3H, d, J=7.1 Hz), 2.95–3.05 (2H, m), 3.18–3.30 (2H, m), 3.45–3.51 (1H, m), 3.70–3.80 (1H, m), 4.02 (3H, s), 4.02–4.10 (1H, m), 4.32–4.42 (1H, m), 5.14 (2H, s), 5.15–5.20 (1H, m), 5.40 (1H, d, J=14.0 Hz), 5.53 (1H, d, J=14.0 Hz), 7.57 (2H, d, J=8.7 Hz), 7.73 (2H, d, J=8.5 Hz), 8.18–8.26 (4H, m), 8.74 (1H, s), 9.73 (1H, s)

c) (1S,5R,6S)-2-[7-(2-Aminoethyl)thio-6-methylimidazo[5,1-b]thiazolium-2-yl]-6-((1R)-1-hydroxyethyl)-1-methyl-1-carbapen-2-em-3-carboxylate (intramolecular salt)

The procedure of Example 3b) was repeated, except that the whole quantity of 4-nitrobenzyl (1S,5R,6S)-6-((1R)-1-hydroxyethyl)-1-methyl-2-[6-methyl-7-[2-(4-nitrobenzyloxycarbonyl)aminoethyl]thioimidazo[5,1-b]thiazolium-2-yl]-1-carbapen-2-em-3-carboxylate iodide prepared in step b) was used as the starting compound. Thus, 7.5 mg of the title compound was prepared.

NMR (D$_2$O) δ (HOD=4.80 ppm): 1.27 (3H, d, J=7.4 Hz), 1.32 (3H, d, J=6.3 Hz), 3.10–3.26 (4H, m), 3.57 (1H, dd, J$_1$=6.1 Hz, J$_2$=2.8 Hz), 3.60–3.73 (1H, m), 4.09 (3H, s), 4.23–4.32 (1H, m), 4.35 (1H, dd, J$_1$=9.4 Hz, J$_2$=2.8 Hz), 8.17 (1H, s), 9.38 (1H, s)

Example 30
(5R,6S)-6-((1R)-1-Hydroxyethyl)-2-(3-hydroxymethyl-6-methyl-7-methylthioimidazo[5,1-b]-thiazolium-2-yl)-1-carbapen-2-em-3-carboxylate (intramolecular salt)

a) 4-Nitrobenzyl (5R,6S)-2-(3-t-butyldimethyl-silyloxymethyl-7-methylthioimidazo[5,1-b]thiazol-2-yl)-6-((1R)-1-hydroxyethyl)-1-carbapen-2-em-3-carboxylate The procedure of Example 1a) was repeated, except that 522 mg of 4-nitrobenzyl (3R,5R,6S)-6-((1R)-1-hydroxyethyl)-2-oxo-1-carbapenam-3-carboxylate and 995 mg of 3-t-butyldimethylsilyloxymethyl-7-methylthio-2-(tri-n-butylstannyl)imidazo[5,1-b]thiazole were used as the starting compounds. Thus, 561 mg of 4-nitrobenzyl (5R,6S)-2-(3-t-butyldimethylsilyloxymethyl-7-methylthio-imidazo[5,1-b]thiazol-2-yl)-6-((1R)-1-hydroxyethyl)-1-carbapen-2-em-3-carboxylate was prepared.

NMR (CDCl$_3$) δ: 0.01 (6H, s), 0.83 (9H, s), 1.39 (3H, d, J=6.3 Hz), 2.43 (3H, s), 3.1–3.2 (2H, m), 3.34 (1H, dd, J$_1$=6.5 Hz, J$_2$=3.0 Hz), 4.25–4.45 (2H, m), 4.49 (2H, s), 5.21 (1H, d, J=13.7 Hz), 5.41 (1H, d, J=13.7 Hz), 7.56 (2H, d, J=8.8 Hz), 8.07 (1H, s), 8.17 (2H, d, J=8.8 Hz)

b) 4-Nitrobenzyl (5R,6S)-6-((1R)-1-hydroxyethyl)-2-(3-hydroxymethyl-7-methylthioimidazo[5,1-b]thiazol-2-yl)-1-carbapen-2-em-3-carboxylate The procedure of Example 12b) was repeated, except that 561 mg of 4-nitrobenzyl (5R,6S)-2-(3-t-butyldimethylsilyloxymethyl-7-methylthioimidazo[5,1-b]-thiazol-2-yl)-6-((1R)-1-hydroxyethyl)-1-carbapen-2-em-3-carboxylate was used as the starting compound. Thus, 315 mg of 4-nitrobenzyl (5R,6S)-6-((1R)-1-hydroxyethyl)-2-(3-hydroxymethyl-7-methylthioimidazo[5,1-b]thiazol-2-yl)-1-carbapen-2-em-3-carboxylate was prepared.

NMR (CDCl$_3$) δ: 1.39 (3H, d, J=6.3 Hz), 2.43 (3H, s), 3.1–3.25 (2H, m), 3.36 (1H, dd, J$_1$=6.4 Hz, J$_2$=3.1 Hz), 4.25–4.45 (2H, m), 4.45–4.6 (2H, m), 5.26 (1H, d, J=13.6 Hz), 5.47 (1H, d, J=13.6 Hz), 7.63 (2H, d, J=8.9 Hz), 8.18 (1H, s), 8.23 (2H, d, J=8.9 Hz)

c) 4-Nitrobenzyl (5R,6S)-6-((1R)-1-hydroxyethyl)-2-(3-hydroxymethyl-6-methyl-7-methylthioimidazo[5,1-b]thiazolium-2-yl)-1-carbapen-2-em-3-carboxylate iodide The procedure of Example 12c) was repeated, except that the reaction was carried out in a mixed solvent composed of dichloromethane and DMF and 100 mg of 4-nitrobenzyl (5R,6S)-6-((1R)-1-hydroxyethyl)-2-(3-hydroxymethyl-7-methylthioimidazo[5,1-b]thiazol-2-yl)-1-carbapen-2-em-3-carboxylate was used as the starting compound. Thus, 4-nitrobenzyl (5R,6S)-6-((1R)-1-hydroxyethyl)-2-(3-hydroxymethyl-6-methyl-7-methylthio-imidazo[5,1-b]thiazolium-2-yl)-1-carbapen-2-em-3-carboxylate iodide was prepared.

NMR (DMSO-d$_6$) δ: 1.16 (3H, d, J=6.2 Hz), 2.41 (3H, s), 3.1–3.45 (2H, m), 3.60 (1H, dd, J$_1$=5.8 Hz, J$_2$=3.1 Hz), 4.03 (3H, s), 4.0–4.1 (1H, m), 4.3–4.4 (1H, m), 4.4–4.6 (2H, m), 5.15 (1H, d, J=5.0 Hz), 5.24 (1H, d, J=12.9 Hz), 5.33 (1H, d, J=12.9 Hz), 5.84 (1H, t, J=5.5 Hz), 7.55 (2H, d, J=8.8 Hz), 8.10 (2H, d, J=8.8 Hz), 9.82 (1H, s)

d) (5R,6S)-6-((1R)-1-Hydroxyethyl)-2-(3-hydroxymethyl-6-methyl-7-methylthioimidazo[5,1-b]thiazolium-2-yl)-1-carbapen-2-em-3-carboxylate (intramolecular salt)

The procedure of Example 3b) was repeated, except that the whole quantity of 4-nitrobenzyl (5R,6S)-6-((1R)-1-hydroxyethyl)-2-(3-hydroxymethyl-6-methyl-7-methylthioimidazo[5,1-b]thiazolium-2-yl)-1-carbapen-2-em-3-carboxylate iodide prepared in step c) was used as the starting compound. Thus, 19.4 mg of the title compound was prepared.

NMR (D$_2$O) δ (HOD=4.80 ppm): 1.30 (3H, d, J=6.3 Hz), 2.42 (3H, s), 3.20 (1H, dd, J$_1$=17.3 Hz, J$_2$=10.1 Hz), 3.34 (1H, dd, J$_1$=17.3 Hz, J$_2$=8.3 Hz), 3.61 (1H, dd, J$_1$=5.8 Hz, J$_2$=3.0 Hz), 4.09 (3H, s), 4.2–4.3 (1H, m), 4.35–4.45 (1H, m), 4.72 (2H, s), 9.41 (1H, s)

Example 31
(1S,5R,6S)-2-[6-(2-Bromoethyl)-7-methyl-thioimidazo[5,1-b]thiazolium-2-yl]-6-((1R)-1-hydroxyethyl)-1-methyl-1-carbapen-2-em-3-carboxylate (intramolecular salt)

a) 4-Nitrobenzyl (1S,5R,6S)-2-[6-(2-bromoethyl)-7-methylthioimidazo[5,1-b]thiazolium-2-yl]-6-((1R)-1-hydroxyethyl)-1-methyl-1-carbapen-2-em-3-carboxylate trifluoromethanesulfonate 2-Bromoethanol (0.021 ml) was dissolved in 1 ml of dichloromethane. The solution was cooled to −60° C. 2,6-

Lutidine (0.038 ml) and 0.053 ml of trifluoromethanesulfonic anhydride were then added to the cooled solution. The mixture was stirred for 20 min. Water (5 ml) was added to the reaction solution, and the mixture was extracted with 5 ml of dichloromethane. The extract was dried over anhydrous magnesium sulfate. 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (130 mg) was then added thereto. The solvent was removed by concentration until the volume of the solution was brought to 3 ml. The residue was stirred at room temperature for 18 hr. The solvent was then removed by distillation under the reduced pressure. Thus, 210 mg of 4-nitrobenzyl (1S,5R,6S)-2-[6-(2-bromoethyl)-7-methylthioimidazo[5,1-b]thiazolium-2-yl]-6-((1R)-1-hydroxyethyl)-1-methyl-1-carbapen-2-em-3-carboxylate trifluoromethanesulfonate as a crude product was prepared.

b) (1S,5R,6S)-2-[6-(2-Bromoethyl)-7-methylthioimidazo[5,1-b]thiazolium-2-yl]-6-((1R)-1-hydroxyethyl)-1-methyl-1-carbapen-2-em-3-carboxylate (intramolecular salt)

The procedure of Example 5b) was repeated, except that 210 mg of 4-nitrobenzyl (1S,5R,6S)-2-[6-(2-bromoethyl)-7-methylthioimidazo[5,1-b]thiazolium-2-yl]-6-((1R)-1-hydroxyethyl)-1-methyl-1-carbapen-2-em-3-carboxylate trifluoromethanesulfonate as the crude product was used as the starting compound. Thus, 10 mg of the title compound was prepared.

NMR (D$_2$O) δ (HOD=4.65 ppm): 1.16 (3H, d, J=7.3 Hz), 1.22 (3H, d, J=6.3 Hz), 2.33 (3H, s), 3.47 (1H, dd, J$_1$=6.1 Hz, J$_2$=2.9 Hz), 3.50–3.60 (1H, m), 3.83 (2H, t, J=7.7 Hz), 4.15–4.22 (1H, m), 4.26 (1H, dd, J$_1$=9.5 Hz, J$_2$=2.9 Hz), 4.80 (2H, t, J=5.7 Hz), 8.06 (1H, s)

Example 32

(5R,6S)-2-[6-(3-Aminopropyl)-3-methyl-7-methylthioimidazo[5,1-b]thiazolium-2-yl]-6-((1R)-1-hydroxyethyl)-1-carbapen-2-em-3-carboxylate (intramolecular salt)

a) 4-Nitrobenzyl (5R,6S)-6-((1R)-1-hydroxyethyl)-2-(3-methyl-7-methylthioimidazo[5,1-b]thiazol-2-yl)-1-carbapen-2-em-3-carboxylate The procedure of Example 1a) was repeated, except that 1.044 g of 4-nitrobenzyl (3R,5R,6S)-6-((1R)-1-hydroxyethyl)-2-oxo-1-carbapenam-3-carboxylate and 1.56 g of 3-methyl-7-methylthio-2-(tri-n-butylstannyl)imidazo[5,1-b]thiazole were used as the starting compounds. Thus, 927 mg of 4-nitrobenzyl (5R,6S)-6-((1R)-1-hydroxyethyl)-2-(3-methyl-7-methylthioimidazo-[5,1-b]thiazol-2-yl)-1-carbapen-2-em-3-carboxylate was prepared.

NMR (CDCl$_3$) δ: 1.40 (3H, d, J=6.3 Hz), 2.19 (3H, s), 2.43 (3H, s), 3.1–3.3 (2H, m), 3.36 (1H, dd, J$_1$=6.4 Hz, J$_2$=3.1 Hz), 4.25–4.45 (2H, m), 5.24 (1H, d, J=13.7 Hz), 5.43 (1H, d, J=13.7 Hz), 7.57 (2H, d, J=8.7 Hz), 7.85 (1H, s), 8.18 (2H, d, J=8.7 Hz)

b) 4-Nitrobenzyl (5R,6S)-6-((1R)-1-hydroxyethyl)-2-[3-methyl-7-methylthio-6-[3-(4-nitrobenzyloxycarbonyl)aminopropyl]imidazo[5,1-b]thiazolium-2-yl]-1-carbapen-2-em-3-carboxylate trifluoromethanesulfonate 3-(4-Nitrobenzyloxycarbonyl)amino-1-propanol (75.6 mg) was suspended in 2 ml of dichloromethane. 2,6-Lutidine (0.038 ml) and 0.052 ml of trifluoromethanesulfonic anhydride were added to the suspension at −60° C. under an argon atmosphere. The mixture was stirred at that temperature for 15 min. Brine was then added to the reaction solution, and the mixture was extracted with dichloromethane. The organic layer was dried over anhydrous magnesium sulfate, and was concentrated under the reduced pressure until the volume of the organic layer was brought to about 3 ml. 4-Nitrobenzyl (5R,6S)-6-((1R)-1-hydroxyethyl)-2-(3-methyl-7-methylthioimidazo[5,1-b]thiazol-2-yl)-1-carbapen-2-em-3-carboxylate (97.5 mg) was added to the residue. The mixture was stirred at room temperature for 3 hr, and purification was then carried out by column chromatography on Sephadex LH-20 (chloroform:methanol=1:1) to prepare 111 mg of 4-nitrobenzyl (5R,6S)-6-((1R)-1-hydroxyethyl)-2-[3-methyl-7-methylthio-6-[3-(4-nitrobenzyloxycarbonyl)aminopropyl]imidazo[5,1-b]-thiazolium-2-yl]-1-carbapen-2-em-3-carboxylate trifluoromethanesulfonate as a crude product.

c) (5R,6S)-2-[6-(3-Aminopropyl)-3-methyl-7-methylthioimidazo[5,1-b]thiazolium-2-yl]-6-((1R)-1-hydroxyethyl)-1-carbapen-2-em-3-carboxylate (intramolecular salt)

The procedure of Example 3b) was repeated, except that 111 mg of 4-nitrobenzyl (5R,6S)-6-((1R)-1-hydroxyethyl)-2-[3-methyl-7-methylthio-6-[3-(4-nitrobenzyloxycarbonyl)aminopropyl]imidazo[5,1-b]thiazolium-2-yl]-1-carbapen-2-em-3-carboxylate trifluoromethanesulfonate as the crude product was used as the starting compound. Thus, 2.8 mg of the title compound was prepared.

NMR (D$_2$O) δ (HOD=4.80 ppm): 1.30 (3H, d, J=6.3 Hz), 2.15–2.25 (2H, m), 2.36 (3H, s), 2.42 (3H, s), 3.0–3.4 (5H, m), 3.55–3.65 (1H, m), 4.2–4.45 (2H, m), 4.55–4.65 (2H, m), 8.30 (1H, s)

Example 33

(1S5R,6S)-2-[6-(2-Carbamoylethyl)-7-methylthioimidazo[5,1-b]thiazolium-2yl]-6-((1R)-1-hydroxyethyl)-1-methyl-1-carbapen-2-em-3-carboxylate (intramolecular salt)

a) 4-Nitrobenzyl (1S,5R,6S)-2-[6-(2-carbamoylethyl)-7-methylthioimidazo[5,1-b]thiazolium-2-yl]-6-((1R)-1-hydroxyethyl)-1-methyl-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (119 mg) was dissolved in 4 ml of acetone and 1 ml of DMF. 3-Bromopropionamide (351 mg) and 346 mg of sodium iodide were added to the solution. The mixture was stirred at room temperature for 20 days. The solvent was removed by distillation under the reduced pressure. The residue was purified by column chromatography on Sephadex LH-20 (chloroform:methanol=1:1) to prepare 58 mg of 4-nitrobenzyl (1S,5R,6S)-2-[6-(2-carbamoylethyl)-7-methylthioimidazo-[5,1-b]thiazolium-2-yl]-6-((1R)-1-hydroxyethyl)-1-methyl-1-carbapen-2-em-3-carboxylate iodide as a crude product.

b) (1S,5R,6S)-2-[6-(2-Carbamoylethyl)-7-methylthioimidazo[5,1-b]thiazolium-2-yl]-6-((1R)-1-hydroxyethyl)-1-methyl-1-carbpen-2em-3-carboxylate (intramolecular salt)

The procedure of Example 5b) was repeated, except that 58 mg of 4-nitrobenzyl (1S,5R,6S)-2-[6-(2-carbamoylethyl)-7-methylthioimidazo[5,1-b]thiazolium-2-yl]-6-((1R)-1-hydroxyethyl)-1-methyl-1-carbapen-2-em-3-carboxylate iodide as the crude product was used as the starting compound. Thus, 6 mg of the title compound was prepared.

NMR (D$_2$O) δ (HOD=4.65 ppm): 1.14 (3H, d, J=7.0 Hz), 1.20 (3H, d, J=6.3 Hz), 2.31 (3H, s), 2.86 (2H, t, J=6.5 Hz), 3.44 (1H, dd, J$_1$=6.1 Hz, J$_2$=2.7 Hz), 3.48–3.57 (1H, m), 4.13–4.20 (1H, m), 4.23 (1H, dd, J$_1$=9.5 Hz, J$_2$=2.9 Hz), 4.61 (2H, t, J=6.6 Hz), 8.02 (1H, s)

Example 34

(5R,6S)-2-(6-Carbamoylmethyl-3-methyl-7-methylthioimidazo[5,1-b]thiazolium-2-yl)-6-((1R)-1- hydroxyethyl)-1-carbapen-2-em-3-carboxylate (intramolecular salt)

a) 4-Nitrobenzyl (5R,6S)-6-((1R)-1-hydroxyethyl)-2-(6-carbamoylmethyl-3-methyl-7-methylthioimidazo[5,1-b]thiazolium-2-yl)-1-carbapen-2-em-3-carboxylate iodide The procedure of Example 3a) was repeated, except that 115 mg of, 4-nitrobenzyl (5R,6S)-6-((1R)-1-hydroxyethyl)-2-(3-methyl-7-methylthioimidazo[5,1-b]thiazol-2-yl)-1-carbapen-2-em-3-carboxylate was used as the starting compound. Thus, 141 mg of 4-nitrobenzyl (5R,6S)-6-((1R)-1-hydroxyethyl)-2-(6-carbamoylmethyl-3-methyl-7-methylthioimidazo[5,1-b]thiazolium-2-yl)-1-carbapen-2-em-3-carboxylate iodide as a crude product was prepared.

b) (5R,6S)-2-(6-Carbamoylethyl)-3-methyl-7-methylthioimidazo[5,1-b]thiazolium-2-yl)-6-((1R)-1-hydroxyethyl)-1-carbapen-2-em-3-carboxylate (intramolecular salt)

The procedure of Example 3b) was repeated, except that 141 mg of 4-nitrobenzyl (5R,6S)-6-((1R)-1-hydroxyethyl)-2-(6-carbamoylmethyl-3-methyl-7-methylthioimidazo[5,1-b]thiazolium-2-yl)-1-carbapen-2-em-3-carboxylate iodide as the crude product was used as the starting compound. Thus, 19.1 mg of the title compound was prepared.

NMR (D$_2$O) δ (HOD=4.80 ppm): 1.31 (3H, d, J=6.0 Hz), 2.38 (3H, s), 2.39 (3H, s), 3.1–3.25 (1H, m), 3.3–3.4 (1H, m), 3.6–3.7 (1R, m), 4.2–4.45 (2H, m), 5.35 (2H, s), 9.49 (1H, s)

Example 35

(1S,5R,6S)-2-(6-Carbamoylmethyl-7-ethylthioimidazo[5,1-b]thiazolium-2-yl)-6-((1R)-1-hydroxyethyl)-1-methyl-1-carbapen-2-em-3-carboxylate (intramolecular salt)

a) 4-Nitrobenzyl (1S,5R,6S)-2-(7-ethylthioimidazo[5,1-b]thiazol-2-yl)-6-((1R)-1-hydroxyethyl)-1-methyl-1-carbapen-2-em-3-carboxylate The procedure of Example 1a) was repeated, except that 724 mg of 4-nitrobenzyl (1R,3R,5R,6S)-6-((1R)-1-hydroxyethyl)-1-methyl-2-oxo-1-carbapenam-3-carboxylate and 1.04 g of 7-ethylthio-2-(tri-n-butylstannyl)imidazo[5,1-b]thiazole were used as the starting compounds. Thus, 731 mg of 4-nitrobenzyl (1S,5R,6S)-2-(7-ethylthioimidazo[5,1-b]thiazol-2-yl)-6-((1R)-1-hydroxyethyl)-1-methyl-1-carbapen-2-em-3-carboxylate was prepared.

NMR (CDCl$_3$) δ: 1.26 (3H, t, J=7.3 Hz), 1.31 (3H, d, J=7.2 Hz), 1.40 (3H, d, J=6.1 Hz), 2.84 (2H, q, J=7.3 Hz), 3.37 (1H, dd, J$_1$=6.5 Hz, J$_2$=2.8 Hz), 3.4–3.5 (1H, m), 4.25–4.35 (1H, m), 4.38 (1H, dd, J$_1$=9.4 Hz, J$_2$=2.8 Hz), 5.28 (1H, d, J=13.7 Hz), 5.53 (1H, d, J=13.7 Hz), 7.68 (2H, d, J=8.4 Hz), 8.03 (1H, s), 8.24 (2H, d, J=8.4 Hz), 8.30 (1H, s)

b) 4-Nitrobenzyl (1S,5R,6S)-2-(6-carbamoylmethyl-7-ethylthioimidazo[5,1-b]thiazolium-2-yl)-6-((1R)-1-hydroxyethyl)-1-methyl-1-carbapen-2-em-3-carboxylate iodide The procedure of Example 3a) was repeated, except that 106 mg of 4-nitrobenzyl (1S,5R,6S)-2-(7-ethylthioimidazo[5,1-b]thiazol-2-yl)-6-((1R)-1-hydroxyethyl)-1-methyl-1-carbapen-2-em-3-carboxylate was used as the starting compound. Thus, 134 mg of 4-nitrobenzyl (1S,5R,6S)-2-(6-carbamoylmethyl-7-ethylthioimidazo[5,1-b]thiazolium-2-yl)-6-((1R)-1-hydroxyethyl)-1-methyl-1-carbapen-2-em-3-carboxylate iodide was prepared.

NMR (CD$_3$OD) δ: 1.27 (3H, t, J=7.4 Hz), 1.32 (3H, d, J=6.3 Hz), 1.34 (3H, d, J=7.1 Hz), 2.87 (2H, q, J=7.4 Hz), 3.50 (1H, dd, J$_1$=6.5 Hz, J$_2$=2.9 Hz), 3.7–3.85 (1H, m), 4.1–4.2 (1H, m), 4.44 (1H, dd, J$_1$=9.8 Hz, J$_2$=2.9 Hz), 5.31 (2H, s), 5.38 (1H, d, J=13.7 Hz), 5.55 (1H, d, J=13.7 Hz), 7.75 (2H, d, J=8.9 Hz), 8.23 (2H, d, J=8.9 Hz), 8.62 (1H, s)

c) (1S,5R,6S)-2-(6-Carbamoylethyl)-7-ethylthioimidazo[5,1-b]thiazolium-2-yl)-6-((1R)-1-hydroxyethyl)-1-methyl-1-carbapen-2-em-3-carboxylate (intramolecular salt)

The procedure of Example 3b) was repeated, except that 133 mg of 4-nitrobenzyl (1S,5R,6S)-2-(6-carbamoylmethyl-7-ethylthioimidazo[5,1-b]thiazolium-2-yl)-6-((1R)-1-hydroxyethyl)-1-methyl-1-carbapen-2-em-3-carboxylate iodide was used as the starting compound. Thus, 54.4 mg of the title compound was prepared.

NMR (D$_2$O) δ (HOD=4.80 ppm): 1.20 (3H, t, J=7.4 Hz), 1.27 (3H, d, J=7.3 Hz), 1.31 (3H, d, J=6.4 Hz), 2.82 (2H, q, J=7.4 Hz), 3.56 (1H, dd, J$_1$=6.1 Hz, J$_2$=2.7 Hz), 3.6–3.7 (1H, m), 4.25–4.35 (1H, m), 4.35 (1H, dd, J$_1$=9.6 Hz, J$_2$=2.7 Hz), 5.32 (2H, s), 8.19 (1H, s)

Example 36

(5R,6S)-2-[7-(2-Aminoethyl))thio-6-methylimidazo[5,1-b]thiazolium-2-yl]-6-((1R)-1-hydroxyethyl)-1-carbapen-2-em-3-carboxylate (intramolecular salt)

a) 4-Nitrobenzyl (5R,6S)-6-((1R)-1-hydroxyethyl)-2-[7-[2-(4-nitrobenzyloxycarbonyl)aminoethyl]thioimidazo-[5,1-b]thiazol-2-yl]-1-carbapen-2-em-3-carboxylate The procedure of Example 1a) was repeated, except that 201 mg of 4-nitrobenzyl (3R,5R,6S)-6-((1R)-1-hydroxyethyl)-2-oxo-1-carbapenam-3-carboxylate and 424 mg of 7-[2-(4-nitrobenzyloxycarbonyl)aminoethyl]thio-2-(tri-n-butylstannyl)imidazo[5,1-b]thiazole were used as the starting compounds. Thus, 200 mg of 4-nitrobenzyl (5R,6S)-6-((1R)-1-hydroxyethyl)-2-[7-[2-(4-nitrobenzyloxycarbonyl)aminoethyl]thioimidazo-[5,1-b-]thiazol-2-yl-]-1-carbapen-2-em-3-carboxylate was prepared.

NMR (CDCl$_3$) δ: 1.40 (3H, d, J=6.3 Hz), 2.86–2.94 (2H, m), 3.28–3.37 (3H, m), 3.40–3.48 (2H, m), 4.28–4.40 (2H, m), 5.19 (2H, s), 5.31 (1H, d, J=13.5 Hz), 5.54 (1H, d, J=13.5 Hz), 6.10 (1H, br s), 7.48 (2H, d, J=8.6 Hz), 7.69 (2H, d, J=8.9 Hz), 8.00 (1H, s), 8.17 (1H, s), 8.19 (2H, d, J=8.6 Hz), 8.24 (2H, d, J=8.9 Hz)

b) 4-Nitrobenzyl (5R,6S)-6-((1R)-1-hydroxyethyl)-2-[6-methyl-7-[2-(4-nitrobenzyloxycarbonyl)aminoethyl]-thioimidazo[5,1-b]thiazolium-2-yl]-1-carbapen-2-em-3-carboxylate iodide The procedure of Example 12c) was repeated, except that the reaction was carried out in a mixed solvent composed of dichloromethane and DMF and 122 mg of 4-nitrobenzyl (5R,6S)-6-((1R)-1-hydroxyethyl)-2-[7-[2-(4-nitrobenzyloxycarbonyl)aminoethyl]thioimidazo[5,1-b]thiazol-2-yl]-1-carbapen-2-em-3-carboxylate was used as the starting compound. Thus, 4-nitrobenzyl (5R,6S)-6-((1R)-1-hydroxyethyl)-2-[6-methyl-7-[2-(4-nitrobenzyloxycarbonyl)aminoethyl]thioimidazo[5,1-b]thiazolium-2-yl]-1-carbapen-2-em-3-carboxylate iodide was prepared.

NMR (DMSO-d$_6$) δ: 1.17 (3H, d, J=6.5 Hz), 2.9–3.0 (2H, m), 3.15–3.25 (2H, m), 3.4–3.5 (2H, m), 3.55–3.65 (1H, m), 3.95–4.05 (1H, m), 4.02 (3H, s), 4.25–4.35 (1H, m), 5.12 (2H, s), 5.15–5.25 (1H, m), 5.43 (1H, d, J=13.8 Hz), 5.55 (1H, d, J=13.8 Hz), 7.55 (2H, d, J=8.6 Hz), 7.62 (1H, br s), 7.75 (2H, d, J=8.5 Hz), 8.2–8.3 (4H, m), 8.66 (1H, s), 9.75 (1H, s)

c) (5R,6S)-2-[7-(2-Aminoethyl)thio-6-methylimidazo[5,1-b]thiazolium-2-yl]-6-((1R)-1-hydroxyethyl)-1-carbapen-2-em-3-carboxylate (intramolecular salt)

The procedure of Example 3b) was repeated, except that the whole quantity of 4-nitrobenzyl (5R,6S)-6-((1R)-1-hydroxyethyl)-2-[6-methyl-7-[2-(4-nitrobenzyloxycarbonyl)aminoethyl]thioimidazo[5,1-b]thiazolium-2-yl]-1-carbapen-2-em-3-carboxylate iodide prepared in step b) was used as the starting compound. Thus, 15.6 mg of the title compound was prepared.

NMR (D$_2$O) δ (HOD=4.80 ppm): 1.31 (3H, d, J=6.2 Hz), 3.1–3.25 (4H, m), 3.3–3.5 (2H, m), 3.5–3.6 (1H, m), 4.08 (3H, s), 4.2–4.4 (2H, m), 8.02 (1H, s), 9.37 (1H, s)

Example 37
(5R,6S)-2-[5,7-Bis(methylthio)-6-methylimidazo[5,1-b]thiazolium-2-yl]-6-((1R)-1-hydroxyethyl)-1-carbapen-2-em-3-carboxylate (intramolecular salt)

a) 4-Nitrobenzyl (5R,6S)-2-[5,7-bis(methylthio)imidazo[5,1-b]thiazol-2-yl]-6-((1R)-1-hydroxyethyl)-1-carbapen-2-em-3-carboxylate The procedure of Example 1a) was repeated, except that 803 mg of 4-nitrobenzyl (3R,5R,6S)-6-((1R)-1-hydroxyethyl)-2-oxo-1-carbapenam-3-carboxylate and 1.18 g of 5,7-bis(methylthio)-2-(tri-n-butylstannyl)imidazo[5,1-b]thiazole were used as the starting compounds. Thus, 810 mg of 4-nitrobenzyl (5R,6S)-2-[5,7-bis(methylthio)imidazo[5,1-b]thiazol-2-yl]-6-((1R)-1-hydroxyethyl)-1-carbapen-2-em-3-carboxylate was prepared.

NMR (CDCl$_3$) δ: 1.39 (3H, d, J=6.3 Hz), 2.42 (3H, s), 2.58 (3H, s), 3.30–3.40 (3H, m), 4.29–4.37 (2H, m), 5.33 (1H, d, J=13.7 Hz), 5.56 (1H, d, J=13.4 Hz), 7.69 (2H, d, J=9.0 Hz), 7.96 (1H, s), 8.25 (2H, d, J=9.0 Hz)

b) 4-Nitrobenzyl (5R,6S)-2-[5,7-bis(methylthio)-6-methylimidazo[5,1-b]thiazolium-2-yl]-6-((1R)-1-hydroxyethyl)-1-carbapen-2-em-3-carboxylate trifluoromethanesulfonate 4-Nitrobenzyl (5R,6S)-2-[5,7-bis(methylthio)imidazo[5,1-b]thiazol-2-yl]-6-((1R)-1-hydroxyethyl)-1-carbapen-2-em-3-carboxylate (86 mg) was dissolved in 1.5 ml of dichloromethane. Methyl trifluoromethanesulfonate (0.018 ml) was added to the solution. The mixture was stirred at room temperature for 30 min. The reaction solution was added dropwise to 10 ml of hexane. The precipitated solid was collected by filtration to prepare 70 mg of 4-nitrobenzyl (5R,6S)-2-[5,7-bis(methylthio)-6-methylimidazo[5,1-b]thiazolium-2-yl]-6-((1R)-1-hydroxyethyl)-1-carbapen-2-em-3-carboxylate trifluoromethanesulfonate.

NMR (DMSO-d$_6$) δ: 1.17 (3H, d, J=6.1 Hz), 2.44 (3H, s), 2.63 (3H, s), 3.50–3.67 (3H, m), 3.99–4.07 (4H, m), 4.29–4.36 (1H, m), 5.46 (1H, d, J=13.9 Hz), 5.58 (1H, d, J=13.9 Hz), 7.77 (2H, d, J=9.1 Hz), 8.25 (2H, d, J=9.1 Hz), 8.63 (1H, s)

c) (5R,6S)-2-[5,7-Bis(methylthio)-6-methylimidazo[5,1-b]thiazolium-2-yl]-6-((1R)-1-hydroxyethyl)-1-carbapen-2-em-3-carboxylate (intramolecular salt)

The procedure of Example 5b) was repeated, except that 70 mg of 4-nitrobenzyl (5R,6S)-2-[5,7-bis(methylthio)-6-methylimidazo[5,1-b]thiazolium-2-yl]-6-((1R)-1-hydroxyethyl)-1-carbapen-2-em-3-carboxylate trifluoromethanesulfonate was used as the starting compound. Thus, 19 mg of the title compound was prepared.

NMR (D$_2$O) δ (HOD=4.65 ppm): 1.22 (3H, d, J=6.3 Hz), 2.33 (3H, s), 2.46 (3H, s), 3.25–3.36 (2H, m), 3.48 (1H, dd, J$_1$=5.8 Hz, J$_2$=3.1 Hz), 4.01 (3H, s), 4.15–4.27 (2H, m), 7.99 (1H, s)

Example 38
(1S,5R,6S)-2-[7-Ethylthio-6-(2-hydroxyethyl)imidazo[5,1-b]thiazolium-2-yl]-6-((1R)-1-hydroxyethyl)-1-methyl-1-carbapen-2-em-3-carboxylate (intramolecular salt)

a) 4-Nitrobenzyl (1S,5R,6S)-2-[7-ethylthio-6-[2-(4-nitrobenzyloxy)carbonyloxyethyl)imidazo[5,1-b]thiazolium-2-yl]-6-((1R)-1-hydroxyethyl)-1-methyl-1-carbapen-2-em-3-carboxylate trifluoromethanesulfonate 2-(4-Nitrobenzyloxy)carbonyloxyethanol (66 mg) was dissolved in 2 ml of dichloromethane. 2,6-Lutidine (0.035 ml) and 0.048 ml of trifluoromethanesulfonic anhydride were added to the solution at −50° C. under an argon atmosphere. The mixture was stirred at that temperature for 15 min. Brine and a 1 N aqueous hydrochloric acid solution were then added to the reaction solution, and the mixture was extracted with dichloromethane. The organic layer was dried over anhydrous magnesium sulfate, and was concentrated under the reduced pressure until the volume of the organic layer was brought to about 3 ml. 4-Nitrobenzyl (1S,5R,6S)-2-(7-ethylthioimidazo[5,1-b]thiazol-2-yl)-6-((1R)-1-hydroxyethyl)-1-methyl-1-carbapen-2-em-3-carboxylate (122 mg) was added to the residue. The mixture was stirred at room temperature for 7 hr. The solvent was removed by distillation under the reduced pressure. The residue was washed with 3 ml of diethyl ether, and was then purified by column chromatography on Sephadex LH-20 (chloroform:methanol=1:1) to prepare 130 mg of 4-nitrobenzyl (1S,5R,6S)-2-[7-ethylthio-6-[2-(4-nitrobenzyloxy)carbonyloxyethyl]imidazo[5,1-b]thiazolium-2-yl]-6-((1R)-1-hydroxyethyl)-1-methyl-1-carbapen-2-em-3-carboxylate trifluoromethanesulfonate as a crude product.

b) (1S,5R,6S)-2-[7-Ethylthio-6-(2-hydroxyethyl)imidazo 5,1-b]thiazolium-2-yl]-6-((1R)-1-hydroxyethyl)-1-methyl-1-carbapen-2-em-3-carboxylate (intramolecular salt)

The procedure of Example 3b) was repeated, except that 130 mg of 4-nitrobenzyl (1S,5R,6S)-2-[7-ethylthio-6-[2-(4-nitrobenzyloxy)carbonyloxyethyl]imidazo[5,1-b]thiazolium-2-yl]-6-((1R)-1-hydroxyethyl)-1-methyl-1-carbapen-2-em-3-carboxylate trifluoromethanesulfonate as the crude product was used as the starting compound. Thus, 19.9 mg of the title compound was prepared.

NMR (D$_2$O) δ (HOD=4.80 ppm): 1.22 (3H, t, J=7.4 Hz), 1.27(3H, d, J=7.1 Hz), 1.32 (3H, d, J=6.5 Hz), 2.87 (2H, q, J=7.4 Hz), 3.56 (1H, dd, J$_1$=6.0 Hz, J$_2$=3.0 Hz), 3.6–3.7 (1H, m), 3.95–4.05 (2H, m), 4.2–4.4 (2H, m), 4.55–4.65 (2H, m), 8.16 (1H, s), 9.39 (1H, s)

Example 39
(1S,5R,6S)-2-[6-((3S,5S)-5-Carboxypyrrolidin-3-yl)-7-methylthioimidazo[5,1-b]thiazolium-2-yl]-6-((1R)-1-hydroxyethyl)-1-methyl-1-carbapen-2-em-3-carboxylate (intramolecular salt)

a) 4-Nitrobenzyl (1S,5R,6S)-6-((1R)-1-hydroxyethyl)-1-methyl-2-[7-methylthio-6-[(3S,5S)-5-(4-nitrobenzyl-oxycarbonyl)-1-(4-nitrobenzyloxycarbonyl)pyrrolidin-3-yl]imidazo[5,1-b]thiazolium-2-yl]-1-carbapen-2-em-3-carboxylate trifluoromethanesulfonate (2S,4R)-4-Hydroxy-1-(4-nitrobenzyloxycarbonyl)proline 4-nitrobenzyl ester (149 mg) was dissolved in 3 ml of dichloromethane. The solution was cooled to −60° C. 2,6-Lutidine (0.043 ml) and 0.059 ml of trifluoromethanesulfonic anhydride were then added to the cooled solution. The mixture was stirred for 30 min. Water (10 ml) was added to the reaction solution, and the mixture was extracted with 10 ml of dichloromethane. The extract was dried over anhydrous magnesium sulfate. 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (157 mg) was then added thereto. The solvent was removed by concentration until the volume of the solution was brought to 3 ml. The residue was stirred at room temperature for 20 hr. The solvent was then removed by distillation under the reduced pressure. The residue was purified by column chromatography on Sephadex LH-20 (chloroform:methanol=1:1) to prepare 192 mg of 4-nitrobenzyl (1S,5R,6S)-6-((1R)-1-hydroxyethyl)-1-methyl-2-[7-methylthio-6-[(3S,5S)-5-(4-nitrobenzyloxycarbonyl)-1-(4-nitrobenzyloxycarbonyl)pyrrolidin-3-yl]imidazo[5,1-b]-thiazolium-2-yl]-1-carbapen-2-em-3-carboxylate trifluoromethanesulfonate as a crude product.

b) (1S,5R,6S)-2-[6-((3S,5S)-5-Carboxypyrrolidin-3-yl)-7-methylthioimidazo[5,1-b]thiazolium-2-yl]-6-((1R)-1-hydroxyethyl)-1-methyl-1-carbapen-2-em-3-carboxylate (intramolecular salt)

The procedure of Example 5b) was repeated, except that 192 mg of 4-nitrobenzyl (1S,5R,6S)-6-((1R)-1-hydroxyethyl)-1-methyl-2-[7-methylthio-6-[(3S,5S)-5-(4-nitrobenzyloxycarbonyl)-1-(4-nitrobenzyloxycarbonyl)pyrrolidin-3-yl]imidazo[5,1-b]thiazolium-2-yl]-1-carbapen-2-em-3-carboxylate trifluoromethanesulfonate as the crude product was used as the starting compound. Thus, 26 mg of the title compound was prepared.

NMR (D$_2$O) δ (HOD=4.65 ppm): 1.14 (3H, d, J=7.1 Hz), 1.19 (3H, d, J=6.2 Hz), 2.14–2.21 (1H, m), 2.29 (3H, s), 2.87–2.97 (1H, m), 3.26–3.32 (1H, m), 3.42–3.58 (1H, m), 3.76–3.82 (1H, m), 4.12–4.19 (1H, m), 4.23 (1H, dd, J$_1$=9.5 Hz, J$_2$=2.7 Hz), 5.36–5.43 (1H, m), 8.05 (1H, s)

Example 40
(1S,5R,6S)-2-(7,8-Dihydroimidazo[5,1-b:4,3-b']bisthiazol-2-yl)-6-((1R)-1-hydroxyethyl)-1-methyl-1-carbapen-2-em-3-carboxylic acid (intramolecular salt)

a) 4-Nitrobenzyl (1S,5R,6S)-6-((1R)-1-hydroxyethyl)-2-[7-(2-methanesulfonyloxyethyl)thioimidazo[5,1-b]thiazol-2-yl]-1-methyl-1-carbapen-2-em-3-carboxylate 4-Nitrobenzyl (1S,5R,6S)-6-((1R)-1-hydroxyethyl)-2-[7-(2-hydroxyethyl)thioimidazo[5,1-b]thiazol-2-yl]-1-methyl-1-carbapen-2-em-3-carboxylate (62.8 mg) was dissolved in 2 ml of dichloromethane. N,N-Diisopropylethylamine (0.040 ml) and 0.011 ml of methanesulfonyl chloride were added to the solution at −50° C. The mixture was stirred at that temperature for 40 min. The reaction solution was then diluted with dichloromethane, and the diluted solution was washed with water. The organic layer was dried over anhydrous magnesium sulfate. The solvent was then removed by distillation under the reduced pressure. The residue was purified by column chromatography on silica gel (dichloromethane:methanol=20:1) to prepare 40.9 mg of 4-nitrobenzyl (1S,5R,6S)-6-((1R)-1-hydroxyethyl)-2-[7-(2-methanesulfonyloxyethyl)thioimidazo [5,1-b]thiazol-2-yl]-1-methyl-1-carbapen-2-em-3-carboxylate.

NMR (DCDl$_3$) δ: 1.32 (3H, d, J=7.2 Hz), 1.40 (3H, d, J=6.2 Hz), 3.08 (3H, s), 3.05–3.15 (2H, m), 3.38 (1H, dd, J$_1$=6.6 Hz, J$_2$=2.8 Hz), 3.4–3.5 (1H, m), 4.25–4.45 (4H, m), 5.28 (1H, d, J=13.8 Hz), 5.53 (1H, d, J=13.8 Hz), 7.68 (2H, d, J=8.5 Hz), 8.03 (1H, s), 8.24 (2H, d, J=8.5 Hz), 8.30 (1H, s)

b) (1S,5R,6S)-2-(7,8-Dihydroimidazo[5,1-b:4,3-b']bisthiazol-2-yl)-6-((1R)-1-hydroxyethyl)-1-methyl-1-carbapen-2-em-3-carboxylic acid (intramolecular salt)

4-Nitrobenzyl (1S,5R,6S)-6-((1R)-1-hydroxyethyl)-2-[7-(2-methanesulfonyloxyethyl)thioimidazo[5,1-b]thiazol-2-yl]-1-methyl-1-carbapen-2-em-3-carboxylate (77.6 mg) was dissolved in 4 ml of pyridine. The solution was stirred at room temperature for 3 days. The reaction solution was concentrated under the reduced pressure. The residue was purified by column chromatography on Sephadex LH-20 (chloroform:methanol=1:1). The purified product was allowed to react in the same manner, as in Example 3b);, and purification was performed by column chromatography on Cosmosil 40C$_{18}$-PREP (a 5 to 30% aqueous methanol solution). In this case, a first fraction was collected to obtain 2.6 mg of the title compound.

NMR (D$_2$O) δ (HOD=4.80 ppm): 1.31 (3H, d, J=6.3 Hz), 3.5–3.7 (2H, m), 3.95–4.05 (2H, m), 4.2–4.4 (2H, m), 4.15–4.3 (2H, m), 8.01 (1H, s), 9.23 (1H, s)

Example 41
(1S,5R,6S)-2-[6-(N,N-Dimethylcarbamoylmethyl)-7-methylthioimidazo[5,1-b]thiazolium-2-yl]6-((1R)-1-hydroxyethyl)-1-methyl-1-carbapen-2-em-3-carboxylate (intramolecular salt)

a) 4-Nitrobenzyl (1S,5R,6S)-2-[6-(N,N-dimethylcarbamoylmethyl)-7-methylthioimidazo[5,1-b]thiazolium-2-yl]-6-((1R)-1-hydroxyethyl)-1-methyl-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (100 mg) was dissolved in 2 ml of dichloromethane. N,N-Dimethyl-2-iodoacetamide (396 mg) was added to the solution. The mixture was stirred at room temperature for 3 days. The reaction solution was added dropwise to 30 ml of diethyl ether. The precipitated solid was collected by filtration to prepare 155 mg of 4-nitrobenzyl (1S,5R,6S)-2-[6-(N,N-dimethylcarbamoylmethyl)-7-methylthioimidazo[5,1-b]-thiazolium-2-yl]-6-((1R)-1-hydroxyethyl)-1-methyl-1-carbapen-2-em-3-carboxylate iodide as a crude product.

b) (1S,5R,6S)-2-[6-(N,N-Dimethylcarbamoylmethyl)-7-methylthioimidazo[5,1-b]thiazolium-2-yl]-6-((1R)-1-hydroxyethyl)-1-methyl-1-carbapen-2-em-3-carboxylate (intramolecular salt)

The procedure of Example 5b) was repeated, except that 155 mg of 4-nitrobenzyl (1S,5R,6S)-2-[6-(N,N-dimethylcarbamoylmethyl)-7-methylthioimidazo[5,1-b]-thiazolium-2-yl]-6-((1R)-1-hydroxyethyl)-1-methyl-1-carbapen-2-em-3-carboxylate iodide as the crude product was used as the starting compound. Thus, 37 mg of the title compound was prepared.

NMR (D$_2$O) δ (HOD=4.65 ppm): 1.10 (3H, d, J=7.1 Hz), 1.14 (3H, d, J=6.6 Hz), 2.16 (3H, s), 2.84 (3H, s), 3.05 (3H, s), 3.40 (1H, dd, J$_1$=5.8 Hz, J$_2$=2.7 Hz), 3.45–3.55 (1H, m), 4.08–4.15 (1H, m), 4.18 (1H, dd, J$_1$=9.4 Hz, J$_2$=2.8 Hz), 5.35 (2H, s), 8.03 (1H, s)

Example 42
(1S,5R,6S)-6-((1R)-1-Hydroxyethyl)-1-methyl-2-[7-methylthio-6-(4-morpholinecarbonylmethyl)imidazo-[5,1-b]thiazolium-2-yl]-1-carbapen-2-em-3-carboxylate (intramolecular salt)

a) 4-Nitrobenzyl (1S,5R,6S)-6-((1R)-1-hydroxyethyl)-1-methyl-2-[7-methylthio-6-(4-morpholinecarbonylmethyl) imidazo[5,1-b]thiazolium-2-yl]-1-carbapen-2-em-3-carboxylate bromide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (100 mg) was dissolved in 1 ml of dichloromethane and 1 ml of DMF. 4-Bromoacetylmorpholine (412 mg) was added to the solution. The mixture was stirred at room temperature for 4 days. The solvent was removed by distillation under the reduced pressure. The residue was purified by column chromatography on Sephadex LH-20 (chloroform:methanol=1:1) to prepare 126 mg of 4-nitrobenzyl (1S,5R,6S)-6-((1R)-1-hydroxyethyl)-1-methyl-2-[7-methylthio-6-(4-morpholinecarbonylmethyl)imidazo[5,1-b]thiazolium-2-yl]-1-carbapen-2-em-3-carboxylate bromide as a crude product.

b) (1S,5R,6S)-6-((1R)-1-Hydroxyethyl)-1-methyl-2-[7-methylthio-6-(4-morpholinecarbonylmethyl)imidazo[5,1-b]thiazolium-2-yl]-1-carbapen-2-em-3-carboxylate (intramolecular salt)

The procedure of Example 5b) was repeated, except that 126 mg of 4-nitrobenzyl (1S,5R,6S)-6-((1R)-1-hydroxyethyl)-1-methyl-2-[7-methylthio-6-(4- morpholinecarbonylmethyl)imidazo[5,1-b]thiazolium-2-yl]-1-carbapen-2-em-3-carboxylate bromide as the crude product was used as the starting compound. Thus, 49 mg of the title compound was prepared.

NMR (D$_2$O) δ (HOD=4.65 ppm): 1.14 (3H, d, J=7.1 Hz), 1.19 (3H, d, J=6.3 Hz), 2.22 (3H, s), 3.45 (1H, dd, J$_1$=6.0 Hz, J$_2$=2.9 Hz), 3.50–3.59 (3H, m), 3.62 (2H, t, J=4.7 Hz), 3.68 (2H, t, J=4.5 Hz), 3.75 (2H, t, J=4.7 Hz), 4.12–4.20 (1H, m), 4.23 (1H, dd, J$_1$=9.5 Hz, J$_2$=2.7 Hz), 5.45 (2H, s), 8.07 (1H, s)

Example 43

(1S,5R,6S)-2-(7-Benzoyl-6-methylimidazo[5,1-b]thiazolium-2-yl)-6-((1R)-1-hydroxyethyl)-1-methyl-1-carbapen-2-em-3-carboxylate (intramolecular salt)

a) 4-Nitrobenzyl (1S,5R,6S)-2-(7-benzoylimidazo[5,1-b]thiazol-2-yl)-6-((1R)-1-hydroxyethyl)-1-methyl-1-carbapen-2-em-3-carboxylate The procedure of Example 1a) was repeated, except that 543 mg of 4-nitrobenzyl (1R,3R,5R,6S)-6-((1R)-1-hydroxyethyl)-1-methyl-2-oxo-1-carbapenam-3-carboxylate and 931 mg of 7-benzoyl-2-(tri-n-butylstannyl)imidazo[5,1-b]thiazole were used as the starting compounds. Thus, 288 mg of 4-nitrobenzyl (1S,5R,6S)-2-(7-benzoylimidazo[5,1-b]thiazol-2-yl)-6-((1R)-1-hydroxyethyl)-1-methyl-1-carbapen-2-em-3-carboxylate was prepared.

NMR (DMSO-d$_6$) δ: 1.19 (3H, d, J=6.2 Hz), 1.25 (3H, d, J=7.1 Hz), 3.45 (1H, dd, J$_1$=5.7 Hz, J$_2$=2.7 Hz), 3.77 (1H, m), 4.04 (1H, m), 4.37 (1H, dd, J$_1$=10.1 Hz, J$_2$=2.7 Hz), 5.41 (1H, d, J=14.0 Hz), 5.55 (1H, d, J=14.0 Hz), 7.58 (3H, m), 7.75 (2H, d, J=8.8 Hz), 8.22 (2H, d, J=8.8 Hz), 8.44 (1H, s), 8.49 (2H, m), 8.62 (1H, 5)

b) 4-Nitrobenzyl (1S,5R,6S)-2-(7-benzoyl-6-methylimidazo[5,1-b]thiazolium-2-yl)-6-((1R)-1-hydroxyethyl)-1-methyl-1-carbapen-2-em-3-carboxylate hydrogencarbonate The procedure of Example 13b) was repeated, except that 97.2 mg of 4-nitrobenzyl (1S,5R,6S)-2-(7-benzoylimidazo[5,1-b]thiazol-2-yl)-6-((1R)-1-hydroxyethyl)-1-methyl-1-carbapen-2-em-3-carboxylate was used as the starting compound. Thus, 117 mg of 4-nitrobenzyl (1S,5R,6S)-2-(7-benzoyl-6-methylimidazo[5,1-b]-thiazolium-2-yl)-6-((1R)-1-hydroxyethyl)-1-methyl-1-carbapen-2-em-3-carboxylate hydrogencarbonate as a crude product was prepared.

c) (1S,5R,6S)-2-(7-Benzoyl-6-methylimidazo[5,1-b]thiazolium-2-yl)-6-((1R)-1-hydroxyethyl)-1-methyl-1-carbapen-2-em-3-carboxylate (intramolecular salt)

The procedure of Example 3b) was repeated, except that 117 mg of 4-nitrobenzyl (1S,5R,6S)-2-(7-benzoyl-6-methylimidazo[5,1-b]thiazolium-2-yl)-6-((1R)-1-hydroxyethyl)-1-methyl-1-carbapen-2-em-3-carboxylate hydrogencarbonate as the crude product was used as the starting compound. Thus, 24.6 mg of the title compound was prepared.

NMR (D$_2$O) δ (HOD=4.80 ppm): 1.20 (3H, d, J=6.9 Hz), 1.30 (3H, d, J=6.3 Hz), 3.5–3.65 (2H, m), 4.2–4.3 (2H, m), 4.32 (3H, s), 7.6–7.7 (2H, m), 7.75–7.85 (3H, m), 8.23 (1H, s), 9.50 (1H, s)

Example 44

(1S,5R,6S)-6-(1R)-1-Hydroxyethyl)-1-methyl-2-[7-methylthio-6-(pyrrolidin-3-yl)imidazo[5,1-b]-thiazolium-2-yl]-1-carbapen-2-em-3-carboxylate (intramolecular salt) hydrochloride (a mixture of diastereomers)

a) 4-Nitrobenzyl (1S,5R,6S)-6-((1R)-1-hydroxyethyl)-1-methyl-2-[7-methylthio-6-[1-(4-nitrobenzyloxycarbonyl)pyrrolidin-3-yl]imidazo[5,1-b]thiazolium-2-yl]-1-carbapen-2-em-3-carboxylate chloride (a mixture of diastereomers)

3-Hydroxy-1-(4-nitrobenzyloxycarbonyl)pyrrolidine (200 mg) was dissolved in 10 ml of dichloromethane. The solution was cooled to −60° C. 2,6-Lutidine (0.096 ml) and 0.132 ml of trifluoromethanesulfonic anhydride were then added to the cooled solution. The mixture was stirred for 15 min. Water (30 ml) was added to the reaction solution, and the mixture was extracted with 30 ml of dichloromethane. The extract was dried over anhydrous magnesium sulfate. 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (213 mg) was then added thereto. The solvent was removed by concentration until the volume of the solution was brought to 10 ml. The residue was stirred at room temperature for 2 days. The solvent was then removed by distillation under. the reduced pressure. The residue was purified by column chromatography on Sephadex LH-20 (chloroform:methanol=1:1), and was then subjected to column chromatography (methanol) on Amberlyst A-26 as an ion-exchange resin (chloro form) to prepare 386 mg of 4-nitrobenzyl (1S,5R,6S)-6-((1R)-1-hydroxyethyl)-1-methyl-2-[7-methylthio-6-[1-(4-nitrobenzyloxycarbonyl)pyrrolidin-3-yl]imidazo[5,1-b]thiazolium-2-yl]-1-carbapen-2-em-3-carboxylate chloride (a mixture of diastereomers) as a crude product.

b) (1S,5R,6S)-6-((1R)-1-Hydroxyethyl)-1-methyl-2-[7-methylthio-6-(pyrrolidin-3-yl)imidazo[5,1-b]-thiazolium-2-yl]-1-carbapen-2-em-3-carboxylate (intramolecular salt) hydrochloride (a mixture of diastereomers)

4-Nitrobenzyl (1S,5R,6S)-6-((1R)-1-hydroxyethyl)-1-methyl-2-[7-methylthio-6-[1-(4-nitrobenzyloxycarbonyl)pyrrolidin-3-yl]imidazo[5,1-b]thiazolium-2-yl]-1-carbapen-2-em-3-carboxylate chloride (a mixture of diastereomers) as the crude product (182 mg) was dissolved in 6 ml of THF and 6 ml of water. 10% Pd—C (120 mg) was added to the solution. The air in the reaction vessel was replaced by hydrogen, and the contents of the reaction vessel were stirred at room temperature for 3 hr. The catalyst was removed by filtration on Celite, and washed with water. The filtrate was washed with ethyl acetate, and was then concentrated under the reduced pressure until the volume of the filtrate was brought to about 5 ml. The residue was purified by column chromatography on Cosmosil 40C$_{18}$-PREP (a 20% aqueous methanol solution) to prepare 19 mg of the title compound.

NMR (D$_2$O) δ (HOD=4.65 ppm): 1.11 (3H, d, J=7.3 Hz), 1.15 (3H, d, J=6.3 Hz), 2.28 (3H, s), 2.44–2.54 (1H, m), 2.70–2.81 (1H, m), 3.39–3.55 (3H, m), 3.56–3.68 (2H, m), 3.93–4.01 (1H, m), 4.08–4.15 (1H, m), 4.19 (1H, dd, J$_1$=9.3 Hz, J$_2$=2.9 Hz), 5.50–5.58 (1H, m), 8.05 (1H, s), 9.40 (1H, s)

Example 45

(1S,5R,6S)-6-((1R)-1-Hydroxyethyl)-1-methyl-2-[6-(N-methylcarbamoylmethyl)-7-methylthioimidazo[5,1-b]thiazolium-2-yl]-1-carbapen-2-em-3-carboxylate (intramolecular salt)

a) 4-Nitrobenzyl (1S,5R,6S)-6-((1R)-1-hydroxyethyl)-1-methyl-2-[6-(N-methylcarbamoylmethyl)-7-methylthioimidazo[5,1-b]thiazolium-2-yl]-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (70 mg) was dissolved in 1.5 ml of acetone. 2-Iodo-N-methylacetamide (120 mg) was added to the solution. The mixture was stirred at room temperature for 5 days. The reaction solution was added dropwise to 20 ml of diethyl ether. The precipitated solid was collected by filtration to prepare 85 mg of 4-nitrobenzyl (1S,5R,6S)-6-((1R)-1-hydroxyethyl)-1-methyl-2-[6-(N-methylcarbamoylmethyl)-7-methylthioimidazo[5,1-b]thiazolium-2-yl]-1-carbapen-2-em-3-carboxylate iodide as a crude product.

b) (1S,5R,6S)-6-((1R)-1-Hydroxyethyl)-1-methyl-2-[6-(N-methylcarbamoylmethyl)-7-methylthioimidazo[5,1-b]thiazolium-2-yl]-1-carbapen-2-em-3-carboxylate (intramolecular salt)

The procedure of Example 5b) was repeated, except that 85 mg of 4-Nitrobenzyl (1S,5R,6S)-6-((1R)-1-hydroxyethyl)-1-methyl-2-[6-(N-methylcarbamoylmethyl)-7-methylthioimidazo[5,1-b]thiazolium-2-yl]-1-carbapen-2-em-3-carboxylate iodide as the crude product was used as the starting compound. Thus, 12 mg of the title compound was prepared.

NMR (D$_2$O) δ (HOD=4.65 ppm): 1.14 (3H, d, J=7.3 Hz), 1.19 (3H, d, J=6.4 Hz), 2.22 (3H, 8), 2.70 (3H, s), 3.44 (1H, dd, J$_1$=6.1 Hz, J$_2$=2.7 Hz), 3.49–3.58 (1H, m), 4.12–4.20 (1H, m), 4.23 (1H, dd, J$_1$=9.2 Hz, J$_2$=2.7 Hz), 5.14 (2H, s), 8.06 (1H, s)

Example 46
(1S,5R,6S)-6-((1R)-1-Hydroxyethyl)-2-[6-(4-hydroxyaminobenzyl)-7-methylthioimidazo[5,1-b]-thiazolium-2-yl]-1-methyl-1-carbapen-2-em-3-carboxylate (intramolecular salt)

a) 4-Nitrobenzyl (1S,5R,6S)-6-((1R)-1-hydroxyethyl)-1-methyl-2-[7-methylthio-6-(4-nitrobenzyl)imidazo[5,1-b]thiazolium-2-yl]-1-carbapen-2-em-3-carboxylate bromide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (87 mg) was dissolved in 3 ml of dichloromethane. 4-Nitrobenzyl bromide (307 mg) was added to the solution. The mixture was stirred at room temperature for 3 days. The solvent was removed by distillation under the reduced pressure. The residue was purified by column chromatography on Sephadex LH-20 (chloroform:methanol=1:1) to prepare 87 mg of 4-nitrobenzyl (1S,5R,6S)-6-((1R)-1-hydroxyethyl)-1-methyl-2-[7-methylthio-6-(4-nitrobenzyl)imidazo[5,1-b]-thiazolium-2-yl]-1-carbapen-2-em-3-carboxylate bromide as a crude product.

b) (1S,5R,6S)-6-((1R)-1-Hydroxyethyl)-2-[6-(4-hydroxyaminobenzyl)-7-methylthioimidazo[5,1-b]-thiazolium-2-yl]-1-methyl-1-carbapen-2-em-3-carboxylate (intramolecular salt)

The procedure of Example 44b) was repeated, except that 87 mg of 4-nitrobenzyl (1S,5R,6S)-6-((1R)-1-hydroxyethyl)-1-methyl-2-[7-methylthio-6-(4-nitrobenzyl)imidazo[5,1-b]thiazolium-2-yl]-1-carbapen-2-em-3-carboxylate bromide as the crude product was used as the starting compound. Thus, 6 mg of the title compound was prepared.

NMR (D$_2$O) δ (HOD=4.65 ppm): 1.11 (3H, d, J=6.1 Hz), 1.19 (3H, d, J=7.1 Hz), 2.02 (3H, s), 3.41–3.55 (2H, m), 4.12–4.25 (2H, m), 5.42 (2H, s), 6.96 (2H, d, J=7.8 Hz), 7.24 (2H, d, J=7.8 Hz), 7.97 (1H, s), 9.20 (1H, s)

Example 47
(1S,5R,6S)-6-((1R)-1-Hydroxyethyl)-1-methyl-2-(6-methyl-7-propylthioimidazo[5,1-b]thiazolium-2-yl)-1-carbapen-2-em-3-carboxylate (intramolecular salt)

a) 4-Nitrobenzyl (1S,5R,6S)-6-((1R)-1-hydroxyethyl)-1-methyl-2-(7-propylthioimidazo[5,1-b]thiazol-2-yl)-1-carbapen-2-em-3-carboxylate The procedure of Example 1a) was repeated, except that 724 mg of 4-nitrobenzyl (1R,3R,5R,6S)-6-((1R)-1-hydroxyethyl)-1-methyl-2-oxo-1-carbapenam-3-carboxylate and 1.07 g of 7-propylthio-2-(tri-n-butylstannyl)imidazo[5,1-b]thiazole were used as the starting compounds. Thus, 369 mg of 4-nitrobenzyl (1S,5R,6S)-6-((1R)-1-hydroxyethyl)-1-methyl-2-(7-propylthioimidazo[5,1-b]thiazol-2-yl)-1-carbapen-2-em-3-carboxylate was prepared.

NMR (CDCl$_3$) δ: 0.99 (3H, t, J=7.4 Hz), 1.31 (3H, d, J=7.1 Hz), 1.40 (3H, d, J=6.3 Hz), 1.5–1.7 (2H, M), 2.75–2.85 (2H, m), 3.37 (1H, dd, J$_1$=6.3 Hz, J$_2$=2.7 Hz), 3.4–3.55 (1H, m), 4.3–4.4 (2H, m), 5.28 (1H, d, J=13.7 Hz), 5.53 (1H, d, J=13.7 Hz), 7.68 (2H, d, J=8.5 Hz), 8.02 (1H, s), 8.25 (2H, d, J=8.5 Hz), 8.31 (1H, s)

b) 4-Nitrobenzyl (1S,5R,6S)-6-((1R)-1-hydroxyethyl)-1-methyl-2-(6-methyl-7-propylthioimidazo[5,1-b]thiazolium-2-yl)-1-carbapen-2-em-3-carboxylate trifluoromethanesulfonate 4-Nitrobenzyl (1S,5R,6S)-6-((1R)-1-hydroxyethyl)-1-methyl-2-(7-propylthioimidazo[5,1-b]thiazol-2-yl)-1-carbapen-2-em-3-carboxylate (91.5 mg) was dissolved in 2 ml of dichloromethane. Methyl trifluoromethanesulfonate (0.023 ml) was added to the solution. The mixture was stirred at room temperature for 15 min. The reaction solution was concentrated under the reduced pressure to prepare 4-nitrobenzyl (1S,5R,6S)-6-((1R)-1-hydroxyethyl)-1-methyl-2-(6-methyl-7-propylthioimidazo[5,1-b]thiazolium-2-yl)-1-carbapen-2-em-3-carboxylate trifluoromethanesulfonate.

NMR (CDCl$_3$) δ: 1.04 (3H, t, J=7.4 Hz), 1.33 (3H, d, J=7.1 Hz), 1.38 (3H, d, J=6.2 Hz), 1.6–1.7 (2H, m), 2.7–2.8 (2H, m), 3.40 (1H, dd, J$_1$=6.7 Hz, J$_2$=2.8 Hz), 3.75–3.85 (1H, m), 4.09 (3H, s), 4.2–4.35 (1H, m), 4.41 (1H, dd, J$_1$=9.6 Hz, J$_2$=2.8 Hz), 5.32 (1H, d, J=13.5 Hz), 5.55 (1H, d, J=13.5 Hz), 7.69 (2H, d, J=8.7 Hz), 8.24 (2H, d, J=8.7 Hz), 8.70 (1H, s), 9.80 (1H, s)

c) (1S,5R,6S)-6-((1R)-1-Hydroxyethyl)-1-methyl-2-(6-methyl-7-propylthioimidazo[5,1-b]thiazolium-2-yl)-1-carbapen-2-em-3-carboxylate (intramolecular salt)

The procedure of Example 3b) was repeated, except that the whole quantity of 4-nitrobenzyl (1S,5R,6S )-6-((1R)-1-hydroxyethyl)-1-methyl-2-(6-methyl-7-propylthioimidazo[5,1-b]thiazolium-2-yl)-1-carbapen-2-em-3-carboxylate trifluoromethanesulfonate prepared in step b) was used as the starting compound. Thus, 31.5 mg of the title compound was prepared.

NMR (D$_2$O) δ (HOD=4.80 ppm): 0.97 (3H, t, J=7.2 Hz), 1.26 (3H, d, J=7.1 Hz), 1.32 (3H, d, J=6.4 Hz), 1.45–1.6 (2H, m), 2.75–2.85 (2H, m), 3.5–3.7 (2H, m), 4.05 (3H, s), 4.25–4.4 (2H, m), 8.13 (1H, s), 9.28 (1H, s)

Example 48
(1S,5R,6S)-6-((1R)-1-Hydroxyethyl)-1-methyl-2-[7-methylthio-6-(2-nitroethyl)imidazo[5,1-b]-thiazolium-2-yl]-1-carbapen-2-em-3-carboxylate (intramolecular salt)

a) 4-Nitrobenzyl (1S,5R,6S)-6-((1R)-1-hydroxyethyl)-1-methyl-2-[7-methylthio-6-(2-nitroethyl)imidazo[5,1-b]thiazolium-2-yl]-1-carbapen-2-em-3-carboxylate trifluoromethanesulfonate 2-Nitroethanol (47 mg) was dissolved in 5 ml of dichloromethane. The solution was cooled to −60° C. 2,6-Lutidine (0.066 ml) and 0.091 ml of trifluoromethanesulfonic anhydride were then added to the solution. The mixture was stirred for 20 min. Water (10 ml) was added to the reaction solution, and the mixture was extracted with 10 ml of dichloromethane. The extract was dried over anhydrous magnesium sulfate. 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (233 mg) was then added thereto. The solvent was removed by concentration until the volume of the solution was brought to 5 ml. The residue was stirred at room temperature for one hr. The reaction solution was added dropwise to 40 ml of diethyl ether. The precipitated solid was collected by filtration to prepare 269 mg of 4-nitrobenzyl (1S,5R,6S)-6-((1R)-1-hydroxyethyl)-1-methyl-2-[7-methylthio-6-(2-nitroethyl) imidazo[-[5,1-b-]thiazolium-2-yl]-1-carbapen-2-em-3-carboxylate trifluoromethanesulfonate as a crude product.

b) (1S,5R,6S)-6-((1R)-1-Hydroxyethyl)-1-methyl-2-[7-methylthio-6-(2-nitroethyl)imidazo[5,1-b]thiazolium-2-yl]-1-carbapen-2-em-3-carboxylate (intramolecular salt)

The procedure of Example 44b) was repeated, except that 101 mg of 4-nitrobenzyl (1S,5R,6S)-6-((1R)-1-hydroxyethyl)-1-methyl-2-[7-methylthio-6-(2-nitroethyl) imidazo[5,1-b]thiazolium-2-yl]-1-carbapen-2-em-3-carboxylate trifluoromethanesulfonate as the crude product was used as the starting compound. Thus, 12 mg of the title compound was prepared.

NMR (D$_2$O) δ (HOD=4.65 ppm): 1.12 (3H, d, J=7.1 Hz), 1.18 (3H, d, J=6.1 Hz), 2.30 (3H, s), 3.43 (1H, dd, J$_1$=6.4 Hz, J$_2$=2.7 Hz), 3.46–3.56. (1H, m), 4.10–4.18 (1H, m), 4.22 (1H, dd, J$_1$=9.5 Hz, J$_2$=2.7 Hz), 4.62–4.70 (2H, m), 4.91–5.05 (2H, m), 8.01 (1H, s), 9.34 (1H, s)

Example 49

(1S,5R,6S )-6-((1R)-1-Hydroxyethyl)-1-methyl-2-[6-[2-(N-methylamino)ethyl]-7-methylthioimidazo[5.1-b] thiazolium-2-yl]-1-carbapen-2-em-3-carboxylate (intramolecular salt)

a) 4-Nitrobenzyl (1S,5R,6S)-6-((1R)-1-hydroxyethyl)-1-methyl-2-[6-[2-N-methyl-N-(4-nitrobenzyloxycarbonyl) amino]ethyl]-7-methylthioimidazo[5,1-b]-thiazolium-2-yl]-1-carbapen-2-em-3-carboxylate trifluoromethanesulfonate 2-[N-Methyl-N-(4-nitrobenzyloxycarbonyl)amino]-ethanol (191 mg) was dissolved in 7 ml of dichloromethane. The solution was cooled to −60° C. 2,6-Lutidine (0.096 ml) and 0.133 ml of trifluoromethanesulfonic anhydride were then added to the cooled solution. The mixture was stirred for 20 min. Water (25 ml) was added to the reaction solution, and the mixture was extracted with 25 ml of dichloromethane. The extract was dried over anhydrous magnesium sulfate. 4-Nitrobenzyl (1S,5R,6S)-6-((1R)-1-hydroxyethyl)-1-methyl-2-(7-methylthioimidazo[5,1-b] thiazol-2-yl)-1-carbapen-2-em-3-carboxylate (174 mg) was then added thereto. The solvent was removed by concentration until the volume of the solution was brought to 3 ml. The residue was stirred at room temperature for 30 min. The solvent was then removed by distillation under the reduced pressure. The residue was purified by column chromatography on Sephadex LH-20 (chloroform:methanol=1:1) to prepare 214 mg of 4-nitrobenzyl (1S,5R,6S)-6-((1R)-1-hydroxyethyl)-1-methyl-2-[6-[2-[N-methyl-N-(4-nitrobenzyloxycarbonyl)amino]ethyl]-7-methylthioimidazo [5,1-b]thiazolium-2-yl]-1-carbapen-2-em-3-carboxylate trifluoromethanesulfonate as a crude product.

b) (1S,5R,6S)-6-((1R)-1-Hydroxyethyl)-1-methyl-2-[6-[2-(N-methylamino)ethyl]-7-methylthioimidazo[5,1-b] thiazolium-2-yl]-1-carbapen-2-em-3-carboxylate (intramolecular salt)

The procedure of Example 44b) was repeated, except that 214 mg of 4-nitrobenzyl (1S,5R,6S)-6-((1R)-1-hydroxyethyl)-1-methyl-2-[6-[2-[N-methyl-N-(4-nitrobenzyloxycarbonyl)amino]ethyl]-7-methylthioimidazo [5,1-b]thiazolium-2-yl]-1-carbapen-2-em-3-carboxylate trifluoromethanesulfonate as the crude product was used as the starting compound. Thus, 10 mg of the title compound was prepared.

NMR (D$_2$O) δ (HOD=4.65 ppm): 1.14 (3H, d, J=7.3 Hz), 1.17 (3H, d, J=6.3 Hz), 2.30 (3H, s), 2.66 (3H, s), 3.44 (1H, dd, J$_1$=5.9 Hz, J$_2$=2.9 Hz), 3.51–3.58 (3H, m), 4.11–4.19 (1H, m), 4.23 (1H, dd, J$_1$=9.2 Hz, J$_2$=2.7 Hz), 4.74 (2H, t, J=6.0 Hz), 8.07 (1H, s)

Example 50

(1S,5R,6S)-6-((1R)-1-Hydroxyethyl)-1-methyl-2-[7-methylthio-6-((3S)-pyrrolidin-3-yl)imidazo[5,1-b] thiazolium-2-yl]-1-carbapen-2-em-3-carboxylate (intramolecular salt) hydrochloride a) 4-Nitrobenzyl (1S,5R,6S)-6-((1R)-1-hydroxyethyl)-1-methyl-2-[7-methylthio-6-[(3S)-1-(4-nitrobenzyloxy-carbonyl)pyrrolidin-3-yl]imidazo[5,1-b]thiazolium-2-yl]-1-carbapen-2-em-3-carboxylate trifluoromethanesulfonate (3R)-3-Hydroxy-1-(4-nitrobenzyloxycarbonyl) pyrrolidine (3.43 g) was dissolved in 120 ml of dichloromethane. The solution was cooled to −60° C. 2,6-Lutidine (1.80 ml) and 2.39 ml of trifluoromethanesulfonic anhydride were then added to the cooled solution. The mixture was stirred for 20 min. Water (100 ml) was added to the reaction solution. The mixture was extracted with 100 ml of dichloromethane. The extract was dried over anhydrous magnesium sulfate. 4-Nitrobenzyl (1S,5R,6S)-6-((1R)-1-hydroxyethyl)-1-methyl-2-(7-methylthioimidazo[5,1-b] thiazol-2-yl)-1-carbapen-2-em-3-carboxylate (5.56 g) was then added thereto. The solvent was removed by concentration until the volume of the solution was brought to 100 ml. The residue was stirred at room temperature for 2 days. The reaction solution was then added dropwise to 550 ml of diethyl ether. The precipitated solid was collected by filtration to prepare 8.40 g of 4-nitrobenzyl (1S,5R,6S)-6-((1R)-1-hydroxyethyl)-1-methyl-2-[7-methylthio-6-[(3S)-1-(4-nitrobenzyloxycarbonyl)pyrrolidin-3-yl]imidazo[5,1-b] thiazolium-2-yl]-1-carbapen-2-em-3-carboxylate trifluoromethanesulfonate as a crude product.

b) (1S,5R,6S)-6-((1R)-1-Hydroxyethyl)-1-methyl-2-[7-methylthio-6-((3S)-pyrrolidin-3-yl)imidazo[5,1-b]-thiazolium-2-yl]-1-carbapen-2-em-3-carboxylate (intramolecular salt hydrochloride 4-Nitrobenzyl (1S,5R,6S)-6-((1R)-1-hydroxyethyl)-1-methyl-2-[7-methylthio-6-[(3S)-1-(4-nitrobenzyloxy-carbonyl)pyrrolidin-3-yl]imidazo[5,1-b]thiazolium-2-yl]-1-carbapen-2-em-3-carboxylate trifluoromethanesulfonate as the crude product (6.86 g) was dissolved in 150 ml of THF and 150 ml of water. 10% Pd—C (5.30 g) was added to the solution. The air in the reaction vessel was replaced by hydrogen, and the contents of the reaction vessel were stirred at room temperature for 3 hr. The catalyst was removed by filtration on Celite, and washed with water. The filtrate was washed with ethyl acetate, and was then concentrated under the reduced pressure until the volume of the filtrate was brought to about 30 ml. The residue was purified by column chromatography on Cosmosil 40C$_{18}$-PREP (a 20% aqueous methanol solution), and was then subjected to column chromatography (water) on Amberlyst A-26 as an ion-exchange resin (chloro form) to prepare 634 mg of the title compound.

NMR (D$_2$O) δ (HOD=4.65 ppm): 1.11 (3H, d, J=7.3 Hz), 1.15 (3H, d, J=6.3 Hz), 2.28 (3H, s), 2.44–2.54 (1H, m), 2.70–2.81 (1H, m), 3.39–3.55 (3H, m), 3.56–3.68 (2H, m), 3.93–4.01 (1H, m), 4.09–4.15 (1H, m), 4.19 (1H, dd, J$_1$=9.3 Hz, J$_2$=2.9. Hz), 5.50–5.58 (1H, m), 8.05 (1H, s), 9.40 (1H, s)

Example 51

(1S,5R,6S)-6-((1R)-1-Hydroxyethyl)-1-methyl-2-[6-((3S,5S)-5-methoxycarbonylpyrrolidin-3-yl)-7-methylthioimidazo[5,1-b]thiazolium-2-yl]-1-carbapen-2-em-3-carboxylate (intramolecular salt) hydrochloride a) 4-Nitrobenzyl (1S,5R,6S)-6-((1R)-1-hydroxyethyl)-1-methyl-2-[6-[(3S,5S)-5-methoxycarbonyl-1-(4-nitrobenzyloxycarbonyl)pyrrolidin-3-yl]-7-methylthioimidazo[5,1-b]thiazolium-2-yl]-1-carbapen-2-em-3-carboxylate chloride (2S,4R)-4-Hydroxy-1-(4-nitrobenzyloxycarbonyl)proline methyl ester (200 mg) was dissolved in 6 ml of dichloromethane. The solution was cooled to −60° C. 2,6-Lutidine (0.079 ml) and 0.109 ml of trifluoromethanesulfonic anhydride were then added to the cooled solution. The mixture was stirred for 30 min. Water (20 ml) was added to the reaction solution, and the mixture was extracted with 20 ml of dichloromethane. The extract was dried over anhydrous magnesium sulfate. 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (240 mg) was then added thereto. The solvent was removed by concentration until the volume of the solution was brought to 5 m. The residue was stirred at room temperature for 20 hr. The reaction solution was then added dropwise to 35 ml of diisopropyl ether. The precipitated solid was collected by filtration, and was subjected to column chromatography (methanol) on Amberlyst A-26 as an ion-exchange resin (chloro form) to prepare 367 mg of 4-nitrobenzyl (1S,5R,6S)-6-((1R)-1-hydroxyethyl)-1-methyl-2-[6-[(3S,5S)-5-methoxycarbonyl-1-(4-nitrobenzyloxycarbonyl)pyrrolidin-3-yl]-7-methylthioimidazo[5,1-b]thiazolium-2-yl]-1-carbapen-2-em-3-carboxylate chloride as a crude product.

b) (1S,5R,6S)-6-((1R)-1-Hydroxyethyl)-1-methyl-2-[6-((3S,5S)-5-methoxycarbonylpyrrolidin-3-yl)-7-methylthioimidazo[5,1-b]thiazolium-2-yl]-1-carbapen-2-em-3-carboxylate (intramolecular salt) hydrochloride 4-Nitrobenzyl (1S,5R,6S)-6-((1R)-1-hydroxyethyl)-1-methyl-2-[7-methylthio-6-[(3S,5S)-5-methoxycarbonyl-1-(4-nitrobenzyloxycarbonyl)pyrrolidin-3-yl]imidazo[5,1-b]thiazolium-2-yl]-1-carbapen-2-em-3-carboxylate chloride as the crude product (367 mg) was dissolved in 12 ml of THF and 12 ml of water. 10% Pd—C (369 mg) was added to the solution. The air in the reaction vessel was replaced by hydrogen, and the contents of the reaction vessel were stirred at room temperature for 3 hr. The catalyst was removed by filtration on Celite, and washed with water. The filtrate was washed with ethyl acetate, and was then concentrated under the reduced pressure until the volume of the filtrate was brought to about 5 ml. The residue was purified by column chromatography on Cosmosil 40$C_{18}$-PREP (a 20% aqueous methanol solution). Thus, 49 mg of the title compound was obtained from a fraction which had been eluted as the first fraction.

NMR ($D_2O$) δ (HOD=4.65 ppm): 1.10 (3H, d, J=7.1 Hz), 1.16 (3H, d, J=6.3 Hz), 2.21–2.29 (4H, m), 2.88–2.97 (1H, m), 3.15 (1H, dd, $J_1$=12.0 Hz, $J_2$=5.2 Hz), 3.41 (1H, dd, $J_1$=6.1 Hz, $J_2$=2.9 Hz), 3.45–3.54 (2H, m), 3.65 (3H, s), 4.00–4.06 (1H, m), 4.09–4.16 (1H, n), 4.20 (1H, dd, $J_1$=9.3 Hz, $J_2$=2.7 Hz), 5.29–5.37 (1H, m), 8.01 (1H, s)

Example 52

(1S,5R,6S)-6-((1R)-1-Hydroxyethyl)-1-methyl-2-[6-((3S,5S)-5-methoxycarbonylpyrrolidin-3-yl)-7-methylthioimidazo[5,1-b]thiazolium-2-yl]-1-carbapen-2-em-3-carboxylate (intramolecular salt) hydrochloride A latter fraction was collected which had been eluted after (1S,5R,6S)-6-((1R)-1-hydroxyethyl)-1-methyl-2-[6-((3S,5S)-5-methoxycarbonylpyrrolidin-3-yl)-7-methylthioimidazo[5,1-b]thiazolium-2-yl]-1-carbapen-2-em-3-carboxylate (intramolecular salt) hydrochloride in the column chromatography on Cosmosil 40$C_{18}$-PREP (a 20% aqueous methanol solution) in Example 51b). The title compound (11 mg) was obtained from this latter fraction.

NMR ($D_2O$) δ (HOD=4.65 ppm): 1.11 (3H, d, J=7.3 Hz), 1.16 (3H, d, J=6.3 Hz), 2.27 (3H, s), 2.43–2.52 (1H, m), 2.62–2.72 (1H, m), 3.14 (1H, dd, $J_1$=12.1 Hz, $J_2$=4.0 Hz), 3.42 (1H, dd, $J_1$=5.8 Hz, $J_2$=2.7 Hz), 3.47–3.56 (2H, m), 3.65 (3H, s), 4.10–4.23 (3H, m), 5.30–5.37 (1H, m), 8.01 (1H, s)

Example 53

(1S,5R,6S)-2-[6-(2-Aminoethyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride a) 4-Nitrobenzyl (1S,5R,6S)-2-[6-(2-azidoethyl)-7-methylthioimidazo[5,1-b]thiazolium-2-yl]-6-((1R)-1-hydroxyethyl)-1-methyl-1-carbapen-2-em-3-carboxylate trifluoromethanesulfonate 2-Azidoethanol (220 mg) was dissolved in 10 ml of dichloromethane. The solution was cooled to −60° C. 2,6-Lutidine (0.323 ml) and 0.446 ml of trifluoromethanesulfonic anhydride were then added to the cooled solution. The mixture was stirred for 20 min. Water (30 ml) was added to the reaction solution, and the mixture was extracted with 30 ml of dichloromethane. The extract was dried over anhydrous magnesium sulfate. 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (1.05 g) was then added thereto. The solvent was removed by concentration until the volume of the solution was brought to 20 ml. The residue was stirred at room temperature for 7 hr. The reaction solution was added dropwise to 50 ml of diethyl ether. The precipitated solid was collected by filtration. Thus, 1.47 g of 4-nitrobenzyl (1S,5R,6S)-2-[6-(2-azidoethyl)-7-methylthioimidazo[5,1-b]thiazolium-2-yl]-6-((1R)-1-hydroxyethyl)-1-methyl-1-carbapen-2-em-3-carboxylate trifluoromethanesulfonate as a crude product was prepared.

b) (1S,5R,6S)-2-[6-(2-Aminoethyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride The procedure of Example 50b) was repeated, except that 1.35 g of 4-nitrobenzyl (1S,5R,6S)-2-[6-(2-azidoethyl)-7-methylthioimidazo[5,1-b]thiazolium-2-yl]-6-((1R)-1-hydroxyethyl)-1-methyl-1-carbapen-2-em-3-carboxylate trifluoromethanesulfonate, as the crude product was used as the starting compound. Thus, 448 mg of the title compound was prepared.

NMR ($D_2O$) δ (HOD=4.65 ppm): 1.13 (3H, d, J=7.1 Hz), 1.17 (3H, d, J=6.4 Hz), 2.29 (3H, s), 3.43 (1H, dd, $J_1$=5.8 Hz, $J_2$=2.7 Hz), 3.46–3.54 (3H, m), 4.10–4.18 (1H, m), 4.22 (1H, dd, $J_1$=9.3 Hz, $J_2$=2.7 Hz), 4.68 (2H, t, J=6.2 Hz), 8.06 (1H, s)

Example 54

(1S,5R,6S)-6-((1R)-1-Hydroxyethyl)-2-[6-((3R,5S)-5-hydroxymethylpyrrolidin-3-yl)-7-methylthioimidazo-[5,1-b]thiazolium-2-yl]-1-methyl-1-carbapen-2-em-3-carboxylate (intramolecular salt) hydrochloride a) 4-Nitrobenzyl (1S,5R,6S)-6-((1R)-1-hydroxyethyl)-1-methyl-2-[7-methylthio-6-[(3R,5S)-1-(4-nitrobenzyloxycarbonyl)-5-(4-nitrobenzyloxycarbonyl)oxymethylpyrrolidin-3-yl]imidazo[5,1-b]thiazolium-2-yl]-1-carbapen-2-em-3-carboxylate chloride (2S,4S)-4-Hydroxy-1-(4-nitrobenzyloxycarbonyl)-2-(4-nitrobenzyloxycarbonyl)oxymethylpyrrolidine (333 mg)

was dissolved in 7 ml of dichloromethane. The solution was cooled to −60° C. 2,6-Lutidine (0.090 ml) and 0.124 ml of trifluoromethanesulfonic anhydride were then added to the cooled solution. The mixture was stirred for 20 min. Water (25 ml) was added to the reaction solution, and the mixture was extracted with 25 ml of dichloromethane. The extract was dried over anhydrous magnesium sulfate. 4-Nitrobenzyl (1S,5R,6S)-6-((1R)-1-hydroxyethyl)-1-methyl-2-(7-methylthioimidazo[5,1-b]-thiazol-2-yl)-1-carbapen-2-em-3-carboxylate (255 mg) was then added thereto. The solvent was removed by concentration until the volume of the solution was brought to 5 ml. The residue was stirred at room temperature for 20 hr. The reaction solution was then added dropwise to 40 ml of diisopropyl ether. The precipitated solid was collected by filtration, and was subjected to column chromatography (methanol) on Amberlyst A-26 as an ion-exchange resin (chloro form) to prepare 490 mg of 4-nitrobenzyl (1S,5R,6S)-6-((1R)-1-hydroxyethyl)-1-methyl-2-[7-methylthio-6-[(3R,5S)-1-(4-nitrobenzyloxycarbonyl)-5-(4-nitrobenzyloxycarbonyl)oxymethylpyrrolidin-3-yl]imidazo[5,1-b]thiazolium-2-yl]-1-carbapen-2-em-3-carboxylate chloride as a crude product.

b) (1S,5R,6S)-6-((1R)-1-Hydroxyethyl)-2-[6-((3R,5S)-5-hydroxymethylpyrrolidin-3-yl)-7-methylthioimidazo-[5,1-b]thiazolium-2-yl]-1-methyl-1-carbapen-2-em-3-carboxylate (intramolecular salt) hydrochloride The procedure of Example 44b) was repeated, except that 490 mg of 4-nitrobenzyl (1S,5R,6S)-6-((1R)-1-hydroxyethyl)-1-methyl-2-[7-methylthio-6-[(3R,5S)-5-methoxycarbonyl-1-(4nitrobenzyloxycarbonyl)pyrrolidin-3-yl]imidazo[5,1-b]thiazolium-2-yl]-1-carbapen-2-em-3-carboxylate chloride as the crude product was used as the starting compound. Thus, 22 mg of the title compound was prepared.

NMR (D$_2$O) δ (HOD 4.65 ppm): 1.13 (3H, d, J=7.3 Hz), 1.18 (3H, d, J=6.3 Hz), 2.30 (3H, s), 2.31–2.41 (1H, m), 2.80–2.89 (1H, m), 3.43 (1H, dd, J$_1$=6.1 Hz, J$_2$=2.7 Hz), 3.47–3.63 (2H, m), 3.75–3.80 (1H, m), 3.89–3.98 (1H, m), 4.01–4.07 (1H, m), 4.11–4.18 (1H, m), 4.22 (1H, dd, J$_1$=9.5 Hz, J$_2$=2.7 Hz), 5.58–5.69 (1H, m), 8.08 (1H, s), 9.47 (1H, s)

Example 55

(1S,5R,6S)-2-[6-[2-[N-(2-Aminoethyl)amino]ethyl]-7-methylthioimidazo[5,1-b]thiazolium-2-yl]-6-((1R)-1-hydroxyethyl)-1-methyl-1-carbapen-2-em-3-carboxylate (intramolecular salt) methanesulfonate a) 4-Nitrobenzyl (1S,5R,6S)-6-((1R)-1-hydroxyethyl)-1-methyl-2-[7-methylthio-6-[2-[N-(4-nitrobenzyloxycarbonyl)-N-[2-(4-nitrobenzyloxycarbonyl)aminoethyl]amino]ethyl]imidazo[5,1-b]thiazolium-2-yl]-1-carbapen-2-em-3-carboxylate methanesulfonate 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (47 mg) was dissolved in 2 ml of dichloromethane. 1-Methanesulfonyloxy-2-[N-(4-nitrobenzyloxycarbonyl)-N-[2-(4-nitrobenzyloxycarbonyl)aminoethyl]amino]ethane (228 mg) was added to the solution. The mixture was stirred at room temperature for 3 days. The solvent was removed by distillation under the reduced pressure. The residue was purified by column chromatography on Sephadex LH-20 (chloroform methanol=1:1) to prepare 65 mg of 4-nitrobenzyl (1S,5R,6S)-6-((1R)-1-hydroxyethyl)-1-methyl-2-[7-methylthio-6-[2-[N-(4-nitrobenzyloxycarbonyl)-N-[2-(4-nitrobenzyloxycarbonyl)aminoethyl]amino]ethyl]imidazo[5,1-b]thiazolium-2-yl]-1-carbapen-2-em-3-carboxylate methanesulfonate as a crude product.

b) (1S,5R,6S)-2-[6-[2-[N-(2-Aminoethyl)amino]ethyl-7-methylthioimidazo[5,1-b]thiazolium-2-yl]-6-((1R)-1-hydroxyethyl)-1-methyl-1-carbapen-2-em-3-carboxylate (intramolecular salt) methanesulfonate The procedure of Example 44b) was repeated, except that 175 mg of 4-nitrobenzyl (1S,5R,6S)-6-((1R)-1-hydroxyethyl)-1-methyl-2-[7-methylthio-6-[2-[N-(4-nitrobenzyloxycarbonyl)-N-[2-(4-nitrobenzyloxycarbonyl)aminoethyl]amino]ethyl]imidazo[5,1-b]thiazolium-2-yl]-1-carbapen-2-em-3-carboxylate methanesulfonate as the crude product was used as the starting compound. Thus, 12 mg of the title compound was prepared.

NMR (D$_2$O) δ (HOD=4.65 ppm): 1.12 (3H, d, J=7.3 Hz), 1.17 (3H, d, J=6.3 Hz), 2.28 (3H, s), 2.68 (3H, s), 2.84 (2H, t, J=6.5 Hz), 2.98 (2H, t, J=6.3 Hz), 3.08 (2H, t, J=6.0 Hz), 3.42 (1H, dd, J$_1$=6.0 Hz, J$_2$=2.7 Hz), 3.45–3.55 (1H, m), 4.08–4.18 (1H, m), 4.20 (1H, dd, J$_1$=9.3 Hz, J$_2$=2.7 Hz), 4.46 (2H, t, J=6.5 Hz), 8.01 (1H, s)

Example 56

(1S,5R,6S)-6-((1R)-1-Hydroxyethyl)-2-(7-isopropylthio-6-methylimidazo[5,1-b]thiazolium-2-yl)-1-methyl-1-carbapen-2-em-3-carboxylate (intramolecular salt)

a) 4-Nitrobenzyl (1S,5R,6S)-6-((1R)-1-hydroxyethyl)-2-(7-isopropylthioimidazo[5,1-b]thiazol-2-yl)-1-methyl-1-carbapen-2-em-3-carboxylate The procedure of Example 1a) was repeated, except that 629 mg of 4-nitrobenzyl (1R,3R,5R,6S)-6-((1R)-1-hydroxyethyl)-1-methyl-2-oxo-1-carbapenam-3-carboxylate and 890 mg of 7-isopropylthio-2-(tri-n-butylstannyl)imidazo[5,1-b]thiazole were used as the starting compounds. Thus, 557 mg of 4-nitrobenzyl (1S,5R,6S)-6-((1R)-1-hydroxyethyl)-2-(7-isopropylthioimidazo[5,1-b]thiazol-2-yl)-1-methyl-1-carbapen-2-em-3-carboxylate was prepared.

NMR (CDCl$_3$) δ: 1.28 (6H, d, J=6.7 Hz), 1.31 (3H, d, J=7.2 Hz), 1.40 (3H, d, J=6.3 Hz), 3.28 (1H, sept, J=6.7 Hz), 3.37 (1H, dd, J$_1$=6.6 Hz, J$_2$=2.9 Hz), 3.4–3.5 (1H, m), 4.3–4.4 (2H, m), 5.28 (1H, d, J=13.7 Hz), 5.53 (1H, d, J=13.7 Hz), 7.68 (2H, d, J=8.8 Hz), 8.03 (1H, s), 8.25 (2H, d, J=8.8 Hz), 8.31 (1H, s)

b) 4-Nitrobenzyl (1S,5R6 S)-6-((1R)-1-hydroxyethyl)-2-(7-isopropylthio-6-methylimidazo[5,1-b]-thiazolium-2-yl)-1-methyl-1-carbapen-2-em-3-carboxylate trifluoromethanesulfonate The procedure of Example 47b) was repeated, except that 102 mg of 4-nitrobenzyl (1S,5R,6S)-6-((1R)-1-hydroxyethyl)-2-(7-isopropylthioimidazo[5,1-b]thiazol-2-yl)-1-methyl-1-carbapen-2-em-3-carboxylate was used as the starting compound. Thus, 4-nitrobenzyl (1S,5R,6S)-6-((1R)-1-hydroxyethyl)-2-(7-isopropylthio-6-methylimidazo [5,1-b]thiazolium-2-yl)-1-methyl-1-carbapen-2-em-3-carboxylate trifluoromethanesulfonate was prepared.

NMR (CDCl$_3$) δ: 1.34 (6H, d, J=6.7 Hz), 1.35 (3H, d, J=7.1 Hz), 1.39 (3H, d, J=6.2 Hz), 3.3–3.45 (2H, m), 3.8–3.9 (1H, m), 4.08 (3H, 8), 4.25–4.45 (2H, m), 5.32 (1H, d, J=13.2 Hz), 5.55 (1H, d, J=13.2 Hz), 7.69 (2H, d, J=8.9 Hz), 8.25 (2H, d, J=8.9 Hz), 8.76 (1H, s), 9.88 (1H, s)

c) (1S,5R,6S)-6-((R)-1-Hydroxyethyl)-2-(7-isopropylthio-6-methylimidazo[5,1-b]thiazolium-2-yl)-1-methyl-1-carbapen-2-em-3-carboxylate (intramolecular salt)

The procedure of Example 3b) was repeated, except that the whole quantity of 4-nitrobenzyl (1S,5R,6S)-6-((1R)-1-hydroxyethyl)-2-(7-isopropylthio-6-methylimidazo[5,1-b]thiazolium-2-yl)-1-methyl-1-carbapen-2-em-3-carboxylate trifluoromethanesulfonate prepared in step b) was used as the starting compound. Thus, 24.0 mg of the title compound was prepared.

NMR (D₂O) δ (HOD=4.80 ppm): 1.2–1.4 (12H, m), 3.3–3.75 (3H, m), 4.06 (3H, s), 4.25–4.4 (2H, m), 8.15 (1H, s,), 9.33 (1H, s)

Example 57
(1S,5R,6S)-2-[6-(4-Aminobutyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride a) 4-Nitrobenzyl (1S,5R,6S)-2-[6-(4-azidobutyl)-7-methylthioimidazo[5,1-b]thiazolium-2-yl]-6-((1R)-1-hydroxyethyl)-1-methyl-1-carbapen-2-em-3-carboxylate trifluoromethanesulfonate 4-Azido-1-butanol (128 mg) was dissolved in 10 ml of dichloromethane. The solution was cooled to −60° C. 2,6-Lutidine (0.154 ml) and 0.206 ml of trifluoromethanesulfonic anhydride were then added to the cooled solution. The mixture was stirred for 20 min. Water (30 ml) was added to the reaction solution, and the mixture was extracted with 30 ml of dichloromethane. The extract was dried over anhydrous magnesium sulfate. 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (470 mg) was then added thereto. The solvent was removed by concentration until the volume of the solution was brought to 10 ml. The residue was stirred at room temperature for 15 hr. The solvent was removed by distillation under the reduced pressure. The residue was purified by column chromatography on Sephadex LH-20 (chloroform:methanol 1:1) to prepare 390 mg of 4-nitrobenzyl (1S,5R,6S)-2-[6-(4-azidobutyl)-7-methylthioimidazo[5,1-b]-thiazolium-2-yl]-6-((1R)-1-hydroxyethyl)-1-methyl-1-carbapen-2-em-3-carboxylate trifluoromethanesulfonate as a crude product.

b) (1S,5R,6S)-2-[6-(4-Aminobutyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride The procedure of Example 50b) was repeated, except that 116 mg of 4-nitrobenzyl (1S,5R,6S)-2-[6-(4-azidobutyl)-7-methylthioimidazo[5,1-b]thiazolium-2-yl]-6-((1R)-1-hydroxyethyl)-1-methyl-1-carbapen-2-em-3-carboxylate trifluoromethanesulfonate as a crude product was used as the starting compound. Thus, 13 mg of the title compound was prepared.

NMR (D₂O) δ (HOD=4.65 ppm): 1.10 (3H, d, J=7.3 Hz), 1.15 (3H, d, J=6.3 Hz), 1.56–1.65 (2H, m), 1.84–1.93 (2H, m), 2.25 (3H, s), 2.91 (2H, t, J=7.0 Hz), 3.39–3.43 (1H, m), 3.45–3.52 (1H, m), 4.09–4.21 (2H, m), 4.34 (2H, t, J=7.2 Hz), 7.99 (1H, s), 9.19 (1H, s)

Example 58
(1S,5R,6S)-2-[7-(2-Aminoethyl)thio-6-methyl-5-methylthioimidazo[5,1-b]thiazolium-2-yl-6-((1R)-1-hydroxyethyl)-1-methyl-1-carbapen-2-em-3-carboxylate (intramolecular salt)

a) 4-Nitrobenzyl (1S,5R,6S)-2-[7-(2-azidoethyl)thio-5-methylthioimidazo[5,1-b]thiazol-2-yl]-6-((1R)-1-hydroxyethyl)-1-methyl-1-carbapen-2-em-3-carboxylate The procedure of Example 1a) was repeated, except that 300 mg of 4-nitrobenzyl (1R,3R,5R,6S)-6-((1R)-1-hydroxyethyl)-1-methyl-2-oxo-1-carbapenam-3-carboxylate and 485 mg of 7-(2-azidoethyl)thio-5-methylthio-2-(tri-n-butylstannyl)imidazo[5,1-b]thiazole were used as the starting compounds. Thus, 272 mg of 4-nitrobenzyl (1S,5R,6S)-2-[7-(2-azidoethyl)thio-5-methylthioimidazo-[5,1-b]thiazol-2-yl]-6-((1R)-1-hydroxyethyl)-1-methyl-1-carbapen-2-em-3-carboxylate was prepared.

NMR (CDCl₃) δ: 1.33 (3H, d, J=7.4 Hz), 1.40 (3H, d, J=6.3 Hz), 2.61 (3H, s), 2.9–3.0 (2H, m), 3.37 (1H, dd, J₁=6.5 Hz, J₂=2.9 Hz), 3.45–3.55 (3H, m), 4.3–4.4 (2H, m), 5.29 (1H, d, J=13.7 Hz), 5.55 (1H, d, J=13.7 Hz), 7.68 (2H, d, J=8.9 Hz), 8.14 (1H, s), 8.25 (2H, d, J=8.9 Hz)

b) 4-Nitrobenzyl (1S,5R,6S)-2-[7-(2-azidoethyl)thio-6-methyl-5-methylthioimidazo[5,1-b]thiazolium-2-yl]-6-((1R)-1-hydroxyethyl)-1-methyl-1-carbapen-2-em-3-carboxylate trifluoromethanesulfonate The procedure of Example 47b) was repeated, except that 72.3 mg of 4-nitrobenzyl (1S,5R,6S)-2-[7-(2-azidoethyl)thio-5-methylthioimidazo[5,1-b]thiazol-2-yl]-6-((1R)-1-hydroxyethyl)-1-methyl-1-carbapen-2-em-3-carboxylate was used as the starting compound. Thus, 4-nitrobenzyl (1S,5R,6S)-2-[7-(2-azidoethyl)thio-6-methyl-5-methylthioimidazo[5,1-b]thiazolium-2-yl]-6-((1R)-1-hydroxyethyl)-1-methyl-1-carbapen-2-em-3-carboxylate trifluoromethanesulfonate was prepared.

NMR (CDCl₃) δ: 1.32 (3H, d, J=7.4 Hz), 1.38 (3H, d, J=6.3 Hz), 2.74 (3H, s), 3.1–3.15 (2H, m), 3.40 (1H, dd, J₁=6.8 Hz, J₂=3.0,Hz), 3.55–3.65 (2H, m), 3.75–3.85 (1H, m), 4.16 (3H, s), 4.25–4.35 (1H, m), 4.40 (1H, dd, J₁=9.4 Hz, J₂=3.0 Hz), 5.25 (1H, d, J=13.5 Hz), 5.54 (1H, d, J=13.5 Hz), 7.67 (2H, d, J=8.5 Hz), 8.22 (2H, d, J=8.5 Hz), 8.38 (1H, s)

c) (1S,5R,6S)-2-[7-(2-Aminoethyl)thio-6-methyl-5-methylthioimidazo[5,1-b]thiazolium-2-yl]-6-((1R)-1-hydroxyethyl)-1-methyl-1-carbapen-2-em-3-carboxylate (intramolecular salt)

The procedure of Example 3b) was repeated, except that the reaction was carried out in a mixed solvent composed of THF and water and the whole quantity of 4-nitrobenzyl (1S,5R,6S)-2-[7-(2-azidoethyl)thio-6-methyl-5-methylthioimidazo[5,1-b]thiazolium-2-yl]-6-((1R)-1-hydroxyethyl)-1-methyl-1-carbapen-2-em-3-carboxylate trifluoromethanesulfonate prepared in step b) was used as the starting compound. Thus, 16.5 mg of the title compound was prepared.

NMR (D₂O) δ (HOD=4.80 ppm): 1.25–1.4 (6H, m), 2.59 (3H, 8), 3.1–3.25 (4H, m), 3.55–3.65 (1H, m), 3.7–3.8 (1H, m), 4.16 (3H, s), 4.25–4.45 (2H, m), 8.29 (1H, s)

Example 59
(1S,5R,6S)-2-[7-(2-Aminoethyl)thio-6-(3-aminopropyl)imidazo[5,1-b]thiazolium-2-yl]-6-((1R)-1-hydroxyethyl)-1-methyl-1-carbapen-2-em-3-carboxylate (intramolecular salt) dihydrochloride a) 4-Nitrobenzyl (1S,5R,6S)-2-[7-(2-azidoethyl)thioimidazo[5,1-b]thiazol-2-yl]-6-((1R)-1-hydroxyethyl)-1-methyl-1-carbapen-2-em-3-carboxylate The procedure of Example 1a) was repeated, except that 3.10 g of 4-nitrobenzyl (1R,3R,5R,6S)-6-((1R)-1-hydroxyethyl)-1-methyl-2-oxo-1-carbapenam-3-carboxylate and 4.62 g of 7-(2-azidoethyl)thio-2-(tri-n-butylstannyl)imidazo[5,1-b]thiazole were used as the starting compounds. Thus, 3.41 g of 4-nitrobenzyl (1S,5R,6S)-2-[7-(2-azidoethyl)thioimidazo[5,1-b]thiazol-2-yl]-6-((1R)-1-hydroxyethyl)-1-methyl-1-carbapen-2-em-3-carboxylate was prepared.

NMR (CDCl₃) δ: 1.31 (3H, d, J=7.4 Hz), 1.40 (3H, d, J=6.3 Hz), 2.95–3.05 (2H, m), 3.37 (1H, dd, J₁=6.5 Hz, J₂=2.8 Hz), 3.4–3.55 (3H, m), 4.25–4.35 (1H, m), 4.38 (1H, dd, J₁=9.6 Hz, J₂=2.8 Hz), 5.28 (1H, d, J=13.7 Hz), 5.53 (1H, d, J=13.7 Hz), 7.68 (2H, d, J=8.6 Hz), 8.03 (1H, s), 8.25 (2H, d, J=8.6 Hz), 8.32 (1H, s)

b) 4-Nitrobenzyl (1S,5R,6S)-2-[7-(2-azidoethyl)thio-6-(3-azidopropyl)imidazo[5,1-b]thiazolium-2-yl]-6-((1R)-1-hydroxyethyl)-1-methyl-1-carbapen-2-em-3-carboxylate chloride 3-Azido-1-propanol (64.5 mg) was suspended in 2 ml of dichloromethane. 2,6-Lutidine (0.082 ml) and 0.113 ml of trifluoromethanesulfonic anhydride were added to the suspension at −60° C. under an argon atmosphere. The mixture was stirred at that temperature for 30 min. Brine was then added to the reaction solution. The mixture was extracted with dichloromethane, followed by washing with a dilute aqueous hydrochloric acid solution and brine in that order. The organic layer was dried over anhydrous magnesium sulfate, and was concentrated under the reduced pressure until the volume of the organic layer was brought to about 5 ml. 4-Nitrobenzyl (1S,5R,6S)-2-[7-(2-azidoethyl)thioimidazo[5,1-b]thiazol-2-yl]-6-((1R)-1-hydroxyethyl)-1-methyl-1-carbapen-2-em-3-carboxylate (303 mg) was added to the residue under cooling in ice. The mixture was stirred at that temperature for 13 hr. Ethyl acetate (20 ml) was added to the reaction solution, and the mixture was concentrated under the reduced pressure until the volume of the mixture was brought to about 3 ml. The residue was added dropwise to 15 ml of diethyl ether. The resultant precipitate was washed with 5 ml of isopropyl ether twice, and was subjected to column chromatography (methanol) on Amberlyst A-26 as an ion-exchange resin (chloro form) to prepare 382 mg of 4-nitrobenzyl (1S,5R,6S)-2-[7-(2-azidoethyl)thio-6-(3-azidopropyl)imidazo[5,1-b]thiazolium-2-yl]-6-((1R)-1-hydroxyethyl)-1-methyl-1-carbapen-2-em-3-carboxylate chloride.

NMR (CDCl$_3$) δ: 1.3–1.45 (6H, m), 2.2–2.45 (2H, m), 2.9–3.0 (2H, m), 3.37 (1H, dd, J$_1$=7.1 Hz, J$_2$=2.5 Hz), 3.5–3.65 (4H, m), 4.1–4.25 (2H, m), 4.58 (1H, dd, J$_1$=9.6 Hz, J$_2$=2.5 Hz), 4.4–4.65 (2H, m), 5.29 (1H, d, J=13.7 Hz), 5.53 (1H, d, J=13.7 Hz), 7.69 (2H, d, J=8.8 Hz), 8.24 (2H, d, J=8.8 Hz), 9.41 (1H, s), 10.88 (1H, s)

c) (1S,5R,6S)-2-[7-(2-Aminoethyl)thio-6-(3-aminopropyl)imidazo[5,1-b]thiazolium-2-yl]-6-((1R)-1-hydroxyethyl)-1-methyl-1-carbapen-2-em-3-carboxylate (intramolecular salt) dihydrochloride The procedure of Example 3b) was repeated, except that the reaction was carried out in a mixed solvent composed of THF and water and 382 mg of 4-nitrobenzyl (1s,5R,6S)-2-[7-(2-azidoethyl)thio-6-(3-azidopropyl)imidazo[5,1-b]thiazolium-2-yl]-6-((1R)-1-hydroxyethyl)-1-methyl-1-carbapen-2-em-3-carboxylate chloride was used as the starting compound. Purification was then carried out by column chromatography on Cosmosil 40C$_{18}$-PREP (a 5% aqueous methanol solution). In this case, a main product was collected which had been eluted as the first fraction. Thus, 72.4 mg of the title compound was prepared.

NMR (D$_2$O) δ (HOD=4.80 ppm): 1.28 (3H, d, J=7.1 Hz), 1.32 (3H, d, J=6.4 Hz), 2.3–2.45 (2H, m), 3.0–3.3 (6H, m), 3.58 (1H, dd, J$_1$=6.1 Hz, J$_2$=2.9 Hz), 3.65–3.75 (1H, m), 4.25–4.35 (1H, m), 4.37 (1H, dd, J$_1$=9.2 Hz, J$_2$=2.9 Hz), 4.55–4.65 (2H, m), 8.22 (1H, s), 9.52 (1H, s)

Example 60
(1S,5R,6S)-2-[6-(3-Aminopropyl)-7-(2-hydroxyethyl)thioimidazo[5,1-b]thiazolium-2-yl]-6-((1R)-1-hydroxyethyl)-1-methyl-1-carbapen-2-em-3-carboxylate (intramolecular salt) hydrochloride A fraction was collected which had been eluted as the latter fraction in the column chromatography on Cosmosil 40C$_{18}$-PREP (a 5% aqueous methanol solution) in Example 59c). Thus, 5.7 mg of the title compound was prepared.

NMR (D$_2$O) δ (HOD=4.80 ppm): 1.28 (3H, d, J=7.3 Hz), 1.32 (3H, d, J=6.3 Hz), 2.3–2.45 (2H, m), 2.95–3.05 (2H, m), 3.1–3.2 (2H, m), 3.58 (1H, dd, J$_1$=5.8 Hz, J$_2$=2.9 Hz), 3.65–3.75 (3H, m), 4.25–4.35 (1H, m), 4.36 (1H, dd, J$_1$=9.5 Hz, J$_2$=2.9 Hz), 4.55–4.65 (2H, m), 8.19 (1H, s), 9.44 (1H, s)

Example 61
(1S,5R,6S)-2-[7-(2-Formylaminoethyl)thio-6-methylimidazo[5,1-b]thiazolium-2-yl]-6-((1R)-1-hydroxyethyl)-1-methyl-1-carbapen-2-em-3-carboxylate (intramolecular salt)

a) 4-Nitrobenzyl (1S,5R,6S)-2-[7-(2-formylaminoethyl)thioimidazo[5,1-b]thiazol-2-yl]-6-((1R)-1-hydroxyethyl)-1-methyl-1-carbapen-2-em-3-carboxylate The procedure of Example 1a) was repeated, except that 1.06 g of 4-nitrobenzyl (1R,3R,5R,6S)-6-((1R)-1-hydroxyethyl)-1-methyl-2-oxo-1-carbapenam-3-carboxylate and 1.665 g of 7-(2-formylaminoethyl)thio-2-(tri-n-butylstannyl)imidazo[5,1-b]thiazole were used as the starting compounds. Thus, 818 mg of 4-nitrobenzyl (1S,5R,6S)-2-[7-(2-formylaminoethyl)thioimidazo[5,1-b]thiazol-2-yl]-6-((1R)-1-hydroxyethyl)-1-methyl-1-carbapen-2-em-3-carboxylate was prepared.

NMR (CDCl$_3$) δ: 1.32 (3H, d, J=7.4 Hz), 1.40 (3H, d, J=6.3 Hz), 2.85–2.95 (2H, m), 3.38 (1H, dd, J$_1$=6.6 Hz, J$_2$=2.8 Hz), 3.4–3.6 (3H, m), 4.25–4.35 (1H, m), 4.39 (1H, dd, J$_1$=9.6 Hz, J$_2$=2.8 Hz), 5.28 (1H, d, J=13.5 Hz), 5.53 (1H, d, J=13.5 Hz), 7.1–7.2 (1H, br s), 7.68 (2H, d, J=8.9 Hz), 8.03 (1H, s), 8.21 (1H, s), 8.25 (2H, d, J=8.9 Hz), 8.30 (1H, s)

b) 4-Nitrobenzyl (1S,5R,6S)-2-[7-(2-formylaminoethyl)thio-6-methylimidazo[5,1-b]thiazolium-2-yl]-6-((1R)-1-hydroxyethyl)-1-methyl-1-carbapen-2-em-3-carboxylate trifluoromethanesulfonate The procedure of Example 47b) was repeated, except that 115 mg of 4-nitrobenzyl (1S,5R,6S)-2-[7-(2-formylaminoethyl)thioimidazo[5,1-b]thiazol-2-yl]-6-((1R)-1-hydroxyethyl)-1-methyl-1-carbapen-2-em-3-carboxylate was used as the starting compound. Thus, 4-nitrobenzyl (1S,5R,6S)-2-[7-(2-formylaminoethyl)thio-6-methylimidazo[5,1-b]thiazolium-2-yl]6-((1R)-1-hydroxyethyl)-1-methyl-1-carbapen-2-em-3-carboxylate trifluoromethanesulfonate was prepared.

NMR (CD$_3$OD) δ: 1.31 (3H, d, J=6.2 Hz), 1.32 (3H, d, J=7.4 Hz), 2.95–3.05 (2H, m), 3.35–3.45 (2H, m), 3.50 (1H, dd, J$_1$=6.2 Hz, J$_2$=2.9 Hz), 3.7–3.85 (1H, m), 4.11 (3H, s), 4.15–4.25 (1H, m), 4.42 (1H, dd, J$_1$=9.7 Hz, J$_2$=2.9 Hz), 5.34 (1H, d, J=13.7 Hz), 5.52 (1H, d, J=13.7 Hz), 7.71 (2H, d, J=8.9 Hz), 8.08 (1H, s), 8.17 (2H, d, J=8.9 Hz), 8.54 (1H, s), 9.52 (1H, s)

c) (1S,5R,6S)-2-[7-(2-Formylaminoethyl)thio-6-methylimidazo[5,1-b]thiazolium-2-yl]-6-((1R)-1-hydroxyethyl)-1-methyl-1-carbapen-2-em-3-carboxylate (intramolecular salt)

The procedure of Example 3b) was repeated, except that the whole quantity of 4-nitrobenzyl (1S,5R,6S)-2-[7-(2-formylaminoethyl)thio-6-methylimidazo[5,1-b]-thiazolium-2-yl]-6-((1R)-1-hydroxyethyl)-1-methyl-1-carbapen-2-em-3-carboxylate trifluoromethanesulfonate prepared in step b) was used as the starting compound. Thus, 46.0 mg of the title compound was prepared.

NMR (D$_2$O) δ (HOD=4.80 ppm): 1.27 (3H, d, J=7.3 Hz), 1.33 (3H, d, J=6.3 Hz), 3.0–3.1 (2H, m), 3.3–3.45 (2H, m), 3.56 (1H, dd, J$_1$=5.9 Hz, J$_2$=2.7 Hz), 3.6–3.7 (1H, m), 4.07 (3H, s), 4.25–4.35 (1H, m), 4.34 (1H, dd, J$_1$=9.5 Hz, J$_2$ 2.7 Hz), 8.08 (1H, s), 8.15 (1H, s)

Example 62
(1S,5R,6S)-6-((1R)-1-Hydroxyethyl)-1-methyl-2-[7-methylthio-6-((2R)-pyrrolidin-2-yl)methylimidazo-[5,1-b]

thiazolium-2-yl]-1-carbapen-2-em-3-carboxylate (intramolecular salt) hydrochloride a) 4-Nitrobenzyl (1S,5R,6S)-6-((1R)-1-hydroxyethyl)-1-methyl-2-[7-methylthio-6-[(2R)-1-(4-nitrobenzyloxycarbonyl)pyrrolidin-2-yl]methylimidazo[5,1-b]thiazolium-2-yl]-1-carbapen-2-em3-carboxylate trifluoromethanesulfonate (2R)-2-Hydroxymethyl-1-(4-nitrobenzyloxycarbonyl) pyrrolidine (160 mg) was dissolved in 5 ml of dichloromethane. The solution was cooled to −60° C. 2,6-Lutidine (0.080 ml) and 0.106 ml of trifluoromethanesulfonic anhydride were then added to the cooled solution. The mixture was stirred for 20 min. Water (20 ml) was added to the reaction solution, and the mixture was extracted with 20 ml of dichloromethane. The extract was dried over anhydrous magnesium sulfate. 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (240 mg) was then added thereto. The solvent was removed by concentration until the volume of the solution was brought to 5 ml. The residue was stirred at room temperature for 15 hr. The reaction solution was added dropwise to 35 ml of diisopropyl ether. The precipitated solid was collected by filtration to prepare 443 mg of 4-nitrobenzyl (1S,5R,6S)-6-((1R)-1-hydroxyethyl)-1-methyl-2-[7-methylthio-6-[(2R)-1-(4-nitrobenzyloxycarbonyl)pyrrolidin-2-yl]methylimidazo[5,1-b]thiazolium-2-yl]-1-carbapen-2-em-3-carboxylate trifluoromethanesulfonate as a crude product.

b) (1S,5R,6S)-6-((1R)-1-hydroxyethyl)-1-methyl-2-[7-methylthio-6-((2R)-pyrrolidin-2-yl]methylimidazo[5,1-b]thiazolium-2-yl]-1-carbapen-2-em-3-carboxylate (intramolecular salt) hydrochloride The procedure of Example 50b) was repeated, except that 443 mg of 4-nitrobenzyl (1S,5R,6S)-6-((1R)-1-hydroxyethyl)-1-methyl-2-[7-methylthio-6-[(2R)-1-(4-nitrobenzyloxycarbonyl)pyrrolidin-2-yl]methylimidazo-[5,1-b]thiazolium-2-yl]-1-carbapen-2-em-3-carboxylate trifluoromethanesulfonate as the crude product was used as the starting compound. Thus, 33 mg of the title compound was prepared.

NMR (D$_2$O) δ (HOD=-4.65 ppm): 1.12–1.18 (6H, m), 1.72–1.84 (1H, m), 1.88–2.12 (2H, m), 2.19–2.28 (4H, m), 3.19–3.28 (1H, m), 3.33–3.42 (1H, m), 3.42–3.46 (1H, m), 3.50–3.60 (1H, m), 3.98–4.07 (1H, m), 4.10–4.17 (1H, m), 4.21. (1H, dd, J$_1$=9.5 Hz, J$_2$=2.7 Hz), 4.62–4.80 (2H, m), 8.11 (1H, s)

Example 63

(1S,5R,6S)-2-[6-(6-Aminohexyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride a) 4-Nitrobenzyl (1S,5R,6S)-2-[6-(6-azidohexyl)-7-methylthioimidazo[5,1-b]thiazolium-2-yl]-6-((1R)-1-hydroxyethyl)-1-methyl-1-carbapen-2-em-3-carboxylate trifluoromethanesulfonate 6-Azido-1-hexanol (80 mg) was dissolved in 5 ml of dichloromethane. The solution was cooled to −60° C. 2,6-Lutidine (0.078 ml) and 0.104 ml of trifluoromethanesulfonic anhydride were then added to the cooled solution. The mixture was stirred for 20 min. Water (15 ml) was added to the reaction solution, and the mixture was extracted with 15 ml of dichloromethane. The extract was dried over anhydrous magnesium sulfate. 4-Nitrobenzyl (1S,5R,6S)-6-((1R)-1-hydroxyethyl)-1-methyl-2-(7methylthioimidazo[5,1-b]thiazol-2-yl)-1-carbapen-2-em-3-carboxylate (218 mg) was then added thereto. The solvent was removed by concentration until the volume of the solution was brought to 5 ml. The residue was stirred at room temperature for 6 hr. The reaction solution was added dropwise to 35 ml of diethyl ether. The precipitated solid was collected by filtration to prepare 264 mg of 4-nitrobenzyl (1S,5R,6S)-2-[6-(6-azidohexyl)-7-methylthioimidazo[5,1-b]thiazolium-2-yl]-6-((1R)-1-hydroxyethyl)-1-methyl-1-carbapen-2-em-3-carboxylate trifluoromethanesulfonate as a crude product.

b) (1S,5R,6S)-2-[6-(6-Aminohexyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride The procedure of Example 50b) was repeated, except that 264 mg of 4-nitrobenzyl (1S,5R,6S)-2-[6-(6-azidohexyl)-7-methylthioimidazo[5,1-b]thiazolium-2-yl]-6-((1R)-1-hydroxyethyl)-1-methyl-1-carbapen-2-em-3-carboxylate trifluoromethanesulfonate as the crude product was used as the starting compound. Thus, 70 mg of the title compound was prepared.

NMR (D$_2$O) δ (HOD=4.65 ppm): 1.11 (3H, d, J=7.3 Hz), 1.18 (3H, d, J=6.4 Hz), 1.25–1.40 (4H, m), 1.51–1.61 (2H, m), 1.80–1.90 (2H, m), 2.25 (3H, s), 2.87 (2H, t, J=7.7 Hz), 3.42 (1H, dd, J$_1$=5.9 Hz, J$_2$=2.9 Hz), 3.46–3.57 (1H, m), 4.11–4.19 (1H, m), 4.21 (1H, dd, J$_1$=9.5 Hz, J$_2$=2.7 Hz), 4.25–4.38 (2H, m), 7.98 (1H, s), 9.19 (1H, s)

Example 64

(1S,5R,6S)-2-[7-(3-Aminopropyl)thio-6-methylimidazo[5,1-b]thiazolium-2-yl]-6-((1R)-1-hydroxyethyl)-1-methyl-1-carbapen-2-em-3-carboxylate (intramolecular salt) hydrochloride a) 4-Nitrobenzyl (1S,5R,6S)-6-((1R)-1-hydroxyethyl)-1-methyl-2-[7-[3-(4-nitrobenzyloxycarbonyl)aminopropyl]thioimidazo[5,1-b]thiazol-2-yl]-1-carbapen-2-em-3-carboxylate The procedure of Example 1a) was repeated, except that 628 mg of 4-nitrobenzyl (1R,3R,5R,6S)-6-((1R)-1-hydroxyethyl)-1-methyl-2-oxo-1-carbapenam-3-carboxylate and 1.24 g of 7-[3-(4-nitrobenzyloxycarbonyl)-aminopropyl]thio-2-(tri-n-butylstannyl)imidazo[5,1-b]thiazole were used as the starting compounds. Thus, 812 mg of 4-nitrobenzyl (1S,5R,6S)-6-((1R)-1-hydroxyethyl)-1-methyl-2-[7-[3-(4-nitrobenzyloxycarbonyl)aminopropyl]thioimidazo[5,1-b]thiazol-2-yl]-1-carbapen-2-em-3-carboxylate was prepared.

NMR (CDCl$_3$) δ: 1.31 (3H, d, J=7.4 Hz), 1.40 (3H, d, J=6.2 Hz), 1.8–1.9 (2H, m), 2.8–2.95 (2H, m), 3.35–3.5 (4H, m), 4.3–4.4 (2H, m), 5.18 (2H, s), 5.27 (1H, d, J=13.5 Hz), 5.42 (1H, br s), 5.52 (1H, d, J=13.5 Hz), 7.50 (2H, d, J=8.8 Hz), 7.68 (2H, d, J=8.8 Hz), 8.02 (1H, s), 8.20 (2H, d, J=8.8 Hz), 8.24 (2H, d, J=8.8 Hz), 8.28 (1H, s)

b) 4-Nitrobenzyl (1S,5R,6S)-6-((1R)-1-hydroxyethyl)-1-methyl-2-[6-methyl-7-[3-(4-nitrobenzyloxycarbonyl)aminopropyl]thioimidazo[5,1-b]thiazolium-2-yl]-1-carbapen-2-em-3-carboxylate chloride The procedure of Example 47b) was repeated, except that 111 mg of 4-nitrobenzyl (1S,5R,6S)-6-((1R)-1-hydroxyethyl)-1-methyl-2-[7-[3-(4-nitrobenzyloxycarbonyl)aminopropyl]thioimidazo[5,1-b]thiazol-2-yl]-1-carbapen-2-em-3-carboxylate was used as the starting compound. The residue was subjected to column chromatography (methanol) on Amberlyst A-26 as an ion-exchange resin (chloro form) to prepare 120 mg of 4-nitrobenzyl (1S,5R,6S)-6-((1R)-1-hydroxyethyl)-1-methyl-2-[6-methyl-7-[3-(4-nitrobenzyloxycarbonyl)aminopropyl]-thioimidazo[5,1-b]thiazolium-2-yl]-1-carbapen-2-em-3-carboxylate chloride.

c) (1S,5R,6S)-2-[7-(3-Aminopropyl)thio-6-methylimidazo[5,1-b]thiazolium-2-yl]-6-((1R)-1- hydroxyethyl)-1methyl-1-carbapen-2-em-3-carboxylate (intramolecular salt) hydrochloride The procedure of Example 3b) was repeated, except that 120 mg of 4-nitrobenzyl (1S,5R,6S)-6-((1R)-1-hydroxyethyl)-1-methyl-2-[6-methyl-7-[3-(4-nitrobenzyloxycarbonyl)aminopropyl]thioimidazo[5,1-b]thiazolium-2-yl]-1-carbapen-2-em-3-carboxylate chloride was used as the starting compound. Thus, 16.5 mg of the title compound was prepared.

NMR (D$_2$O) δ (HOD=4.80 ppm): 1.27 (3H, d, J=7.2 Hz), 1.31 (3H, d, J=6.3 Hz), 1.85–2.0 (2H, m), 2.85–2.95 (2H, m), 3.1–3.2 (2H, m), 3.5–3.6 (1H, m), 3.6–3.75 (1H, m), 4.06 (3H, s), 4.25–4.4 (2H, m), 8.15 (1H, s), 9.33 (1H, s)

Example 65

(1S,5R,6S)-6-((1R)-1-Hydroxyethyl)-2-[7-methylthio-6-[2-oxo-2-(piperazin-1-yl)ethyl]imidazo[5,1-b]thiazolium-2-yl]-1-methyl-1-carbapen-2-em-3-carboxylate (intermolecular salt) hydroiodide a) 4-Nitrobenzyl (1S,5R,6S)-6-((1R)-1-hydroxyethyl)-2-[7-methylthio-6-[2-[4-(4-nitrobenzyloxycarbonyl)piperazin-1-yl]-2-oxoethyl]imidazo[5,1-b]-thiazolium-2-yl]-1-methyl-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (379 mg) was dissolved in 18 ml of acetone. 4-Chloroacetyl-1-(4-nitrobenzyloxycarbonyl)piperazine (1.34 g) and 600 mg of sodium iodide were added to the solution. The mixture was stirred at room temperature for 2 days. The solvent was removed by distillation under the reduced pressure. The residue was purified by column chromatography on Sephadex LH-20 (chloroform:methanol=1:1) to prepare 342 mg of 4-nitrobenzyl (1S,5R,6S)-6-((1R)-1-hydroxyethyl)-2-[7-methylthio-6-[2-[4-(4-nitrobenzyloxycarbonyl)piperazin-1-yl]-2-oxoethyl]imidazo[5,1-b]-thiazolium-2-yl]-1-methyl-1-carbapen-2-em-3-carboxylate iodide as a crude product.

b) (1S,5R,6S)-6-((1R)-1-Hydroxyethyl)-2-[7-methylthio-6-[2-oxo-2-(piperazin-1-yl)ethyl]imidazo[5,1-b]-thiazolium-2-yl]-1-methyl-1-carbapen-2-em-3-carboxylate (intramolecular salt) hydroiodide The procedure of Example 44b) was repeated, except that 320 mg of 4-nitrobenzyl (1S,5R,6S)-6-((1R)-1-hydroxyethyl)-2-[7-methylthio-6-[2-[4-(4-nitrobenzyloxycarbonyl)piperazin-1-yl]-2-oxoethyl]imidazo[5,1-b]-thiazolium-2-yl]-1-methyl-1-carbapen-2-em-3-carboxylate iodide as the crude product was used as the starting compound. Thus, 110 mg of the title compound was prepared.

NMR (D$_2$O) δ (HOD=4.65 ppm): 1.11 (3H, d, J=7.0 Hz), 1.16 (3H, d, J=6.3 Hz), 2.19 (3H, s), 3.20 (2H, t, J=5.4 Hz), 3.31 (2H, t, J=5.1 Hz), 3.42 (1H, dd, J$_1$=6.0 Hz, J$_2$=2.7 Hz), 3.46–3.56 (1H, m), 3.74 (2H, t, J=5.3 Hz), 3.84 (2H, t, J=5.1 Hz), 4.09–4.17 (1H, m), 4.20 (1H, dd, J$_1$=9.5 Hz, J$_2$=2.7 Hz), 5.46 (2H, s), 8.04 (1H, s), 9.19 (1H, s)

Example 66

(1S,5R,6S)-2-[6-[N-(3-Aminopropyl)carbamoylmethyl]-7-methylthioimidazo[5,1-b]thiazolium-2-yl]-6-((1R)-1-hydroxyethyl)-1-methyl-1-carbapen-2-em-3-carboxylate (intramolecular salt) hydrochloride a) 4-Nitrobenzyl (1S,5R,6S)-2-[6-[N-(3-azidopropyl)carbamoylmethyl]-7-methylthioimidazo[5,1-b]-thiazolium-2-yl]-6-((1R)-1-hydroxyethyl)-1-methyl-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (932 mg) was dissolved in 25 ml of acetone. 2-Iodo-N-(3-azidopropyl)acetamide (2.88 g) and 2.45 g of sodium iodide were added to the solution. The mixture was stirred at room temperature for 3 days. The solvent was removed by distillation under the reduced pressure. The residue was purified by column chromatography on Sephadex LH-20 (chloroform:methanol=1:1) to prepare 1.21 g of 4-nitrobenzyl (1S,5R,6S)-2-[6-[N-(3-azidopropyl)carbamoylmethyl]-7-methylthioimidazo[5,1-b]thiazolium-2-yl]-6-((1R)-1-hydroxyethyl)-1-methyl-1-carbapen-2-em-3-carboxylate iodide as a crude product.

b) (1S,5R,6S)-2-[6-[N-(3-Aminopropyl)carbamoylmethyl]-7-methylthioimidazo[5,1-b]thiazolium-2-yl]-6-((1R)-1-hydroxyethyl)-1-methyl-1-carbapen-2-em-3-carboxylate (intramolecular salt) hydrochloride 4-Nitrobenzyl (1S,5R,6S)-2-[6-[N-(3-azidopropyl)carbamoylmethyl]-7-methylthioimidazo[5,1-b]thiazolium-2-yl]-6-((1R)-1-hydroxyethyl)-1-methyl-1-carbapen-2-em-3-carboxylate iodide as the crude product (1.20 g) was dissolved in 35 ml of THF and 35 ml of water. 10% Pd—C (1.05 g) was added to the solution. The air in the reaction vessel was replaced by hydrogen, and the contents of the reaction vessel were stirred at room temperature for 3 hr. The catalyst was removed by filtration on Celite, and washed with water. The filtrate was washed with ethyl acetate, and was concentrated under the reduced pressure until the volume of the filtrate was brought to about 5 ml. The residue was purified by column chromatography on Cosmosil 40C$_{18}$-PREP (a 20% aqueous methanol solution). A fraction eluted as the first fraction was subjected to column chromatography (water) on Amberlyst A-26 as an ion-exchange resin (chloro form). Thus, 276 mg of the title compound was prepared.

NMR (D$_2$O) δ (HOD=4.65 ppm): 1.12 (3H, d, J=7.3 Hz), 1.17 (3H, d, J=6.3 Hz), 1.74–1.84 (2H, m), 2.22 (3H, s), 2.87–2.92 (2H, m), 3.24 (2H, t, J=6.8 Hz), 3.42 (1H, dd, J$_1$=6.1 Hz, J$_2$=2.9Hz), 3.47–3.57 (1H, m), 4.09–4.17 (1H, m), 4.22 (1H, dd, J$_1$=9.3 Hz, J$_2$=2.7 Hz), 5.14 (2H, s), 8.05 (1H, s)

Example 67

(1S,5R,6S)-6-((1R)-1-Hydroxyethyl)-2-[6-[N-(3-hydroxypropyl)carbamoylmethyl]-7-methylthioimidazo-[5,1-b]thiazolium-2-yl]-1-methyl-1-carbapen-2-em-3-carboxylate (intramolecular salt)

A latter fraction was collected which had been eluted after (1S,5R,6S)-2-[6-[N-(3-aminopropyl)carbamoylmethyl]-7-methylthioimidazo[5,1-b]thiazolium-2-yl]-6-((1R)-1-hydroxyethyl)-1-methyl-1-carbapen-2-em-3-carboxylate (intramolecular salt) hydrochloride in the column chromatography on Cosmosil 40C$_{18}$-PREP (a 20% aqueous methanol solution) in Example 66b). Thus, 30 mg of the title compound was prepared.

NMR (D$_2$O) δ (HOD=4.65 ppm): 1.12 (3H, d, J=7.3 Hz), 1.17 (3H, d, J=6.4 Hz), 1.61–1.69 (2H, m), 2.20 (3H, s), 3.21 (2H, t, J=6.8 Hz), 3.42 (1H, dd, J$_1$=6.0 Hz, J$_2$=2.9 Hz), 3.47–3.55 (3H, m), 4.09–4.17 (1H, m), 4.21 (1H, dd, J$_1$=9.2 Hz, J$_2$=2.7 Hz), 5.12 (2H, s), 8.04 (1H, s)

Example 68

(1S,5R,6S)-2-[6-(3-Acetimidoylaminopropyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride (1S,5R,6S)-2-[6-(3-Aminopropyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride (290 mg) was dissolved in 15 ml of water. Ethylacetimidate hydrochloride (380 mg) was added to the solution under cooling in ice. The mixture was adjusted to pH 8 to 8.5 by the addition of a 1 N aqueous sodium hydroxide solution. The mixture was stirred for 45 min. The reaction solution was adjusted to pH 3.4 by the addition of a 1 N aqueous hydrochloric acid solution, and was purified by column chromatography on Cosmosil 40C$_{18}$-PREP (a 10% aqueous methanol solution) to prepare 197 mg of the title compound.

NMR (D$_2$O) δ (HOD=4.65 ppm): 1.11 (3H, d, J=7.1 Hz), 1.16 (3H, d, J=6.3 Hz), 2.08 (3H, s), 2.15 (2H, m), 2.26 (3H, s), 3.24 (2H, t, J=6.8 Hz), 3.42 (1H, m), 3.49 (1H, m), 4.13 (1H, m), 4.20 (1H, m), 4.41 (2H, t, J=6.8 Hz), 8.01 (1H, s), 9.23 (1H, s)

Example 69

(1S,5R,6S)-2-[6-((3S)-1-Acetimidoylpyrrolidin-3-yl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride (1S,5R,6S)-6-((1R)-1-Hydroxyethyl)-1-methyl-2-[7-methylthio-6-((3S)-pyrrolidin-3-yl)imidazo[5,1-b]-thiazolium-2-yl]-1-carbapen-2-em-3-carboxylate (intramolecular salt) hydrochloride (58 mg) was dissolved in 3 ml of water. Ethyl acetimidate hydrochloride (57 mg) was added to the solution. The mixture was adjusted to pH 8.6 by the addition of a 1 N sodium hydroxide solution under cooling in ice, and was stirred for 20 min. The pH value of the reaction solution was returned to 3.6 by the addition of 1 N hydrochloric acid. Purification was then carried out by column chromatography on Cosmosil 40C$_{18}$-PREP (a 20% aqueous methanol solution) to prepare 39 mg of the title compound.

NMR (D$_2$O) δ (HOD=4.65 ppm): 1.10 (3H, d, J=7.3 Hz), 1.15 (3H, d, J=6.3 Hz), 2.18–2.23 (3H, m), 2.28 (3H, s), 2.44–2.56 (1H, m), 2.65–2.81 (1H, m), 3.38–3.42 (1H, m), 3.47–3.55 (1H, m), 3.60–3.99 (3H, m), 4.08–4.22 (2H, m), 4.27–4.33 (1H, m), 5.53–5.64 (1H, m), 8.02 (1H, s), 9.32 (1H, s)

Example 70

(1S,5R,6S)-2-[6-((3S)-1-Amidinopyrrolidin-3-yl)-7-methylthioimidazo[5,1-b]thiazolium-2-yl-6-((1R)-1-hydroxyethyl)-1-methyl-1-carbapen-2-em-3-carboxylate (intramolecular salt) hydrochloride a) (3S,4R)-1-[(Allyloxycarbonyl)(triphenylphosphoranilidene)methyl]-3-[(1R)-1-(t-butyldimethylsilyloxy)ethyl]-4-[(1R)-1-(pivaloyloxycarbonyl)ethyl]azetidin-2-one A solution of 3.30 g of (3S,4R)-1-[(allyloxycarbonyl)(triphenylphosphoranilidene)methyl]-3-[(1R)-1-(t-butyldimethylsilyloxy)ethyl]-4-[(1R)-1-(carboxy)ethyl]azetidin-2-one in 20 ml of toluene was cooled in an ice-cold water bath. Triethylamine (0.70 ml) was added to the cooled solution. Pivaloyl chloride (0.62 ml) was added dropwise thereto, and the mixture was stirred at that temperature for 30 min. The reaction mixture was brought to ambient temperature. The insolubles were then collected by filtration, and were washed with 5 ml of toluene. The filtrates were combined, and the solvent was removed by distillation to prepare 3.72 g of (3S,4R)-1-[(4-allyloxycarbonyl)(triphenylphosphoranilidene)methyl]-3-[(1R)-1-(t-butyldimethylsilyloxy)ethyl]-4-[(1R)-1-(pivaloyloxy-carbonyl)ethyl]-azetidin-2-one as a crude product.

NMR (CDCl$_3$) δ:−0.20–0.10 (6H, m), 0.60–0.65, 0.95–1.05 (3H, m), 0.75–0.90 (9H, m), 1.24, 1.25 (9H, m), 1.30–1.35, 1.45–1.55 (3H, m), 2.45–3.10 (2H, m), 4.05–4.25 (2H, m), 4.40–4.70 (2H, m), 5.10–5.20 (1H, m), 5.25–5.40 (1H, m), 5.84–6.05 (1H, m), 7.45–7.60 (9H, m), 7.70–7.85 (6H, m)

b) (3S,4R)-1-[(Allyloxycarbonyl)(triphenyl-phosphoranilidene)methyl]-3-[(1R)-1-(t-butyl-dimethysilyloxy)ethyl]-4-[(1R)-1-methyl-2-(7-methylthioimidazo-[5,1-b]thiazol-2-yl)-2-oxoethyl] azetidin-2-one A solution of 0.16 g of 2-iodo-7-methylthioimidazo[5,1-b]thiazole in 2 ml of THF was cooled to −30° C. An ethylmagnesium bromide/THF solution (0.6 ml) was added to the cooled solution. The mixture was stirred at that temperature for 30 min. A solution of 0.37 g of (3S,4R)-1-[(allyloxycarbonyl)(triphenylphosphoranilidene)methyl]-3-[(1R)-1-(t-butyldimethylsilyloxy)ethyl]-4-[(1R)-1-(pivaloyloxycarbonyl)ethyl]azetidin-2-one in 1.5 ml of THF was added to the reaction mixture. The mixture was stirred at ambient temperature for 30 min. This reaction mixture was added to 50 ml of a saturated aqueous ammonium chloride solution, and the mixture was extracted with 50 ml of ethyl acetate. The organic layer was washed with dilute hydrochloric acid, a dilute aqueous sodium hydrogencarbonate solution, and a saturated aqueous sodium chloride solution in that order, and was dried over anhydrous magnesium sulfate. The solvent was removed by distillation, and the residue was purified by column chromatography on silica gel (ethyl acetate) to prepare 81 mg of (3S,4R)-1-[(allyloxycarbonyl)(triphenylphosphoranilidene)methyl]-3-[(1R)-1-(t-butyl-dimethylsilyloxy)ethyl]-4-[(1R)-1-methyl-2-(7-methylthioimidazo[5,1-b]thiazol-2-yl)-2-oxoethyl] azetidin-2-one.

NMR (CDCl$_3$) δ: −0.08 (3H, s), −0.06 (3H, s), 0.80 (9H, s), 0.90 (3H, d, J=5.8 Hz), 1.46 (3H, d, J=6.7 Hz), 2.43 (3H, s), 2.55–2.60 (1H, m), 2.65–2.90 (2H, m), 3.75–3.80, 3.90–4.00 (1H, m), 4.15–4.25 (1H, m), 4.55–4.70 (2H, m), 5.10–5.25 (1H, m), 5.35–5.50, 6.00–6.10 (1H, m), 7.45–7.65 (9H, m), 7.70–7.85 (6H, m), 8.00–8.10 (2H, m), 8.56 (1H, s)

c) Allyl (1S,5R,6S)-6-[(1R)-1-(t-butyldimethylsilyloxy)ethyl]-1-methyl-2-(7-methylthioimidazo[5,1-b]thiazol-2-yl)-1-carbapen-2-em-3-carboxylate A solution of 0.81 g (3S,4R)-1-[(allyloxycarbonyl)(triphenylphosphoranilidene)methyl]-3-[(1R)-1-(t-butyldimethylsilyloxy)ethyl]-4-[(1R)-1-methyl-2-(7-methylthioimidazo[5,1-b]thiazol-2-yl)-2-oxoethyl]-azetidin-2-one in 4 ml of toluene was stirred with heating at 90° C. for 7 hr. The reaction mixture was concentrated. The residue was purified by column chromatography on silica gel (hexane:ethyl acetate=2:3) to prepare 0.46 g of allyl (1S,5R,6S)-6-[(1R)-1-(t-butyldimethylsilyloxy)ethyl]-1-methyl-2-(7-methylthioimidazo[5,1-b]thiazol-2-yl)-1-carbapen-2-em-3-carboxylate.

NMR (CDCl$_3$) δ: 0.10 (6H, s), 0.90 (9H, s), 1.25–1.30 (6H, m), 2.42 (3H, s), 3.29 (1H, dd, J$_1$=5.5 Hz, J$_2$=2.8 Hz), 3.35–3.43 (1H, m), 4.25–4.35 (2H, m), 4.68–4.86 (2H, m), 5.25–5.30 (1H, m), 5.40–5.50 (1H, m), 5.90–6.15 (1H, m), 8.00 (1H, s), 8.30 (1H, s)

d) Allyl (1S,5R,6S)-6-((1R)-1-Hydroxyethyl)-1-methyl-2-(7-methylthioimidazo[5,1-b]thiazol-2-yl)-1-carbapen-2-em-3-carboxylate A solution of 0.97 g of allyl (1S,5R,6S)-6-[(1R)-1-(t-butyldimethylsilyloxy)ethyl]-1-methyl-2-(7-methylthioimidazo[5,1-b]thiazol-2-yl)-1-carbapen-2-em-3-carboxylate in 9 ml of THF was cooled in an ice-cold water bath. Acetic acid (1.7 ml) and 9.1 ml of a 1 M tetra-n-butylammonium fluoride/THF solution were added to the cooled solution. The mixture was then stirred at ambient temperature for 40 hr. Ethyl acetate (50 ml) was added to the reaction mixture. The mixture was washed with a saturated aqueous sodium hydrogencarbonate solution and a saturated aqueous sodium chloride solution in that order, and was dried over anhydrous magnesium sulfate. The solvent was removed by distillation, and the residue was purified by column chromatography on silica gel (5% methanol/ethyl acetate) to prepare 0.72 g of allyl (1S,5R,6S)-6-((1R)-1-hydroxyethyl)-1-methyl-2-(7-methylthioimidazo[5,1-b]-thiazol-2-yl)-1-carbapen-2-em-3-carboxylate.

NMR (CDCl$_3$) δ: 1.29 (3H, d, J=7.2 Hz), 1.38 (3H, d, J=6.3 Hz), 2.44 (3H, s), 3.33 (1H, dd, J$_1$=6.8 Hz, J$_2$=2.8 Hz), 3.40–3.50 (1H, m), 4.24–4.40 (2H, m), 4.70–4.90 (2H, m), 5.28–5.32 (1H, m), 5.43–5.50 (1H, m), 5.90–6.05 (1H, m), 8.02 (1H, s), 8.30 (1H, s)

e) Allyl (1S,5R,6S)-2-[6-[(3S)-1-N,N'-bis(allyloxycarbonyl)amidinopyrrolidin-3-yl]-7-methylthioimidazo-[5,1-b]thiazolium-2-yl]-6-((1R)-1-hydroxyethyl)-1-methyl-1-carbapen-2-em-3-carboxylate trifluoromethane-sulfonate (3R)-1-N,N'-Bis(allyloxycarbonyl)amidino-3-hydroxypyrrolidine, (230 mg) was dissolved in 7 ml of dichloromethane. The solution was cooled to −60° C. 2,6-Lutidine (0.108 ml) and 0.143 ml of trifluoromethanesulfonic anhydride were then added to the cooled solution. The mixture was stirred for 20 min. Water (15 ml) was added to the reaction solution, and the mixture was extracted with 15 ml of dichloromethane. The extract was dried over anhydrous magnesium sulfate. Allyl (1S,5R,6S)-6-((1R)-1-hydroxyethyl)-1-methyl-2-(7-methylthioimidazo-[5,1-b]thiazol-2-yl)-1-carbapen-2-em-3-carboxylate (230 mg) was then added thereto. The solvent was removed by concentration until the volume of the solution was brought to 7 ml. The residue was stirred at room temperature for 16 hr. The solvent was removed by distillation under the reduced pressure. The residue was purified by column chromatography on Sephadex LH-20 (chloroform:methanol=1:1) to prepare 170 mg of allyl (1S,5R,6S)-2-[6-[(3S)-1-N,N'-bis(allyloxycarbonyl)amidinopyrrolidin-3-yl]-7-methylthioimidazo[5,1-b]thiazolium-2-yl]-6-((1R)-1-hydroxyethyl)-1-methyl-1-carbapen-2-em-3-carboxylate trifluoromethane-sulfonate as a crude product.

f) (1S,5R,6S)-2-[6-((3S)-1-Amidinopyrrolidin-3-yl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride Allyl (1S,5R,6S)-2-[6-[(3S)-1-N,N'-bis(allyloxycarbonyl)amidinopyrrolidin-3-yl]-7-methylthioimidazo[5,1-b]thiazolium-2-yl]-6-((1R)-1-hydroxyethyl)-1-methyl-1-carbapen-2-em-3-carboxylate trifluoromethane-sulfonate as the crude product (80 mg) was dissolved in 2 ml of THF and 1 ml of methanol under an argon atmosphere. Triphenylphosphine (11 mg), 0.025 ml of morpholine, and 11 mg of tetrakis(triphenylphosphine) palladium(0) were added to the solution. The mixture was stirred at room temperature for 2 hr. The reaction solution was washed with ethyl acetate, and was concentrated under the reduced pressure until the volume of the solution was brought to about 5 ml. The residue was then purified by column chromatography on Cosmosil 40C$_{18}$-PREP (a 20% aqueous methanol solution), and was then subjected to column chromatography (water) on Amberlyst A-26 as an ion-exchange resin (chloro form) to prepare 9 mg of the title compound.

NMR (D$_2$O) δ (HOD=4.65 ppm): 1.11 (3H, d, J=7.3 Hz), 1.16 (3H, d, J=6.5 Hz), 2.29 (3H, s), 2.36–2.47 (1H, m), 2.61–2.72 (1H, m), 3.40–3.43 (1H, m), 3.45–3.55 (1H, m), 3.59–3.74 (3H, m), 4.05–4.16 (2H, m), 4.20 (1H, dd, J$_1$=9.2 Hz, J$_2$=2.7 Hz), 5.52–5.60 (1H, m), 8.01 (1H, s)

Example 71
(1S,5R,6S)-2-[6-Carbamoylmethyl-7-(piperidin-4-yl)thioimidazo[5,1-b]thiazolium-2-yl]-6-((1R)-1-hydroxyethyl)-1-methyl-1-carbapen-2-em-3-carboxylate (intramolecular salt) hydrochloride a) 4-Nitrobenzyl (1S,5R,6S)-6-((1R)-1-hydroxyethyl)-1-methyl-2-[7-[1-(4-nitrobenzyloxycarbonyl)piperidin-4-yl]thioimidazo[5,1-b]thiazol-2-yl]-1-carbapen-2-em-3-carboxylate The procedure of Example 1a) was repeated, except that 410 mg of 4-nitrobenzyl (1R,3R,5R,6S)-6-((1R)-1-hydroxyethyl)-1-methyl-2-oxo-1-carbapenam-3-carboxylate and 881 mg of 7-[1-(4-nitrobenzyloxycarbonyl)piperidin-4-yl]thio-2-(tri-n-butylstannyl)imidazo[5,1-b]thiazole were used as the starting compounds. Thus, 450 mg of 4-nitrobenzyl (1S,5R,6S)-6-((1R)-1-hydroxyethyl)-1-methyl-2-[7-[1-(4-nitrobenzyloxycarbonyl)piperidin-4-yl]thioimidazo[5,1-b]thiazol-2-yl]-1-carbapen-2-em-3-carboxylate was prepared.

NMR (CDCl$_3$) δ: 1.31 (3H, d, J=7.5 Hz), 1.40 (3H, d, J=6.3 Hz), 1.5–1.7 (2H, m), 1.9–2.1 (2H, m), 2.9–3.2 (3H, m), 3.35–3.5 (2H, m), 4.0–4.15 (2H, m), 4.25–4.4 (2H, m), 5.19 (2H, s), 5.27 (1H, d, J=13.5 Hz), 5.53 (1H, d, J=13.5 Hz), 7.48 (2H, d, J=8.7 Hz), 7.68 (2H, d, J=8.7 Hz), 8.21 (2H, d, J=8.7 Hz), 8.24 (2H, d, J=8.7 Hz), 8.28 (1H, s)

b) 4-Nitrobenzyl (1S,5R,6S)-2-[6-carbamoylmethyl-7-[1-(4-nitrobenzyloxycarbonyl)piperidin-4-yl]thioimidazo-[5,1-b]thiazolium-2-yl]-6-((1R)-1-hydroxyethyl)-1-methyl-1-carbapen-2-em-3-carboxylate iodide The procedure of Example 3a) was repeated, except that the reaction was carried out at 40° C. and 104 mg of 4-nitrobenzyl (1S,5R,6S)-6-((1R)-1-hydroxyethyl)-1-methyl-2-[7-[1-(4-nitrobenzyloxycarbonyl)piperidin-4-yl]thioimidazo-[5,1-b]thiazol-2-yl]-1-carbapen-2-em-3-carboxylate was used as the starting compound. Thus, 118 mg of 4-nitrobenzyl (1S,5R,6S)-2-[6-carbamoylmethyl-7-[1-(4-nitrobenzyloxycarbonyl)piperidin-4-yl]thioimidazo-[5,1-b]thiazolium-2-yl]-6-((1R)-1-hydroxyethyl)-1-methyl-1-carbapen-2-em-3-carboxylate iodide was prepared.

NMR (CD$_2$OD) δ: 1.32 (3H, d, J=6.3 Hz), 1.34 (3H, d, J=7.2 Hz), 1.45–1.65 (2H, m), 1.95–2.05 (2H, m), 2.85–3.1 (2H, m), 3.3–3.4 (1H, m), 3.50 (1H, dd, J$_1$=6.3 Hz, J$_2$=2.7 Hz), 3.7–3.85 (1H, m), 4.0–4.2 (3H, m), 4.43 (1H, dd, J$_1$=9.9 Hz, J$_2$=2.7 Hz), 5.23 (2H, s), 5.31 (2H, s), 5.37 (1H, d, J=13.8 Hz), 5.54 (1H, d, J=13.8 Hz), 7.57 (2H, d, J=9.3 Hz), 7.74 (2H, d, J=8.7 Hz), 8.15–8.25 (4H, m), 8.62 (1H, s)

c) (1S,5R,6S)-2-[6-Carbamoylmethyl-7-(piperidin-4-yl)thioimidazo[5,1-b]thiazolium-2-yl]-6-((1R)-1-hydroxyethyl)-1-methyl-1-carbapen-2-em-3-carboxylate (intramolecular salt) hydrochloride The procedure of Example 3b) was repeated, except that the reaction was carried out in a mixed solvent composed of THF and water and 118 mg of 4-nitrobenzyl (1S,5R,6S)-2-[6-carbamoylmethyl-7-(1-(4-nitrobenzyloxycarbonyl)piperidin-4-yl]thioimidazo[5,1-b]thiazolium-2-yl]-6-((1R)-1-hydroxyethyl)-1-methyl-1-carbapen-2-em-3-carboxylate iodide was used as the starting compound. Purification was then carried out by column chromatography on Cosmosil 40C$_{18}$-PREP (a 5% aqueous methanol solution), followed by column chromatography (water) on Amberlyst A-26 as an ion-exchange resin (chloro form) to prepare 26.6 mg of the title compound.

NMR (D$_2$O) δ (HOD=4.80 ppm): 1.28 (3H, d, J=7.2 Hz), 1.32 (3H, d, J=6.6 Hz), 1.75–1.95 (2H, m), 2.1–2.25 (2H, m), 2.95–3.1 (2H, m), 3.35–3.5 (3H, m), 3.57 (1H, dd, J$_1$=6.3 Hz, J$_2$=2.7 Hz), 3.6–3.75 (1H, m), 4.25–4.35 (1H, m), 4.46 (1H, dd, J$_1$=9.3 Hz, J$_2$=2.7 Hz), 5.34 (2H, s), 8.21 (1H, s)

Example 72
(1S,5R,6S)-2-[6-(3-Formimidoylaminopropyl)-7-methylthioimidazo-[5,1-b]thiazolium-2-yl]-6-((1R)-1- hydroxyethyl)-1-methyl-1-carbapen-2-em-3-carboxylate (intramolecular salt) hydrochloride (1S,5R,6S)-2-[6-(3-Aminopropyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride (60 mg) was dissolved in 3 ml of water. Ethyl formimidate hydrochloride (140 mg) was added six times at intervals of 2 to 3 min to the solution under cooling in ice. Each time when the ethyl formimidate hydrochloride was added to the solution, the solution was adjusted to pH 8 to 8.5 by the addition of a 1 N aqueous sodium hydroxide solution. The mixture was stirred for 30 min. The reaction solution was adjusted to pH 3.6 by the addition of a 1 N aqueous hydrochloric acid solution, was purified by column chromatography on Cosmosil 40C$_{18}$-PREP (a 20% aqueous methanol solution), and was then subjected to column chromatography (water) on Amberlyst A-26 as an ion-exchange resin (chloro form) to prepare 5 mg of the title compound.

NMR (D$_2$O) δ (HOD=4.65 ppm): 1.09 (3H, d, J=7.3 Hz), 1.16 (3H, d, J=6.4 Hz), 2.18 (2H, m), 2.25 (3H, s), 3.30 (2H, t, J=6.9 Hz), 3.40 (1H, m), 3.46 (1H, m), 4.12 (1H, m), 4.18 (1H, m), 4.39 (2H, m), 7.73 (1H, br s), 7.96 (1H, s), 9.20 (1H, s)

Example 73

(1S,5R,6S)-2-[6-[N-(3-Acetimidoylaminopropyl) carbamoylmethyl]-7-methylthioimidazo[5,1-b]-thiazolium-2-yl]-6-((1R)-1-hydroxyethyl)-1-methyl-1-carbapen-2-em-3-carboxylate (intramolecular salt) hydrochloride The procedure of Example 69 was repeated, except that 50 mg of (1S,5R,6S)-2-[6-[N-(3-aminopropyl) carbamoylmethyl]-7-methylthioimidazo[5,1-b]thiazolium-2-yl]-6-((1R)-1-hydroxyethyl)-1-methyl-1-carbapen-2-em-3-carboxylate (intramolecular salt) hydrochloride was used as the starting compound. Thus, 16 mg of the title compound was prepared.

NMR (D$_2$O) δ (HOD=4.65 ppm): 1.12 (3H, d, J=7.3 Hz), 1.16 (3H, d, J=6.4 Hz), 1.72–1.81 (2H, m), 2.05 (3H, s), 2.21 (3H, s), 3.15 (2H, t, J=6.8 Hz), 3.23 (2H, t, J=6.8 Hz), 3.42 (1H, dd, J$_1$=6.1 Hz, J$_2$ 2.9 Hz), 3.47–3.56 (1H, m), 4.10–4.17 (1H, m), 4.21 (1H, dd, J$_1$=9.3 Hz, J$_2$=2.7 Hz), 5.13 (2H, s), 8.05 (1H, s)

Example 74

(1S,5R,6S)-2-[6-[N-(3-Aminopropyl)-N-methylcarbamoylmethyl]-7-methylthioimidazo[5,1-b]thiazolium-2-yl]-6-((1R)-1-hydroxyethyl)-1-methyl-1-carbapen-2-em-3-carboxylate (intramolecular salt) hydrochloride a) 4-Nitrobenzyl (1S,5R,6S)-2-[6-[N-(3-azidopropyl)-N-methylcarbamoylmethyl]-7-methylthioimidazo-[5,1-b] thiazolium-2-yl]-6-((1R)-1-hydroxyethyl)-1-methyl-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (120 mg) was dissolved in 5 ml of acetone. 2-Iodo-N-(3-azidopropyl)-N-methylacetamide (400 mg) and 320 mg of sodium iodide were added to the solution. The mixture was stirred at room temperature for 2 days. The solvent was removed by distillation under the reduced pressure. The residue was purified by column chromatography on Sephadex LH-20 (chloroform:methanol=1:1) to prepare 188 mg of 4-nitrobenzyl (1S,5R,6S)-2-[6-[N-(3-azidopropyl)-N-methylcarbamoylmethyl]-7-methylthioimidazo[5,1-b]thiazolium-2-yl]-6-((1R)-1-hydroxyethyl)-1-methyl-1-carbapen-2-em-3-carboxylate iodide as a crude product.

b) (1S,5R,6S)-2-[6-[N-(3-Aminopropyl)-N-methylcarbamoylmethyl]-7-methylthioimidazo[5,1-b] thiazolium-2-yl]-6-((1R)-1-hydroxyethyl)-1-methyl-1-carbapen-2-em-3-carboxylate (intramolecular salt) hydrochloride The procedure of Example 50b) was repeated, except that 180 mg of 4-nitrobenzyl (1S,5R,6S)-2-[6-[N-(3-azidopropyl)-N-methylcarbamoylmethyl]-7-methylthioimidazo[5,1-b]thiazolium-2-yl]-6-((1R)-1-hydroxyethyl)-1-methyl-1-carbapen-2-em-3-carboxylate iodide as the crude product was used as the starting compound. Thus, 38 mg of the title compound was prepared.

NMR (D$_2$O) δ (HOD=4.65 ppm): 1.12 (3H, d, J=7.3 Hz), 1.17 (3H, d, J=6.3 Hz), 1.79–2.07 (2H, m), 2.18, 2.22 (total 3H, s each), 2.83–3.03 (2H, m), 2.87, 3.08 (total 3H, s each), 3.37–3.56 (3H, m), 4.10–4.17 (1H, m), 4.22 (1H, dd, J$_1$=9.5 Hz, J$_2$=2.5 Hz), 5.37 (2H, s), 8.05 (1H, s)

Example 75

(1S,5R,6S)-2-[6-((3S,5S)-5-N,N-Dimethylcarbamoylpyrrolidin-3-yl)-7-methylthioimidazo[5,1-b]-thiazolium-2-yl]-6-((1R)-1-hydroxyethyl)-1-methyl-1-carbapen-2-em-3-carboxylate (intramolecular salt) hydrochloride a) Allyl (1S,5R,6S)-2-[6-((3S,5S)-1-allyloxycarbonyl-5-N,N-dimethylcarbamoylpyrrolidin-3-yl)-7-methylthioimidazo[5,1-b]thiazolium-2-yl]-6-((1R)-1-hydroxyethyl)-1-methyl-1-carbapen-2-em-3-carboxylate trifluoromethanesulfonate (2S,4R)-1-Allyloxycarbonyl-2-N,N-dimethylcarbamoyl-4-hydroxypyrrolidine (300 mg) was dissolved in 5 ml of dichloromethane. The solution was cooled to −35° C. 2,6-Lutidine (0.173 ml) and 0.230 ml of trifluoromethanesulfonic anhydride were then added to the cooled solution. The mixture was stirred for 20 min. Water (15 ml) was added to the reaction solution, and the mixture was extracted with 15 ml of dichloromethane. The extract was dried over anhydrous magnesium sulfate. Allyl (1S,5R,6S)-6-((1R)-1-hydroxyethyl)-1-methyl-2-(7-methylthioimidazo[5,1-b] thiazol-2-yl)-1-carbapen-2-em-3-carboxylate (253 mg) was then added thereto. The solvent was removed by concentration until the volume of the solution was brought to 6 ml. The residue was stirred for 2 days. The solvent was removed by distillation under the reduced pressure. The residue was purified by column chromatography on Sephadex LH-20 (chloroform:methanol=1:1) to prepare 189 mg of allyl (1S,5R,6S)-2-[6-((3S,5S)-1-allyloxycarbonyl-5-N,N-dimethylcarbamoylpyrrolidin-3-yl)-7-methylthioimidazo[5,1-b]-thiazolium-2-yl]-6-((1R)-1-hydroxyethyl)-1-methyl-1-carbapen-2-em-3-carboxylate trifluoromethanesulfonate as a crude product.

b) (1S,5R,6S)-2-[6-((3S,5S)-5-N,N-Dimethylcarbamoylpyrrolidin-3-yl)-7-methylthioimidazo[5,1-b]-thiazolium-2-yl]-6-((1R)-1-hydroxyethyl)-1-methyl-1-carbapen-2-em-3-carboxylate (intramolecular salt) hydrochloride The procedure of Example 70f) was repeated, except that 90 mg of allyl (1S,5R,6S)-2-[6-((3S,5S)-1-allyloxycarbonyl-5-N,N-dimethylcarbamoylpyrrolidin-3-yl)-7-methylthioimidazo[5,1-b]thiazolium-2-yl]-6-((1R)-1-hydroxyethyl)-1-methyl-1-carbapen-2-em-3-carboxylate trifluoromethanesulfonate as a crude product was used as the starting compound. Thus, 27 mg of the title compound was prepared.

NMR (D$_2$O) δ (HOD=4.65 ppm): 1.11 (3H, d, J=7.1 Hz), 1.16 (3H, d, J=6.4 Hz), 2.27 (3H, s), 2.48–2.54 (2H, m), 2.83 (3H, s), 2.96 (3H, s), 2.80–2.89 (1H, m), 3.11 (1H, dd, J$_1$=12.4 Hz, J$_2$=5.4 Hz), 3.42 (1H, dd, J$_1$=5.9 Hz, J$_2$=2.7 Hz), 3.45–3.55 (1H, m), 3.64 (1H, dd, J$_1$=12.4 Hz, J$_2$=6.6 Hz), 4.09–4.16 (1H, m), 4.20 (1H, dd, J$_1$=9.5 Hz, J$_2$=2.7 Hz), 4.41–4.46 (1H, m), 5.29–5.36 (1H, m), 8.02 (1H, s)

Example 76
(1S,5R,6S)-2-[6-(2-Acetimidoylaminoethyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride The procedure of Example 69 was repeated, except that 150 mg of (1S,5R,6S)-2-[6-(2-aminoethyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride was used as the starting compound. Thus, 71 mg of the title compound was prepared.

NMR (D$_2$O) δ (HOD=4.65 ppm): 1.12 (3H, d, J=7.3 Hz), 1.17 (3H, d, J=6.4 Hz), 2.09 (3H, s), 2.27 (3H, s), 3.43 (1H, dd, J$_1$=6.0 Hz, J$_2$=2.7 Hz), 3.46–3.55 (1H, m), 3.71–3.75 (2H, m), 4.10–4.17 (1H, m), 4.21 (1H, dd, J$_1$=9.5 Hz, J$_2$=2.7 Hz), 4.56–4.60 (2H, m), 8.04 (1H, s)

Example 77
(1S,5R,6S)-6-((1R)-1-Hydroxyethyl)-1-methyl-2-(6-methyl-7-trifluoromethylthioimidazo[5,1-b]-thiazolium-2-yl)-1-carbapen-2-em-3-carboxylate (intramolecular salt)

a) 4-Nitrobenzyl (1S,5R,6S)-6-((1R)-1-hydroxyethyl)-1-methyl-2-(7-trifluoromethylthioimidazo[5,1-b]-thiazol-2-yl)-1-carbapen-2-em-3-carboxylate The procedure of Example 1a) was repeated, except that 4-nitrobenzyl (1R,3R,5R,6S)-6-((1R)-1-hydroxyethyl)-1-methyl-2-oxo-1-carbapenam-3-carboxylate (743 mg) and 1.06 g of 2-(tri-n-butylstannyl)-7-trifluoroethylthioimidazo[5,1-b]thiazole were used as the starting compounds. Thus, 172 mg of 4-nitrobenzyl (1S,5R,6S)-6-((1R)-1-hydroxyethyl)-1-methyl-2-(7-trifluoromethylthioimidazo[5,1-b]thiazol-2-yl)-1-carbapen-2-em-3-carboxylate was prepared.

NMR (CDCl$_3$) δ: 1.32 (3H, d, J=7.3 Hz), 1.40 (3H, d, J=6.3 Hz), 3.36–3.41 (1H, m), 3.45–3.54 (1H, m), 4.28–4.42 (2H, m), 5.28 (1H, d, J=13.0 Hz), 5.53 (1H, d, J=13.0 Hz), 7.67 (2H, d, J=8.8 Hz), 8.09 (1H, s), 8.24 (2H, d, J=8.8 Hz), 8.33 (1H, s)

b) 4-Nitrobenzyl (1S,5R,6S)-2-(6-methyl-7-trifluoromethylthioimidazo[5,1-b]thiazolium-2-yl)-6-((1R)-1-hydroxyethyl)-1-methyl-1-carbapen-2-em-3-carboxylate trifluoromethanesulfonate 4-Nitrobenzyl (1S,5R,6S)-6-((1R)-1-hydroxyethyl)-1-methyl-2-(7-trifluoromethylthioimidazo[5,1-b]thiazol-2-yl)-1-carbapen-2-em-3-carboxylate (50 mg) was dissolved in 1 ml of dichloromethane. Methyl trifluoromethanesulfonate (0.011 ml) was added to the solution. The mixture was stirred at room temperature for one hr. The reaction solution was added dropwise to 30 ml of hexane. The precipitated solid was collected by filtration to prepare 55 mg of 4-nitrobenzyl (1S,5R,6S)-2-(6-methyl-7-trifluoromethylthioimidazo[5,1-b]-thiazolium-2-yl)-6-((1R)-1-hydroxyethyl)-1-methyl-1-carbapen-2-em-3-carboxylate trifluoromethanesulfonate.

NMR (acetone-d$_6$) δ: 1.29 (3H, d, J=6.3 Hz), 1.37 (3H, d, J=7.3 Hz), 3.56 (1H, dd, J$_1$=6.0 Hz, J$_2$=3.1 Hz), 3.88–3.96 (1H, m), 4.18–4.25 (1H, m), 4.33 (3H, s), 4.53 (1H, dd, J$_1$=9.5 Hz, J$_2$=2.7 Hz), 5.45 (1H, d, J=13.6 Hz), 5.64 (1H, d, J=13.6 HZ), 7.84 (2H, d, J=8.8 Hz), 8.26 (2H, d, J=8.8 Hz), 8.85 (1H, s), 9.96 (1H, s)

c) (1S,5R,6S)-6-((1R)-1-Hydroxyethyl)-1-methyl-2-(6-methyl-7-trifluoromethylthioimidazo[5,1-b]-thiazolium-2-yl)-1-carbapen-2-em-3-carboxylate (intramolecular salt)

The procedure of Example 5b) was repeated, except that 55 mg of 4-nitrobenzyl (1S,5R,6S)-2-(6-methyl-7-trifluoromethylthioimidazo[5,1-b]-thiazolium-2-yl)-6-((1R)-1-hydroxyethyl)-1-methyl-1-carbapen-2-em-3-carboxylate trifluoromethanesulfonate was used as the starting compound. Thus, 20 mg of the title compound was prepared.

NMR (D$_2$O) δ (HOD 4.65 ppm): 1.11 (3H, d, J=7.3 Hz), 1.16 (3H, d, J=6.3 Hz), 3.41 (1H, dd, J$_1$=6.1 Hz, J$_2$=2.7 Hz), 3.47–3.56 (1H, m), 3.96 (3H, s), 4.08–4.16 (1H1, m), 4.19 (1H, dd, J$_1$=9.5 Hz, J$_2$=2.7 Hz), 8.09 (1H, s)

Example 78
(1S,5R,6S)-2-[7-(2-Guanidinoethyl)thio-6-methylimidazo[5,1-b]-thiazolium-2-yl]-6-((1R)-1-hydroxyethyl)-1-methyl-1-carbapen-2-em-3-carboxylate (intramolecular salt) hydrochloride a) 4-Nitrobenzyl (1S,5R,6S)-2-[7-[2-N,N'-bis(4-nitrobenzyloxycarbonyl)guanidinoethyl]thioimidazo[5,1-b]thiazol-2-yl]-6-((1R)-1-hydroxyethyl)-1-methyl-1-carbapen-2-em-3-carboxylate The procedure of Example 1a) was repeated, except that 101 mg of 4-nitrobenzyl (1R,3R,5R,6S)-6-((1R)-1-hydroxyethyl)-1-methyl-2-oxo-1-carbapenam-3-carboxylate and 260 mg of 7-[2-N,N'-bis(4-nitrobenzyloxycarbonyl)-guanidinoethyl]thio-2-(tri-n-butylstannyl)imidazo[5,1-b]thiazole were used as the starting compounds. Thus, 85.6 mg of 4-nitrobenzyl (1S,5R,6S)-2-[7-[2-N,N'-bis(4-nitrobenzyloxycarbonyl)guanidinoethyl]thioimidazo[5,1-b]thiazol-2-yl]-6-((1R)-1-hydroxyethyl)-1-methyl-1-carbapen-2-em-3-carboxylate was prepared.

NMR (CDCl$_3$) δ: 1.30 (3H, d, J=7.2 Hz), 1.41 (3H, d, J=6.0 Hz), 2.9–3.05 (2H, m), 3.35–3.5 (2H, m), 3.6–3.7 (2H, m), 4.25–4.4 (2H, m), 5.20 (2H, s), 5.26 (1H, d, J=13.5 Hz), 5.31 (2H, s), 5.51 (1H, d, J=13.5 Hz), 7.5–7.6 (4H, m), 7.67 (2H, d, J=8.7 Hz), 8.01 (1H, s), 8.15–8.3 (6H, m), 8.8–8.9 (1H, m), 11.8 (1H, s)

b) 4-Nitrobenzyl (1S,5R,6S)-2-[7-[2-N,N'-bis(4-nitrobenzyloxycarbonyl)guanidinoethyl]thio-6-methylimidazo[5,1-b]thiazolium-2-yl]-6-((1R)-1-hydroxyethyl)-1-methyl-1-carbapen-2-em-3-carboxylate trifluoromethane-sulfonate The procedure of Example 47b) was repeated, except that 39.8 mg of 4-nitrobenzyl (1S,5R,6S)-2-[7-[2-N,N'-bis(4-nitrobenzyloxycarbonyl)guanidinoethyl]thioimidazo-[5,1-b]thiazol-2-yl]-6-((1R)-1-hydroxyethyl)-1-methyl-1-carbapen-2-em-3-carboxylate was used as the starting compound. Thus, 4-nitrobenzyl (1S,5R,6S)-2-[7-[2-N,N'-bis(4-nitrobenzyloxycarbonyl)guanidinoethyl]thio-6-methylimidazo[5,1-b]thiazolium-2-yl]-6-((1R)-1-hydroxyethyl)-1-methyl-1-carbapen-2-em-3-carboxylate trifluoromethanesulfonate was prepared.

NMR (CDCl$_3$) δ: 1.29 (3H, d, J=6.9 H2), 1.37 (3H, d, J=6.6 Hz), 3.0–3.1 (2H, m), 3.35–3.4 (2H, m), 3.6–3.8 (4H, m), 4.10 (3H, s), 4.2–4.4 (2H, m), 5.2–5.35 (5H, m), 5.51 (1H, d, J=13.8 Hz), 7.45–7.6 (4H, m), 7.67 (2H, d, J=9.0 Hz), 8.15–8.3 (6H, m), 8.5–8.6 (1H, m), 8.69 (1H, s), 9.79 (1H, s)

c) (1S,5R,6S)-2-[7-(2-Guanidinoethyl)thio-6-methylimidazo[5,1-b]thiazolium-2-yl]-6-((1R)-1-hydroxyethyl)-1-methyl-1-carbapen-2-em-3-carboxylate (intramolecular salt) hydrochloride The procedure of Example 3b) was repeated, except that the reaction was carried out in a mixed solvent composed of THF and water and the whole quantity of 4-nitrobenzyl (1S,5R,6S)-2-[7-[2-N,N'-bis(4-nitrobenzyloxycarbonyl)guanidinoethyl]thio-6-methylimidazo[5,1-b]thiazolium-2-yl]-6-((1R)-1-hydroxyethyl)-1-methyl-1-carbapen-2-em-3-carboxylate trifluoromethanesulfonate prepared in step b) was used as the starting compound for the reaction. Purification was then carried out by column chromatography on Cosmosil 40C$_{18}$-PREP (a 5% aqueous methanol solution), followed by column chromatography (water) on Amberlyst A-26 as an ion-exchange resin (chloro form) to prepare 6.8 mg of the title compound.

NMR (D$_2$O) δ (HOD=4.80 ppm): 1.27 (3H, d, J=7.2 Hz), 1.32 (3H, d, J=6.6 Hz), 3.05–3.15 (2H, m), 3.3–3.4 (2H, m), 3.57 (1H, dd, J$_1$=6.0 Hz, J$_2$=2.7 Hz), 3.6–3.7 (1H, m), 4.07 (3H, s), 4.2–4.3 (1H, m), 4.35 (1H, dd, J$_1$=9.3 Hz, J$_2$=2.7 Hz), 8.15 (1H, s)

Example 79
(1S,5R,6S)-2-(7-Fluoromethylthio-6-methylimidazo[5,1-b]thiazolium-2-yl)-6-((1R)-1-hydroxyethyl)-1-methyl-1-carbapen-2-em-3-carboxylate (intramolecular salt)

a) 4-Nitrobenzyl (1S,5R,6S)-2-(7-fluoromethylthioimidazo[5,1-b]thiazol-2-yl)-6-((1R)-1-hydroxyethyl)-1-methyl-1-carbapen-7-em-3-carboxylate The procedure of Example 1a) was repeated, except that 868 mg of 4-nitrobenzyl (1R,3R,5R,6S)-6-((1R)-1-hydroxyethyl)-1-methyl-2-oxo-1-carbapenam-3-carboxylate and 1.16 g of 7-fluoromethylthio-2-(tri-n-butylstannyl)imidazo[5,1-b]thiazole were used as the starting compounds. Thus, 285 mg of 4-nitrobenzyl (1S,5R,6S)-2-(7-fluoromethylthioimidazo[5,1-b]thiazol-2-yl)-6-((1R)-1-hydroxyethyl)-1-methyl-1-carbapen-2-em-3-carboxylate was prepared.

NMR (CDCl$_3$) δ: 1.31 (3H, d, J=7.3 Hz), 1.40 (3H, d, J=6.4 Hz), 3.37 (1H, dd, J$_1$=6.0 Hz, J$_2$=2.7 Hz), 3.42–3.51 (1H, m), 4.29–4.35 (1H, m), 4.37 (1H, dd, J$_1$=9.7 Hz, J$_2$=3.0 Hz), 5.28 (1H, d, J=13.6 Hz), 5.52 (1H, d, J=13.6 Hz), 5.56 (1H, s), 5.69 (1H, s), 7.68 (2H, d, J=9.0 Hz), 8.04 (1H, s), 8.24 (2H, d, J=9.0 Hz), 8.32 (1H, s)

b) 4-Nitrobenzyl (1S,5R,6S)-2-(7-fluoromethylthio-6-methylimidazo[5,1-b]thiazolium-2-yl)-6-((1R)-1-hydroxyethyl)-1-methyl-1-carbapen-2-em-3-carboxylate trifluoromethanesulfonate 4-Nitrobenzyl (1S,5R,6S)-2-(7-fluoromethylthioimidazo[5,1-b]thiazol-2-yl)-6-((1R)-1-hydroxyethyl)-1-methyl-1-carbapen-2-em-3-carboxylate (58 mg) was dissolved in 1 ml of dichloromethane. Methyl trifluoromethanesulfonate (0.013 ml) was added to the solution. The mixture was stirred at room temperature for one hr. The reaction solution was added dropwise to 20 ml of hexane. The precipitated solid was collected by filtration to prepare 66 mg of 4-nitrobenzyl (1S,5R,6S)-2-(7-fluoromethylthio-6-methylimidazo[5,1-b]thiazolium-2-yl)-6-((1R)-1-hydroxyethyl)-1-methyl-1-carbapen-2-em-3-carboxylate trifluoromethanesulfonate as a crude product.

c) (1S,5R,6S)-2-(7-Fluoromethylthio-6-methylimidazo[5,1-b]thiazolium-2-yl)-6-((1R)-1-hydroxyethyl)-1-methyl-1-carbapen-2-em-3-carboxylate (intramolecular salt)

The procedure of Example 5b) was repeated, except that 66 mg of 4-nitrobenzyl (1S,5R,6S)-2-(7-fluoromethylthio-6-methylimidazo[5,1-b]thiazolium-2-yl)-6-((1R)-1-hydroxyethyl)-1-methyl-1-carbapen-2-em-3-carboxylate trifluoromethanesulfonate as the crude product was used as the starting compound. Thus, 13 mg of the title compound was prepared.

NMR (D$_2$O) δ (HOD=4.65 ppm): 1.12 (3H, d, J=7.3 Hz), 1.17 (3H, d, J=6.3 Hz), 3.42 (1H, dd, J$_1$=6.1 Hz, J$_2$=2.7 Hz), 3.46–3.56 (1H, m), 3.92 (3H, s), 4.08–4.18 (1H, m), 4.21 (1H, dd, J$_1$=9.2 Hz, J$_2$=2.7 Hz), 5.47 (1H, s), 5.60 (1H, s), 8.03 (1H, s)

Example 80
(1S,5R,6S)-6-((1R)-1-Hydroxyethyl)-1-methyl-2-[6-methyl-7-((3S)-pyrrolidin-3-yl)thioimidazo[5,1-b]thiazolium-2-yl]-1-carbapen-2-em-3-carboxylate (intramolecular salt) hydrochloride a) 4-Nitrobenzyl (1S,5R,6S)-6-((1R)-1-hydroxyethyl)-1-methyl-2-[7-[(3S)-1-(4-nitrobenzyloxycarbonyl)pyrrolidin-3-yl]thioimidazo[5,1-b]thiazol-2-yl-1-carbapen-2-em-3-carboxylate The procedure of Example 1a) was repeated, except that 143 mg of 4-nitrobenzyl (1R,3R,5R,6S)-6-((1R)-1-hydroxyethyl)-1-methyl-2-oxo-1-carbapenam-3-carboxylate and 287 mg of 7-[(3S)-1-(4-nitrobenzyloxycarbonyl)pyrrolidin-3-yl]thio-2-(tri-n-butylstannyl)imidazo [5,1-b]thiazole were used as the starting compounds. Thus, 136 mg of 4-nitrobenzyl (1S,5R,6S)-6-((1R)-1-hydroxyethyl)-1-methyl-2-[7-[(3S)-1-(4-nitrobenzyloxycarbonyl)pyrrolidin-3-yl]thioimidazo-[5,1-b]thiazol-2-yl]-1-carbapen-2-em-3-carboxylate was prepared.

NMR (CDCl$_3$) δ: 1.29 (3H, d, J=6.6 Hz), 1.40 (3H, d, J=6.3 Hz), 1.9–2.3 (2H, m), 3.35–3.6 (4H, m), 3.6–3.8 (3H, m), 4.25–4.4 (2H, m), 5.21 (2H, s), 5.27 (1H, d, J=13.5 Hz), 5.52 (1H, d, J=13.5 Hz), 7.4–7.55 (2H, m), 7.6–7.7 (2H, m), 8.03, 8.04 (total 1H, s each), 8.1–8.3 (5H, m)

b) 4-Nitrobenzyl (1S,5R,6S)-6-((1R)-1-hydroxyethyl)-1-methyl-2-[6-methyl-7-[(3S)-1-(4-nitrobenzyloxycarbonyl)pyrrolidin-3-yl]thioimidazo[5,1-b]thiazolium-2-yl]-1-carbapen-2-em-3-carboxylate trifluoromethane-sulfonate The procedure of Example 47b) was repeated, except that 60.3 mg of 4-nitrobenzyl (1S,5R,6S)-6-((1R)-1-hydroxyethyl)-1-methyl-2-[7-[(3S)-1-(4-nitrobenzyl-oxycarbonyl)pyrrolidin-3-yl]thioimidazo[5,1-b]thiazol-2-yl]-1-carbapen-2-em-3-carboxylate was used as the starting compound. Thus, 4-nitrobenzyl (1S,5R,6S)-6-((1R)-1-hydroxyethyl)-1-methyl-2-[6-methyl-7-[(3S)-1-(4-nitrobenzyloxycarbonyl)pyrrolidin-3-yl]thioimidazo[5,1-b]thiazolium-2-yl]-1-carbapen-2-em-3-carboxylate trifluoromethanesulfonate was prepared.

NMR (CDCl$_3$) δ: 1.09 (3H, d, J=6.9 Hz), 1.34 (3H, d, J=6.3 Hz), 1.9–2.1 (1H, m), 2.2–2.4 (2H, m), 3.3–4.2 (8H, m), 4.18 (3H, s), 4.45–4.55 (1H, m), 5.06 (1H, d, J=13.5 Hz), 5.24 (2H, s), 5.53 (1H, d, J=13.5 Hz), 7.52 (2H, d, J=8.7 Hz), 7.58 (2H, d, J=8.7 Hz), 7.95 (2H, d, J=8.7 Hz), 8.19 (2H, d, J=8.7 Hz), 8.52 (1H, s), 9.62 (1H, s)

c) (1S,5R,6S)-6-((1R)-1-Hydroxyethyl)-1-methyl-2-[6-methyl-7-((3S)-pyrrolidin-3-yl)thioimidazo[5,1-b]thiazolium-2-yl]-1-carbapen-2-em-3-carboxylate (intramolecular salt) hydrochloride The procedure of Example 3b) was repeated, except that the reaction was carried out in a mixed solvent composed of THF and water and the whole quantity of 4-nitrobenzyl (1S,5R,6S)-6-((1R)-1-hydroxyethyl)-1-methyl-2-[6-methyl-7-[(3S)-1-(4-nitrobenzyloxycarbonyl)pyrrolidin-3-yl]thioimidazo[5,1-b]thiazolium-2-yl]-1-carbapen-2-em-3-carboxylate trifluoromethanesulfonate prepared in step b) was used as the starting compound for the reaction. Purification was performed by column chromatography on Cosmosil 40C$_{18}$-PREP (a 5% aqueous methanol solution), followed by column chromatography (water) on Amberlyst A-26 as an ion-exchange resin (chloro form) to prepare 1.7 mg of the title compound.

NMR (D$_2$O) δ (HOD=4.80 ppm): 1.28 (3H, d, J=7.2 Hz), 1.32 (3H, d, J=6.3 Hz), 2.0–2.15 (1H, m), 2.4–2.55 (1H, m), 3.3–3.5 (2H, m), 3.55–3.8 (4H, m), 4.0–4.1 (1H, m), 4.09 (3H, s), 4.25–4.4 (2H, m), 8.18 (1H, s)

Example 81
(1S,5R,6S)-2-[6-[2-(4-Hydroxyaminophenyl)-2-oxoethyl]-7-methylthioimidazo[5,1-b]thiazolium-2-yl]6-((1R-1hydroxyethyl)-1-methyl-1-carbapen-2-em-3-carboxylate (intramolecular salt)

a) 4-Nitrobenzyl (1S,5R,6S)-6-((1R)-1-hydroxyethyl)-1-methyl-2-[7-methylthio-6-[2-(4-nitrophenyl)-2-oxoethyl]imidazo[5,1-b]thiazolium-2-yl]-1-carbapen-2-em-3-carboxylate bromide 4-Nitrobenzyl (1S,5R,6S)-6-((1R)-1-hydroxyethyl)-1-methyl-2-(7-methylthioimidazo[5,1-b]thiazol-2-yl)-1- carbapen-2-em-3-carboxylate (170 mg) was dissolved in 2 ml of acetone and 4 ml of acetonitrile. 4-Nitrophenacyl bromide (787 mg) was added to the solution. The mixture was stirred at room temperature for 20 hr. The solvent was removed by distillation under the reduced pressure. The residue was purified by column chromatography on Sephadex LH-20 (chloroform:methanol=1:1) to prepare 132 mg of 4-nitrobenzyl (1S,5R,6S)-6-((1R)-1-hydroxyethyl)-1-methyl-2-[7-methylthio-6-[2-(4-nitrophenyl)-2-oxoethyl] imidazo[5,1-b]thiazolium-2-yl]-1-carbapen-2-em-3-carboxylate bromide as a crude product.

b) (1S,5R,6S)-2-[6-[2-(4-Hydroxyaminophenyl)-2-oxoethyl]-7-methylthioimidazo[5,1-b]thiazolium-2-yl]-6-((1R)-1-hydroxyethyl)-1-methyl-1-carbapen-2-em-3-carboxylate (intramolecular salt)

The procedure of Example 44b) was repeated, except that 132 mg of 4-nitrobenzyl (1S,5R,6S)-6-((1R)-1-hydroxyethyl)-1-methyl-2-[7-methylthio-6-[2-(4-nitrophenyl)-2-oxoethyl]imidazo[5,1-b]thiazolium-2-yl]-1-carbapen-2-em-3-carboxylate bromide as the crude product was used as the starting compound. Thus, 13 mg of the title compound was prepared.

NMR (DMSO-$d_6$) δ: 1.15–1.19 (6H, m), 2.30 (3H, s), 3.17 (1H, dd, $J_1$=6.8Hz, $J_2$=2.7 Hz), 3.40–3.49 (1H, m), 3.90–3.99 (1H, m), 4.11 (1H, dd, $J_1$=9.5 Hz, $J_2$=2.7 Hz), 5.05 (1H, d, J=4.8 Hz), 6.07 (2H, s), 6.88 (2H, d, J=8.8 Hz), 7.95 (2H, d, J=8.8 Hz), 8.37 (1H, s), 8.90 (1H, s), 9.48 (1H, s), 9.61 (1H, s)

Example 82

(1S,5R,6S)-2-(6-Benzyl-7-methylthioimidazo-[5,1-b]thiazolium-2-yl)-6-((1R)-1-hydroxyethyl)-1-methyl-1-carbapen-2-em-3-carboxylate (intramolecular salt)

a) 4-Nitrobenzyl (1S,5R,6S)-2-(6-benzyl-7-methylthioimidazo[5,1-b]thiazolium-2-yl)-6-((1R)-1-hydroxyethyl)-1-methyl-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (78 mg) was dissolved in 3.0 ml of acetonitrile. Benzyl bromide (0.119 ml) and 150 mg of sodium iodide were added to the solution. The mixture was stirred at room temperature for 3 days. The solvent was removed by distillation under the reduced pressure. The residue was purified by column chromatography on Sephadex LH-20 (methylene chloride:methanol=1:1) to prepare 83 mg of 4-nitrobenzyl (1S,5R,6S)-2-(6-benzyl-7-methylthioimidazo[5,1-b]thiazolium-2-yl)-6-((1R)-1-hydroxyethyl)-1-methyl-1-carbapen-2-em-3-carboxylate iodide.

NMR (DMSO-$d_6$) δ: 1.17 (3H, d, J=6.1 Hz), 1.23 (3H, d, J=7.1 Hz), 2.13 (3H, s), 3.49 (1H, m), 3.77 (1H, m), 4.04 (1H, m), 4.39, (1H, dd, $J_1$=10.0 Hz, $J_2$=2.9 Hz), 5.18 (1H, d, J=5.1 Hz), 5.41 (1H, d, J=13.7 Hz), 5.53 (1H, d, J=13.7 Hz), 5.70 (2H, s), 7.36–7.44 (5H, m), 7.73 (2H, d, J=9.0 Hz), 8.23 (2H, d, J=9.0 Hz), 8.71 (1H, s), 9.85 (1H, s); MS (m/z) 605 (M)$^+$.

b) (1S,5R,6S)-2-(6-Benzyl-7-methylthioimidazo[5,1-b]thiazolium-2-yl)-6-((1R)-1-hydroxyethyl)-1-methyl-1-carbapen-2-em-3-carboxylate (intramolecular salt)

4-Nitrobenzyl (1S,5R,6S)-2-(6-benzyl-7-methylthioimidazo[5,1-b]thiazolium-2-yl)-6-((1R)-1-hydroxyethyl)-1-methyl-1-carbapen-2-em-3-carboxylate iodide (80 mg) was dissolved in THF (4.0 ml)-water (4.0 ml). 10% Pd—C (64 mg) was added to the solution. The air in the reaction vessel was replaced by hydrogen, and the contents of the reaction vessel were stirred at room temperature for 2 hr. The catalyst was removed by filtration on Celite, and washed with water. The filtrate was washed with ethyl acetate, and was then concentrated under the reduced pressure until the volume of the filtrate was brought to about 3 ml. The residue was purified by column chromatography on Cosmosil 40C$_{18}$-PREP (a 5% aqueous acetonitrile solution to a 20% aqueous acetonitrile solution) to prepare 39 mg of the title compound.

NMR (DMSO-$d_6$) δ: 1.08 (3H, d, J=8.5 Hz), 1.10 (3H, d, J=6.4 Hz), 2.06 (3H, s), 3.10 (1H, dd, $J_1$=6.7 Hz, $J_2$=3.0 Hz), 3.40 (1H, m), 3.88 (1H, m), 4.03 (1H, dd, $J_1$=9.5 Hz, $J_2$=2.7 Hz), 5.01 (1H, d, J=4.9 Hz), 5.59 (2H, s), 7.29–7.38 (5H, m), 8.25 (1H, s), 9.60 (1H, s); MS (m/z) 470 (M+H)$^+$.

Example 83

(1S,5R,6S)-6-((1R)-1-Hydroxyethyl)-2-[6-(3-methoxybenzyl)-7-methylthioimidazo[5,1-b]thiazolium-2-yl]-1-methyl-1-carbapen-2-em-3-carboxylate (intramolecular salt)

a) 4-Nitrobenzyl (1S,5R,6S)-6-((1R)-1-hydroxyethyl)-2-[6-(3-methoxybenzyl)-7-methylthioimidazo[5,1-b] thiazolium-2-yl]-1-methyl-1-carbapen-2-em-3-carboxylate iodide The procedure of Example 82a) was repeated, except that 78 mg of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate, 0.14 ml of 3-methoxybenzyl bromide, and 150 mg of sodium iodide were used as the starting compounds. Thus, 80 mg of 4-nitrobenzyl (1S,5R,6S)-6-((1R)-1-hydroxyethyl)-2-[6-(3-methoxybenzyl)-7-methylthioimidazo[5,1-b]thiazolium-2-yl]-1-methyl-1-carbapen-2-em-3-carboxylate iodide was prepared.

NMR (DMSO-$d_6$) δ: 1.19 (3H, d, J=7.1 Hz), 1.21 (3H, d, J=7.1 Hz), 2.14 (3H, s), 3.41 (1H, dd, $J_1$=7.1 Hz, $J_2$=2.7 Hz), 3.82 (3H, s), 4.03 (1H, m), 4.27 (1H, m), 4.52 (1H, dd, $J_1$=9.5 Hz, $J_2$=2.7 Hz), 5.33 (1H, d, J=13.7 Hz), 5.53 (1H, J=13.7 Hz), 5.70 (2H, s), 6.88 (1H, m), 6.91–7.01 (2H, m), 7.23–7.33 (2H, m), 7.68 (2H, d, J=9.0 Hz), 8.24 (2H, d, J=9.0 Hz), 9.43 (1H, s), 10.85 (1H, s); MS (m/z) 635 (M)$^+$.

b) (1S,5R,6S)-6-((1R)-1-Hydroxyethyl)-2-[6-(3-methoxybenzyl)-7-methylthioimidazo[5,1-b]thiazolium-2-yl]-1-methyl-1-carbapen-2-em-3-carboxylate (intramolecular salt)

The procedure of Example 82b) was repeated, except that 4-nitrobenzyl (1S,5R,6S)-6-((1R)-1-hydroxyethyl)-2-[6-(3-methoxybenzyl)-7-methylthioimidazo[5,1-b]-thiazolium-2-yl]-1-methyl-1-carbapen-2-em-3-carboxylate iodide (77 mg) was used as the starting compound. Thus, 9 mg of the title compound was prepared.

NMR (DMSO-$d_6$) δ: 1.13 (3H, d, J=6.8 Hz), 1.16 (3H, d, J=6.0 Hz), 2.16 (3H, s), 3.45 (1H, m), 3.75 (3H, s), 3.94 (1H, m), 4.10 (1H, m), 5.03 (1H, d, J=4.9 Hz), 5.60 (2H, s), 6.91–6.99 (3H, m), 7.30–7.55 (2H, m), 8.31 (1H, s), 9.58 (1H, s); MS (m/z) 500 (M+H)$^+$.

Example 84

(1S,5R,6S)-2-[6-(4-Chlorobenzyl)-7-methyl-thioimidazo[5,1-b]thiazolium-2-yl]-6-((1R)-1-hydroxyethyl)-1-methyl-1-carbapen-2-em-3-carboxylate (intramolecular salt)

a) 4-Nitrobenzyl (1S,5R,6S)-2-[6-(4-chlorobenzyl)-7-methylthioimidazo[5,1-b]thiazolium-2-yl]-6-((1R)-1-hydroxyethyl)-1-methyl-1-carbapen-2-em-3-carboxylate iodide The procedure of Example 82a) was repeated, except that 78 mg of 4-nitrobenzyl (1S,5R,6S)-6-((1R)-1-hydroxyethyl)-1-methyl-2-(7-methylthioimidazo[5,1-b] thiazol-2-yl)-1-carbapen-2-em-3-carboxylate, 205 mg of 4-chlorobenzyl bromide, and 150 mg of sodium iodide were used as the starting compounds. Thus, 89 mg of 4-nitrobenzyl (1S,5R,6S)-2-[6-(4-chlorobenzyl)-7-methylthioimidazo[5,1-b]thiazolium-2-yl]-6-((1R)-1-hydroxyethyl)-1-methyl-1-carbapen-2-em-3-carboxylate iodide was prepared.

NMR (DMSO-d$_6$) δ: 1.39 (3H, d, J=6.6 Hz), 1.39 (3H, d, J=6.6 Hz), 2.07 (3H, s), 2.74 (1H, d, J=4.4 Hz), 3.41 (1H, dd, J$_1$=6.6 Hz, J$_2$=2.7 Hz), 3.94 (1H, m), 4.30 (1H, m), 4.48 (1H, dd, J$_1$=9.5 Hz, J$_2$=3.0 Hz), 5.32 (1H, d, J=13.7 Hz), 5.54 (1H, d, J=13.7 Hz), 5.69 (2H, s), 7.40 (2H, d, J=6.6 Hz), 7.45 (2H, d, J=6.6 Hz), 7.68 (2H, d, J=8.8 Hz), 8.24 (2H, d, J=8.8 Hz), 9.42 (1H, s), 11.05 (1H, s); MS (m/z) 639 (M)$^+$.

b) (1S,5R,6S)-2-[6-(4-Chlorobenzyl)-7-methylthioimidazo[5,1-b]thiazolium-2-yl]-6-((1R)-1-hydroxyethyl)-1-methyl-1-carbapen-2-em-3-carboxylate (intramolecular salt)

The procedure of Example 82b) was repeated, except that 77 mg of 4-nitrobenzyl (1S,5R,6S)-2-[6-(4-chlorobenzyl)-7-methylthioimidazo[5,1-b]thiazolium-2-yl]-6-((1R)-1-hydroxyethyl)-1-methyl-1-carbapen-2-em-3-carboxylate iodide was used as the starting compound. Thus, 23 mg of the title compound was prepared.

NMR (DMSO-d$_6$) δ: 1.13 (3H, d, J=7.1 Hz), 1.15 (3H, d, J=6.4 Hz), 2.16 (3H, s), 3.16 (1H, m), 3.45 (1H, m), 3.94 (1H, m), 4.08 (1H, dd, J$_1$=9.5 Hz, J$_2$=2.7 Hz), 5.05 (1H, d, J=5.1 Hz), 5.64 (2H, s), 7.41 (2H, d, J=8.8 Hz), 7.48 (2H, d, J=8.8 Hz), 8.29 (1H, s), 9.61 (1H, s); MS (m/z). 504 (M+H)$^+$.

Example 85

(1S,5R,6S)-2-(6-Carbamoylmethyl-7-fluoromethylthioimidazo[5,1-b]thiazolium-2-yl)-6-((1R)-1-hydroxyethyl)-1-methyl-1-carbapen-2-em-3-carboxylate (intramolecular salt)

a) 4-Nitrobenzyl (1S,5R,6S)-2-(6-carbamoylmethyl-7-fluoromethylthioimidazo[5,1-b]thiazolium-2-yl)-6-((1R)-1-hydroxyethyl)-1-methyl-1-carbapen-2-em-3-carboxylate iodide 4-Nitrobenzyl (1S,5R,6S)-2-(6-fluoromethylthioimidazo[5,1-b]thiazol-2-yl)-6-((1R)-1-hydroxyethyl)-1-methyl-1-carbapen-2-em-3-carboxylate (58 mg) was dissolved in 2 ml of acetone. 2-Iodoacetamide (179 mg) was added to the solution. The mixture was stirred at room temperature for 6 days. The solvent was removed by distillation under the reduced pressure. The residue was purified by column chromatography on Sephadex LH-20 (chloroform:methanol=1:1) to prepare 56 mg of 4-nitrobenzyl (1S,5R,6S)-2-(6-carbamoylmethyl-7-fluoromethylthioimidazo[5,1-b]thiazolium-2-yl)-6-((1R)-1-hydroxyethyl)-1-methyl-1-carbapen-2-em-3-carboxylate iodide as a crude product.

b) (1S,5R6S)-2-(6-Carbamoylmethyl-7-fluoromethylthioimidazo[5,1-b]thiazolium-2-yl)-6-((1R)-1-hydroxyethyl)-1-methyl-1-carbapen-2-em-3-carboxylate (intramolecular salt)

The procedure of Example 5b) was repeated, except that 56 mg of 4-nitrobenzyl (1S,5R,6S)-2-(6-carbamoylmethyl-7-fluoromethylthioimidazo[5,1-b]-thiazolium-2-yl)-6-((1R)-1-hydroxyethyl)-1-methyl-1-carbapen-2-em-3-carboxylate iodide as the crude product was used as the starting compound. Thus, 14 mg of the title compound was prepared.

NMR (D$_2$O) δ (HOD=4.65 ppm): 1.10 (3H, d, J=7.3 Hz), 1.15 (3H, d, J=6.3 Hz), 3.39–3.42 (1H, m), 3.45–3.54 (1H, m), 4.08–4.15 (1H, m), 4.17–4.21 (1H, m), 5.18 (2H, s), 5.41 (1H, s), 5.54 (1H, s), 8.06 (1H, s)

Example 86

(1S,5R,6S)-6-((1R)-1-Hydroxyethyl)-1-methyl-2-(7-methylthio-6-phenethylimidazo[5,1-b]thiazolium-2-yl)-1-carbapen-2-em-3-carboxylate (intramolecular salt)

a) 4-Nitrobenzyl (1S,5R,6S)-6-((1R)-1-hydroxyethyl)-1-methyl-2-(7-methylthio-6-phenethylimidazo[5,1-b]thiazolium-2-yl)-1-carbapen-2-em-3-carboxylate iodide The procedure of Example 82a) was repeated, except that 78 mg of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate, 0.204 ml of (2-bromoethyl)benzene, and 225 mg of sodium iodide were used as the starting compounds. Thus, 45 mg of 4-nitrobenzyl (1S,5R,6S)-6-((1R)-1-hydroxyethyl)-1-methyl-2-(7-methylthio-6-phenethylimidazo[5,1-b]thiazolium-2-yl)-1-carbapen-2-em-3-carboxylate iodide was prepared.

NMR (CDCl$_3$) δ: 1.29–1.32 (6H, m), 2.27 (3H, s), 3.30 (2H, t, J=7.6 Hz), 3.42 (1H, dd, J$_1$=6.7 Hz, J$_2$=2.7 Hz), 3.90 (1H, m), 4.31 (1H, m), 4.50 (1H, dd, J$_1$=9.6 Hz, J$_2$=2.9 Hz), 4.70 (2H, t, J=8.0 Hz), 5.32 (1H, d, J=13.4 Hz), 5.54 (1H, d, J=13.4 Hz), 7.24–7.34 (5H, m), 7.69 (2H, d, J=8.8 Hz), 8.23 (2H, d, J=8.8 Hz), 9.53 (1H, s), 10.77 (1H, s); MS (m/z) 619 (M)$^+$.

b) (1S5R,6S)-6-((1R)-1-Hydroxyethyl)-1-methyl-2-(7-methylthio-6-phenethylimidazo[5,1-b]thiazolium-2-yl)-1-carbapen-2-em-3-carboxylate (intramolecular salt)

The procedure of Example 82a) was repeated, except that 45 mg of 4-nitrobenzyl (1S,5R,6S)-6-((1R)-1-hydroxyethyl)-1-methyl-2-(7-methylthio-6-phenethylimidazo[5,1-b]thiazolium-2-yl)-1-carbapen-2-em-3-carboxylate iodide was used as the starting compound. Thus, 13 mg of the title compound was prepared.

NMR (DMSO-d$_6$) δ: 1.06 (3H, d, J=7.1 Hz), 1.10 (3H, d, J=6.1 Hz), 2.27 (3H, s), 3.08–3.11 (3H, m), 3.18 (1H, m), 3.88 (1H, m), 4.02 (1H, dd, J$_1$=13.4 Hz, J$_2$=2.9 Hz), 4.56 (2H, t, J=8.0 Hz), 4.97 (1H, d, J=5.1 Hz), 7.17–7.28 (5H, m), 8.22 (1H, s), 9.41 (1H, s); MS (m/z) 484 (M+H)$^+$.

Example 87

(1S,5R,6S)-2-[6-((3RS)-3-Amino-3-carbamoylpropyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride a) (2RS)-2-Allyloxycarbonylamino-4-iodobutaneamide (2RS)-2-Allyloxycarbonylamino-4-hydroxybutaneamide (202 mg) was dissolved in 2 ml of DMF. N,N-Diisopropylethylamine (0.192 ml) and 0.0813 ml of methanesulfonyl chloride were added to the solution at −5° C. to 0° C. The mixture was allowed to react at that temperature for one hr. The reaction solution was diluted with 20 ml of ethyl acetate. The diluted solution was washed with 15% brine, 15% brine+a 1 N aqueous hydrochloric acid solution, a saturated aqueous sodium hydrogencarbonate solution, and 15% brine in that order, and was dried over anhydrous magnesium sulfate. The solvent was then removed by distillation under the reduced pressure. The residue was dissolved in 5 ml of acetonitrile. Sodium iodide (265 mg) was added to the solution. The mixture was stirred at room temperature for 3 hr. Ethyl acetate (20 ml) was added to the reaction solution, was washed with 15% brine, a 5% aqueous sodium thiosulfate solution, and 15% brine in that order, and was dried over anhydrous magnesium sulfate. The solvent was then removed by distillation under the reduced pressure. The residue was crystallized from ethyl acetate-ether to prepare 95 mg of (2RS)-2-allyloxycarbonylamino-4-iodobutaneamide.

NMR (DMSO-d$_6$) δ: 2.27 (1H, m), 2.60 (1H, m), 4.55 (2H, m), 4.69 (1H, m), 4.94 (1H, m), 5.0–5.5 (3H, m), 5.95 (1H, m), 8.11 (1H, d, J=8.0 Hz), 11.40 (2H, br s)

b) (1S,5R,6S)-2-[6-((3RS)-3-Amino-3-carbamoyl-propyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride Allyl (1S,5R,6S)-6-((1R)-1-hydroxyethyl)-1-methyl-2-(7-methylthioimidazo[5,1-b]thiazol-2-yl)-1-carbapen-2-em-3-carboxylate (90 mg) and 200 mg of (2RS)-2-allyloxycarbonylamino-4-iodobutaneamide were dissolved in 2 ml of acetone. The solution was stirred at room temperature for 2 days. The solvent was removed by distillation under the reduced pressure. The residue was purified by column chromatography on Sephadex LH-20 (chloroform:methanol=1:1) to prepare 60 mg of allyl (1S, 5R,6S)-2-[6-((3RS)-3-allyloxycarbonylamino-3-carbamoylpropyl)-7-methylthioimidazo[5,1-b]thiazolium-2-yl]-6-((1R)-1-hydroxyethyl)-1-methyl-1-carbapen-2-em-3-carboxylate iodide as a crude product. This product was dissolved in 2 ml of THF and 2 ml of methanol. Triphenylphosphine (7.9 mg), 8.7 mg of tetrakistriphenylphosphinepalladium, and 0.0157 ml of morpholine were added to the solution. A reaction was allowed to proceed at room temperature under an argon atmosphere for 1.5 hr. Ethyl acetate (6 ml) was added to the reaction solution, and the mixture was extracted with 6 ml of water twice. The extract was concentrated under the reduced pressure until the volume of the extract was brought to about 2 to 3 ml. The residue was adjusted to pH 2.5 by the addition of a 1 N aqueous hydrochloric acid solution, and was purified by column chromatography on Cosmosil 40C$_{18}$-PREP (a 10% aqueous methanol solution). Thus, 7 mg of the title compound was prepared.

NMR (D$_2$O) δ (HOD=4.65 ppm): 1.10 (3H, d, J=7.3 Hz), 1.15 (3H, d, J=6.3 Hz), 2.23 (3H, s), 2.40 (2H, m), 3.40 (1H, m), 3.48 (1H, m), 4.03 (1H, m), 4.11 (1H, m), 4.19 (1H, m), 4.34 (2H, ,), 7.84 (2H, s), 9.08 (1H, s)

Example 88

(1S,5R,6S)-6-((1R)-1-Hydroxyethyl)-1-methyl-2-[7-methylthio-6-(2-oxo-2-phenylethyl)imidazo[5,1-b]-thiazolium-2-yl]-1-carbapen-2-em-3-carboxylate (intramolecular salt)

a) 4-Nitrobenzyl (1S,5R,6S)-6-((1R)-1-hydroxyethyl)-1-methyl-2-[7-methylthio-6-(2-oxo-2-phenylethyl)imidazo[5,1-b]-thiazolium-2-yl]-1-carbapen-2-em-3-carboxylate bromide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (103 mg) was dissolved in 2 ml of acetone. Phenacyl bromide (398 mg) was added to the solution. The mixture was stirred at room temperature for 3 days. The reaction solution was added dropwise to 30 ml of diethyl ether. The resultant precipitate was collected by filtration to prepare 124 mg of 4-nitrobenzyl (1S,5R,6S)-6-((1R)-1-hydroxyethyl)-1-methyl-2-[7-methylthio-6-(2-oxo-2-phenylethyl)imidazo[5,1-b]thiazolium-2-yl]-1-carbapen-2-em-3-carboxylate bromide as a crude product.

b) (1S,5R,6S)-6-((1R)-1-Hydroxyethyl)-1-methyl-2-[7-methylthio-6-(2-oxo-2-phenylethyl)imidazo[5,1-b]-thiazolium-2-yl]-1-carbapen-2-em-3-carboxylate (intramolecular salt)

The procedure of Example 5b) was repeated, except that 124 mg of 4-nitrobenzyl (1S,5R,6S)-6-((1R)-1-hydroxyethyl)-1-methyl-2-[7-methylthio-6-(2-oxo-2-phenylethyl)imidazo[5,1-b]thiazolium-2-yl]-1-carbapen-2-em-3-carboxylate bromide as the crude product was used as the starting compound. Thus, 21 mg of the title compound was prepared.

NMR (DMSO-d$_6$) δ: 1.16–1.19 (6H, m), 2.32 (3H, s), 3.15–3.20 (1H, m), 3.41–3.49 (1H, m), 3.90–3.99 (1H, m), 4.08–4.14 (1H, m), 5.04 (1H, d, J=5.1 Hz), 6.24 (2H, s), 7.63–7.69 (2H, m), 7.77–7.82 (1H, m), 8.12–8.17 (2H, m), 8.36 (1H, s), 9.48 (1H, s)

Example 89

(1S,5R,6S)-2-[6-(4-cyanobenzyl)-7-methylthioimidazo[5,1-b]thiazolium-2-yl]-6-((1R)-1-hydroxyethyl)-1-methyl-1-carbapen-2-em-3-carboxylate (intramolecular salt)

a) 4-Nitrobenzyl (1S,5R,6S)-2-[6-(4-cyanobenzyl)-7-methylthioimidazo[5,1-b]thiazolium-2-yl]-6-((1R)-1-hydroxyethyl)-1-methyl-1-carbapen-2-em-3-carboxylate iodide The procedure of Example 82a) was repeated, except that 78 mg of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate, 196 mg of 4-bromomethylbenzonitrile, and 150 mg of sodium iodide were used as the starting compounds. Thus, 55 mg of 4-nitrobenzyl (1S,5R,6S)-2-[6-(4-cyanobenzyl)-7-methylthioimidazo[5,1-b]thiazolium-2-yl]-6-((1R)-1-hydroxyethyl)-1-methyl-1-carbapen-2-em-3-carboxylate iodide was prepared.

NMR (DMSO-d$_6$) δ: 1.19 (3H, d, J=7.1 Hz), 1.21 (3H, d, J=7.1 Hz), 2.15 (3H, s), 2.73 (1H, br s), 3.41 (1H, dd, J$_1$=6.7 Hz, J$_2$=2.7 Hz), 3.93 (1H, m), 4.29 (1H, m), 4.48 (1H, dd, J$_1$=9.4 Hz, J$_2$=3.0 Hz), 5.32 (1H, d, J=13.6 Hz), 5.53 (1H, d, J=13.7 Hz), 5.86 (2H, s), 7.63–7.72 (6H, m), 8.24 (2H, d, J=8.8 Hz), 9.33 (1H, s), 11.21 (1H, s); MS (m/z) 630 (M)$^+$.

b) (1S,5R,6S)-2-[6-(4-cyanobenzyl)-7-methylthioimidazo[5,1-b]thiazolium-2-yl]-6-((1R)-1-hydroxyethyl)-1-methyl-1-carbapen-2-em-3-carboxylate (intramolecular salt)

The procedure of Example 82b) was repeated, except that 50 mg of 4-nitrobenzyl (1S,5R,6S)-2-[6-(4-cyanobenzyl)-7-methylthioimidazo[5,1-b]thiazolium-2-yl]-6-((1R)-1-hydroxyethyl)-1-methyl-1-carbapen-2-em-3-carboxylate iodide was used as the starting compound. Thus, 24 mg of the title compound was prepared.

NMR (DMSO-d$_6$) δ: 1.14 (3H, d, J=7.1 Hz), 1.16 (3H, d, J=6.1 Hz), 2.20 (3H, s), 3.16 (1H, dd, J$_1$=6.5 Hz, J$_2$=2.7 Hz), 3.46 (1H, m), 3.95 (1H, m), 4.09 (1H, dd, J$_1$=9.5 Hz, J$_2$=2.7 Hz), 5.04 (1H, d, J=5.1 Hz), 5.76 (2H, s), 7.54 (2H, d, J=8.3 Hz), 7.88 (2H, d, J=8.5 Hz), 8.33 (1H, s), 9.66 (1H, s); MS (m/z) 495 (M+H)$^+$.

Example 90

(1S,5R,6S)-2-[6-(3-Hydroxybenzyl)-7-methyl-thioimidazo[5,1-b]thiazolium-2-yl]-6-((1R)-1-hydroxyethyl)-1-methyl-1-carbapen-2-em-3-carboxylate (intramolecular salt)

a) 4-Nitrobenzyl (1S,5R,6S)-2-[6-(3-t-butyldimethylsilyloxy)benzyl-7-methylthioimidazo[5,1-b]-thiazolium-2-yl]-6-((1R)-1-hydroxyethyl)-1-methyl-1-carbapen-2-em-3-carboxylate bromide The procedure of Example 82a) was repeated, except that 78 mg of 4-nitrobenzyl (1S,5R,6S)-6-((1R)-1-hydroxyethyl)-1-methyl-2-(7-methylthioimidazo[5,1-b]-thiazol-2-yl)-carbapen-2-em-3-carboxylate and 382 mg of 3-t-butyldimethylsilyloxybenzyl bromide were used as the starting compounds. Thus, 82 mg of 4-nitrobenzyl (1S,5R,6S)-2-[6-(3-t-butyldimethylsilyloxy)benzyl-7-methylthioimidazo[5,1-b]thiazolium-2-yl]-6-((1R)-1-hydroxyethyl)-1-methyl-1-carbapen-2-em-3-carboxylate bromide was prepared.

NMR (DMSO-d$_6$) δ: 0.20 (6H, s), 0.96 (9H, s), 1.39 (3H, d, J=6.1 Hz), 1.40 (3H, d, J=7.1 Hz), 2.18 (3H, s), 3.44 (1H, m), 3.62 (1H, br s), 3.96 (1H, m), 4.27 (1H, m), 4.57 (1H, dd, J=J$_1$=9.5 Hz, J$_2$=2.7 Hz), 5.31 (1H, d, J=13.6 Hz), 5.52 (1H, d, J=13.6 Hz), 5.67 (2H, s), 6.83 (1H, m), 6.97 (1H, s), 7.20 (1H, J=8.0 Hz), 7.26 (1H, d, J=8.0 Hz), 7.67 (2H, d, J=8.5 Hz), 8.22 (2H, d, J=8.5 Hz), 9.45 (1H, s), 10.84 (1H, s); MS (m/z) 735 (M)$^+$.

b) (1S,5R,6S)-2-[6-(3-Hydroxybenzyl)-7-methylthioimidazo[5,1-b]thiazolium-2-yl]-6-((1R)-1-hydroxyethyl)-1-methyl-1-carbapen-2-em-3-carboxylate (intramolecular salt)

4-Nitrobenzyl (1S,5R,6S)-2-[6-(3-t-butyldimethylsilyloxy)benzyl-7-methylthioimidazo[5,1-b]thiazolium-2-yl]-6-((1R)-1-hydroxyethyl)-1-methyl-1-carbapen-2-em-3-carboxylate bromide (82 mg) was dissolved in THF (3 ml)-water (3 ml). A 1 M tetra-n-butylammonium fluoride/THF solution (0.12 ml) was added to the solution. The mixture was stirred at room temperature for 30 min. The reaction solution was adjusted to pH 7 by the addition of a saturated aqueous sodium hydrogencarbonate solution. 10% Pd—C (80 mg) was added thereto. The air in the reaction vessel was replaced by hydrogen, and the procedure of Example 82b) was then repeated to prepare 3 mg of the title compound.

NMR (DMSO-d$_6$) δ: 1.08 (3H, d, J=7.1 Hz), 1.10 (3H, d, J=6.1 Hz), 2.18 (3H, s), 3.10 (1H, dd, J$_1$=6.7 Hz, J$_2$=2.9 Hz), 3.39 (1H, m), 3.88 (1H, m), 4.03 (1H, dd, J$_1$=9.4 Hz, J$_2$=2.9 Hz), 4.96 (1H, d, J=5.1 Hz), 5.49 (2H, s), 6.67–6.72 (3H, m), 7.13 (1H, t, J=7.6 Hz), 8.21 (1H, s), 9.52 (1H, s); MS (m/z) 486 (M+H)$^+$.

Example 91

(1S,5R,6S)-6-((1R)-1-Hydroxyethyl]-1-methyl-2-[7-methylthio-6-(N-phenyl)carbamoylmethyl]imidazo[5,1-b]thiazolium-2-yl]-1-carbapen-2-em-3-carboxylate (intramolecular salt)

a) 4-Nitrobenzyl (1S,5R,6S)-6-((1R)-1-hydroxyethyl)-1-methyl-2-[7-methylthio-6-(N-phenyl)carbamoylmethyl]imidazo[5,1-b]thiazolium-2-yl]-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (112 mg) was dissolved in 4 ml of acetonitrile. 2-chloro-N-phenylacetamide (353 mg) and 322 mg of sodium iodide were added to the solution. The mixture was stirred at room temperature for 2 days. The solvent was removed by distillation under the reduced pressure. The residue was purified by column chromatography on Sephadex LH-20 (chloroform:methanol=1:1) to prepare 125 mg of 4-nitrobenzyl (1S,5R,6S)-6-((1R)-1-hydroxyethyl)-1-methyl-2-[7-methylthio-6-(N-phenyl)carbamoylmethyl]imidazo[5,1-b]thiazolium-2-yl]-1-carbapen-2-em-3-carboxylate iodide as a crude product.

b) (1S,5R,6S)-6-((1R)-1-Hydroxyethyl)-1-methyl-2-[7-methylthio-6-(N-phenyl)carbamoylmethyl]imidazo[5,1-b]thiazolium-2-yl]-1-carbapen-2-em-3-carboxylate (intramolecular salt)

The procedure of Example 5b) was repeated, except that 1.21 g of 4-nitrobenzyl (1S,5R,6S)-6-((1R)-1-hydroxyethyl)-1-methyl-2-[7-methylthio-6-(N-phenyl)carbamoylmethyl]imidazo[5,1-b]thiazolium-2-yl]-1-carbapen-2-em-3-carboxylate iodide as the crude product was used as the starting compound. Thus, 29 mg of the title compound was prepared.

NMR (DMSO-d$_6$) δ: 1.14–1.19 (6H, m), 2.35 (3H, s), 3.16–3.19 (1H, m), 3.41–3.50 (1H, m), 3.90–3.99 (1H, m), 4.12 (1H, dd, J$_1$=9.5 Hz, J$_2$=2.7 Hz), 5.04 (1H, d, J=5.1 Hz), 5.42 (2H, s), 7.07–7.13 (1H, m), 7.31–7.37 (2H, m), 7.56–7.61 (2H, m), 8.36 (1H, 5), 9.59 (1H, s), 10.77 (1H, s)

Example 92

(1S,5R,6S)-6-((1R)-1-Hydroxyethyl)-2-(6-N-methoxy-N-methylcarbamoylmethyl-7-methylthioimidazo[5,1-b]thiazolium-2-yl)-1-methyl-1-carbapen-2-em-3-carboxylate (intramolecular salt).

a) 4-Nitrobenzyl (1S,5R,6S)-6-((1R)-1-hydroxyethyl)-2-(6-N-methoxy-N-methylcarbamoylmethyl-7-methylthioimidazo[5,1-b]thiazolium-2-yl)-1-methyl-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (100 mg) was dissolved in 3 ml of acetone. 2-Iodo-N-methoxy-N-methylacetamide (229 mg) was added to the solution, and the mixture was stirred at 60° C. for 3 days. The solvent was removed by distillation under the reduced pressure. The residue was purified by column chromatography on Sephadex LH-20 (chloroform:methanol=1:1) to prepare 48 mg of 4-nitrobenzyl (1S,5R,6S)-6-((1R)-1-hydroxyethyl)-2-(6-N-methoxy-N-methylcarbamoylmethyl-7-methylthioimidazo[5,1-b]thiazolium-2-yl)-1-methyl-1-carbapen-2-em-3-carboxylate iodide.

NMR (acetone-d$_6$) δ: 1.31 (3H, d, J=6.3 Hz), 1.39 (3H, d, J=6.9 Hz), 2.46 (3H, s), 3.27 (3H, s), 3.55 (1H, dd, J$_1$=5.6, Hz, J$_2$=3.2 Hz), 3.86–3.91 (1H, m), 3.97 (3H, s), 4.20–4.25 (1H, m), 4.57 (1H, dd, J$_1$=9.9 Hz, J$_2$=3.2 Hz), 5.46 (1H, d, J=13.7 Hz), 5.64 (1H, d, J=13.7 Hz), 5.90 (2H, 6), 7.84 (2H, d, J=8.5 Hz), 8.25 (2H, d, J=8.5 Hz), 9.18 (1H, s), 10.22 (1H, s)

b) (1S,5R,6S)-6-((1R)-1-Hydroxyethyl)-2-(6-N-methoxy-N-methylcarbamoylmethyl-7-methylthioimidazo[5,1-b]thiazolium-2-yl)-1-methyl-1-carbapen-2-em-3-carboxylate (intramolecular salt)

The procedure of Example 3b) was repeated, except that 45 mg of 4-nitrobenzyl (1S,5R,6S)-6-((1R)-1-hydroxyethyl)-2-(6-N-methoxy-N-methylcarbamoylmethyl-7-methylthioimidazo[5,1-b]thiazolium-2-yl)-1-methyl-1-carbapen-2-em-3-carboxylate iodide was used as the starting compound. Thus, 8.1 mg of the title compound was prepared.

NMR (D$_2$O) δ (HOD=4.80 ppm).: 1.14 (3H, d, J=7.1 Hz), 1.19 (3H, d, J=6.1 Hz), 2.23 (3H, s), 3.18 (3H, s), 3.45 (1H, dd, J$_1$=6.2 Hz, J$_2$=2.7 Hz), 3.51–3.56 (1H, m), 3.81 (3H, s), 4.13–4.17 (1H, m), 4.23 (1H, dd, J$_1$=9.5 Hz, J$_2$=2.7 Hz), 5.47 (2H, s), 8.07 (1H, s)

Example 93

(1S,5R,6S)-2-[6-((1S)-2-Amino-1-hydroxymethyl)ethyl-7-methylthioimidazo[5,1-b]thiazolium-2-yl]-6-((1R)-1-hydroxyethyl)-1-methyl-1-carbapen-2-em-3-carboxylate (intramolecular salt) hydrochloride a) (2R)-3-Azido-1-triethylsilyloxy-2-propanol (2R)-3-Azido-1,2-propanediol (260 mg) was dissolved in 6 ml of DMF. Imidazole (166 mg) and 0.373 ml of triethylsilyl chloride were added to the solution under cooling in ice. The mixture was stirred for 30 min. Brine (30 ml) was added to the reaction solution, and the mixture was then extracted with 30 ml of diethyl ether three times. The combined organic layers were dried over anhydrous magnesium sulfate, and were filtered. The solvent was removed by distillation under the reduced pressure. The residue was purified by column chromatography on silica gel (hexane:ethyl acetate=3:1) to prepare 370 mg of (2R)-3-azido-1-triethylsilyloxy-2-propanol.

NMR (CDCl$_3$) δ: 0.63 (6H, q, J=7.5 Hz), 0.97 (9H, t, J=7.5 Hz), 2.51 (1H, d, J=5.3 Hz), 3.37 (2H, d, J=5.6 Hz), 3.58–3.69 (2H, m), 3.79–3.86 (1H, m)

b) 4-Nitrobenzyl (1S,5R,6S)-2-[6-((1S)-2-azido-1-triethylsilyloxymethyl)ethyl-7-methylthioimidazo[5,1-b]thiazolium-2-yl]-6-((1R)-1-hydroxyethyl)-1-methyl-1-carbapen-2-em-3-carboxylate trifluoromethanesulfonate (2R)-3-Azido-1-triethylsilyloxy-2-propanol (150 mg) was dissolved in 3 ml of dichloromethane. The solution was cooled to −60° C. 2,6-Lutidine (0.090 ml) and 0.115 ml of trifluoromethanesulfonic anhydride were then added to the cooled solution. The mixture was stirred for 20 min. Water (15 ml) was added to the reaction solution, and the mixture was extracted with 15 ml of dichloromethane. The extract was dried over anhydrous magnesium sulfate. 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (277 mg) was then added thereto. The solvent was removed by concentration until the volume of the solution was brought to 5 ml. The residue was stirred at 35° C. for 7 days. The solvent was removed by distillation under the reduced pressure. The residue was purified by column chromatography on Sephadex LH-20 (chloroform:methanol=1:1) to prepare 126 mg of 4-nitrobenzyl (1S,5R,6S)-2-[6-((1S)-2-azido-1-triethylsilyloxymethyl)ethyl-7-methylthioimidazo[5,1-b]-thiazolium-2-yl]-6-((1R)-1-hydroxyethyl)-1-methyl-1-carbapen-2-em-3-carboxylate trifluoromethanesulfonate as a crude product.

c) (1S,5R,6S)-2-[6-((1S)-2-Amino-1-hydroxymethyl)ethyl-7-methylthioimidazo[5,1-b]thiazolium-2-yl]-6-((1R)-1-hydroxyethyl)-1-methyl-1-carbapen-2-em-3-carboxylate (intramolecular salt) hydrochloride The procedure of Example 50b) was repeated, except that 120 mg of 4-nitrobenzyl (1S,5R,6S)-2-[6-((1S)-2-azido-1-triethylsilyloxymethyl)ethyl-7-methylthio-imidazo[5,1-b]thiazolium-2-yl]-6-((1R)-1-hydroxyethyl)-1-methyl-1-carbapen-2-em-3-carboxylate trifluoromethane-sulfonate as the crude product was used as the starting compound. Thus, 17 mg of the title compound was prepared.

NMR (D$_2$O) δ (HOD=4.65 ppm): 1.13 (3H, d, J=7.1 Hz), 1.19 (3H, d, J=6.6 Hz), 2.31 (3H, s), 3.45 (1H, dd, J$_1$=5.6 Hz, J$_2$=2.7 Hz), 3.49–3.61 (3H, m), 3.87–4.02 (2H, m), 4.12–4.21 (1H, m), 4.23 (1H, dd, J$_1$=9.5 Hz, J$_2$=3.0 Hz), 5.19–5.28 (1H, m), 8.11 (1H, s)

Example 94

(1S,5R,6S)-2-[6-((2R)-3-Amino-2-methylpropyl)-7-methylthioimidazo[5,1-b]thiazolium-2yl]-6-((1R)-1-hydroxyethyl)-1-methyl-1-carbapen-2-em-3-carboxylate (intramolecular salt) hydrochloride a) 4-Nitrobenzyl (1S,5R,6S)-2-[6-((2R)-3-azido-2-methylpropyl)-7-methylthioimidazo[5,1-b]thiazolium-2-yl]-6-((1R)-1-hydroxyethyl)-1-methyl-1-carbapen-2-em-3-carboxylate trifluoromethanesulfonate (2R)-3-Azido-2-methyl-1-propanol (28 mg) was dissolved in 5 ml of dichloromethane. The solution was cooled to −60° C. 2,6-Lutidine (0.031 ml) and 0.043 ml of trifluoromethanesulfonic anhydride were then added to the cooled solution. The mixture was stirred for 20 min. Water (10 ml) was added to the reaction solution, and the mixture was extracted with 10 ml of dichloromethane. The extract was dried over anhydrous magnesium sulfate. 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (102 mg) was then added thereto. The solvent was removed by concentration until the volume of the solution was brought to 2 ml. The residue was stirred at 35° C. for 7 hr. The reaction solution was added dropwise to 30 ml of diethyl ether. The precipitated solid was collected by filtration to prepare 109 mg of 4-nitrobenzyl (1S,5R,6S)-2-[6-((2R)-3-azido-2-methylpropyl)-7-methylthioimidazo[5,1-b]-thiazolium-2-yl]-6-((1R)-1-hydroxyethyl)-1-methyl-1-carbapen-2-em-3-carboxylate trifluoromethanesulfonate as a crude product.

b) (1S,5R,6S)-2-[6-((2R)-3-Amino-2-methylpropyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride The procedure of Example 50b) was repeated, except that 109 mg of 4-nitrobenzyl (1S,5R,6S)-2-[6-((2R)-3-azido-2-methylpropyl)-7-methylthioimidazo[5,1-b]-thiazolium-2-yl]-6-((1R)-1-hydroxyethyl)-1-methyl-1-carbapen-2-em-3-carboxylate trifluoromethanesulfonate as the crude product was used as the starting compound. Thus, 21 mg of the title compound was prepared.

NMR (D$_2$O) δ (HOD=4.65 ppm): 0.96 (3H, d, J=6.8 Hz), 1.14 (3H, d, J=7.1 Hz), 1.19 (3H, d, J=6.3 Hz), 2.29 (3H, s), 2.41–2.50 (1H, m), 2.83–3.07 (2H, m), 3.44 (1H, dd, J$_1$=5.9 Hz, J$_2$=2.7 Hz), 3.48–3.58 (1H, m), 4.11–4.19 (1H, m), 4.20–4.44 (3H, m), 8.04 (1H, s), 9.28 (1H, s)

Example 95

(1S,5R,6S)-2-(6-Ethoxycarbonylmethyl-7-methyl-thioimidazo[5,1-b]-thiazolium-2-yl)-6-((1R)-1-hydroxyethyl)-1-methyl-1-carbapen-2-em-3-carboxylate (intramolecular salt)

The procedure of Example 82a) was repeated, except that 78 mg of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate and 0.166 ml of bromoethyl acetate were used as the starting compounds. Thus, a crude quaternary salt (76 mg) was prepared. The procedure of Example 82b) was repeated, except that 55 mg of the crude quaternary salt was used as the starting compound and the solvent for the reaction was THF-1/15 M sodium phosphate buffer (pH 6.8) (1:1). Thus, 19 mg of the title compound was prepared.

NMR (D$_2$O) δ (HOD=4.80 ppm): 1.15–1.19 (9H, m), 2.20 (3H, s), 3.44 (1H, m), 3.53 (1H, m), 4.12–4.23 (4H, m), 5.28 (2H, s), 8.06 (1H, s); MS (m/z) 468 (M+H)$^+$ (measured as D$_2$O solution)

Example 96

(1S,5R,6S)-2-[6-(2-Acetylamino)ethyl-7-methyl-thioimidazo[5,1-b]thiazolium-2-yl]-6-((1R)-1-hydroxyethyl)-1-methyl-1-carbapen-2-em-3-carboxylate (intramolecular salt)

The procedure of Example 82a) was repeated, except that −156 mg of 4-nitrobenzyl (1S,5R,6S)-6-((1R)-1-hydroxyethyl)-1-methyl-2-(7-methylthioimidazo[5,1-b]-thiazol-2-yl)-1-carbapen-2-em-3-carboxylate, 491 mg of N-(2-bromoethyl)acetamide, and 225 mg of sodium iodide were used as the starting compounds. Thus, a crude quaternary salt (38 mg) was prepared. The procedure of Example 82b) was repeated, except that 55 mg of this crude quaternary salt was used as the starting compound and the solvent for the reaction was THF-1/15 M sodium phosphate buffer (pH 6.8) (1:1). Thus, the title compound (9 mg) was prepared.

NMR (D$_2$O) δ (HOD=4.80 ppm): 1.12 (3H, d, J=7.3 Hz), 1.18 (3H, d, J=5.3 Hz), 1.18 (3H, s), 2.29 (3H, s), 3.35 (1H, m), 3.43 (1H, m), 3.57 (2H, t, J=5.8 Hz), 4.13 (1H, m), 4.20 (1H, dd, J$_1$=9.5 Hz, J$_2$=2.7 Hz), 4.44 (2H, t, J=5.9 Hz), 8.01 (1H, s); MS (m/z) 468 (M+H)$^+$ (measured as D$_2$O solution)

Example 97

(1S,5R,6S)-6-((1R)-1-Hydroxyethyl)-2-[7-methylthio-6-(thiazol-4-yl)methylimidazo[5,1-b]-thiazolium-2-yl]-1-methyl-1-carbapen-2-em-3-carboxylate (intramolecular salt)

4-Nitrobenzyl (1S,5R,6S)-6-((1R)-1-hydroxyethyl)-1-methyl-2-(7-methylthioimidazo[5,1-b]thiazol-2-yl)-1- carbapen-2-em-3-carboxylate (154 mg) was dissolved in 2 ml of acetonitrile. 4-Chloromethylthiazole (130 mg) and 135 mg of sodium iodide were added to the solution. The mixture was stirred at 35° C. for 3 days. The solvent was removed by distillation under the reduced pressure. Dichloromethane (8 ml) was added to the residue. The insolubles were removed by filtration. The filtrate was concentrated under the reduced pressure. Ethyl acetate was added to the residue. The resultant precipitate was collected by filtration, and was dissolved in 7.5 ml of THF and 7.5 ml of a 1/15 M sodium phosphate buffer (pH 7). 10% Pd—C (200: mg) was added to the solution. The air in the reaction vessel was replaced by hydrogen, and the contents of the reaction vessel were stirred at room temperature for 1.5 hr. The catalyst was removed by filtration on Celite, and washed with water. The filtrate was washed with ethyl acetate, and was then concentrated under the reduced pressure until the volume of the filtrate was brought to about 3 to 4 ml. The residue was purified by column chromatography on Cosmosil 40C$_{18}$-PREP (a 50% aqueous methanol solution) to prepare 58 mg of the title compound.

NMR (D$_2$O) δ (HOD=4.65 ppm): 1.07 (3H, d, J=7.3 Hz), 1.13 (3H, d, J=6.3 Hz), 2.00 (3H, s), 3.29 (1H, dd, J$_1$=5.8 Hz, J$_2$=2.7 Hz), 3.49 (1H, m), 4.12 (1H, m), 4.17 (1H, dd, J$_1$=9.5 Hz, J$_2$=2.7 Hz), 5.65 (2H, s), 7.65 (1H, s), 7.97 (1H, s), 8.87 (1H, s), 9.28 (1H, s)

Example 98

(1S,5R,6S)-2-[6-(2-Aminosulfonylaminoethyl)-7-methylthioimidazo[5,1-b]thiazolium-2-yl]-6-((1R)-1-hydroxyethyl)-1-methyl-1-carbapen-2-em-3-carboxylate (intramolecular salt)

a) 4-Nitrobenzyl (1S,5R,6S)-6-((1R)-1-hydroxyethyl)-1-methyl-2-[7-methylthio-6-[2-(4-nitrobenzyloxycarbonyl-aminosulfonylamino)ethyl]imidazo[5,1-b]-thiazolium-2-yl]-1-carbapen-2-em-3-carboxylate trifluoromethanesulfonate The procedure of Example 20a) was repeated, except that 51 mg of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate and 68 mg of 2-(4-nitrobenzyloxycarbonylaminosulfonylamino)ethanol were used as the starting compounds. Thus, 66 mg of 4-nitrobenzyl (1S,5R,6S)-6-((1R)-1-hydroxyethyl)-1-methyl-2-[7-methylthio-6-[2-(4-nitrobenzyloxycarbonyl-aminosulfonylamino)ethyl]imidazo[5,1-b]thiazolium-2-yl]-1-carbapen-2-em-3-carboxylate trifluoromethanesulfonate was prepared.

NMR (acetone-d$_6$) δ: 1.30 (3H, d, J=6.0 Hz), 1.37 (3H, d, J=7.4 Hz), 2.56 (3H, s), 3.56 (1H, dd, J$_1$=6.0 Hz, J$_2$=3.3 Hz), 3.80 (2H, t, J=6.3 Hz), 3.87–3.91 (1H, m), 4.20–4.24 (1H, m), 4.52 (1H, dd, J$_1$=10.2 Hz, J$_2$=3.0 Hz), 4.84 (2H, t, J=6.3 Hz), 5.34 (2H, s), 5.45 (1H, d, J=13.7 Hz), 5.64 (1H, d, J=13.7 Hz), 7.68 (2H, d, J=8.8 Hz), 7.85 (2H, d, J=8.8 Hz), 8.23–8.28 (4H, m), 8.77 (1H, s), 9.79 (1H, s)

b) (1S,5R,6S)-2-[6-(2-Aminosulfonylaminoethyl)-7-methylthioimidazo[5,1-b]thiazolium-2-yl]-6-((1R)-1-hydroxyethyl)-1-methyl-1-carbapen-2-em-3-carboxylate (intramolecular salt)

The procedure of Example 3b) was repeated, except that 28 mg of 4-nitrobenzyl (1S,5R,6S)-6-((1R)-1-hydroxyethyl)-1-methyl-2-[6-[2-(4-nitrobenzyloxy-carbonylaminosulfonylamino)ethyl]-7-methylthioimidazo-[5,1-b]thiazolium-2-yl]-1-carbapen-2-em-3-carboxylate trifluoromethanesulfonate was used as the starting compound to prepare 4.7 mg of the title compound.

NMR (D$_2$O) δ (HOD=4.80 ppm): 1.12 (3H, d, J=7.3 Hz), 1.17 (3H, d, J=6.3 Hz), 2.29 (3H, s), 3.41–3.47 (3H, m), 3.48–3.53 (1H, m), 4.10–4.17 (1H, m), 4.21 (1H, dd, J$_1$=9.5 Hz, J$_2$=2.7 Hz), 4.46 (2H, t, J=5.6 Hz), 8.01 (1H, s)

Example 99

(1S,5R,6S)-2-[6-((2R)-3-Amino-2-hydroxy)propyl-7-methylthioimidazo[5,1-b]thiazolium-2-yl]-6-((1R)-1-hydroxyethyl)-1-methyl-1-carbapen-2-em-3-carboxylate (intramolecular salt) hydrochloride a) (2R)-3-Azido-1,2-bis(triethylsilyloxy)propane (2S)-3-Chloro-1,2-propanediol (3.30 g) was dissolved in 15 ml of DMF. Sodium azide (2.33 g) was added to the solution. The mixture was stirred at 100° C. for 20 hr. DMF (15 ml) was added to the reaction solution. Imidazole (2.03 g) and 5.67 ml of triethylsilyl chloride were added thereto under cooling in ice. The mixture was stirred for 10 min. Imidazole (2.23 g) and 5.95 ml of triethylsilyl chloride were added thereto. The mixture was stirred for 10 min. Brine (120 ml) was then added to the reaction solution, and the mixture was extracted with 120 ml of diethyl ether three times. The combined organic layers were dried over anhydrous magnesium sulfate, and were filtered. The solvent was removed by distillation under the reduced pressure. Thus, 11.21 g of (2R)-3-azido-1,2-bis(triethylsilyloxy)propane was prepared.

NMR (CDCl$_3$) δ: 0.57–0.67 (18H, m), 0.91–1.01 (12H, m), 3.19–3.43 (2H, m), 3.49–3.61 (2H, m), 3.80–3.87 (1H, m)

b) (2R)-3-Azido-2-triethylsilyloxy-1-propanol (2R)-3-Azido-1,2-bis(triethylsilyloxy)propane (9.55 g) was dissolved in 50 ml of THF, 50 ml of methanol, and 10 ml of water. The solution was adjusted to pH 3.4 by the addition of 1 N hydrochloric acid. The mixture was stirred at room temperature for 2 hr. Brine (100 ml) was added to the reaction solution, and the mixture was extracted with 150 ml of diethyl ether. The organic layer was dried over anhydrous magnesium sulfate, and was filtered. The solvent was removed by distillation under the reduced pressure. The residue was purified by column chromatography on silica gel (hexane:ethyl acetate=4:1) to prepare 2.70 g of (2R)-3-azido-2-triethylsilyloxy-1-propanol.

NMR (CDCl$_3$) δ: 0.66 (6H, q, J=7.5 Hz), 0.98 (9H, t, J=7.5 Hz), 1.79–1.84 (1H, m), 3.28–3.40 (2H, m), 3.55–3.67 (2H, m), 3.84–3.90 (1H, m)

c) 4-Nitrobenzyl (1S,5R,6S)-2-[6-((2R)-3-azido-2-triethylsilyloxy)propyl-7-methylthioimidazo[5,1-b]-thiazolium-2-yl]-6-((1R)-1-hydroxyethyl)-1-methyl-1-carbapen-2-em-3-carboxylate trifluoromethanesulfonate (2R)-3-Azido-2-triethylsilyloxy-1-propanol (341 mg) was dissolved in 7 ml of dichloromethane. The solution was cooled to −60° C. 2,6-Lutidine (0.189 ml) and 0.260 ml of trifluoromethanesulfonic anhydride were then added to the cooled solution. The mixture was stirred for 20 min. A 1/15 M sodium phosphate buffer (pH 6.6) (15 ml) was added to the reaction solution, and the mixture was extracted with 15 ml of dichloromethane. The extract was dried over anhydrous magnesium sulfate. 4-Nitrobenzyl (1S,5R,6S)-6-((1R)-1-hydroxyethyl)-1-methyl-2(7-methyl-thioimidazo[5,1-b]thiazol-2-yl)-1-carbapen-2-em-3-carboxylate (600 mg) was then added thereto. The solvent was removed by concentration until the volume of the solution was brought to 12 ml. The residue was stirred at 35° C. for 12 hr. The reaction solution was added dropwise to a mixed solvent composed of 30 ml of diethyl ether and 30 ml of hexane. The precipitated solid was collected by filtration to prepare 970 mg of 4-nitrobenzyl (1S,5R, 6S)-2-[6-((2R)-3-azido-2-triethylsilyloxy)propyl-7-methylthioimidazo[5,1-b]thiazolium-2-yl]-6-((1R)-1-hydroxyethyl)-1-methyl-1-carbapen-2-em-3-carboxylate trifluoromethanesulfonate as a crude product.

d) (1S,5R,6S)-2-[6-((2R)-3-Amino-2-hydroxy)propyl-7-methylthioimidazo[5,1-b]-thiazolium-2-yl]-6-((1R)-1-hydroxyethyl)-1-methyl-1-carbapen-2-em-3-carboxylate (intramolecular salt) hydrochloride 4-Nitrobenzyl (1S,5R,6S)-2-[6-((2R)-3-azido-2-triethylsilyloxy)propyl-7-methylthioimidazo[5,1-b]-thiazolium-2-yl]-6-((1R)-1-hydroxyethyl)-1-methyl-1-carbapen-2-em-3-carboxylate trifluoromethanesulfonate as the crude product (1.07 g) was dissolved in 30 ml of THF and 30 ml of water. The solution was adjusted to pH 2.1 by the addition of a 1 N aqueous hydrochloric acid solution, and was stirred at room temperature for 5 hr. 10% Pd—C (640 mg) was added thereto. The air in the reaction vessel was replaced by hydrogen, and the contents of the reaction vessel were stirred at room temperature for 2 hr. The catalyst was removed by filtration on Celite, and washed with water. The filtrate was washed with ethyl acetate, and was then concentrated under the reduced pressure until the volume of the filtrate was brought to about 10 ml. The residue was purified by column chromatography on Cosmosil 40$C_{18}$-PREP (a 20% aqueous methanol solution). A first fraction was collected, and was subjected to column chromatography (water) on Amberlyst A-26 as an ion-exchange resin (chloro form). Thus, 271 mg of the title compound was prepared.

NMR (D2O) δ (HOD=4.65 ppm): 1.12 (3H, d, J=7.0 Hz), 1.16 (3H, d, J=6.3 Hz), 2.26.(3H, s), 2.87–2.94 (1H, m), 3.20–3.26 (1H, m), 3.42 (1H, dd, $J_1$=6.0 Hz, $J_2$=2.7 Hz), 3.46–3.55 (1H, m), 4.10–4.23 (3H, m), 4.28–4.35 (1H, m), 4.60–4.63 (1H, m), 8.03 (1H, s)

Example 100

(1S,5R,6S)-2-[6-((2S)-2,3-Dihydroxy)propyl-7-methylthioimidazo[5,1-b]thiazolium-2-yl]-6-((1R)-1-hydroxyethyl)-1-methyl-1-carbapen-2-em-3-carboxylate (intramolecular salt)

A fraction was collected which has been eluted after (1S,5R,6S)-2-[6-((2R)-3-amino-2-hydroxy)propyl-7-methylthioimidazo[5,1-b]-thiazolium-2-yl]-6-((1R)-1-hydroxyethyl)-1-methyl-1-carbapen-2-em-3-carboxylate (intramolecular salt) hydrochloride in the column chromatography on Cosmosil 40$C_{18}$-PREP (a 20% aqueous methanol solution) in Example 99d). Thus, 37 mg of the title compound was prepared.

NMR (D$_2$O) δ (HOD=4.65 ppm): 1.10 (3H, d, J=7.1 Hz), 1.16 (3H, d, J=6.3 Hz), 2.25 (3H, s), 3.41 (1H, dd, $J_1$=5.8 Hz, $J_2$=2.7 Hz), 3.45–3.62 (3H, m), 3.94–4.01 (1H, m), 4.09–4.16 (1H, m), 4.19 (1H, dd, $J_1$=9.5 Hz, $J_2$=2.7 Hz), 4.22–4.30 (1H, m), 4.48–4.55 (1H, m), 8.00 (1H, s), 9.18 (1H, s)

Example 101

(1S,5R,6S)-6-((1R)-1-Hydroxyethyl)-1-methyl-2-[6-[2-(pyridin-2-yl)ethyl]-7-methylthio-imidazo[5,1-b]thiazolium-2-yl]-1-carbapen-2-em-3-carboxylate (intramolecular salt)

a) 4-Nitrobenzyl (1S,5R,6S)-6-((1R)-1-hydroxyethyl)-1-methyl-2-[6-[2-(pyridin-2-yl)ethyl]-7-methylthioimidazo[5,1-b]-thiazolium-2-yl]-1-carbapen-2-em-3-carboxylate trifluoromethanesulfonate The procedure of Example 20a) was repeated, except that 150 mg of 4-nitrobenzyl (1S,5R,6S)-6-((1R)-1-hydroxyethyl)-1-methyl-2-(7-methylthioimidazo[5,1-b]-thiazol-2-yl)-1-carbapen-2-em-3-carboxylate and 62 mg of 2-(2-hydroxyethyl)pyridine were used as the starting compounds. Thus, 143 mg of 4-nitrobenzyl (1S,5R,6S)-6-((1R)-1-hydroxyethyl)-1-methyl-2-[6-[2-(pyridin-2-yl)ethyl]-7-methylthioimidazo[5,1-b]thiazolium-2-yl]-1-carbapen-2-em-3-carboxylate trifluoromethanesulfonate was prepared.

NMR (DMSO-$d_6$) δ: 1.18 (3H, d, J=6.2 Hz), 1.22 (3H, d, J=6.7 Hz), 2.41 (3H, s), 3.35–3.50 (3H, m), 3.70–3.80 (1H, m), 4.01–4.11 (1H, m), 4.39 (1H, dd, $J_1$=9.3 Hz, $J_2$=2.5 Hz), 4.85 (2H, t, J=7.1 Hz), 5.42 (1H, d, J=13.8 Hz), 5.54 (1H, d, J=13.8 Hz), 7.30–7.40 (2H, m), 7.74 (2H, d, J=8.8 Hz), 7.77–7.82 (1H, m), 8.24 (2H, d, J=8.8 Hz), 8.50–8.54 (1H, m), 8.69 (1H, s), 9.74 (1H, s)

b) (1S,5R,6S)-6-((1R)-1-Hydroxyethyl)-1-methyl-2-[6-[2-(pyridin-2-yl)ethyl]-7-methylthioimidazo[5,1-b]thiazolium-2-yl]-1-carbapen-2-em-3-carboxylate (intramolecular salt)

The procedure of Example 3b) was repeated, except that 77 mg of 4-nitrobenzyl (1S,5R,6S)-6-((1R)-1-hydroxyethyl)-1-methyl-2-[6-[2-(pyridin-2-yl)ethyl]-7-methylthioimidazo[5,1-b]thiazolium-2-yl]-1-carbapen-2-em-3-carboxylate trifluoromethanesulfonate was used as the starting compound. Thus, 26 mg of the title compound was prepared.

NMR (D$_2$O) δ (HOD=4.80 ppm): 1.26 (3H, d, J=7.1 Hz), 1.33 (3H, d, J=6.3Hz), 2.31 (3H, s), 3.43 (2H, t, J=6.6 Hz), 3.57 (1H, dd, $J_1$=5.7 Hz, $J_2$=2.7 Hz), 3.60–3.68 (1H, m), 4.26–4.32 (1H, m), 4.35 (1H, dd, $J_1$=9.3 Hz, $J_2$=2.5 Hz), 4.83 (2H, t, J=6.6 Hz), 7.27 (7H, d, J=7.7 Hz), 7.33–7.38 (1H, m), 7.74–7.81 (1H, m), 8.08 (1H, s), 8.43–8.46 (1H, m)

Example 102

(1S,5R,6S)-6-((1R)-1-Hydroxyethyl)-1-methyl-2-[6-[2-(1-methylpyridinium-2-yl)ethyl]-7-methylthioimidazo[5,1-b]thiazolium-2-yl]-1-carbapen-2-em-3-carboxylate chloride (intramolecular salt)

a) 4-Nitrobenzyl (1S,5R,6S)-6-((1R)-1-hydroxyethyl)-1-methyl-2-[6-[2-(1-methylpyridinium-2-yl)ethyl]-7-methylthioimidazo[5,1-b]thiazolium-2-yl]-1-carbapen-2-em-3-carboxylate trifluoromethanesulfonate iodide 4-Nitrobenzyl (1S,5R,6S)-6-((1R)-1-hydroxyethyl)-1-methyl-2-[6-[2-(pyridin-2-yl)ethyl]-7-methylthio-imidazo[5,1-b]thiazolium-2-yl]-1-carbapen-2-em-3-carboxylate trifluoromethanesulfonate (77 mg) was dissolved in 2 ml of acetonitrile. Iodomethane (142 mg) was added thereto, and the mixture was stirred at room temperature for 2 days. The solvent was removed by distillation under the reduced pressure. The residue was purified by column chromatography on Sephadex LH-20 (chloroform:methanol=1:1) to prepare 70 mg of 4-nitrobenzyl (1S,5R,6S)-6-((1R)-1-hydroxyethyl)-1-methyl-2-[6-[2-(1-methylpyridinium-2-yl)ethyl]-7-methylthioimidazo[5,1-b]thiazolium-2-yl]-1-carbapen-2-em-3-carboxylate trifluoromethanesulfonate iodide.

NMR (DMSO-$d_6$) δ: 1.19 (3H, d, J=6.3 Hz), 1.24 (3H, d, J=7.1 Hz), 2.43 (3H, s), 3.52 (1H, dd, $J_1$=5.5 Hz, $J_2$=3.0 Hz), 3.70 (2H, t, J=7.1 Hz), 3.75–3.83 (1H, m), 4.02–4.10 (1H, m), 4.38 (3H, s), 4.42 (1H, dd, $J_1$=9.3 Hz, $J_2$=2.5 Hz), 4.89 (2H, t, J=7.1 Hz), 5.43 (1H, d, J=14.0 Hz), 5.55 (1H, d, J=14.0 Hz), 7.76 (2H, d, J=8.8 Hz), 7.98 (1H, d, J=8.2 Hz), 8.04–8.10 (1H, m), 8.26 (2H, d, J=8.8 Hz), 8.50–8.57 (1H, m), 8.77 (1H, s), 9.08 (1H, d, J=5.2 Hz), 9.73 (1H, s)

b) (1S,5R,6S)-6-((1R)-1-Hydroxyethyl)-1-methyl-2-[6-[2-(1-methylpyridinium-2-yl)ethyl]-7-methylthio-imidazo[5,1-b]thiazolium-2-yl]-1-carbapen-2-em-3-carboxylate chloride (intramolecular salt)

The procedure of Example 3b) was repeated to treat 65 mg of 4-nitrobenzyl (1S,5R,6S)-6-((1R)-1-hydroxyethyl)-1-methyl-2-(6-(2-(1-methylpyridinium-2-yl)ethyl)-7-methylthioimidazo[5,1-b]thiazolium-2-yl)-1-carbapen-2-em-3-carboxylate trifluoromethanesulfonate iodide, and was then subjected to column chromatography (water) on Amberlyst A-26 as an ion-exchange resin (chloro form). Thus, 7.2 mg of the title compound was prepared.

NMR (D$_2$O) δ (HOD=4.80 ppm): 1.27 (3H, d, J=7.1 Hz), 1.31 (3H, d, J=6.3 Hz), 2.39 (3H, s), 3.58–3.68 (2H, m), 3.81 (2H, t, J=7.1 Hz), 3.98–4.02 (1H, m), 4.36 (1H, dd, J$_1$=9.3 Hz, J$_2$=2.7 Hz), 4.44 (3H, s), 4.96 (2H, t, J=7.1 Hz), 7.84 (1H, d, J=8.0 Hz), 7.93–7.99 (1H, m), 8.17 (1H, s), 8.40–8.46 (1H, m), 8.85 (1H, d, J=6.3 Hz), 9.49 (1H, s)

Example 103

(1S,5R,6S)-2-[6-((2R)-3-Acetimidoylamino-2-hydroxypropyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride The procedure of Example 69 was repeated, except that 25 mg of (1S,5R,6S)-2-[6-((2R)-3-amino-2-hydroxypropyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride was used as the starting compound. Thus, 15 mg of the title compound was prepared.

NMR (D$_2$O) δ (HOD=4.65 ppm): 1.11 (3H, d, J=7.1 Hz), 1.15 (3H, d, J=6.3 Hz), 2.10 (3H, s), 2.25 (3H, s), 3.23–3.54 (4H, m), 4.08–4.34 (4H, m), 4.48–4.53 (1H, m), 8.00 (1H, s)

Example 104

(1S,5R,6S)-2-[6-(3-Aminosulfonylaminopropyl)-7-methylthioimidazo[5,1-b]thiazolium-2-yl]-6-((1R)-1-hydroxyethyl)-1-methyl-1-carbapen-2-em-3-carboxylate (intramolecular salt)

a) 4-Nitrobenzyl (1S,5R,6S)-6-((1R)-1-hydroxyethyl)-1-methyl-2-[6-[3-(4-nitrobenzyloxycarbonylaminosulfonylamino)propyl]-7-methylthioimidazo[5,1-b]-thiazolium-2-yl]-1-carbapen-2-em-3-carboxylate trifluoromethanesulfonate The procedure of Example 20a) was repeated, except that 87 mg of 4-nitrobenzyl (1S,5R,6S)-6-((1R)-1-hydroxyethyl)-1-methyl-2-(7-methylthioimidazo[5,1-b]-thiazol-2-yl)-1-carbapen-2-em-3-carboxylate and 80 mg of 3-(4-nitrobenzyloxycarbonylaminosulfonylamino)propanol were used as the starting compounds. Thus, 93 mg of 4-nitrobenzyl (1S,5R,6S)-6-((1R)-1-hydroxyethyl)-1-methyl-2-[6-[3-(4-nitrobenzyloxycarbonylaminosulfonylamino)propyl]-7-methylthioimidazo[5,1-b]thiazolium-2-yl]-1-carbapen-2-em-3-carboxylate trifluoromethanesulfonate was prepared.

NMR (DMSO-d$_6$) δ: 1.17 (3H, d, J=6.1 Hz), 1.21 (3H, d, J=7.1 Hz), 2.00–2.10 (2H, m), 2.41 (3H, s), 2.90–3.07 (2H, m), 3.49 (1H, dd, J$_1$=5.6 Hz, J$_2$=3.2 Hz), 3.74–3.82 (1H, m), 4.00–4.10 (1H, m), 4.39 (1H, dd, J$_1$=10.2 Hz, J$_2$=3.2 Hz), 4.43 (2H, t, J=7.1 Hz), 5.29 (2H, s), 5.41 (1H, d, J=13.6 Hz), 5.53 (1H, d, J=13.6 Hz), 7.62 (2H, d, J=8.8 Hz), 7.74 (2H, d, J=8.8 Hz), 8.03 (1H, br s), 8.21–8.27 (4H, m), 8.68 (1H, s), 9.68 (1H, s), 11.52 (1H, br s)

b) (1S,5R,6S)-2-[6-(3-Aminosulfonylaminopropyl)-7-methylthioimidazo[5,1-b]thiazolium-2-yl]-6-((1R)-1-hydroxyethyl)-1-methyl-1-carbapen-2-em-3-carboxylate (intramolecular salt)

The procedure of Example 3b) was repeated, except that 85 mg of 4-nitrobenzyl (1S,5R,6S)-6-((1R)-1-hydroxyethyl)-1-methyl-2-[6-[3-(4-nitrobenzyloxycarbonylaminosulfonylamino)propyl]-7-methylthio-imidazo-[5,1-b]thiazolium-2-yl]-1-carbapen-2-em-3-carboxylate trifluoromethanesulfonate was used as the starting compound. Thus, 23 mg of the title compound was prepared.

NMR (D$_2$O) δ (HOD=4.80 ppm): 1.11 (3H, d, J=7.3 Hz), 1.16 (3H, d, J=6.4 Hz), 2.02–2.11 (2H, m), 2.27 (3H, s), 3.01 (2H, t, J=7.1 Hz), 3.41 (1H, dd, J$_1$=6.1 Hz, J$_2$=2.7 Hz), 3.45–3.54 (1H, m), 4.09–4.16 (1H, m), 4.20 (1H, dd, J$_1$=9.5 Hz, J$_2$=2.9 Hz), 4.41 (2H, t, J=7.1 Hz), 7.99 (1H, s)

Example 105

(1S,5R,6S)-6-((1R)-1-Hydroxyethyl)-1-methyl-2-[7-methylthio-6-(pyridin-2-yl)methylimidazo[5,1-b]-thiazolium-2-yl]-1-carbapen-2-em-3-carboxylate (intramolecular salt)

The procedure of Example 82a) was repeated, except that 78 mg of 4-nitrobenzyl (1S,5R,6S)-6-((1R)-1-hydroxyethyl)-1-methyl-2-(7-methylthioimidazo[5,1-b]-thiazol-2-yl)-1-carbapen-2-em-3-carboxylate and 137 mg of 2-bromomethylpyridine were used as the starting compounds. Thus, a crude quaternary salt (59 mg) was prepared. The procedure of Example 82b) was repeated, except that 59 mg of the crude quaternary salt was used as the starting compound and the solvent for the reaction was THF-1/15 M sodium phosphate buffer (pH 6.8) (1:1). Thus, 25 mg of the title compound was prepared.

NMR (DMSO-d$_6$) δ: 1.16 (3H, d, J=6.8 Hz), 1.17 (3H, d, J=6.1 Hz), 2.14 (3H, s), 3.16 (1H, dd, J$_1$=6.8 Hz, J$_2$=2.7 Hz), 3.45 (1H, m), 3.95 (1H, m), 4.10 (1H, dd, J$_1$=9.5 Hz, J$_2$=2.7 Hz), 5.03 (1H, d, J=5.1 Hz), 5.80 (2H, s), 7.37 (1H, m), 7.53 (1H, d, J=7.8 Hz), 7.78 (1H, dt, J$_1$=7.6 Hz, J$_2$=1.7 Hz), 8.33 (1H, s), 8.51 (1H, m), 9.68 (1H, s); MS (m/z) 471 (M+H)$^+$

Example 106

(1S,5R,6S)-2-[6-(4-Benzyloxy)benzyl-7-methylthioimidazo[5,1-b]thiazolium-2-yl]-6-((1R)-1-hydroxyethyl)-1-methyl-1-carbapen-2-em-3-carboxylate (intramolecular salt)

The procedure of Example 82a) was repeated, except that 78 mg of 4-nitrobenzyl (1S,5R,6S)-6-((1R)-1-hydroxyethyl)-1-methyl-2-(7-methylthioimidazo[5,1-b]-thiazol-2-yl)-1-carbapen-2-em-3-carboxylate, 233 mg of 4-benzyloxybenzyl chloride, and 150 mg of sodium iodide were used as the starting compounds. Thus, a crude quaternary salt (103 mg) was prepared. The procedure of Example 82b) was repeated, except that 103 mg of the crude quaternary salt was used as the starting compound. Thus, 22 mg of the title compound was prepared.

NMR (DMSO-d$_6$) δ: 1.15–1.20 (6H, m), 2.13 (3H, s), 3.42 (1H, m), 3.70 (1H, m), 4.02 (1H, m), 4.30 (1H, m), 5.11 (2H, s), 5.15 (1H, d, J=5.1 Hz), 5.60 (2H, s), 7.05 (2H, d, J=8.8 Hz), 7.31–7.43 (7H, m), 8.61 (1H, s), 9.75 (1H, s); MS (m/z) 576 (M+H)$^+$

Example 107

(1S,5R,6S)-6-((1R)-1-Hydroxyethyl)-1-methyl-2-[7-methylthio-6-[3-(4-phenylpiperazin-1-yl)carbonyl-aminopropyl]imidazo[5,1-b]thiazolium-2-yl]-1-carbapen-2-em-3-carboxylate (intramolecular salt)

The procedure of Example 82a) was repeated, except that 156 mg of 4-nitrobenzyl (1S,5R,6S)-6-((1R)-1-hydroxyethyl)-1-methyl-2-(7-methylthioimidazo[5,1-b]-thiazol-2-yl)-1-carbapen-2-em-3-carboxylate, 975 mg of N-(3-bromopropyl)-4-phenylpiperazinecarboxamide, and 225 mg of sodium iodide were used as the starting compounds. Thus, a crude quaternary salt (75 mg) was prepared. The procedure of Example 82b) was repeated, except that 75 mg of the crude quaternary salt was used as the starting compound and the solvent for the reaction was THF—1/15 M sodium phosphate buffer (pH 6.8) (1:1). Thus, 10 mg of the title compound was prepared.

NMR (D$_2$O) δ (HOD=4.80 ppm): 1.02 (1H, d, J=7.3 Hz), 1.23 (3H, d, J=6.4 Hz), 2.19 (2H, m), 2.36 (3H, s), 2.87 (4H, t, J=5.2 Hz), 3.26–3.38 (8H, m), 3.97 (1H, dd, J$_1$=9.3 Hz, J$_2$=2.7 Hz), 4.21 (1H, m), 4.72 (2H, m), 6.99–7.02 (3H, m), 7.32 (2H, t, J=8.3 Hz), 8.14 (1H, s); MS (m/z) 625 (M+H)$^+$

Example 108
(1S,5R,6S)-2-(6-N-Benzyloxycarbamoylmethyl-7-methylthioimidazo[5,1-b]thiazolium-2-yl)-6-((1R)-1-hydroxyethyl)-1-methyl-1-carbapen-2-em-3-carboxylate (intramolecular salt)

a) 4-Nitrobenzyl (1S,5R,6S)-2-(6-N-benzyloxycarbamoylmethyl-7-methylthioimidazo[5,1-b]thiazolium-2-yl)-6-((1R)-1-hydroxyethyl)-1-methyl-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (103 mg) was dissolved in 3 ml of acetone. 2-Iodo-N-benzyloxyacetamide (291 mg) was added to the solution. The mixture was stirred at 60° C. for 2 days. The solvent was removed by distillation under the reduced pressure. The residue was purified by column chromatography on Sephadex LH-20 (chloroform:methanol=1:1) to prepare 111 mg of 4-nitrobenzyl (1S,5R,6S)-2-(6-N-benzyloxycarbamoylmethyl-7-methylthioimidazo[5,1-b]thiazolium-2-yl)-6-((1R)-1-hydroxyethyl)-1-methyl-1-carbapen-2-em-3-carboxylate iodide.

NMR (acetone-$d_6$) δ: 1.31 (3H, d, J=6.1 Hz), 1.41 (3H, d, J=7.1 Hz), 2.49 (3H, s), 3.57 (1H, dd, $J_1$=6.1 Hz, $J_2$=2.9 Hz), 3.82–3.95 (1H, m), 4.20–4.26 (1H, m), 4.37 (1H, d, J=4.9 Hz), 4.56 (1H, dd, $J_1$=10.0 Hz, $J_2$=2.9 Hz), 4.97 (2H, s), 5.46 (1H, d, J=13.9 Hz), 5.50 (1H, s), 5.64 (1H, d, J=13.9 Hz), 7.32–7.49 (5H, m), 7.85 (2H, d, J=8.7 Hz), 8.27 (2H, d, J=8.7 Hz), 9.00 (1H, s), 10.06 (1H, s)

b) (1S,5R,6S)-2-(6-N-Benzyloxycarbamoylmethyl-7-methylthioimidazo[5,1-b]thiazolium-2-yl)-6-((1R)-1-hydroxyethyl)-1-methyl-1-carbapen-2-em-3-carboxylate (intramolecular salt)

The procedure of Example 3b) was repeated, except that 85 mg of 4-nitrobenzyl (1S,5R,6S)-2-(6-N-benzyloxycarbamoylmethyl-7-methylthioimidazo[5,1-b]thiazolium-2-yl)-6-((1R)-1-hydroxyethyl)-1-methyl-1-carbapen-2-em-3-carboxylate iodide was used as the starting compound. Thus, 35 mg of the title compound was prepared.

NMR ($D_2O$) δ (HOD=4.80 ppm): 1.27 (3H, d, J=6.8 Hz), 1.33 (3H, d, J=6.3 Hz), 2.29 (3H, s), 3.58 (1H, dd, $J_1$=6.1 Hz, $J_2$=2.9 Hz), 3.60–3.70 (1H, m), 4.16–4.26 (1H, m), 4.36 (1H, dd, $J_1$=10.0 Hz, $J_2$=2.9 Hz), 4.96 (2H, s), 5.14 (2H, s), 7.38–7.43 (5H, m), 8.17 (1H, s), 9.34 (1H, s)

Example 109
(1S,5R,6S)-6-((1R)-1-Hydroxyethyl)-2-[6-(4-methylthiazol-5-yl)methyl-7-methylthioimidazo[5,1-b]thiazolium-2-yl]-1-methyl-1-carbapen-2-em-3-carboxylate (intramolecular salt)

a) 4-Nitrobenzyl (1S,5R,6S)-6-((1R)-1-hydroxyethyl)-2-[6-(4-methylthiazol-5-yl)methyl-7-methylthioimidazo[5,1-b]thiazolium-2-yl]-1-methyl-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (103 mg) was dissolved in 2 ml of acetonitrile. 5-Chloromethyl-4-methylthiazole (60 mg) and 60 mg of sodium iodide were added to the solution. The mixture was stirred at room temperature for 2 days. The solvent was removed by distillation under the reduced pressure. The residue was purified by column chromatography on Sephadex LH-20 (chloroform:methanol=1:1) to prepare 123 mg of 4-nitrobenzyl (1S,5R,6S)-6-((1R)-1-hydroxyethyl)-2-[6-(4-methylthiazol-5-yl)methyl-7-methylthioimidazo[5,1-b]thiazolium-2-yl]-1-methyl-1-carbapen-2-em-3-carboxylate iodide.

NMR (DMSO-$d_6$) δ: 1.19 (3H, d, J=6.7 Hz), 1.23 (3H, d, J=7.1 Hz), 2.31 (3H, s), 2.55 (3H, s), 3.48 (1H, m), 3.75 (1H, m), 4.06 (1H, m), 4.20 (1H, dd, $J_1$=9.5 Hz, $J_2$=2.7 Hz), 5.41 (1H, d, J=13.5 Hz), 5.54 (1H, d, J=13.5 Hz), 5.91 (2H, s), 7.75 (2H, d, J=8.8 Hz), 8.23 (2H, d, J=8.8 Hz), 8.63 (1H, s), 9.08 (1H, s), 9.76 (1H, s)

b) (1S,5R,6S)-6-((1R)-1-Hydroxyethyl)-2-[6-(4-methylthiazol-5-yl)methyl-7-methylthioimidazo[5,1-b]thiazolium-2-yl]-1-methyl-1-carbapen-2-em-3-carboxylate (intramolecular salt)

4-Nitrobenzyl (1S,5R,6S)-6-((1R)-1-hydroxyethyl)-2-[6-(4-methylthiazol-5-yl)methyl-7-methylthioimidazo[5,1-b]thiazolium-2-yl]-1-methyl-1-carbapen-2-em-3-carboxylate iodide (120 mg) was treated in the same manner as in Example 3b). Thus, 28 mg of the title compound was prepared.

NMR ($D_2O$) δ (HOD=4.65 ppm): 1.05 (3H, d, J=7.3 Hz), 1.16 (3H, d, J=6.4 Hz), 2.02 (3H, s), 2.41 (3H, s), 3.41 (1H, dd, $J_1$=5.8 Hz, $J_2$=2.7 Hz), 3.49 (1H, m), 4.13 (1H, m), 4.21 (1H, dd, $J_1$=9.4 Hz, $J_2$=2.7 Hz), 5.68 (2H, s), 7.92 (1H, s), 8.84 (1H, s), 9.25 (1H, s)

Example 110
(1S,5R,6S)-6-((1R)-1-Hydroxyethyl)-2-[6-(imidazol-4-yl)methyl-7-methylthioimidazo[5,1-b]thiazolium-2-yl]-1-methyl-1-carbapen-2-em-3-carboxylate (intramolecular salt) hydrochloride a) 4-Nitrobenzyl (1S,5R,6S)-6-((1R)-1-hydroxyethyl)-1-methyl-2-[7-methylthio-6-[1-(4-nitrobenzyloxy-carbonyl)imidazol-4-yl]methylimidazo[5,1-b]thiazolium-2-yl]-1-carbapen-2-em-3-carboxylate iodide The procedure of Example 109a) was repeated, except that 643 mg of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate, 554 mg of 4-chloromethyl-1-(4-nitrobenzyloxycarbonyl)imidazole, and 280 mg of sodium iodide were used as the starting compounds. Thus, 854 mg of 4-nitrobenzyl (1S,5R,6S)-6-((1R)-1-hydroxyethyl)-1-methyl-2-[7-methylthio-6-[1-(4-nitrobenzyloxycarbonyl)imidazol-4-yl]methylimidazo[5,1-b]thiazolium-2-yl]-1-carbapen-2-em-3-carboxylate iodide was prepared.

NMR (DMSO-$d_6$) δ: 1.17 (3H, d, J=6.4 Hz), 1.23 (3H, d, J=7.1 Hz), 2.36 (3H, s), 3.48 (1H, m), 3.75 (1H, m), 4.05 (1H, m), 4.40 (1H, dd, $J_1$=9.5 Hz, $J_2$=2.7 Hz), 5.21 (1H, d, J=6.4 Hz), 5.41 (1H, d, J=13.4 Hz), 5.54 (1H, d, J=13.4 Hz), 5.60 (2H, s), 5.65 (2H, s), 7.73 (2H, d, J=8.8 Hz), 7.79 (2H, d, J=8.8 Hz), 7.87 (1H, s), 8.22 (2H, d, J=8.8 Hz), 8.27 (2H, d, J=8.8 Hz), 8.42 (1H, s), 8.73 (1H, s), 9.88 (1H, s)

b) (1S,5R,6S)-6-((1R)-1-Hydroxyethyl)-2-[6-(imidazol-4-yl)methyl-7-methylthioimidazo[5,1-b]thiazolium-2-yl]-1-methyl-1-carbapen-2-em-3-carboxylate (intramolecular salt) hydrochloride 4-Nitrobenzyl (1S,5R,6S)-6-((1R)-1-hydroxyethyl)-1-methyl-2-[7-methylthio-6-[1-(4-nitrobenzyloxycarbonyl)-imidazol-4-yl]methylimidazo[5,1-b]thiazolium-2-yl]-1-carbapen-2-em-3-carboxylate iodide (850 mg) was dissolved in 20 ml of THF and 20 ml of water. 10%Pd—C (850 mg) was added to the solution. The air in the reaction vessel was replaced by hydrogen, and the contents of the reaction vessel were stirred at room temperature for 1.5 hr. The catalyst was removed by filtration on Celite, and was washed with a 50% aqueous THF solution. The filtrate was washed with ethyl acetate, and was then concentrated under the reduced pressure until the volume of the filtrate was brought to about 10 ml. The residue was purified by column chromatography on Cosmosil 40$C_{18}$-PREP (a 20% aqueous methanol solution), and was then subjected to column chromatography (water) on Amberlyst A-26 as an ion-exchange resin (chloro form) to prepare 210 mg of the title compound.

NMR (D$_2$O) δ (HOD=4.65 ppm): 1.13 (3H, d, J=7.1 Hz), 1.20 (3H, d, J=6.4 Hz), 2.13 (3H, s), 3.44 (1H, dd, J$_1$=5.9 Hz, J$_2$=2.7 Hz), 3.52 (1H, m), 4.16 (1H, m), 4.23 (1H, dd, J$_1$=9.4 Hz, J$_2$=2.7 Hz), 5.48 (2H, s), 7.30 (1H, s), 7.70 (1H, s), 8.00 (1H, s), 9.14 (1H, s)

Example 111

(1S,5R,6S)-2-[7-(3-Aminopropyl)thio-6-carbamoyl-methylimidazo[5,1-b]thiazolium-2-yl]-6-((1R)-1-hydroxyethyl)-1-methyl-1-carbapen-2-em-3-carboxylate (intramolecular salt) hydrochloride a) 4-Nitrobenzyl (1S,5R,6S)-2-[7-(3-azidopropyl)thioimidazo[5,1-b]thiazol-2-yl]-6-((1R)-1-hydroxyethyl)-1-methyl-1-carbapen-2-em-3-carboxylate The procedure of Example 1a) was repeated, except that 2.42 g of 4-nitrobenzyl (1S,5R,6S)-6-((1R)-1-hydroxyethyl)-1-methyl-2-oxo-1-carbapenam-3-carboxylate and 3.70 g of 7-(3-azidopropyl)thio-2-(tri-n-butylstannyl)imidazo[5,1-b]thiazole were used as the starting compounds. Thus, 2.38 g of 4-nitrobenzyl (1S,5R,6S)-2-[7-(3-azidopropyl)thioimidazo[5,1-b]-thiazol-2-yl]-6-((1R)-1-hydroxyethyl)-1-methyl-1-carbapen-2-em-3-carboxylate was prepared.

NMR (CDCl$_3$) δ: 1.31 (3H, d, J=7.2 Hz), 1.40 (3H, d, J=6.0 Hz), 1.8–1.9 (2H, m), 2.8–2.9 (2H, m), 3.37 (1H, dd, J$_1$=6.6 Hz, J$_2$=2.7 Hz), 3.4–3.55 (3H, m), 4.25–4.4 (2H, m), 5.28 (1H, d, J=13.8 Hz), 5.53 (1H, d, J=13.8 Hz), 7.68 (2H, d, J=8.7 Hz), 8.02 (1H, s), 8.24 (2H, d, J=8.7 Hz), 8.30 (1H, s)

b) 4-Nitrobenzyl (1S,5R,6S)-2-[7-(3-azidopropyl)thio-6-carbamoylmethylimidazo[5,1-b]thiazolium-2-yl]-6-((1R)-1-hydroxyethyl)-1-methyl-1-carbapen-2-em-3-carboxylate iodide The procedure of Example 3a) was repeated, except that the reaction was carried out at 40° C. and 1.48 g of 4-nitrobenzyl (1S,5R,6S)-2-[7-(3-azidopropyl)thioimidazo[5,1-b]thiazol-2-yl]-6-((1R)-1-hydroxyethyl)-1-methyl-1-carbapen-2-em-3-carboxylate was used as the starting compound. Thus, 1.85 g of 4-nitrobenzyl (1S,5R,6S)-2-[7-(3-azidopropyl)thio-6-carbamoylmethylimidazo[5,1-b]thiazolium-2-yl]-6-((1R)-1-hydroxyethyl)-1-methyl-1-carbapen-2-em-3-carboxylate iodide was prepared.

NMR (DMSO-d$_6$) δ: 1.18 (3H, d, J=6.0 Hz), 1.25 (3H, d, J=6.9 Hz), 1.65–1.8 (2H, m), 2.8–2.9 (2H, m), 3.35–3.45 (2H, m), 3.45–3.55 (1H, m), 3.7–3.85 (1H, m), 4.0–4.15 (1H:, m), 4.35–4.45 (1H, m), 5.19 (2H, s), 5.42 (1H, d, J=13.5 Hz), 5.55 (1H, d, J=13.5 Hz), 7.70 (1H, s), 7.74 (2H, d, J=9.0 Hz), 7.96 (1H, s), 8.24 (2H, d, J=9.0 Hz), 8.75 (1H, s), 9.76 (1H, s)

c) (1S,5R,6S)-2-[7-(3-Aminopropyl)thio-6-carbamoyl-methylimidazo[5,1-b]thiazolium-2-yl]-6-((1R)-1-hydroxyethyl)-1-methyl-1-carbapen-2-em-3-carboxylate intramolecular salt) hydrochloride The procedure of Example 3b) was repeated, except that the reaction was carried out in a mixed solvent composed of THF and water and 1.85 g of 4-nitrobenzyl (1S,5R,6S)-2-[7-(3-azidopropyl)thio-6-carbamoylmethylimidazo[5,1-b]thiazolium-2-yl]-6-((1R)-1-hydroxyethyl)-1-methyl-1-carbapen-2-em-3-carboxylate iodide was used as the starting compound. Purification was then carried out by column chromatography on Cosmosil 40C$_{18}$-PREP (5 to 25% aqueous methanol solution). In this case, a main product eluted as a first fraction was collected, and was subjected to column chromatography (water) on Amberlyst A-26 as an ion-exchange resin (chloro form) to prepare 418 mg of the title compound.

NMR (D$_2$O) δ (HOD=4.80 ppm): 1.27 (3H, d, J=6.9 Hz), 1.31 (3H, d, J=6.3 Hz), 1.85–2.0 (2H, m), 2.8–2.9 (2H, m), 3.05–3.15 (2H, m), 3.57 (1H, dd, J$_1$=6.0 Hz, J$_2$=2.7 Hz), 3.6–3.75 (1H, m), 4.2–4.3 (1H, m), 4.35 (1H, dd, J$_1$=9.3 Hz, J$_2$=2.7 Hz), 5.33 (2H, s), 8.20 (1H, s), 9.46 (1H, s)

Example 112

(1S,5R,6S)-2-[7-(3-Hydroxypropyl)thio-6-carbamoylmethylimidazo[5,1-b]thiazolium-2-yl]-6-((1R)-1-hydroxyethyl)-1-methyl-1-carbapen-2-em-3-carboxylate (intramolecular salt)

A fraction was collected which had been eluted as the latter fraction in the column chromatography on Cosmosil 40C$_{18}$-PREP (5 to 25% aqueous methanol solution) in Example 111c) to, prepare 58 mg of the title compound.

NMR (D$_2$O) δ (HOD=4.80 ppm): 1.26 (3H, d, J=7.2 Hz), 1.31 (3H, d, J=6.6 Hz), 1.7–1.85 (2H, m), 2.8–2.9 (2H, m), 3.56 (1H, dd, J$_1$=6.0 Hz, J$_2$=2.7 Hz), 3.6–3.7 (3H, m), 4.25–4.35 (1H, m), 4.35 (1H, dd, J$_1$=9.3 Hz, J$_2$=2.7 Hz), 5.32 (2H, s), 8.19 (1H, s), 9.43 (1H, s)

Example 113

(1S,5R,6S)-2-[6-((2S)-3-Amino-2-hydroxy)propyl-7-methylthioimidazo[5,1-b]thiazolium-2-yl]-6-((1R)-1-hydroxyethyl)-1-methyl-1-carbapen-2-em-3-carboxylate (intramolecular salt) hydrochloride a) (2S)-3-Azido-2-triethylsilyloxy-1-propanol The procedures of Example 99a) and Example 99b) were repeated, except that 1.35 g of (2R)-3-chloro-1,2-propanediol was used as the starting compound. Thus, 520 mg of (2S)-3-azido-2-triethylsilyloxy-1-propanol was prepared.

NMR (CDCl$_3$) δ: 0.66 (6H, q, J=7.5 Hz), 0.98 (9H, t, J=7.5 Hz), 1.79–1.84 (1H, m), 3.28–3.40 (2H, m), 3.55–3.67 (2H, m), 3.84–3.90 (1H, m)

b) 4-Nitrobenzyl (1S,5R,6S)-2-[6-((2S)-3-azido-2-triethylsilyloxy)propyl-7-methylthioimidazo[5,1-b]-thiazolium-2-yl]-6-((1R)-1-hydroxyethyl)-1-methyl-1-carbapen-2-em-3-carboxylate trifluoromethanesulfonate The procedure of Example 99c) was repeated, except that 270 mg of (2S)-3-azido-2-triethylsilyloxy-1-propanol and 517 mg of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate were used as the starting compounds. Thus, 765 mg of 4-nitrobenzyl (1S,5R,6S)-2-[6-((2S)-3-azido-2-triethylsilyloxy)propyl-7-methylthioimidazo[5,1-b]thiazolium-2-yl]-6-((1R)-1-hydroxyethyl)-1-methyl-1-carbapen-2-em-3-carboxylate trifluoromethanesulfonate as a crude product was prepared.

c) (1S,5R,6S)-2-[6-((2S)-3-Amino-2-hydroxy)propyl-7-methylthioimidazo[5,1-b]thiazolium-2-yl]-6-((1R)-1-hydroxyethyl)-1-methyl-1-carbapen-2-en-3-carboxylate (intramolecular salt) hydrochloride The procedure of Example 99d) was repeated, except that 765 mg of 4-nitrobenzyl (1S,5R,6S)-2-[6-((2S)-3-azido-2-triethylsilyloxy)propyl-7-methylthioimidazo[5,1-b]thiazolium-2-yl]-6-((1R)-1-hydroxyethyl)-1-methyl-1-carbapen-2-em-3-carboxylate trifluoromethanesulfonate as the crude product was used as the starting compound. Thus, 173 mg of the title compound was prepared.

NMR (D$_2$O) δ (HOD=4.65 ppm): 1.12 (3H, d, J=7.0 Hz), 1.16 (3H, d, J=6.3 Hz), 2.26 (3H, s), 2.87–2.94 (1H, m), 3.20–3.26 (1H, m), 3.42 (1H, dd, J$_1$=6.0 Hz, J$_2$=2.7 Hz), 3.46–3.55 (1H, m), 4.10–4.23 (3H, m), 4.28–4.35 (1H, m), 4.60–4.63 (1H, m), 8.03 (1H, s)

Example 114
(1S,5R,6S)-2-[6-((2R-2,3-Dihydroxy)propyl-7-methylthioimidazo[5,1-b]thiazolium-2-yl]-6-((1R)-1-hydroxyethyl)-1-methyl-1-carbapen-2-em-3-carboxylate (intramolecular salt)

The latter fraction was colleted which had been eluted after (1S,5R,6S)-2-[6-((2S)-3-amino-2-hydroxy)propyl-7-methylthioimidazo[5,1-b]thiazolium-2-yl]-6-((1R)-1-hydroxyethyl)-1-methyl-1-carbapen-2-em-3-carboxylate (intramolecular salt) hydrochloride in the column chromatography on Cosmosil 40C$_{18}$-PREP (a 20% aqueous methanol solution) in Example 113c). The title compound (23 mg) was obtained from this fraction.

NMR (D$_2$O) δ (HOD=4.65 ppm): 1.10 (3H, d, J=7.1 Hz), 1.16 (3H, d, J=6.3 Hz), 2.25 (3H, s), 3.41 (1H, dd, J$_1$=5.8 Hz, J$_2$=2.7 Hz), 3.45–3.62 (3H, m), 3.94–4.01 (1H, m), 4.09–4.16 (1H, m), 4.19 (1H, dd, J$_1$=9.5 Hz, J$_2$=2.7 Hz), 4.22–4.30 (1H, m), 4.48–4.55 (1H, m), 8.00 (1H, s), 9.18 (1H, s)

Example 115
(1S,5R,6S)-2-[6-((2R)-3-Amino-2-hydroxy)-propyl-7-methanesulfinylimidazo[5,1-b]thiazolium-2-yl]-6-((1R)-1-hydroxyethyl)-1-methyl-1-carbapen-2-em-3-carboxylate (intramolecular salt) hydrochloride (a mixture of diastereomers)

4-Nitrobenzyl (1S,5R,6S)-2-[6-((2R)-3-azido-2-triethylsilyloxy)propyl-7-methylthioimidazo[5,1-b]thiazolium-2-yl]-6-((1R)-1-hydroxyethyl)-1-methyl-1-carbapen-2-em-3-carboxylate trifluoromethanesulfonate as the crude product (115 mg) was dissolved in 4 ml of THF and 4 ml of water. OXONE (manufactured by E.I. du Pont de Nemours & Co.) (109 mg) was added to the solution. The mixture was stirred at room temperature for 4 hr, and was adjusted to pH 4.6 by the addition of a saturated aqueous sodium hydrogencarbonate solution. 10%Pd—C (60 mg) was then added thereto. The air in the reaction vessel was replaced by hydrogen, and the contents of the reaction vessel were stirred at room temperature for 2 hr. The catalyst was removed by filtration on Celite, and washed with water. The filtrate was washed with ethyl acetate, and was then concentrated under the reduced pressure until the volume of the filtrate was brought to about 5 ml. The residue was purified by column chromatography on Cosmosil 40C$_{18}$-PREP (a 20% aqueous methanol solution). A first fraction was collected, and was subjected to column chromatography (water) on Amberlyst A-26 as an ion-exchange resin (chloro form) to prepare 6 mg of the title compound.

NMR (D$_2$O) δ (HOD=4.65 ppm): 1.24–1.32 (6H, m), 2.95–3.12 (1H, m), 3.24, 3.31 (total 3H, s each), 3.31–3.39 (1H, m), 3.55–3.59 (1H, m), 3.63–3.72 (1H, m), 4.25–4.38 (3H, m), 4.48–4.60 (1H, m), 4.77–4.85 (1H, m), 8.03 (1H, s), 8.30, 8.32 (total 1H, s each)

Example 116
(1S,5R,6S)-6-((1R)-1-Hydroxyethyl)-2-[6-(2-hydroxyethyl)-7-methanesulfinylimidazo[5,1-b]thiazolium-2-yl]-1-methyl-1-carbapen-2-em-3-carboxylate (intramolecular salt) (a mixture of diastereomers)

a) 4-Nitrobenzyl (1S,5R,6S)-2-[6-(2-azidoethyl)-7-methanesulfinylimidazo[5,1-b]thiazolium-2-yl]-6-((1R)-1-hydroxyethyl)-1-methyl-1-carbapen-2-em-3-carboxylate trifluoromethanesulfonate The procedure of Example 6a) was repeated, except that 110 mg of 4-nitrobenzyl (1S,5R,6S)-2-[6-(2-azidoethyl)-7-methylthioimidazo[5,1-b]thiazolium-2-yl]-6-((1R)-1-hydroxyethyl)-1-methyl-1-carbapen-2-em-3-carboxylate trifluoromethanesulfonate was used as the starting compound. Thus, 128 mg of 4-nitrobenzyl (1S,5R,6S)-2-[6-(2-azidoethyl)-7-methanesulfinylimidazo[5,1-b]thiazolium-2-yl]-6-((1R)-1-hydroxyethyl)-1-methyl-1-carbapen-2-em-3-carboxylate trifluoromethanesulfonate as a crude product was prepared.

b) (1S,5R,6S)-6-((1R)-1-Hydroxyethyl)-2-[6-(2-hydroxyethyl)-7-methanesulfinylimidazo[5,1-b]thiazolium-2-yl]-1-methyl-1-carbapen-2-em-3-carboxylate (intramolecular salt) (a mixture of diastereomers)

The procedure of Example 44b) was repeated, except that 128 mg of 4-nitrobenzyl (1S,5R,6S)-2-[6-(2-azidoethyl)-7-methanesulfinylimidazo[5,1-b]thiazolium-2-yl]-6-((1R)-1-hydroxyethyl)-1-methyl-1-carbapen-2-em-3-carboxylate trifluoromethanesulfonate as a crude product was used as the starting compound. Thus, 6 mg of the title compound was prepared.

NMR (D$_2$O) δ (HOD=4.65 ppm): 1.15–1.23 (6H, m), 3.17, 3.19 (total 3H, s each), 3.45–3.49 (1H, m), 3.54–3.64 (1H, m), 3.84–3.96 (2H, m), 4.14–4.21 (1H, m), 4.23–4.29 (1H, m), 4.53–4.61 (2H, m), 8.20, 8.22 (total 1H, s each)

Example 117
(1S,5R,6S)-2-[6-(2-Aminothiazol-4-yl)methyl-7-methylthioimidazo[5,1-b]thiazolium-2-yl]-6-((1R)-1-hydroxyethyl)-1-methyl-1-carbapen-2-em-3-carboxylate (intramolecular salt)

a) 4-Nitrobenzyl (1S,5R,6S)-6-((1R)-1-hydroxyethyl)-2-[7-methylthio-6-[2-(4-nitrobenzyloxycarbonyl)aminothiazol-4-yl]methylimidazo[5,1-b]-thiazolium-2-yl]-1-methyl-1-carbapen-2-em-3-carboxylate iodide The procedure of Example 109a) was repeated, except that 103 mg of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate, 100 mg of 4-chloromethyl-2-(4-nitrobenzyloxycarbonyl)aminothiazole, and 46 mg of sodium iodide were used as the starting compounds. Thus, 70 mg of 4-nitrobenzyl (1S,5R,6S)-6-((1R)-1-hydroxyethyl)-2-[7-methylthio-6-[2-(4-nitrobenzyloxycarbonyl)aminothiazol-4-yl]methylimidazo[5,1-b]thiazolium-2-yl]-1-methyl-1-carbapen-2-em-3-carboxylate iodide was prepared.

NMR (DMSO-d$_6$) δ: 1.19 (3H, d, J=6.4 Hz), 1.24 (3H, d, J=7.2 Hz), 2.32 (3H, s), 3.49 (1H, m), 3.76 (1H, m), 4.07 (1H, m), 4.20 (1H, dd, J$_1$=9.5 Hz, J$_2$=2.7 Hz), 5.19 (1H, d, J=6.4 Hz), 5.39 (2H, s), 5.42 (1H, d, J=13.5 Hz), 5.54 (1H, d, J=13.5 Hz), 5.68 (2H, s), 7.31 (1H, s), 7.67 (2H, d, J=8.8 Hz), 7.75 (2H, d, J=8.8 Hz), 8.23 (2H, d, J=8.8 Hz), 8.26 (2H, d, J=8.8 Hz), 8.71 (1H, s), 9.40 (1H, s)

b) (1S,5R,6S)-2-[6-(2-Aminothiazol-4-yl)methyl-7-methylthioimidazo[5,1-b]thiazolium-2-yl]-6-((1R)-1-hydroxyethyl)-1-methyl-1-carbapen-2-em-3-carboxylate (intramolecular salt) hydrochloride 4-Nitrobenzyl (1S,5R,6S)-6-((1R)-1-hydroxyethyl)-2-[7-methylthio-6-[2-(4-nitrobenzyloxycarbonyl)aminothiazol-4-yl]methylimidazo[5,1-b]thiazolium-2-yl]-1-methyl-1-carbapen-2-em-3-carboxylate iodide (65 mg) was treated in the same manner as in Example 110b). Thus, 9 mg of the title compound was prepared.

NMR (D$_2$O) δ (HOD=4.65 ppm): 1.07 (3H, d, J=7.3 Hz), 1.14 (3H, d, J=6.4 Hz), 2.12 (3H, s), 3.43 (1H, m), 3.50 (1H, m), 4.14 (1H, m), 4.20 (1H, dd, J$_1$=9.5 Hz, J$_2$=2.7 Hz), 5.32 (2H, s), 6.65 (1H, s), 7.98 (1H, s) 9.19 (1H, s)

Example 118
(1S,5R,6S)-6-((1R)-1-Hydroxyethyl)-1-methyl-2-[7-methylthio-6-(1-phenylethyl)imidazo[5,1-b]thiazolium-2-yl]-1-carbapen-2-em-3-carboxylate (intramolecular salt) (a mixture of diastereomers)

The procedure of Example 82a) was repeated, except that 78 mg of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate, 0.204 ml of (1-bromoethyl)benzene, and 150 mg of sodium iodide were used as the starting compounds. Thus, 25 mg of a crude quaternary salt was prepared. The procedure of Example 82b) was repeated, except that 25 mg of the crude quaternary salt was used as the starting compound. Thus, 10 mg of the title compound was prepared. Both the isomers can be separated by reversed phase HPLC.

NMR (DMSO-$d_6$) δ: 1.32–1.36 (6H, m), 2.13 (3H, d, J=7.1 Hz), 2.17 (3H, s), 3.35 (1H, m), 3.68 (1H, m), 4.29 (1H, m), 4.39 (1H, dd, $J_1$=9.4 Hz, $J_2$=2.4 Hz), 5.21 (1H, d, J=5.1 Hz), 6.25 (1H, m), 7.52–7.62 (5H, m), 8.37 (0.5H, s), 8.40 (0.5H, s), 9.95 (0.5H, s), 9.96 (1H, s); MS (m/z) 484 $(M+H)^+$

Example 119
(1S,5R,6S)-6-((1R)-1Hydroxyethyl)-1-methyl-2-[7-methylthio-6-(carboxy)(phenyl)methylimidazo[5,1-b]thiazolium]-2-yl-1-carbapen-2-em-3-carboxylate (intramolecular salt) (a mixture of diastereomers)

The procedure of Example 82a) was repeated, except that 52 mg of 4-nitrobenzyl (1S,5R,6S)-6-((1R)-1-hydroxyethyl)-1-methyl-2-(7-methylthioimidazo[5,1-b]-thiazol-2-yl)-1-carbapen-2-em-3-carboxylate and 280 mg of 4-nitrobenzyl bromophenylacetate were used as the starting compounds. Thus, a crude quaternary salt (64 mg) was prepared. The crude quaternary salt (25 mg) was dissolved in THF (2.5 ml)—1/15 M sodium phosphate buffer (pH 6.8) (2.5 ml). 10%Pd—C (6.0 mg) was added to the solution. The air in the reaction vessel was replaced by hydrogen, and the contents of the reaction vessel were stirred at room temperature for 2 hr. The reaction solution was adjusted to pH 7 by the addition of a saturated aqueous sodium hydrogencarbonate solution. Post-treatment and purification were then carried out in the same manner as in Example 82b). Thus, 15 mg of a sodium salt of the title compound was prepared. Both the isomers can be separated by reversed phase HPLC.

NMR (DMSO-$d_6$) δ: 1.05–1.10 (6H, m), 2.18 (1.5H, s), 2.27 (1.5H, s), 3.10 (1H, m), 3.25 (1H, m), 3.88 (1H, m), 4.03 (1H, m), 4.96 (1H, m), 5.97 (1H, d, J=5.1 Hz), 7.26–7.40 (5H, m), 8.04 (0.5H, s), 8.05 (0.5H, s), 9.44 (0.5H, s), 9.49 (0.5H, s); MS (m/z) 514 $(M+H)^+$

Example 120
(1S,5R,6S)-2-[6-(4-Carboxybenzyl)-7-methyl-thioimidazo[5,1-b]thiazolium-2-yl]-6-((1R)-1-hydroxyethyl)-1-methyl-1-carbapen-2-em-3-carboxylate (intramolecular salt)

The procedure of Example 82a) was repeated, except that 78 mg of 4-nitrobenzyl (1S,5R,6S)-6-((1R)-1-hydroxyethyl)-1-methyl-2-(7-methylthioimidazo[5,1-b]-thiazol-2-yl)-1-carbapen-2-em-3-carboxylate and 350 mg of 4-nitrobenzyl 4-bromomethylbenzoate were used as the starting compounds. Thus, a crude quaternary salt (51 mg) was prepared. The procedure of Example 119 was repeated, except that 51 mg of the crude quaternary salt was used as the starting compound. Thus, 4 mg of a sodium salt of the title compound was prepared.

NMR (DMSO-$d_6$) δ: 1.08 (3H, d, J=7.0 Hz), 1.10 (3H, d, J=6.3 Hz), 2.02 (3H, s), 3.10 (1H, m), 3.39 (1H, m), 3.88 (1H, m), 4.03 (1H, m), 4.99 (1H, d, J=4.9 Hz), 5.55 (2H, s), 7.18 (2H, d, J=8.1 Hz), 7.76 (2H, d, J=8.0 Hz), 8.55 (1H, s), 9.52 (1H, s); MS (m/z) 514 $(M+H)^+$

Example 121
(1S,5R,6S)-2-(6-N-Hydroxyaminocarbonylmethyl-7-methylthioimidazo[5,1-b]thiazolium-2-yl)-6-((1R)-1-hydroxyethyl)-1-methyl-1-carbapen-2-em-3-carboxylate (intramolecular salt)

a) 4-Nitrobenzyl (1S,5R,6S)-6-((1R)-1-hydroxyethyl)-1-methyl-2-[7-methylthio-6-N-(4-nitrobenzyloxycarbonyloxy)aminocarbonylmethylimidazo[5,1-b]thiazolium-2-yl]-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (87 mg) was dissolved in 8 ml of acetonitrile. N-(4-Nitrobenzyloxycarbonyl)oxy-2-iodoacetamide (320 mg) was added to the solution. The mixture was stirred at 60° C. for 5 days. The insolubles were removed by filtration. The solvent was then removed by distillation under the reduced pressure. The residue was purified by column chromatography on Sephadex LH-20 (chloroform:methanol=1:1) to prepare 132 mg of 4-nitrobenzyl (1S,5R,6S)-6-((1R)-1-hydroxyethyl)-1-methyl-2-[7-methylthio-6-N-(4-nitrobenzyloxycarbonyloxy)aminocarbonylmethylimidazo[5,1-b]thiazolium-2-yl]-1-carbapen-2-em-3-carboxylate iodide.

NMR (DMSO-$d_6$) δ: 1.18 (3H, d, J=6.6 Hz), 1.25 (3H, d, J=7.1 Hz), 2.35 (3H, s), 3.51 (1H, dd, $J_1$=5.6 Hz, $J_2$=3.2 Hz), 3.71–3.80 (1H, m), 4.03–4.10 (1H, m), 4.41 (1H, dd, $J_1$=9.9 Hz, $J_2$=3.2 Hz), 5.26 (2H, s), 5.42 (1H, d, J=13.7 Hz), 5.55 (1H, d, J=13.7 Hz), 7.62 (2H, d, J=8.5 Hz), 7.75 (2H, d, J=8.5 Hz), 8.24 (4H, d, J=8.5 Hz), 8.77 (1H, s), 9.79 (1H, s)

b) (1S,5R,6S)-2-(6-N-Hydroxyaminocarbonylmethyl-7-methylthioimidazo[5,1-b]thiazolium-2-yl)-6-((1R)-1-hydroxyethyl)-1-methyl-1-carbapen-2-em-3-carboxylate (intramolecular salt)

4-Nitrobenzyl (1S,5R,6S)-6-((1R)-1-hydroxyethyl)-1-methyl-2-[7-methylthio-6-N-(4-nitrobenzyloxycarbonyloxy)aminocarbonylmethylimidazo[5,1-b]thiazolium-2-yl]-1-carbapen-2-em-3-carboxylate iodide (130 mg) was dissolved in 5 ml of THF and 5 ml of a 1/15 M sodium phosphate buffer (pH 6.6). 10%Pd—C (130 mg) was added to the solution. The air in the reaction vessel was replaced b hydrogen, and the contents of the reaction vessel were stirred at room temperature for 2 hr. The catalyst was removed by filtration on Celite, and was washed with water. The filtrate was washed with ethyl acetate, and was then concentrated under the reduced pressure until the volume of the filtrate was brought to about 2 ml. The residue was purified by column chromatography on Cosmosil 40$C_{18}$-PREP (a 20% aqueous methanol solution) to prepare 15 mg of the title compound.

NMR ($D_2O$) δ (HOD=4.80 ppm): 1.28 (3H, d, J=7.1 Hz), 1.33 (3H, d, J=6.6 Hz), 2.36 (3H, s), 3.58 (1H, dd, $J_1$=6.2 Hz, $J_2$=2.9 Hz), 3.65–3.72 (1H, m), 4.27–4.32 (1H, m), 4.37 (1H, dd, $J_1$=9.6 Hz, $J_2$=2.9 Hz), 5.27 (2H, s), 8.20 (1H, s)

Example 122
(1S,5R,6S)-6-((1R)-1-Hydroxyethyl)-1-methyl-2-[6-methyl-7-[2-(4-methyl-1,4-diazoniabicyclo-[2,2,2]oct-1-yl)ethyl]thioimidazo[5,1-b]thiazolium-2-yl]-1-carbapen-2-em-3-carboxylate dichloride (intramolecular salt)

a) 4-Nitrobenzyl (1S,5R,6S)-2-[7-(2-bromoethyl)-thioimidazo[5,1-b]thiazol-2-yl]-6-((1R)-1-hydroxyethyl)-1-methyl-1-carbapen-2-em-3-carboxylate The procedure of Example 1a) was repeated, except that 1.01 g of 4-nitrobenzyl (1R,3R,5R,6S)-6-((1R)-1- hydroxyethyl)-1-methyl-2-oxo-1-carbapenam-3-carboxylate and 1.62 g of 7-(2-bromoethyl)thio-2-(tri-n-butylstannyl)imidazo[5,1-b]thiazole were used as the starting compounds. Thus, 780 mg of 4-nitrobenzyl (1S,5R,6S)-2-[7-(2-bromoethyl)thioimidazo[5,1-b]thiazol-2-yl]-6-((1R)-1-hydroxyethyl)-1-methyl-1-carbapen-2-em-3-carboxylate was prepared.

NMR (CDCl$_3$) δ: 1.32 (3H, d, J=7.2 Hz), 1.40 (3H, d, J=6.3 Hz), 3.1–3.2 (2H, m), 3.38 (1H, dd, J$_1$=6.6 Hz, J$_2$=3.0 Hz), 3.4–3.6 (3H, m), 4.25–4.35 (1H, m), 4.38 (1H, dd, J$_1$=9.3 Hz, J$_2$=3.0 Hz), 5.28 (1H, d, J=13.5 Hz), 5.53 (1H, d, J=13.5 Hz), 7.68 (2H, d, J=(1H, s)

b) 4-Nitrobenzyl (1S,5R,6S)-2-[7-[2-(1-azonia-4-azabicyclo[2,2,2]oct-1-yl)ethyl]thioimidazo[5,1-b]thiazol-2-yl]-6-((1R)-1-hydroxyethyl)-1-methyl-1-carbapen-2-em-3-carboxylate bromide 4-Nitrobenzyl (1S,5R,6S)-2-[7-(2-bromoethyl)thioimidazo[5,1-b]thiazol-2-yl]-6-((1R)-1-hydroxyethyl)-1-methyl-1-carbapen-2-em-3-carboxylate (177 mg) was dissolved in 5 ml of acetonitrile. 1,4-Diazabicyclo[2,2,2]octane (43 mg) was added to the solution. The mixture was stirred at 50° C. for 12 hr. The reaction solution was concentrated. The residue was purified by column chromatography on Sephadex LH-20 (chloroform:methanol=1:1) to prepare 184 mg of 4-nitrobenzyl (1S,5R,6S)-2-[7-[2-(1-azonia-4-azabicyclo[2,2,2]oct-1-yl)ethyl]thioimidazo[5,1-b]thiazol-2-yl]-6-((1R)-1-hydroxyethyl)-1-methyl-1-carbapen-2-em-3-carboxylate bromide.

NMR (CD$_3$OD) δ: 1.25–1.35 (6H, m), 3.1–3.2 (8H, m), 3.25–3.4 (6H, m), 3.4–3.5 (3H, m), 3.6–3.7 (1H, m), 4.1–4.2 (1H, m), 4.36 (1H, dd, J$_1$=9.6 Hz, J$_2$=2.7 Hz), 5.35 (1H, d, J=13.2 Hz), 5.52 (1H, d, J=13.2 Hz), 7.73 (2H, d, J=8.7 Hz), 8.22 (2H, d, J=8.7 Hz), 8.27 (1H, s), 8.35 (1H, s)

c) (1S,5R,6S)-6-((1R)-1-Hydroxyethyl)-1-methyl-2-[6-methyl-7-[2-(4-methyl-1,4-diazoniabicyclo[2,2,2]oct-1-yl)ethyl]thioimidazo[5,1-b]thiazolium-2-yl]-1-carbapen-2-em-3-carboxylate dichloride intramolecular salt)

A solution of 4-nitrobenzyl (1S,5R,6S)-2-[7-[2-(1-azonia-4-azabicyclo[2,2,2]oct-1-yl)ethyl]thioimidazo-[5,1-b]thiazol-2-yl]-6-((1R)-1-hydroxyethyl)-1-methyl-1-carbapen-2-em-3-carboxylate bromide (60.5 mg) in 2 ml of dichloromethane and 0.5 ml of DMF was cooled in ice. Methyl trifluoromethanesulfonate (0.034 ml) was added to the cooled solution. The mixture was stirred at that temperature for 2 hr and then at room temperature for 5 hr. The solvent was removed by distillation under the reduced pressure. The residue was washed with 2 ml of diethyl ether twice. The residue was purified by column chromatography on Sephadex LH-20 (chloroform:methanol=1:1). The procedure of Example 50b) was then repeated, except that this product was used as the starting compound. Thus, 9.8 mg of the title compound was prepared.

NMR (D$_2$O) δ (HOD=4.65 ppm): 1.13 (3H, d, J=7.3 Hz), 1.17 (3H, d, J=6.4 Hz), 3.15–3.3 (5H, m), 3.42 (1H, dd, J$_1$=6.0 Hz, J$_2$=2.8 Hz), 3.45–3.6 (1H, m), 3.7–3.8 (2H, m), 3.90 (12H, s), 3.94 (3H, 8), 4.1–4.2 (1H, m), 4.21 (1H, dd, J$_1$=9.2 Hz, J$_2$=2.8 Hz), 8.04 (1H, s), 9.25 (1H, s)

Example 123
(1S,5R,6S)-6-((1R)-1-Hydroxyethyl)-1-methyl-2-[7-methylthio-6-(thiophene-2-yl)methylimidazo[5,1-b]thiazolium-2-yl]-1-carbapen-2-em-3-carboxylate (intramolecular salt)

a) 4-Nitrobenzyl (1S,5R,6S)-6-((1R)-1-hydroxyethyl)-1-methyl-2-[7-methylthio-6-(thiophene-2-yl)-methylimidazo[5,1-b]thiazolium-2-yl]-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (103 mg) was dissolved in 3 ml of acetonitrile. 2-Thiophenemethyl chloride (265 mg) and 300 mg of sodium iodide were added to the solution. The mixture was stirred at room temperature for 16 hr. The insolubles were removed by filtration. The solvent was then removed by distillation under the reduced pressure. The residue was purified by column chromatography on Sephadex LH-20 (chloroform:methanol=1:1) to prepare 76 mg of 4-nitrobenzyl (1S,5R,6S)-6-((1R)-1-hydroxyethyl)-1-methyl-2-[7-methylthio-6-(thiophene-2-yl)methylimidazo [5,1-b]thiazolium-2-yl]-1-carbapen-2-em-3-carboxylate iodide.

NMR (DMSO-d$_6$) δ: 1.18 (3H, d, J=60 Hz), 1.23 (3H, d, J=7.1 Hz), 2.32 (3H, s), 3.50 (1H, dd, J$_1$=5.6 Hz, J$_2$=3.2 Hz), 3.70–3.83 (1H, m), 4.0–4.10 (1H, m), 4.40 (1H, dd, J$_1$=9.9 Hz, J$_2$=3.2 Hz), 5.21 (2H, s), 5.42 (1H, d, J=13.7 Hz), 5.55 (1H, d, J=13.7 Hz), 7.08 (1H, dd, J$_1$=5.2 Hz, J$_2$=3.3 Hz), 7.35 (1H, d, J=3.3 Hz), 7.64 (1H, d, J=5.2 Hz), 7.75 (2H, d, J=8.8 Hz), 8.24 (2H, d, J=8.8 Hz), 8.86 (1H, s), 10.0 (1H, s)

b) (1S,5R,6S)-6-((1R)-1-Hydroxyethyl)-1-methyl-2-[7-methylthio-6-(thiophene-2-yl)methylimidazo[5,1-b]thiazolium-2-yl]-1-carbapen-2-em-3-carboxylate (intramolecular salt)

4-Nitrobenzyl (1S,5R,6S)-6-((1R)-1-hydroxyethyl)-1-methyl-2-[7-methylthio-6-(thiophene-2-yl)methylimidazo-[5,1-b]thiazolium-2-yl]-1-carbapen-2-em-3-carboxylate iodide (52 mg) was dissolved in 3 ml of THF and 3 ml of a 1/15 M sodium phosphate buffer (pH 6.6). 10%Pd—C (52 mg) was added to the solution. The air in the reaction vessel was replaced by hydrogen, and the contents of the reaction vessel were stirred at room temperature for 3 hr. The catalyst was removed by filtration on Celite, and was washed with water. The filtrate was washed with ethyl acetate, and was then concentrated under the reduced pressure until the volume of the filtrate was brought to about 2 ml. The residue was purified by column chromatography on Cosmosil 40C$_{18}$-PREP (a 20% aqueous methanol solution) to prepare 12 mg of the title compound.

NMR (D$_2$O) δ (HOD=4.80 ppm): 1.21 (3H, d, J=7.4 Hz), 1.28 (3H, d, J=6.6 Hz), 2.25 (3H, s), 3.53 (1H, dd, J$_1$=6.3 Hz, J$_2$=3.0 Hz), 3.58–3.64 (1H, m), 4.23–4.27 (1H, m), 4.32 (1H, dd, J$_1$=9.3 Hz, J$_2$=3.0 Hz), 5.81 (2H, s), 7.08 (1H, dd, J$_1$=5.2 Hz, J$_2$=3.3 Hz), 7.29 (1H, d, J=3.3 Hz), 7.50 (1H, d, J=5.2 Hz), 8.07 (1H, s)

Example 124
(1S,5R,6S)-6-((1R)-1-Hydroxyethyl)-2-[6-(4-methoxycarbonylbenzyl)-7-methylthioimidazo[5,1-b]-thiazolium-2-yl]-1-methyl-1-carbapen-2-em-3-carboxylate (intramolecular salt)

The procedure of Example 3a) was substantially repeated, except that 78 mg of 4-nitrobenzyl (1S,5R,6S)-6-((1R)-1-hydroxyethyl)-1-methyl-2-(7-methylthio-imidazo[5,1-b]thiazol-2-yl)-1-carbapen-2-em-3-carboxylate and 250 mg of 4-methoxybenzyl bromide were used as the starting compounds. Thus, 20 mg of a corresponding quaternary salt was prepared. The procedure of Example 3b) was substantially repeated, except that this compound was used as the starting compound. Thus, 3.9 mg of the title compound was prepared.

NMR (DMSO-d$_6$) δ: 1.09 (3H, d, J=7.3 Hz), 1.11 (3H, d, J=6.4 Hz), 2.05 (3H, s), 3.10 (1H, m), 3.42 (1H, m), 3.78 (3H, s), 3.87 (1H, m), 4.03 (1H, dd, J$_1$=9.5 Hz, J$_2$=2.7 Hz), 4.97 (1H, d, J=5.1 Hz), 5.69 (2H, s), 7.34 (2H, d, J=8.5 Hz), 7.91 (2H, d, J=8.5 Hz), 8.26 (1H, s), 9.60 (1H, s)

Example 125
(1S,5R,6S)-2-(6-Hydrazinocarbonymethyl-7-methylthioimidazo[5,1-b]thiazolium-2-yl)-6-((1R)-1- hydroxyethyl)-1-methyl-1-carbapen-2-em-3-carboxylate (intramolecular salt)

a) 4-Nitrobenzyl (1S,5R,6S)-2-[7-methylthio-6-[N-(4-nitrobenzyloxycarbonyl)hydrazinocarbonylmethyl]imidazo[5,1-b]thiazolium-2-yl]-6-((1R)-1-hydroxyethyl)-1-methyl-1-carbapen-2-em-3-carboxylate iodide 4-Nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate (103 mg) was dissolved in 3 ml of acetonitrile. N-(4-Nitrobenzyloxycarbonyl)-2-iodoacetylhydrazide (379 mg) was added to the solution. The mixture was stirred at 60° C. for 5 days. The insolubles were removed by filtration. The solvent was then removed by distillation under the reduced pressure. The residue was purified by column chromatography on Sephadex LH-20 (chloroform:methanol=1:1) to prepare 145 mg of 4-nitrobenzyl (1S,5R,6S)-2-[7-methylthio-6-[N-(4-nitrobenzyloxycarbonyl)hydrazinocarbonylmethyl]imidazo[5,1-b]thiazolium-2-yl]-6-((1R)-1-hydroxyethyl)-1-methyl-1-carbapen-2-em-3-carboxylate iodide.

NMR (DMSO-$d_6$) δ: 1.18 (3H, d, J=6.7 Hz), 1.25 (3H, d, J=7.1 Hz), 2.35 (3H, s), 3.51 (1H, dd, $J_1$=5.6 Hz, $J_2$=3.2 Hz), 3.70–3.81 (1H, m), 4.0–4.11 (1H, m), 4.41 (1H, dd, $J_1$=9.9 Hz, $J_2$=3.2 Hz), 5.26 (2H, s), 5.19 (1H, d, J=4.9 Hz), 5.42 (1H, d, J=13.7 Hz), 5.55 (1H, d, J=13.7 Hz), 7.61 (2H, d, J=8.8 Hz), 7.75 (2H, d, J=8.5 Hz), 8.24 (4H, d, J=8.8 Hz), 8.75 (1H, s), 9.71 (1H, s), 9.78 (1H, s), 10.49 (1H, s)

b) (1S,5R,6S)-2-(6-Hydrazinocarbonylmethyl-7-methylthioimidazo[5,1-b]thiazolium-2-yl)-6-((1R)-1-hydroxyethyl)-1-methyl-1-carbapen-2-em-3carboxylate (intramolecular salt)

4-Nitrobenzyl (1S,5R,6S)-2-[7-methylthio-6-[N-(4-nitrobenzyloxycarbonyl)hydrazinocarbonylmethyl]imidazo[5, 1-b]thiazolium-2-yl]-6-((1R)-1-hydroxyethyl)-1-methyl-1-carbapen-2-em-3-carboxylate iodide (120 mg) was dissolved in 5 ml of THF and 5 ml of a 1/15 M sodium phosphate buffer (pH 6.6). 10%Pd—C (120 mg) was added to the solution. The air in the reaction vessel was replaced by hydrogen, and the contents of the reaction vessel were stirred at room temperature for 2 hr. The catalyst was removed by filtration on Celite, and was washed with water. The filtrate was washed with ethyl acetate, and was then concentrated under the reduced pressure until the volume of the filtrate was brought to about 2 ml. The residue was purified by column chromatography on Cosmosil 40$C_{18}$-PREP (a 20% aqueous methanol solution) to prepare 8.8 mg of the title compound.

NMR ($D_2O$) δ (HOD=4.80 ppm): 1.25 (3H, d, J=7.1 Hz), 1.30 (3H, d, J=6.3 Hz), 2.31 (3H, s), 3.57 (1H, dd, $J_1$=6.0. Hz, $J_2$=2.7 Hz), 3.60–3.68 (1H, m), 4.24–4.29 (1H, m), 4.36 (1H, dd, $J_1$=9.3 Hz, $J_2$=2.7 Hz), 5.31 (2H, s), 8.18 (1H, s)

Example 126

(1S,5R,6S)-2-[6-(3-Aminobenzyl)-7-methylthioimidazo[5,1-b]thiazolium-2-yl]-6-((1R)-1-hydroxyethyl)-1-methyl-1-carbapen-2-em-3-carboxylate (intramolecular salt) hydrobromide The procedure of Example 3a) was substantially repeated, except that 78 mg of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate and 421 mg of (4-nitrobenzyl)oxycarbonylaminobenzyl bromide were used as the starting compounds. Thus, 105 mg of a corresponding quaternary salt was prepared. The procedure of Example 3b) was substantially repeated, except that this quaternary salt was used as the starting compound. Thus, 12.7 mg of the title compound was prepared.

NMR (DMSO-$d_6$) δ: 1.09 (3H, d, J=7.4 Hz), 1.11 (3H, d, J=6.5 Hz), 2.12 (3H, s), 3.10 (1H, m), 3.34 (1H, m), 3.88 (1H, m), 4.03 (1H, dd, $J_1$=9.5 Hz, $J_2$=2.8 Hz), 4.98 (1H, d, J=5.1 Hz), 5.14 (2H, br s), 5.44 (2H, s), 6.38–6.46 (3H, m), 6.97 (1H, t, J=8.2 Hz), 8.23 (1H, s), 9.56 (1H, s)

Example 127

(1S,5R,6S)-6-((1R)-1-Hydroxyethyl)-1methyl-2-[6-[2-(4-methylmorpholinium-4-yl)methylbenzyl]-7-methylthioimidazo[5,1-b]thiazolium-2-yl]-1-carbapen-2-em-3-carboxylate bromide (intramolecular salt)

a) 4-Nitrobenzyl (1S,5R,6S)-2-[6-(2-bromomethylbenzyl)-7-methylthioimidazo[5,1-b]thiazolium-2-yl]-6-carboxylate bromide The procedure of Example 3a) was substantially repeated, except that 0.287 g of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate and 0.434 g of o-xylene dibromide were used as the starting compounds. Thus, 0.163 g of 4-nitrobenzyl (1S,5R,6S)-2-[6-(2-bromomethylbenzyl)-7-methylthioimidazo[5,1-b]thiazolium-2-yl]-6-((1R)-1-hydroxyethyl)-1-methyl-1-carbapen-2-em-3-carboxylate bromide was prepared.

NMR ($CDCl_3$) δ: 1.36 (3H, d, J=6.1 Hz), 1.37 (3H, d, J=7.1 Hz), 2.17 (3H, s), 3.41 (1H, m), 3.89 (1H, m), 4.28 (1H, m), 4.50 (1H, dd, $J_1$=9.6 Hz, $J_2$=2.7 Hz), 4.68 (2H, s), 5.32 (1H, d, J=13.6 Hz), 5.54 (1H, d, J=13.6 Hz), 5.88 (2H, s), 7.35 (1H, m), 7.38–7.43 (3H, m), 7.68 (2H, d, J=9.0 Hz), 8.22 (2H, d, J=9.0 Hz), 9.41 (1H, s), 10.82 (1H, s)

b) (1S,5R,6S)-6-((1R)-1-Hydroxyethyl)-1-methyl-2-[6-[2-(4-methylmorpholininm-4-yl)methylbenzyl]-7-methylthioimidazo[5,1-b]thiazolium-2-yl]-1-carbapen-2-em-3-carboxylate bromide (intramolecular salt)

The procedure of Example 3a) was substantially repeated, except that 194 mg of 4-nitrobenzyl (1S,5R,6S)-2-[6-(2-bromomethylbenzyl)-7-methylthioimidazo[5,1-b]thiazolium-2-yl]-6-((1R)-1-hydroxyethyl)-1-methyl-1-carbapen-2-em-3-carboxylate bromide and 81 μl of 4-methylmorpholine were used as the starting compounds. Thus, 86 mg of a corresponding quaternary salt was prepared. The procedure of Example 3b) was substantially repeated, except that this quaternary salt was used as the starting compound. Thus, 29.7 mg of the title compound was prepared.

NMR (DMSO-$d_6$) δ: 1.11 (3H, d, J=6.8 Hz), 1.12 (3H, d, J=6.4 Hz), 1.89 (3H, s), 3.17 (3H, s), 3.21 (1H, m), 3.51–3.61 (5H, m), 3.92–3.96 (5H, m), 4.25 (1H, dd, $J_1$=9.5 Hz, $J_2$=2.8 Hz), 4.93 (1H, d, J=13.7 Hz), 5.01 (1H, d, J=5.1 Hz), 5.13 (1H, d, J=13.7 Hz), 5.83 (1H, d, J=15.6 Hz), 6.02 (1H, d, J=15.6 Hz), 7.09 (1H, m), 7.4.5–7.47 (2H, m), 7.60 (1H, m), 8.22 (1H, s), 9.61 (1H, s)

Example 128

(1S,5R,6S)-6-((1R)-1-Hydroxyethyl)-1-methyl-2-[6-[3-(4-methylmorpholinium-4-yl)methylbenzyl]-7-methylthioimidazo[5,1-b]thiazolium-2-yl]-1-carbapen-2-em-3-carboxylate bromide (intramolecular at a) 4-Nitrobenzyl (1S,5R,6S)-2-[6-(3-bromomethylbenzyl)-7-methylthioimidazo[5,1-b]thiazolium-2-yl]6-((1R)-1-hydroxyethyl)-1-methyl-1-carbapen-2-em-3-carboxylate bromide The procedure of Example 3a) was substantially repeated, except that 0.287 g of 4-nitrobenzyl (1S,5R,6S)-6-((1R)-1-hydroxyethyl)-1-methyl-2-(7-methyl-thioimidazo[5,1-b]thiazol-2-yl)-1-carbapen-2-em-3-carboxylate and 0.434 g of m-xylene dibromide were used as the starting compounds. Thus, 0.260 g of 4-nitrobenzyl (1S,5R,6S)-2-[6-(3-bromomethylbenzyl)-7-methylthioimidazo[5,1-b]thiazolium-2-yl]-6-((1R)-1-hydroxyethyl)-1-methyl-1-carbapen-2-em-3-carboxylate bromide was prepared.

NMR (CDCl$_3$) δ: 1.38 (3H, d, J=6.1 Hz), 1.40 (3H, d, J=7.3 Hz), 2.15 (3H, 8), 3.43 (1H, m), 3.92 (1H, m), 4.30 (1H, m), 4.48–4.51 (3H, m), 5.32 (1H, d, J=13.4 Hz), 5.53 (1H, d, J=13.4 Hz), 5.68 (2H, s), 7.41 (3H, m), 7.51 (1H, s), 7.68 (2H, d, J=8.8 Hz), 8.24 (2H, d, J=8.8 Hz), 9.46 (1H, s), 11.02 (1H, s)

b) (1S,5R,6S)-6-((1R)-1-Hydroxyethyl)-1-methyl-2-[6-[3-(4-methylmorpholinium-4-yl)methylbenzyl]-7-methylthioimidazo[5,1-b]thiazolium-2-yl]-1-carbapen-9-em-3-carboxylate bromide (intramolecular salt)

The procedure of Example 3a) was substantially repeated, except that 216 mg of 4-nitrobenzyl (1S,5R,6S)-2-[6-(3-bromomethylbenzyl)-7-methylthioimidazo[5,1-b]thiazolium-2-yl]-6-((1R)-1-hydroxyethyl)-1-methyl-1-carbapen-2-em-3-carboxylate bromide and 130 µl of 4-methylmorpholine were used as the starting compounds. Thus, 108 mg of a corresponding quaternary salt was prepared. The procedure of Example 3b) was substantially repeated, except that this quaternary salt was used as the starting compound. Thus, 50.9 mg of the title compound was prepared.

NMR (DMSO-d$_6$) δ: 1.08 (3H, d, J=7.8 Hz), 1.10 (3H, d, J=6.8 Hz), 2.13 (3H, s), 2.98 (3H, s), 3.10 (1H, m), 3.23–3.30 (2H, m), 3.38–3.42 (3H, m), 3.85–3.91 (5H, m), 4.04 (1H, dd, J$_1$=9.6 Hz, J$_2$=2.7 Hz), 4.62 (2H, s), 4.99 (1H, d, J=5.1 Hz), 5.63 (2H, s), 7.50 (4H, s), 8.29 (1H, s), 9.64 (1H, s)

Example 129

(1S,5R,6S)-6-((1R)-1-Hydroxyethyl)-1-methyl-2-[6-[4-(4-methylmorpholinium-4-yl)methylbenzyl]-7-methylthioimidazo[5,1-b]thiazolium-2-yl]-1-carbapen-2-em-3-carboxylate bromide (intramolecular salt a) 4-Nitrobenzyl (1S,5R,6S)-2-[6-(4-bromomethylbenzyl)-7-methylthioimidazo[5,1-b]thiazolium-2-yl]-6-((1R)-1-hydroxyethyl)-1-methyl-1-carbapen-2-em-3-carboxylate bromide The procedure of Example 3a) was substantially repeated, except that 0.287 g of 4-nitrobenzyl (1S,5R,6S)-6-((1R)-1-hydroxyethyl)-1-methyl-2-(7-methyl-thioimidazo[5,1-b]thiazol-2-yl)-1-carbapen-2-em-3-carboxylate and 0.434 g of p-xylene dibromide were used as the starting compounds. Thus, 0.242 g of 4-nitrobenzyl (1S,5R,6S)-2-[6-(4-bromomethylbenzyl)-7-methylthioimidazo[5,1-b]thiazolium-2-yl]-6-((1R)-1-hydroxyethyl)-1-methyl-1-carbapen-2-em-3-carboxylate bromide was prepared.

NMR (CDCl$_3$) δ: 1.38 (6H, d, J=6.1 Hz), 2.10 (3H, s), 3.45 (1H, m), 3.98 (1H, m), 4.27 (1H, m), 4.45 (2H, s), 4.53 (1H, dd, J$_1$=9.6 Hz, J$_2$=3.0 Hz), 5.52 (1H, d, J=13.6 Hz), 5.75 (1H, d, J=13.6 Hz), 5.80 (2H, s), 7.42 (2H, d, J=8.5 Hz), 7.48 (2H, d, J=8.5 Hz), 7.67 (2H, d, J=9.0 Hz), 8.23 (2H, d, J=9.0 Hz), 9.41 (1H, s), 10.93 (1H, s)

b) (1S,5R,6S)-6-((1R)-1-Hydroxyethyl)-1-methyl-2-[6-[4-(4-methylmorpholinium-4-yl)methylbenzyl]-7-methyl-thioimidazo[5,1-b]thiazolium-2-yl]-1-carbapen-2-em-3-carboxylate bromide (intramolecular salt)

The procedure of Example 3a) was substantially repeated, except that 216 mg of 4-nitrobenzyl (1S,5R,6S)-2-[6-(-4-bromomethylbenzyl)-7-methylthio-imidazo[5,1-b]thiazolium-2-yl]-6-((1R)-1-hydroxyethyl)-1-methyl-1-carbapen-2-em-3-carboxylate bromide and 122 µl of 4-methylmorpholine were used as the starting compounds. Thus, 113 mg of a corresponding quaternary salt was prepared. The procedure of Example 3b) was substantially repeated, except that this quaternary salt was used as the starting compound. Thus, 41.1 mg of the title compound was prepared.

NMR (DMSO-d$_3$) δ: 1.09 (3H, d, J=6.8 Hz), 1.10 (3H, d, J=6.1 Hz), 2.07 (3H, s), 2.97 (3H, s), 3.11 (1H, m), 3.23–3.30 (2H, m), 3.40–3.45 (3H, m), 3.84–3.93 (5H, m), 4.05 (1H, dd, J$_1$=9.0 Hz, J$_2$=2.4 Hz), 4.68 (2H, s), 5.00 (1H, d, J=5.1 Hz), 5.67 (2H, s), 7.44 (2H, d, J=8.3 Hz), 7.53 (2H, d, J=8.3 Hz), 8.30 (1H, s), 9.66 (1H, s)

Example 130

(1S,5R,6S)-6-((1R)-1-Hydroxyethyl)-1-methyl-2-[7-methylthio-6-[2-(pyridinium-1-yl)methyl-benzyl]imidazo[5,1-b]thiazolium-2-yl]-1-carbapen-2-em-3-carboxylate bromide (intramolecular salt)

The procedure of Example 3a) was substantially repeated, except that 194 mg of 4-nitrobenzyl (1S,5R,6S)-2-[6-(2-bromomethylbenzyl)-7-methylthioimidazo[5,1-b]thiazolium-2-yl]-6-((1R)-1-hydroxyethyl)-1-methyl-1-carbapen-2-em-3-carboxylate bromide and 81 µl of pyridine were used as the starting compounds. Thus, 78 mg of a corresponding quaternary salt was prepared. The procedure of Example 3b) was substantially repeated, except that this quaternary salt was used as the starting compound. Thus, 20.9 mg of the title compound was prepared.

NMR (DMSO-d$_6$) δ: 1.09 (3H, d, J=6.8 Hz), 1.10 (3H, d, J=6.1 Hz), 2.04 (3H, s), 3.14 (1H, m), 3.30 (1H, m), 3.89 (1H, m), 4.07 (1H, m), 4.99 (1H, d, J=5.1 Hz), 5.70 (2H, s), 6.07 (2H, s), 7.10 (1H, m), 7.26 (1H, m), 7.41–7.45 (2H, m), 8.14–8.20 (3H, m), 8.61 (1H, m), 9.07 (1H, m), 9.40 (1H, s)

Example 131

(1S,5R,6S)-6-((1R)-1-Hydroxyethyl)-1-methyl-2-[7-methylthio-6-[3-(pyridinium-1-yl)methyl-benzyl]imidazo[5,1-b]thiazolium-2-yl]-1-carbapen-2-em-3-carboxylate bromide (intramolecular salt)

The procedure of Example 3a) was substantially repeated, except that 216 mg of 4-nitrobenzyl (1S,5R,6S)-2-[6-(3-bromomethylbenzyl)-7-methylthio-imidazo[5,1-b]thiazolium-2-yl]-6-((1R)-1-hydroxyethyl)-1-methyl-1-carbapen-2-em-3-carboxylate bromide and 130 µl of pyridine were used as the starting compounds. Thus, 100 mg of a corresponding quaternary salt was prepared. The procedure of Example 3b) was substantially repeated, except that this quaternary salt was used as the starting compound. Thus, 26.0 mg of the title compound was prepared.

NMR (DMSO-d$_6$) δ: 1.09 (3H, d, J=7.0 Hz), 1.10 (3H, d, J=6.4 Hz), 1.98 (3H, s), 3.12 (1H, m), 3.41 (1H, m), 3.89 (1H, m), 4.06 (1H, dd, J$_1$=9.5 Hz, J$_2$=2.7 Hz), 4.99 (1H, d, J=5.1 Hz), 5.62 (2H, s), 5.79 (2H, s), 7.38 (1H, m), 7.41–7.45 (3H, m), 8.11–8.15 (2H, m), 8.28 (1H, s), 8.57 (1H, m), 9.11 (1H, d, J=5.6 Hz), 9.59 (1H, s)

Example 132

(1S,5R,6S)-6-((1R)-1-Hydroxyethyl)-1-methyl-2-[7-methylthio-6-[4-(pyridinium-1-yl)methyl-benzyl]imidazo[5,1-b]thiazolium-2yl]-1-carbapen-2-em-3-carboxylate bromide (intramolecular salt)

The procedure of Example 3a) was substantially repeated, except that 216 mg of 4-nitrobenzyl (1S,5R,6S)-2-[6-(4-bromomethylbenzyl)-7-methylthio-imidazo[5,1-b]thiazolium-2-yl]-6-((1R)-1-hydroxyethyl)-1-methyl-1-carbapen-2-em-3-carboxylate bromide and 122 µl of pyridine were used as the starting compounds. Thus, 112 mg of a corresponding quaternary salt was prepared. The procedure of Example 3b) was substantially repeated, except that this quaternary salt was used as the starting compound. Thus, 39.5 mg of the title compound was prepared.

NMR (DMSO-d$_6$) δ: 1.08 (3H, d, J=7.1 Hz), 1.10 (3H, d, J=6.1 Hz), 2.06 (3H, s), 3.09 (1H, m), 3.28 (1H, m), 3.89 (1H, m), 4.03 (1H, dd, J$_1$=9.5 Hz, J$_2$=2.9 Hz), 4.98 (1H, d, J=5.1 Hz), 5.60 (2H, s), 5.79 (2H, s), 7.37 (2H, d, J=8.3 Hz), 7.59 (2H, d, J=8.3 Hz), 8.09–8.13 (2H, m), 8.25 (1H, s), 8.56 (1H, m), 9.12 (2H, d, J=5.4 Hz), 9.59 (1H, s)

Example 133
(1S,5R,6S)-2-[6-Carbamoylmethyl-7-(3guanidinopropyl) thioimidazo[5,1-b]thiazolium-2-yl]-6-((1R)-1-hydroxyethyl)-1-methyl-1-carbapen-2-em-3-carboxylate (intramolecular salt) hydrochloride a) 4-Nitrobenzyl (1S,5R,6S)-2-[7-[3-N,N'-bis(4-nitrobenzyloxycarbonyl)guanidinopropyl]thioimidazo[5,1-b]thiazol-2-yl]-6-((1R)-1-hydroxyethyl)-1-methyl-1-carbapen-2-em-1-carboxylate The procedure of Example 1a) was repeated, except that 297 mg of 4-nitrobenzyl (1S,5R,6S)-6-((1R)-1-hydroxyethyl)-1-methyl-2-oxo-1-carbapenam-3-carboxylate and 777 mg of 7-[3-N,N'-bis(4-nitrobenzyloxycarbonyl)-guanidinopropyl]thio-2-(tri-n-butylstannyl)imidazo[5,1-b]thiazole were used as the starting compounds. Thus, 436 mg of 4-nitrobenzyl (1S,5R,6S)-2-[7-[3-N,N'-bis(4-nitrobenzyloxycarbonyl) guanidinopropyl]thioimidazo[5,1-b]thiazol-2-yl]-6-((1R)-1-hydroxyethyl)-1-methyl-1-carbapen-2-em-3-carboxylate was prepared.

NMR (CDCl$_3$) δ: 1.30 (3H, d, J=7.2 Hz), 1.40 (3H, d, J=6.3 Hz), 1.85–1.95 (2H, m), 2.8–2.9 (2H, m), 3.36 (1H, dd, J$_1$=6.3 Hz, J$_2$=2.7 Hz), 3.4–3.5 (1H, m), 3.6–3.7 (2H, m), 4.25–4.4 (2H, m), 5.22 (2H, s), 5.26 (2H, s), 5.27 (1H, d, J=13.8 Hz), 5.52 (1H, d, J=13.8 Hz), 7.5–7.6 (4H, m), 7.68 (2H, d, J=8.4 Hz), 8.01 (1H, s), 8.15–8.3 (7H, m), 8.4–8.5 (1H, m), 11.78 (1H, s)

b) (1S,5R,6S)-2-[6-Carbamoylmethyl-7-(3-guanidinopropyl)thioimidazo[51-b]thiazolium-2-yl]-6-((1R)-1-hydroxyethyl)-1-methyl-1-carbapen-2-em-3-carboxylate (intramolecular salt) hydrochloride The procedures of Examples 3a) and 50b) were repeated, except that 144 mg of 4-nitrobenzyl (1S,5R,6S)-2-[7-[3-N,N'-bis(4-nitrobenzyloxycarbonyl)guanidinopropyl] thioimidazo[5,1-b]thiazol-2-yl]-6-((1R)-1-hydroxyethyl)-1-methyl-1-carbapen-2-em-3-carboxylate was used as the starting compound. Thus, 22.2 mg of the title compound was prepared.

NMR (D$_2$O) δ (HOD=4.80 ppm): 1.29 (3H, d, J=6.9 Hz), 1.33 (3H, d, J=6.6 Hz), 1.8–1.95 (2H, m), 2.85–2.95 (2H, m), 3.3–3.4 (2H, m), 3.59 (1H, dd, J$_1$=6.3 Hz, J$_2$=3.0 Hz), 3.6–3.75 (1H, m), 4.25–4.35 (1H, m), 4.37 (1H, dd, J$_1$=9.6 Hz, J$_2$=3.0 Hz), 5.35 (2H, s), 8.22 (1H, s)

Example 134
(1S,5R,6S)-6-((1R)-1-Hydroxyethyl)-2-[6-(3-isothioureidomethylbenzyl)-7-methylthioimidazo[5,1-b]thiazolium-2-yl]-1-methyl-1-carbapen-2-em-3-carboxylate (intramolecular salt) hydrochloride a) 4-Nitrobenzyl (1S,5R,6S)-6-((1R)-1-hydroxyethyl)-2-[6-(3-isothioureidomethylbenzyl)-7-methylthio-imidazo[5,1-b]thiazolium-2-yl]-1-methyl-1-carbapen-2-em-3-carboxylate bromide hydrobromide 4-Nitrobenzyl (1S,5R,6S)-2-[6-(3-bromomethyl-benzyl)-7-methylthioimidazo[5,1-b]thiazolium-2-yl]-6-((1R)-1-hydroxyethyl)-1-methyl-1-carbapen-2-em-3-carboxylate bromide (80 mg) was dissolved in 2 ml of acetonitrile and 0.5 ml of methanol. Thiourea (12 mg) was added to the solution. The mixture was stirred at room temperature for one day. The reaction solution was added to 30 ml of diethyl ether. The resultant precipitate was collected by filtration to prepare 75 mg of 4-nitrobenzyl (1S,5R,6S)-6-((1R)-1-hydroxyethyl)-2-[6-(3-isothioureidomethylbenzyl)-7-methylthioimidazo-[5,1-b]thiazolium-2-yl]-1-methyl-1-carbapen-2-em-3-carboxylate bromide hydrobromide as a crude product.

b) (1S,5R,6S)-6-((1R)-1-Hydroxyethyl)-2-[6-(3-isothioureidomethylbenzyl)-7-methylthioimidazo[5,1-b] thiazolium-2-yl]-1-methyl-1-carbapen-2-em-3-carboxylate (intramolecular salt) hydrochloride The procedure of Example 50b) was repeated, except that 72 mg of 4-nitrobenzyl (1S,5R,6S)-6-((1R)-1-hydroxyethyl)-2-[6-(3-isothioureidomethylbenzyl)-7-methylthioimidazo[5,1-b]thiazolium-2-yl]-1-methyl-1-carbapen-2-em-3-carboxylate bromide hydrobromide was used as the starting compound. Thus, 26 mg of the title compound was prepared.

NMR (D$_2$O) δ (HOD=4.65 ppm): 1.11 (3H, d, J=7.3 Hz), 1.17 (3H, d, J=6.3 Hz), 1.89 (3H, s), 3.43 (1H, dd, J$_1$=5.9 Hz, J$_2$=2.7 Hz), 3.52 (1H, m), 4.15 (1H, m), 4.23 (1H, dd, J$_1$=9.5 Hz, J$_2$=2.7 Hz), 4.28 (2H, s), 5.51 (2H, s), 7.24–7.36 (4H, m), 7.99 (1H, s)

Example 135
(1S,5R,6S)-6-((1R)-1-Hydroxyethyl)-1-methyl-2-[6-[3-(4-methyl-1,4-diazoniabicyclo(2,2,2)oct-1-yl)methylbenzyl]-7-methylthioimidazo[5,1-b]thiazolium-2yl]-1-carbapen-2-em-3-carboxylate dichloride (intramolecular salt)

a) 4-Nitrobenzyl (1S,5R,6S)-2-[6-[3-(4-aza-1-azoniabicyclo[2,2,2]oct-1-yl)methylbenzyl]-7-methylthioimidazo[5,1-b]thiazolium-2-yl]-6-((1R)-1-hydroxyethyl)-1-methyl-1-carbapen-2-em-3-carboxylate dibromide 4-Nitrobenzyl (1S,5R,6S)-2-[6-(3-bromomethyl-benzyl)-7-methylthioimidazo[5,1-b]thiazolium-2-yl]-6-((1R)-1-hydroxyethyl)-1-methyl-1-carbapen-2-em-3-carboxylate bromide (89 mg) was dissolved in 2 ml of acetonitrile and 1 ml of DMF. Diazabicyclo[2,2,2]octane (16 mg) was added to the solution. The mixture was stirred at room temperature for 3 hr. The reaction solution was added dropwise to 40 ml of diethyl ether. The resultant precipitate was collected by filtration to prepare 96 mg of 4-nitrobenzyl (1S,5R,6S)-2-[6-[3-(4-aza-1-azoniabicyclo[2,2,2]oct-1-yl)methylbenzyl]-7-methylthioimidazo[5,1-b]thiazolium-2-yl]-6-((1R)-1-hydroxyethyl)-1-methyl-1-carbapen-2-em-3-carboxylate dibromide as a crude product.

b) 4-Nitrobenzyl (1S,5R,6S)-6-((1R)-1-hydroxyethyl)-1-methyl-2-[6-[3-(4-methyl-1,4-diazoniabicyclo-[2,2,2]oct-1-yl)methylbenzyl]-7-methylthioimidazo[5,1-b]thiazolium-2-yl]-1-carbapen-2em-3-carboxylate iodide dibromide 4-Nitrobenzyl (1S,5R,6S)-2-[6-[3-(4-aza-1-azoniabicyclo [2,2,2]oct-1-yl)methylbenzyl]-7-methylthioimidazo[5,1-b] thiazolium-2-yl]-6-((1R)-1-hydroxyethyl)-1-methyl-1-carbapen-2-em-3-carboxylate dibromide (94 mg) was dissolved in 1 ml of acetonitrile and 1 ml of DMF. Methyl iodide (0.1 ml) was added to the solution. The mixture was stirred at room temperature for one day. The reaction solution was added dropwise to 30 ml of diethyl ether. The resultant precipitate was collected by filtration to prepare 110 mg of 4-nitrobenzyl (1S,5R,6S)-6-((1R)-1-hydroxyethyl)-1-methyl-2-[6-[3-(4-methyl-1,4-diazoniabicyclo[2,2,2]oct-1-yl)methylbenzyl]-7-methylthioimidazo[5,1-b]thiazolium-2-yl]-1-carbapen-2-em-3-carboxylate iodide dibromide as a crude product.

c) (1S,5R,6S)-6-((1R)-1-Hydroxyethyl)-1-methyl-2-[6-[3-(4-methyl-1,4-diazoniabicyclo[2,2,2]oct-1-yl) methylbenzyl]-7-methylthioimidazo[5,1-b]thiazolium-2-yl]-1-carbapen-2-em-3-carboxylate dichloride (intramolecular salt)

The procedure of Example 50b) was repeated, except that 110 mg of 4-nitrobenzyl (1S,5R,6S)-6-((1R)-1-hydroxyethyl)-1-methyl-2-[6-[3-(4-methyl-1,4-diazoniabicyclo[2,2,2]oct-1-yl)methylbenzyl]-7-methylthioimidazo-[5,1-b]thiazolium-2-yl]-1-carbapen-2-em-3-carboxylate iodide dibromide was used as the starting compound. Thus, 24 mg of the title compound was prepared.

NMR (D$_2$O) δ (HOD=4.65 ppm): 1.10 (3H, d, J=7.3 Hz), 1.16 (3H, d, J=6.3 Hz), 2.01 (3H, s), 3.22 (3H, s), 3.40–3.57 (2H, m), 3.88 (12H, br s), 4.17 (1H, m), 4.22 (1H, m), 4.70 (2H, s), 5.58 (2H, s), 7.42–7.55 (4H, m), 7.97 (1H, s)

Example 136

(1S,5R,6S)-2-[6-(2-Diethylcarbamoylbenzyl)-7-methylthioimidazo[5,1-b]thiazolium-2-yl]-6-((1R)-1hydroxyethyl-)-1-methyl-1-carbapen-2-em-3-carboxylate (intramolecular salt)

The procedure of Example 3a) was substantially repeated, except that 78 mg of 4-nitrobenzyl (1S,5R,6S)-6-((1R)-1-hydroxyethyl)-1-methyl-2-(7-methylthioimidazo-[5,1-b]thiazol-2-yl)-1-carbapen-2-em-3-carboxylate and 278 mg of 2-diethylcarbamoylbenzyl bromide were used as the starting compounds. Thus, 68 mg of a corresponding quaternary salt was prepared. The procedure of Example 3b) was substantially repeated, except that this quaternary salt was used as the starting compound. Thus, 31.7 mg of the title compound was prepared.

NMR (DMSO-d$_6$) δ: 0.98 (3H, t, J=7.1 Hz), 1.05–1.11 (9H, m), 2.15 (3H, s), 3.04–3.09 (3H, m), 3.34–3.40 (3H, m), 3.87 (1H, m), 4.03 (1H, dd, J$_1$=9.5 Hz, J$_2$=2.7 Hz), 4.98 (1H, d, J=5.1 Hz), 5.47 (2H, s), 7.16 (1H, m), 7.30–7.39 (3H, m), 8.24 (1H, s), 9.44 (1H, s)

Example 137

(1S,5R,6S)-2-[6-(4-Diethylcarbamoylbenzyl)-7-methylthioimidazo[5,1-b]thiazolium-2-yl]-6-((1R)-1-hydroxyethyl)-1-methyl-1-carbapen-2-em-3-carboxylate (intramolecular salt)

The procedure of Example 3a) was substantially repeated, except that 78 mg of 4-nitrobenzyl (1S,5R,6S)-6-((1R)-1-hydroxyethyl)-1-methyl-2-(7-methylthio-imidazo[5,1-b]thiazol-2-yl)-1-carbapen-2-em-3-carboxylate and 215 mg of 4-diethylcarbamoylbenzyl bromide were used as the starting compounds. Thus, 27 mg of a corresponding quaternary salt was prepared. The procedure of Example 3b) was substantially repeated, except that this quartenary salt was used as the starting compound. Thus, 7.5 mg of the title compound was prepared.

NMR (DMSO-d$_6$) δ: 0.94–1.11 (12H, m), 2.06 (3H, s), 3.08–3.1 (3H, m), 3.38–3.42 (3H, m), 3.88 (1H, m), 4.03 (1H, dd, J$_1$=9.4 Hz, J$_2$=2.7 Hz), 4.97 (1H, d, J=5.4 Hz), 5.63 (2H, s), 7.31 (2H, d, J=8.3 Hz), 7.36 (2H, d, J=8.3 Hz), 8.24 (1H, s), 9.58 (1H, s)

Example 138

(1S,5R,6S)-2-[7-Acetyl-6-(3-aminopropyl)imidazo[5,1-b]thiazolium-2-yl]-6-((1R)-1-hydroxyethyl)-1-methyl-1-carbapen-2-em-3-carboxylate (intramolecular salt) hydrochloride The procedures of Examples 48a) and 50b) were repeated, except that 153 mg of 4-nitrobenzyl (1S,5R,6S)-2-(7-acetylimidazo[5,1-b]thiazol-2-yl)-6-((1R)-1-hydroxyethyl)-1-methyl-1-carbapen-2-em-3-carboxylate and 169 mg of 3-azidopropanol were used as the starting compounds. Thus, 8.9 mg of the title compound was prepared.

NMR (D$_2$O) δ (HOD=4.80 ppm): 1.28 (3H, d, J=7.2 Hz), 1.31 (3H, d, J=6.3 Hz), 2.2–2.35 (2H, m), 2.65 (3H, s), 3.1–3.2 (2H, m), 3.58 (1H, dd, J$_1$=6.3 Hz, J$_2$=3.0 Hz), 3.6–3.7 (1H, m), 4.2–4.4 (2H, m), 8.34 (1H, s)

Example 139

(1S,5R,6S)-2-(7-Benzylthio-6-carbamoyl-methylimidazo[5,1-b]thiazolium-2-yl)-6-((1R)-1-hydroxyethyl)-1-methyl-1-carbapen-2-em-3-carboxylate (intramolecular salt)

a) 4-Nitrobenzyl (1S,5R,6S)-2-(7-benzylthioimidazo[5,1-b]thiazol-2-yl)-6-((1R)-1-hydroxyethyl)-1-methyl-1-carbapen-2-em-3-carboxylate The procedure of Example 1a) was repeated, except that 424 mg of 4-nitrobenzyl (1S,5R,6S)-6-((1R)-1-hydroxyethyl)-1-methyl-2-oxo-1-carbapenam-3-carboxylate and 658 mg of 7-benzylthio-2-(tri-n-butylstannyl)imidazo[5,1-b]thiazole were used as the starting compounds. Thus, 459 mg of 4-nitrobenzyl (1S,5R,6S)-2-(7-benzylthioimidazo[5,1-b]thiazol-2-yl)-6-((1R)-1-hydroxyethyl)-1-methyl-1-carbapen-2-em-3-carboxylate was prepared.

NMR (CDCl$_3$) δ: 1.24 (3H, d, J=7.5 Hz), 1.40 (3H, d, J=6.3 Hz), 3.3–3.4 (2H, m), 3.99 (2H, s), 4.25–4.4 (2H, m), 5.26 (1H, d, J=13.8 Hz), 5.51 (1H, d, J=13.8 Hz), 7.1–7.25 (5H, m), 7.67 (2H, d, J=8.4 Hz), 8.01 (1H, s), 8.24 (2H, d, J=8.4 Hz), 8.30 (1H, s)

b) (1S,5R,6S)-2-(7-Benzylthio-6-carbamoylmethylimidazo[5,1-b]thiazolium-2-yl)-6-((1R)-1-hydroxyethyl)-1-methyl-1-carbapen-2-em-3-carboxylate (intramolecular salt)

The procedures of Examples 3a) and 3b) were repeated, except that 103 mg of 4-nitrobenzyl (1S,5R,6S)-2-(7-benzylthioimidazo[5,1-b]thiazol-2-yl)-6-((1R)-1-hydroxyethyl)-1-methyl-1-carbapen-2-em-3-carboxylate was used as the starting compound. Thus, 29.1 mg of the title compound was prepared.

NMR (D$_2$O) δ (HOD=4.80 ppm): 1.22 (3H, d, J=6.9 Hz), 1.30 (3H, d, J=6.3 Hz), 3.5–3.6 (2H, m), 3.94 (2H, s), 4.2–4.35 (2H, m), 5.11 (2H, s), 7.0–7.1 (2H, m), 7.2–7.35 (3H, m), 8.05 (1H, s)

Example 140

(1S,5R,6S)-2-[6-((2R)-3-Amino-2-methoxypropyl)-7-methylthioimidazo[5,1-b]thiazolium-2-yl]-6((1R)-1-hydroxyethyl)-1-methyl-1-carbapen-2-em-3-carboxylate (intramolecular salt) hydrochloride The procedures of Examples 50a) and 50b) were repeated, except that 49 mg of (2R)-3-azido-2-methoxypropanol and 161 mg of 4-nitrobenzyl (1S,5R,6S)-6-((1R)-1-hydroxyethyl)-1-methyl-2-(7-methylthioimidazo-[5,1-b]thiazol-2-yl)-1-carbapen-2-em-3-carboxylate were used as the starting compounds. Thus, 45 mg of the title compound was prepared.

NMR (D$_2$O) δ (HOD=4.65 ppm): 1.13 (3H, d, J=7.0 Hz), 1.18 (3H, d, J=6.4 Hz), 2.29 (3H, s), 2.82 (1H, dd, J$_1$=13.4 Hz, J$_2$=9.0 Hz), 3.25 (1H, dd, J$_1$=13.4 Hz, J$_2$=3.2 Hz), 3.31 (3H, s), 3.44 (1H, dd, J$_1$=6.0 Hz, J$_2$=2.7 Hz), 3.53 (1H, m), 3.93 (1H, m), 4.14 (1H, m), 4.22 (1H, dd, J$_1$=9.5 Hz, J$_2$=2.9 Hz), 4.50–4.65 (2H, m), 8.01 (1H, s), 9.25 (1H, s)

Example 141

(1S,5R,6S)-6-((1R)-1-Hydroxyethyl-2-[6-(3-isothioureidopropyl)-7-methylthioimidazo[5,1-b]thiazolium-2-yl]-1-methyl-1-carbapen-2-em-3-carboxylate (intramolecular salt) hydrochloride a) 4-Nitrobenzyl (1S,5R,6S)-2-[6-(3-iodopropyl)-7-methylthioimidazo[5,1-b]thiazolium-2-yl]-6-((1R)-1-hydroxyethyl)-1-methyl-1-carbapen-2-em-3-carboxylate trifluoromethanesulfonate The procedure of Example 50a) was repeated, except that 256 mg of 3-iodopropanol and 609 mg of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate were used as the starting compounds. Thus, 918 mg of 4-nitrobenzyl (1S,5R,6S)-2-[6-(3-iodopropyl)-7-methylthioimidazo[5,1-b]thiazolium-2-yl]-6-((1R)-1-hydroxyethyl)-1-methyl-1-carbapen-2-em-3-carboxylate trifluoromethanesulfonate was prepared.

NMR (acetone-d$_6$) δ: 1.28 (3H, d, J=6.4 Hz), 1.35 (3H, d, J=7.3 Hz), 2.55–2.63 (5H, m), 3.40 (2H, m), 3.54 (1H, dd, $J_1$=6.0 Hz, $J_2$=3.1 Hz), 3.87 (1H, m), 4.21 (1H, m), 4.34 (1H, d, J=5.1 Hz), 4.51 (1H, dd, $J_1$=10.0 Hz, $J_2$=3.2 Hz), 4.76 (2H, m), 5.44 (1H, d, J=13.9 Hz), 5.62 (1H, d, J=13.9 Hz), 7.84 (2H, d, J=8.8 Hz), 8.25 (2H, d, J=8.8 Hz), 8.74 (1H, s), 9.81 (1H, s)

b) (1S,5R,6S)-6-((1R)-1-Hydroxyethyl)-2-[6-(3-isothioureidopropyl)-7-methylthioimidazo[5,1-b]thiazolium-2-yl]-1-methyl-1-carbapen-2-em-3-carboxylate (intramolecular salt) hydrochloride The procedures of Examples 134a) and 134b) were repeated, except that 85 mg of 4-nitrobenzyl (1S,5R,6S)-2-[6-(3-iodopropyl)-7-methylthioimidazo[5,1-b]-thiazolium-2-yl]-6-((1R)-1-hydroxyethyl)-1-methyl-1-carbapen-2-em-3-carboxylate trifluoromethanesulfonate and 10 mg of thiourea were used as the starting compounds. Thus, 15 mg of the title compound was prepared.

NMR ($D_2O$) δ (HOD=4.65 ppm): 1.12 (3H, d, J=7.3 Hz), 1.17 (3H, d, J=6.4 Hz), 2.21–2.31 (5H, m), 3.12 (2H, t, J=7.0 Hz), 3.40 (1H, dd, $J_1$=6.0 Hz, $J_2$=2.9 Hz), 3.51 (1H, m), 4.14 (1H, m), 4.22 (1H, dd, $J_1$=9.5 Hz, $J_2$=2.7 Hz), 4.47 (2H, t, J=7.0 Hz), 8.00 (1H, s), 9.24 (1H, s)

Example 142
(1S,5R,6S)-6-((1R)-1-Hydroxyethyl)-2-[6-(4-isothioureidomethylbenzyl)-7-methylthioimidazo[5,1-b]thiazolium-2-yl]-1-methyl-1-carbapen-2em-3-carboxylate (intramolecular salt) hydrochloride The procedures of Examples 134a) and 50b) were repeated, except that 73 mg of 4-nitrobenzyl (1S,5R,6S)-2-[6-(4-bromomethylbenzyl)-7-methylthioimidazo[5,1-b]thiazolium-2-yl]-6-((1R)-1-hydroxyethyl)-1-methyl-1-carbapen-2-em-3-carboxylate bromide and 9 mg of thiourea were used as the starting compounds. Thus, 20 mg of the title compound was prepared.

NMR ($D_2O$) δ (HOD=4.65 ppm): 1.12 (3H, d, J=7.3 Hz), 1.18 (3H, d, J=6.3 Hz), 1.89 (3H, s), 3.43 (1H, dd, $J_1$=6.1 Hz, $J_2$=2.7 Hz), 3.51 (1H, m), 4.14 (1H, m), 4.22 (1H, dd, $J_1$=9.5 Hz, $J_2$=2.9 Hz), 4.27 (2H, s), 5.52 (2H, s), 7.27 (2H, d, J=8.1 Hz), 7.38 (2H, d, J=8.1 Hz), 8.01 (1H, s)

Example 143
(1S,5R,6S)-6-(1R)-1-Hydroxyethyl)-1-methyl-2-[6-[4-(4-methyl-1,4-diazoniabicyclo[2,2,2]oct-1yl)methylbenzyl]-7-methylthioimidazo[5,1-b]thiazolium-2-yl]-1-carbapen-2-em-3-carboxylate dichloride (intramolecular salt)

The procedures of Examples 135a), 135b), and 50b) were repeated, except that 73 mg of 4-nitrobenzyl (1S,5R,6S)-2-[6-(4-bromomethylbenzyl)-7-methylthio-imidazo[5,1-b]thiazolium-2-yl]-6-((1R)-1-hydroxyethyl)-1-methyl-1-carbapen-2-em-3-carboxylate bromide, 12 mg of 1,4-diazabicyclo[2,2,2]octane, and 0.092 ml of methyl iodide were used as the starting compounds. Thus, 27 mg of the title compound was prepared.

NMR ($D_2O$) δ (HOD=4.65 ppm): 1.11 (3H, d, J=7.1 Hz), 1.17 (3H, d, J=6.3 Hz), 2.06 (3H, s), 3.22 (3H, s), 3.43 (1H, dd, $J_1$=5.8 Hz, $J_2$=2.7 Hz), 3.51 (1H, m), 3.87 (12H, br s), 4.13 (1H, m), 4.22 (1H, dd, $J_1$=9.5 Hz, $J_2$=2.7 Hz), 4.67 (2H, s), 5.61 (2H, s), 7.42 (2H, d, J=8.1 Hz), 7.48 (2H, d, J=8.1 Hz), 8.01 (1H, s)

Example 144
(1S,5R,6S)-2-[7-(3-Aminopropylthio)-6-benzylimidazo[5,1-b]thiazolium-2-yl]-6-((1R)-1-hydroxyethyl)-1-methyl-1-carbapen-2-em-3-carboxylate (intramolecular salt) hydrobromide The procedure of Example 3a) was substantially repeated, except that 80 mg of 4-nitrobenzyl (1S,5R,6S)-6-((1R)-1-hydroxyethyl)-1-methyl-2-[7-(3-azidopropylthio)imidazo[5,1-b]thiazol-2-yl]-1-carbapen-2-em-3-carboxylate and 120 μl of benzyl bromide were used as the starting compounds. Thus, 85 mg of a corresponding quaternary salt was prepared. The procedure of Example 3b) was substantially repeated, except that this quaternary salt was used as the starting compound. Thus, 23.0 mg of the title compound was prepared.

NMR (DMSO-$d_6$) δ: 1.07 (3H, d, J=7.1 Hz), 1.14 (3H, d, J=6.1 Hz), 1.74 (2H, m), 2.65 (2H, m), 2.78 (2H, m), 3.15 (1H, m), 3.42 (1H, m), 3.86 (1H, m), 4.16 (1H, dd, $J_1$=9.6 Hz, $J_2$=2.4 Hz), 4.96 (1H, d, J=5.4 Hz), 5.54 (2H, s), 7.34–7.39 (5H, m), 8.09 (2H, br s), 8.18 (1H, s), 9.30 (1H, s)

Example 145
(1S,5R,6S)-2-[6-(3,5-Dihydroxybenzyl)-7-methylthioimidazo[5,1-b]thiazolium-2-yl]-6-((1R)-1-hydroxyethyl)-1-methyl-1carbapen-3-carboxylate (intramolecular salt)

The procedure of Example 3a) was substantially repeated, except that 78 mg of 4-nitrobenzyl (1S,5R,6S)-6-((1R)-1-hydroxyethyl)-1-methyl-2-(7-methylthioimidazo-[5,1-b]thiazol-2-yl)-1-carbapen-2-em-3-carboxylate and 321 mg of 3,5-bis(triethylsilyloxy)benzyl bromide were used as the starting compounds. Thus, 81 mg of a corresponding quaternary salt was prepared. The triethylsilyl group was removed from this compound in substantially the same manner as in Example 99b). The procedure of Example 3b) was then substantially repeated, except that the quaternary salt with the triethylsilyl group removed therefrom was used. Thus, 5.9 mg of the title compound was prepared.

NMR (DMSO-$d_6$) δ: 1.08 (3H, d, J=7.1 Hz), 1.10 (3H, d, J=6.3 Hz), 2.08 (3H, s), 3.09 (1H, m), 3.24 (1H, m), 3.87 (1H, m), 4.03 (1H, dd, $J_1$=9.5 Hz, $J_2$=2.7 Hz), 4.96 (1H, d, J=5.4 Hz), 5.38 (2H, s), 6.10 (2H, s), 6.12 (1H, s), 8.20 (1H, s), 9.40 (2H, br s), 9.50 (1H, s)

Example 146
(1S,5R,6S)-6-((1R)-1-Hydroxyethyl)-1-methyl-2-[6-[3-(1-methylpyrrolidinium-1-yl)methyl-benzyl]-7-methylthioimidazo[5,1-b]thiazolium-2-yl]-1-carbapen-2-em-3-carboxylate bromide (intramolecular salt)

The procedure of Example 3a) was substantially repeated, except that 78 mg of 4-nitrobenzyl (1S,5R,6S)-2-[6-(3-bromomethylbenzyl)-7-methylthioimidazo[5,1-b]thiazolium-2-yl]-6-((1R)-1-hydroxyethyl)-1-methyl-1-carbapen-2-em-3-carboxylate bromide and 52.0 μl of 1-methylpyrrolidine were used as the starting compounds. Thus, 67 mg of a corresponding quaternary salt was prepared. The procedure of Example 3b) was substantially repeated, except that this quaternary salt was used as the starting compound. Thus, 13.0 mg of the title compound was prepared.

NMR (DMSO-$d_6$) δ: 1.08 (3H, d, J=7.3 Hz), 1.10 (3H, d, J=6.4 Hz), 2.02–2.06 (4H, br s), 2.12 (3H, s), 3.11 (1H, m), 3.32 (2H, m), 3.46–3.61 (3H, m), 3.88 (1H, m), 4.05 (1H, dd, $J_1$=9.5 Hz, $J_2$=2.7 Hz), 4.48 (2H, s), 4.97 (1H, d, J=4.6 Hz), 5.65 (2H, s), 7.47–7.50 (4H, m), 8.29 (1H, s), 9.61 (1H, s)

Example 147
(1S,5R,6S)-6-((1R)-1-Hydroxyethyl)-2-[6-[3-(3-hydroxymethylpyridinium-1-yl)methylbenzyl]-7-methylthioimidazo[5,1-b]thiazolium-2-yl]-1-methyl-1-carbapen-2-em-3-carboxylate bromide (intramolecular salt)

The procedure of Example 3a) was substantially repeated, except that 78 mg of 4-nitrobenzyl (1S,5R,6S)-2-[6-(3-bromomethylbenzyl)-7-methylthioimidazo[5,1-b]-thiazolium-2-yl]-6-((1R)-1-hydroxyethyl)-1-methyl-1- carbapen-2-em-3-carboxylate bromide and 48.5 μl of 3-hydroxymethylpyridine were used as the starting compounds. Thus, 70 mg of a corresponding quaternary salt was prepared. The procedure of Example 3b) was substantially repeated, except that this quaternary salt was used as the starting compound. Thus, 30.6 mg of the title compound was prepared.

NMR (DMSO-$d_6$) δ: 1.08 (3H, d, J=6.8 Hz), 1.10 (3H, d, J=5.8 Hz), 1.98 (3H, s), 3.13 (1H, m), 3.42 (1H, m), 3.91 (1H, m), 4.06 (1H, dd, $J_1$=9.5 Hz, $J_2$=2.4 Hz), 4.65 (2H, s), 4.98 (1H, d, J=5.1 Hz), 5.65 (2H, s), 5.80 (2H, s), 5.95 (1H, br s), 7.37–7.47 (4H, m), 8.08 (1H, m), 8.29 (1H, s), 8.45 (1H, d, J=6.1 Hz), 9.07 (1H, s), 9.61 (1H, s)

Example 148

(1S,5R,6S)-6-((1R)-1-Hydroxyethyl)-2-[6-[3-(4hydroxymethylpyridiniun-1-yl)methylbenzyl]-7-methylthioimidazo[5,1-b]thiazolium-2-yl]-1-methyl-1-carbapen-2-em-3-carboxylate bromide (intramolecular salt)

The procedure of Example 3a) was substantially repeated, except that 78 mg of 4-nitrobenzyl (1S,5R,6S)-2-[6-(3-bromomethylbenzyl)-7-methylthioimidazo[5,1-b]-thiazolium-2-yl]-6-((1R)-1-hydroxyethyl)-1-methyl-1-carbapen-2-em-3-carboxylate bromide and 54.6 mg of 4-hydroxymethylpyridine were used as the starting compounds. Thus, 62 mg of a corresponding quaternary salt was prepared. The procedure of Example 3b) was substantially repeated, except that this quaternary salt was used as the starting compound. Thus, 30.8 mg of the title compound was prepared.

NMR (DMSO-$d_6$) δ: 1.09 (3H, d, J=6.8 Hz), 1.11 (3H, d, J=6.3 Hz), 2.03 (3H, s), 3.12 (1H, m), 3.42 (1H, m), 3.89 (1H, m), 4.07 (1H, dd, $J_1$=9.5 Hz, $J_2$=2.7 Hz), 4.74 (2H, s), 4.98 (1H, d, J=5.1 Hz), 5.60 (2H, s), 5.74 (2H, s), 5.99 (1H, br s), 7.37–7.43 (4H, m), 7.98 (2H, d, J=6.8 Hz), 8.29 (1H, s), 9.00 (2H, d, J=6.8 Hz), 9.61 (1H, s)

Example 149

(1S,5R,6S)-2-[6-[3-[4-(3-Aminopropyl)-1,4-diazoniabicyclo[2,2,2]oct-1-yl]methylbenzyl]-7-methylthioimidazo[5,1-b]thiazolium-2-yl-6-((1R)-1-hydroxyethyl)-1-methyl-1-carbapen-2-em-3-carboxylate dichloride (intramolecular salt) hydrochloride a) 4-Nitrobenzyl (1S,5R,6S)-6-((1R)-1-hydroxyethyl)-1-methyl-2-[6-[3-[4-[3-(4-nitrobenzyloxycarbonylamino)propyl]-1,4-diazoniabicyclo[2,2,2]oct-1-yl]methyl-benzyl]-7-methylthioimidazo[5,1-b]thiazolium-2-yl]-1-carbapen-2-em-3-carboxylate iodide dibromide 4-Nitrobenzyl (1S,5R,6S)-2-[6-(3-bromomethylbenzyl)-7-methylthioimidazo[5,1-b]thiazolium-2-yl]-6-((1R)-1-hydroxyethyl)-1-methyl-1-carbapen-2-em-3-carboxylate bromide (94 mg) and 58 mg of 1-[3-(4-nitrobenzyloxycarbonylamino)propyl]-4-aza-1-azoniabicyclo[2,2,2]octane were dissolved in 3 ml of acetonitrile, 0.5 ml of chloroform, and 0.5 ml of DMF. The mixture was stirred at 35° C. for one day. The reaction solution was added dropwise to 30 ml of diethyl ether. The resultant precipitate was collected by filtration to prepare 132 mg of 4-nitrobenzyl (1S,5R,6S)-6-((1R)-1-hydroxyethyl)-1-methyl-2-[6-[3-[4-[3-(4-nitrobenzyl-oxycarbonylamino)propyl]-1,4-diazoniabicyclo[2,2,2]oct-1-yl]methylbenzyl]-7-methylthioimidazo[5,1-b]thiazolium-2-yl]-1-carbapen-2-em-3-carboxylate iodide dibromide as a crude product.

b) (1S,5R,6S)-2-[6-[3-[4-(3-Aminopropyl)-1,4-diazoniabicyclo[2,2,2]oct-1-yl]methylbenzyl]-7-methylthioimidazo[5,1-b]thiazolium-2-yl]-6-((1R)-1-hydroxyethyl)-1-methyl-1-carbapen-2-em-3-carboxylate dichloride (intramolecular salt) hydrochloride The procedure of Example 50b) was repeated, except that 132 mg of 4-nitrobenzyl (1S,5R,6S)-6-((1R)-1-hydroxyethyl)-1-methyl-2-[6-[3-[4-[3-(4-nitrobenzyl-oxycarbonylamino)propyl]-1,4-diazoniabicyclo[2,2,2]oct-1-yl]methylbenzyl]-7-methylthioimidazo[5,1-b]thiazolium-2-yl]-1-carbapen-2-em-3-carboxylate iodide dibromide was used as the starting compound. Thus, 30 mg of the title compound was prepared.

NMR ($D_2O$) δ (HOD=4.65 ppm): 1.13 (3H, d, J=7.1 Hz), 1.20 (3H, d, J=6.3 Hz), 2.06 (3H, s), 2.15 (2H, m), 3.00 (2H, m), 3.46–3.63 (4H, m), 3.95 (12H, m), 4.17 (1H, m), 4.26 (1H, dd, $J_1$=9.5 Hz, $J_2$=2.7 Hz), 4.77 (2H, m), 5.62 (2H, s), 7.50–7.60 (4H, m), 7.99 (1H, s), 9.35 (1H, s)

Example 150

(1S,5R,6S)-2-[6-[3-(4-carbamoylmethyl-1,4-diazoniabicyclo[2,2,2]oct-1-yl)methylbenzyl]-7-methylthioimidazo[5,1-b]thiazolium-2-yl]-6-((1R)-1-hydroxyethyl)-1-methyl-1-carbapen-2-em-3-carboxylate dichloride (intramolecular salt)

The procedures of Examples 149a) and 50b) were repeated, except that 91 mg of 4-nitrobenzyl (1S,5R,6S)-2-[6-(3-bromomethylbenzyl)-7-methylthioimidazo[5,1-b]-thiazolium-2-yl]-6-((1R)-1-hydroxyethyl)-1-methyl-1-carbapen-2-em-3-carboxylate bromide and 35 mg of 1-carbamoylmethyl-4-aza-1-azoniabicyclo[2,2,2]octane were used as the starting compounds. Thus, 40 mg of the title compound was prepared.

NMR ($D_2O$) δ (HOD=4.65 ppm): 1.14 (3H, d, J=7.5 Hz), 1.20 (3H, d, J=6.3 Hz), 2.05 (3H, s), 3.45–3.57 (2H, m), 3.97 (6H, m), 4.12–4.21 (7H, m), 4.27 (1H, dd, $J_1$=9.5 Hz, $J_2$=2.7 Hz), 4.31 (2H, s), 4.75 (2H, m), 5.62 (2H, s), 7.49–7.57 (4H, m), 8.00 (1H, s)

Example 151

(1S,5R,6S)-6-((1R)-1-Hydroxyethyl)-1-methyl-2-[6-[3-(N-methylisothioureido)methylbenzyl]-7-methylthioimidazo[5,1-b]thiazolium-2-yl]-1-carbapen-2-em-3-carboxylate (intramolecular salt) hydrochloride The procedures of Examples 134a) and 50b) were repeated, except that 100 mg of 4-nitrobenzyl (1S,5R,6S)-2-[6-(3-bromomethylbenzyl)-7-methylthioimidazo[5,1-b]thiazolium-2-yl]-6-((1R)-1-hydroxyethyl)-1-methyl-1-carbapen-2-em-3-carboxylate bromide and 12 mg of N-methylthiourea were used as the starting compounds. Thus, 38 mg of the title compound was prepared.

NMR ($D_2O$) δ (HOD=4.65 ppm): 1.15 (3H, d, J=7.4 Hz), 1.20 (3H, d, J=6.4 Hz), 1.96 (3H, s), 2.75 (3H, s), 3.47 (1H, dd, $J_1$=6.0 Hz, $J_2$=2.9 Hz), 3.54 (1H, m), 4.18 (1H, m), 4.24–4.29 (3H, m), 5.55 (2H, s) 7.26 (2H, m), 7.35 (2H, m), 8.05 (1H, s)

Example 152

(1S,5R,6S)-2-[6-Carbamoylmethyl-7-(pyridin-2-yl)methylthioimidazo[5,1-b]thiazolium-2-yl]-6-((1R)-1-hydroxyethyl)-1-methyl-1-carbapen-2-em-3-carboxylate (intramolecular salt)

a) 4-Nitrobenzyl (1S,5R,6S)-6-((1R)-1-hydroxyethyl)-1-methyl-2-[7-(pyridin-2-yl)methylthioimidazo-[5,1-b]thiazol-2-yl]-1-carbapen-2-em-3-carboxylate The procedure of Example 1a) was repeated, except that 807 mg of 4-nitrobenzyl (1S,5R,6S)-6-((1R)-1-hydroxyethyl)-1-methyl-2-oxo-1-carbapenam-3-carboxylate and 1.255 g of 7-(pyridin-2-yl)methylthio-2-(tri-n-butylstannyl)imidazo[5,1-b]thiazole were used as the starting compounds. Thus, 149 mg of 4-nitrobenzyl (1S,5R,6S)-6-((1R)-1-hydroxyethyl)-1-methyl-2-[7-(pyridin-2-yl)methylthioimidazo[5,1-b]thiazol-2-yl]-1-carbapen-2-em-3-carboxylate was prepared.

NMR (CDCl$_3$) δ: 1.25 (3H, d, J=7.2 Hz), 1.40 (3H, d, J=6.3 Hz), 3.3–3.4 (2H, m), 4.13 (2H, s), 4.25–4.4 (2H, m), 5.26 (1H, d, J=13.8 Hz), 5.51 (1H, d, J=13.8 Hz), 7.1–7.25 (2H, m), 7.5–7.6 (1H, m), 7.67 (2H, d, J=8.7 Hz), 8.00 (1H, s), 8.24 (2H, d, J=8.7 Hz), 8.30 (1H, s), 8.45–8.5 (1H, m)

b) (1S,5R,6S)-2-[6-Carbamoylmethyl-7-(pyridin-2-yl)methylthioimidazo[5,1-b]thiazolium-2-yl]-6-((1R)-1-hydroxyethyl)-1-methyl-1-carbapen-2-em-3-carboxylate (intramolecular salt)

The procedures of Examples 3a) and 3b) were repeated, except that 62.3 mg of 4-nitrobenzyl (1S,5R,6S)-6-((1R)-1-hydroxyethyl)-1-methyl-2-[7-(pyridin-2-yl)methylthioimidazo[5,1-b]thiazol-2-yl]-1-carbapen-2-em-3-carboxylate was used as the starting compound. Thus, 9.9 mg of the title compound was prepared.

NMR (D$_2$O) δ (HOD=4.80 ppm): 1.21 (3H, d, J=7.2 Hz), 1.30 (3H, d, J=6.3 Hz), 3.5–3.6 (2H, m), 4.01 (2H, s), 4.2–4.35 (2H, m), 5.23 (2H, s), 7.07 (1H, d, J=7.5 Hz), 7.3–7.4 (1H, m), 7.6–7.7 (1H, m)

Example 153

(1S,5R,6S)-6-((1R)-1-Hydroxyethyl)-1-methyl-2-[7-methylthio-6-[3-(morpholin-4-yl)methylbenzyl]imidazo[5,1-b]5,1-b]thiazolium-2-yl]-1-carbapen-2-em-3-carboxylate (intramolecular salt) hydrochloride The procedures of Examples 134a) and 50b) were repeated, except that 84 mg of 4-nitrobenzyl (1S,5R,6S)-2-[6-(3-bromomethylbenzyl)-7-methylthioimidazo[5,1-b]-thiazolium-2-yl]-6-((1R)-1-hydroxyethyl)-1-methyl-1-carbapen-2-em-3-carboxylate bromide and 0.010 ml of morpholine were used as the starting compounds. Thus, 18 mg of the title compound was prepared.

NMR (D$_2$O) δ (HOD=4.65 ppm): 1.12 (3H, d, J=7.3 Hz), 1.21 (3H, d, J=6.3 Hz), 1.92 (3H, s), 2.41 (4H, br s), 3.43–3.63 (8H, m), 4.18 (1H, m), 4.24 (1H, dd, J$_1$=9.5 Hz, J$_2$=2.7 Hz), 5.51 (2H, s), 7.21–7.35 (4H, m), 8.01 (1H, s)

Example 154

(1S,5R,6S)-6-(1R)-1-Hydroxyethyl)-1-methyl-2-[6-[4-(1-methylpyrrolidinium-1-yl)methylbenzyl]-7-methylthioimidazo[5,1-b]thiazolium-2-yl]-1-carbapen-2-em-3-carboxylate bromide (intramolecular salt)

The procedure of Example 3a) was substantially repeated, except that 78 mg of 4-nitrobenzyl (1S,5R,6S)-2-[6-(4-bromomethylbenzyl)-7-methylthioimidazo[5,1-b]-thiazolium-2-yl]-6-((1R)-1-hydroxyethyl)-1-methyl-1-carbapen-2-em-3-carboxylate bromide and 52 µl of 1-methylpyrrolidine were used as the starting compounds. Thus, 74 mg of a corresponding quaternary salt was prepared. The procedure of Example 3b) was substantially repeated, except that this quaternary salt was used as the starting compound. Thus, 34.4 mg of the title compound was prepared.

NMR (DMSO-d$_6$) δ: 1.08 (3H, d, J=6.4 Hz), 1.10 (3H, d, J=6.1 Hz), 2.05–2.08 (7H, m), 2.81 (3H, s), 3.24 (1H, m), 3.37–3.48 (5H, m), 3.88 (1H, m), 4.04 (1H, dd, J$_1$=9.5 Hz, J$_2$=2.7 Hz), 4.51 (2H, s), 4.99 (1H, d, J=5.1 Hz), 5.67 (2H, s), 7.42 (2H, d, J=8.3 Hz), 7.55 (2H, d, J=8.3 Hz), 8.31 (1H, s), 9.68 (1H, s)

Example 155

(1S,5R,6S)-6-((1R)-1-Hydroxyethyl)-2-[6-[3-(2-hydromethylpyridinium-1-yl)methylbenzyl]-7-methyl-thiomidazo[5,1-b]thiazolium-2-yl]-methyl-1-carbapen-2-em-3-carboxylate bromide (intramolecular salt)

The procedure of Example 3a) was substantially repeated, except that 777 mg of 4-nitrobenzyl (1S,5R,6S)-2-[6-(3-bromomethylbenzyl)-7-methylthio-imidazo[5,1-b]thiazolium-2-yl]-6-((1R)-1-hydroxyethyl)-1-methyl-1-carbapen-2-em-3-carboxylate bromide and 405 µl of 2-hydroxymethylpyridine were used as the starting compounds. Thus, 742 mg of a corresponding quaternary salt was prepared. The procedure of Example 3b) was substantially repeated, except that this quaternary salt was used as the starting compound. Thus, 279 mg of the title compound was prepared.

NMR (DMSO-d$_6$) δ: 1.08 (3H, d, J=7.3 Hz), 1.10 (3H, d, J=6.3 Hz), 2.07 (3H, s), 3.10 (1H, m), 3.41 (1H, m), 3.88 (1H, m), 4.06 (1H, dd, J$_1$=9.5 Hz, J$_2$=2.7 Hz), 5.02 (1H, d, J=5.1 Hz), 5.57 (2H, s), 5.82 (2H, s), 7.38–7.48 (3H, m), 7.54 (1H, s), 8.10–8.14 (2H, m), 8.30 (1H, s), 8.57 (1H, t, J=7.8 Hz), 9.18 (2H, d, J=5.4 Hz), 9.69 (1H, s)

Example 156

(1S,5R,6S)-6-((1R)-1-Hydroxyethyl)-2-[6-[3-(2-hydroxymethylimidazo[5,1-b]thiazolium-6-yl)methylbenzyl]-7-methylthioimidazo[5,1-b-]thiazolium-2-yl]-1-methyl-1-carbapen-2-em-3-carboxylate bromide (intramolecular salt)

The procedure of Example 3a) was substantially repeated, except that 78 mg of 4-nitrobenzyl (1S,5R,6S)-2-[6-(3-bromomethylbenzyl)-7-methylthioimidazo[5,1-b]-thiazolium-2-yl]-6-((1R)-1-hydroxyethyl)-1-methyl-1-carbapen-2-em-3-carboxylate bromide and 46 mg of 2-hydroxymethylimidazo[5,1-b]thiazole were used as the starting compounds. Thus, 73.9 mg of a corresponding quaternary salt was prepared. The procedure of Example 3b) was substantially repeated, except that this quaternary salt was used as the starting compound. Thus, 24.3 mg of the title compound was prepared.

NMR (DMSO-d$_6$) δ: 1.14 (3H, d, J=5.4 Hz), 1.16 (3H, d, J=5.4 Hz), 2.06 (3H, s), 3.19 (1H, m), 3.47 (1H, m), 3.95 (1H, m), 4.12 (1H, dd, J$_1$=9.5 Hz, J$_2$=2.7 Hz), 4.66 (2H, s), 5.05 (1H, d, J=4.4 Hz), 5.61 (2H, s), 5.66 (2H, s), 6.19 (1H, br s), 7.31 (1H, s), 7.40–7.49 (3H, m), 7.74 (1H, s), 8.08 (1H, s), 8.35 (1H, s), 9.66 (1H, s), 9.68 (1H, s)

Example 157

(1S,5R,6S)-6-((1R)-1-Hydroxyethyl)-2-[6-[3-(imidazo[5,1-b]thiazolium-6-yl)methylbenzyl]-7-methyl-thiomidazo[5,1-b]thiazolium-2-yl)-1-methyl-1-carbapen-2-em-3-carboxylate bromide (intramolecular salt)

The procedure of Example 3a) was substantially repeated, except that 78 mg of 4-nitrobenzyl (1S,5R,6S)-2-[6-(3-bromomethylbenzyl)-7-methylthioimidazo[5,1-b]-thiazolium-2-yl]-6-((1R)-1-hydroxyethyl)-1-methyl-1-carbapen-2-em-3-carboxylate bromide and 37 mg of imidazo[5,1-b]thiazole were used as the starting compounds. Thus, 87.7 mg of a corresponding quaternary salt was prepared. The procedure of Example 3b) was substantially repeated, except that this quaternary salt was used as the starting compound. Thus, 28.7 mg of the title compound was prepared.

NMR (DMSO-d$_6$) δ: 1.09 (3H, d, J=6.3 Hz), 1.14 (3H, d, J=7.3 Hz), 2.06 (3H, s), 3.34 (1H, m), 3.65 (1H, m), 3.96 (1H, m), 4.27 (1H, dd, J$_1$=10.0 Hz, J$_2$=2.9 Hz), 5.10 (1H, br s), 5.60 (2H, s), 5.66 (2H, s), 7.31–7.41 (4H, m), 7.67 (1H, d, J=4.1 Hz), 7.81 (1H, s), 8.16 (1H, d, J=4.1 Hz), 8.68 (1H, s), 9.67 (1H, s), 9.83 (1H, )

Example 158

(1S,5R,6S)-6-((1R)-1-Hydroxyethyl)-2-[6-[4-(imidazo[5,1-b]thiazolium-6-yl)methylbenzyl]-7-methyl-thiomidazo[5,1-b]thiazolium-2-yl]-1-methyl-1-carbapen-2-em-3-carboxylate bromide (intramolecular salt)

The procedure of Example 3a) was substantially repeated, except that 78 mg of 4-nitrobenzyl (1S,5R,6S)-2-[6-(4-bromomethylbenzyl)-7-methylthioimidazo[5,1-b]thiazolium-2-yl]-6-((1R)-1-hydroxyethyl)-1-methyl-1-carbapen-2-em-3-carboxylate bromide and 37 mg of imidazo[5,1-b]thiazole were used as the starting compounds. Thus, 88.5 mg of a corresponding quaternary salt was prepared. The procedure of Example 3b) was substantially repeated, except that this quaternary salt was used as the starting compound. Thus, 36.5 mg of the title compound was prepared.

NMR (DMSO-$d_6$) δ: 1.13 (3H, d, J=7.0 Hz), 1.15 (3H, d, J=6.3 Hz), 2.07 (3H, s), 3.15 (1H, m), 3.45 (1H, m), 3.94 (1H, m), 4.10 (1H, dd, $J_1$=9.5 Hz, $J_2$=2.7 Hz), 5.02 (1H, d, J=5.1 Hz), 5.64 (2H, s), 5.66 (2H, s), 7.41 (2H, d, J=8.3 Hz), 7.48 (2H, d, J=8.3 Hz), 7.71 (1H, d, J=4.1 Hz), 7.86 (1H, s), 8.17 (1H, d, J=4.1 Hz), 8.31 (1H, s), 9.64 (1H, s), 9.68 (1H, s)

Example 159

(1S,5R,6S)-2-[6-[3-(4,5-Dihydro-1H-imidazol-2-yl)thiomethylbenzyl]-7-methylthioimidazo[5,1-b]thiazolium-2-yl]-6-((1R)-1-hydroxyethyl)-1-methyl-1-carbapen-2-em-3-carboxylate (intramolecular salt) hydrochloride The procedures of Examples 134a) and 50b) were repeated, except that 100 mg of 4-nitrobenzyl (1S,5R,6S)-2-[6-(3-bromomethylbenzyl)-7-methylthio-imidazo[5,1-b]thiazolium-2-yl]-6-((1R)-1-hydroxyethyl)-1-methyl-1-carbapen-2-em-3-carboxylate bromide and 16 mg of 2-imidazolidinethione were used as the starting compounds. Thus, 42 mg of the title compound was prepared.

NMR ($D_2O$) δ (HOD=4.65 ppm): 1.14 (3H, d, J=7.3 Hz), 1.20 (3H, d, J=6.3 Hz), 1.97 (3H, s), 3.47 (1H, dd, $J_1$=6.0 Hz, $J_2$=2.9 Hz), 3.54 (1H, m), 3.78 (4H, s), 4.18 (1H, m), 4.27 (1H, dd, $J_1$=9.5 Hz, $J_2$=2.9 Hz), 4.33 (2H, s), 5.55 (2H, s), 7.29 (2H, m), 7.37 (2H, m), 8.04 (1H, s)

Example 160

(1S,5R,6S)-2-[6-[3-(4,5-Dihydro-1H-imidazol-2-yl)thiopropyl]-7-methylthioimidazo[5,1-b]-thiazolium-2yl]-6-((1R)-1-hydroxyethyl)-1-methyl-1-carbapen-2-em-3-carboxylate (intramolecular salt) hydrochloride The procedures of Examples 134a) and 50b) were repeated, except that 90 mg of 4-nitrobenzyl (1S,5R,6S)-2-[6-(3-iodopropyl)-7-methylthioimidazo[5,1-b]thiazolium-2-yl]-6-((1R)-1-hydroxyethyl)-1-methyl-1-carbapen-2-em-3-carboxylate trifluoromethanesulfonate and 11 mg of 2-imidazolidinethione were used as the starting compounds. Thus, 42 mg of the title compound was prepared.

NMR ($D_2O$) δ (HOD=4.65 ppm): 1.16 (3H, d, J=7.3 Hz), 1.21 (3H, d, J=6.3 Hz), 2.28–2.36 (5H, m), 3.18 (2H, t, J=7.0 Hz), 3.46 (1H, dd, $J_1$=6.0 Hz, $J_2$=2.9. Hz), 3.55 (1H, m), 3.86 (4H, s), 4.18 (1H, m), 4.25 (1H, dd, $J_1$=9.5 Hz, $J_2$=2.9 Hz), 4.50 (2H, s), 8.05 (1H, s)

Example 161

(1S,5R,6S)-6-((1R)-1-Hydroxyethyl)-2-[6-[3-[4-(2-hydroxyethyl)-1,4-diazoniabicyclo[2,2,2]oct-1-yl]methylbenzyl]-7-methylthio-imidazo[5,1-b]thiazolium-2-yl]-1-methyl-1-carbapen-2-em-3-carboxylate dichloride (intramolecular salt The procedures of Examples 149a) and 50b) were repeated, except that 101 mg of 4-nitrobenzyl (1S,5R,6S)-2-[6-(3-bromomethylbenzyl)-7-methylthioimidazo[5,1-b]thiazolium-2-yl]-6-((1R)-1-hydroxyethyl)-1-methyl-1-carbapen-2-em-3-carboxylate bromide and 37 mg of 1-(2-hydroxyethyl)-4-aza-1-azoniabicyclo[2,2,2]octane were used as the starting compounds. Thus, 33 mg of the title compound was prepared.

NMR ($D_2O$) δ (HOD=4.65 ppm): 1.15 (3H, d, J=7.3 Hz), 1.21 (3H, d, J=6.3 Hz), 2.07 (3H, s), 3.46–3.59 (2H, m), 3.65 (2H, m), 3.90–4.05 (14H, m), 4.18 (1H, m), 4.26 (1H, dd, $J_1$=9.5 Hz, $J_2$=2.9 Hz), 4.75 (2H, m), 5.63 (2H, s), 7.49–7.59 (4H, m), 8.02 (1H, s)

Example 162

(1S,5R,6S)-6-((1R)-1-Hydroxyethyl)-1-methyl-2-[7-methylthio-6-[3-(thiazolium-3-yl)methyl-benzyl]imidazo[5,1-b]thiazolium-3-yl]-1-carbapen-2-em-3-carboxylate bromide (intramolecular salt)

The procedure of Example 3a) was substantially repeated, except that 78 mg of 4-nitrobenzyl (1S,5R,6S)-2-[6-(3-bromomethylbenzyl)-7-methylthioimidazo[5,1-b]-thiazolium-2-yl]-6-((1R)-1-hydroxyethyl)-1-methyl-1-carbapen-2-em-3-carboxylate bromide and 35.4 μl of thiazole were used as the starting compounds. Thus, 79.1 mg of a corresponding quaternary salt was prepared. The procedure of Example 3b) was substantially repeated, except that this quaternary salt was used as the starting compound. Thus, 16.0 mg of the title compound was prepared.

NMR (DMSO-$d_6$) δ: 1.08 (3H, d, J=6.3 Hz), 1.10 (3H, d, J=5.9 Hz), 2.00 (3H, s), 3.12 (1H, m), 3.39 (1H, m), 3.90 (1H, m), 4.05 (1H, dd, $J_1$=9.4 Hz, $J_2$=2.4 Hz), 4.98 (1H, d, J=5.1 Hz), 5.61 (2H, s), 5.72 (2H, s), 7.36–7.45 (4H, m), 8.27–8.30 (2H, m), 8.47 (1H, m), 9.61 (1H, s), 10.28 (1H, s)

Example 163

(1S,5R,6S)-6-((1R)-1-Hydroxyethyl)-1-methyl-2-[7-methylthio-6-[4-(thiazolium-3-yl)methyl-benzyl]imidazo[5,1-b]thiazolium-2-yl]-1-carbapen-2-em-3-carboxylate bromide (intramolecular salt)

The procedure of Example 3a) was substantially repeated, except that 78mg of 4-nitrobenzyl (1S,5R,6S)-2-[6-(4-bromomethylbenzyl)-7-methylthioimidazo[5,1-b]-thiazolium-2-yl]-6-((1R)-1-hydroxyethyl)-1-methyl-1-carbapen-2-em-3-carboxylate bromide and 35.4 μl of thiazole were used as the starting compounds. Thus, 80.2 mg of a corresponding quaternary salt was prepared. The procedure of Example 3b) was substantially repeated, except that this quaternary salt was used as the starting compound. Thus, 13.3 mg of the title compound was prepared.

NMR (DMSO-$d_6$) δ: 1.08 (3H, d, J=8.2 Hz), 1.10 (3H, d, J=6.6 Hz), 2.07 (3H, s), 3.12 (1H, m), 3.39 (1H, m), 3.88 (1H, m), 4.04 (1H, m), 4.98 (1H, d, J=5.1 Hz), 5.61 (2H, s), 5.72 (2H, s), 7.36 (2H, d, J=8.0 Hz), 7.46 (2H, d, J=8.0 Hz), 8.26–8.28 (2H, m), 8.47 (1H, m), 9.59 (1H, s), 10.26 (1H, s)

Example 164

(1S,6R,6S)-6-((1R)-1-Hydroxyethyl)-2-[6-[3-(isoquinolinium-2-yl)methylbenzyl]-7-methylthioimidazo[5,1-b]thiazolium-2-yl]-1-methyl-1-carbapen-2-em-3-carboxylate bromide (intramolecular salt)

The procedure of Example 3a) was substantially repeated, except that 78 mg of 4-nitrobenzyl (1S,6R,6S)-2-[6-(3-bromomethylbenzyl)-7-methylthioimidazo[5,1-b]thiazolium-2-yl]-6-((1R)-1-hydroxyethyl)-1-methyl-1-carbapen-2-em-3-carboxylate bromide and 65 mg of isoquinoline were used as the starting compounds. Thus, 75.5 mg of a corresponding quaternary salt was prepared. The procedure of Example 3b) was substantially repeated, except that this quaternary compound was used as the starting compound. Thus, 20.6 mg of the title compound was prepared.

NMR (DMSO-d$_6$) δ: 1.09 (3H, d, J=7.8 Hz), 1.11 (3H, d, J=6.6 Hz), 1.95 (3H, 8), 3.12 (1H, m), 3.39 (1H, m), 3.90 (1H, m), 4.06 (1H, dd, J$_1$=9.5 Hz, J$_2$=2.7 Hz), 4.97 (1H, d, J=5.1 Hz), 5.59 (2H, s), 5.90 (2H, s), 7.37 (1H, d, J=7.8 Hz), 7.41–7.46 (2H, m), 7.50 (1H, d, J=7.6 Hz), 8.04 (1H, t, J=7.1 Hz), 8.20–8.29 (3H, m), 8.43 (1H, d, J=8.6 Hz), 8.52 (1H, d, J=6.8 Hz), 8.70 (1H, d, J=6.8 Hz), 9.57 (1H, s), 10.20 (1H, s)

Example 165

(1S,6R,6S)-6-((1R)-1-Hydroxyethyl)-1-methyl-2-[7-methylthio-6-[3-(3H-pyrimidinium-4-one-1-yl)-methylbenzyl]imidazo[5,1-b]thiazolium-2-yl]-1-carbapen-2-em-3-carboxylate bromide (intramolecular salt)

The procedure of Example 3a) was substantially repeated, except that 78 mg of 4-nitrobenzyl (1S,6R,6S)-2-[6-(3-bromomethylbenzyl)-7-methylthioimidazo[5,1-b]-thiazolium-2-yl]-6-((1R)-1-hydroxyethyl)-1-methyl-1-carbapen-2-em-3-carboxylate bromide and 48 mg of 3H-pyrimidin-4-one were used as the starting compounds. Thus, 41.0 mg of a corresponding quaternary salt was prepared. The procedure of Example 3b) was substantially repeated, except that this quaternary salt was used as the starting compound. Thus, 4.4 mg of the title compound was prepared.

NMR (DMSO-d$_6$) δ: 1.08 (3H, d, J=8.0 Hz), 1.10 (3H, d, J=6.4 Hz), 2.04 (3H, s), 3.10 (1H, m), 3.38 (1H, m), 3.88 (1H, m), 4.04 (1H, dd, J$_1$=9.5 Hz, J$_2$=3.0 Hz), 4.96 (1H, br s), 4.99 (2H, s), 5.59 (2H, s), 5.94 (1H, d, J=7.6 Hz), 7.27–7.32 (3H, m), 7.40 (1H, t, J=7.6 Hz), 7.65 (1H, m), 8.25 (1H, s), 8.40 (1H, s), 9.56 (1H, s)

Example 166

(1S,6R,6S)-6-((1R)-1-Hydroxyethyl)-2-[6-[4-(isoquinolinium-2-yl)methylbenzyl]-7-methylthioimidazo[5,1-b]thiazolium-2-yl]-1-methyl-1-carbapen-2-em-3-carboxylate bromide (intramolecular salt)

The procedure of Example 3a) was substantially repeated, except that 78 mg of 4-nitrobenzyl (1S,6R,6S)-2-[6-(4-bromomethylbenzyl)-7-methylthioimidazo[5,1-b]-thiazolium-2-yl]-6-((1R)-1-hydroxyethyl)-1-methyl-1-carbapen-2-em-3-carboxylate bromide and 65 mg of isoquinoline were used as the starting compounds. Thus, 78.1 mg of a corresponding quaternary salt was prepared. The procedure of Example 3b) was substantially repeated, except that this quaternary salt was used as the starting compound. Thus, 27.9 mg of the title compound was prepared.

NMR (DMSO-d$_6$) δ: 1.07 (3H, d, J=7.1 Hz), 1.10 (3H, d, J=6.1 Hz), 2.06 (3H, s), 3.09 (1H, m), 3.39 (1H, m), 3.87 (1H, m), 4.03 (1H, dd, J$_1$=9.5 Hz, J$_2$=2.7 Hz), 4.96 (1H, d, J=5.1 Hz), 5.60 (2H, s), 5.90 (2H, s), 7.37 (2H, d, J=8.0 Hz), 7.54 (2H, d, J=8.0 Hz), 8.20 (1H, t, J=7.0 Hz), 8.19–8.23 (2H, m), 8.27 (1H, d, J=8.3 Hz), 8.44 (1H, d, J=8.8 Hz), 8.51 (1H, d, J=7.1 Hz), 8.71 (1H, d, J=7.1 Hz), 9.56 (1H, s), 10.18 (1H, s)

Example 167

(1S,6R,6S)-2-[7-(3-Aminopropyl)thio-6-(3,5-dihydroxy)benzylimidazo[5,1-b]thiazolium-2-yl]-6-((1R)-1-hydroxyethyl)-1-methyl-1-carbapen-2-em-3-carboxylate (intramolecular salt) hydrochloride a) 4-Nitrobenzyl (1S,6R,6S)-2-[7-(3-azidopropyl)thio-6-[3,5-bis(triethylsilyloxy)]benzylimidazo[5,1-b]thiazolium-2-yl]-6-((1R)-1-hydroxyethyl)-1-methyl-1-carbapen-2-em-3-carboxylate bromide Triphenylphosphine (958 mg) and 1.21 g of carbon tetrabromide were added to a solution of 896 mg of 3,5-bis(triethylsilyloxy)benzyl alcohol in 7 ml of dichloromethane. The mixture was stirred at room temperature for 30 min. The reaction solution was purified by column chromatography on silica gel (dichloromethane) to prepare 3,5-bis(triethylsilyloxy)benzyl bromide. This compound was dissolved in 8 ml of acetonitrile. 4-Nitrobenzyl (1S,6R,6S)-2-[7-(3-azidopropyl)thioimidazo[5,1-b]thiazol-2-yl]-6-((1R)-1-hydroxyethyl)-1-methyl-1-carbapen-2-em-3-carboxylate (245 mg) was added to the solution. The mixture was stirred at room temperature for 4 days. The reaction solution was concentrated. The residue was purified by column chromatography on Sephadex LH-20 (chloroform:methanol=1:1) to prepare 172 mg of 4-nitrobenzyl (1S,6R,6S)-2-[7-(3-azidopropyl)thio-6-[3,5-bis(triethylsilyloxy)]benzylimidazo[5,1-b]thiazolium-2-yl]-6-((1R)-1-hydroxyethyl)-1-methyl-1-carbapen-2-em-3-carboxylate bromide.

NMR (CDCl$_3$) δ: 0.73 (12H, g, J=7.8 Hz), 0.98 (18H, t, J=7.8 Hz), 1.65–1.8 (2H, m), 2.5–2.6 (2H, m), 3.3–3.4 (2H, m), 3.44 (1H, dd, J$_1$=6.3 Hz, J$_2$=2.7 Hz), 3.85–3.95 (1H, m), 4.25–4.35 (1H, m), 4.45–4.55 (1H, m), 5.32 (1H, d, J=13.2 Hz), 5.50 (2H, s), 5.55 (1H, d, J=13.2 Hz), 6.3–6.4 (3H, m), 7.69 (2H, d, J=8.7 Hz), 8.24 (2H, d, J=8.7 Hz), 9.61 (1H, s), 10.81 (1H, s)

b) (1S,6R,6S)-2-[7-(3-Aminopropyl)thio-6-3,5-dihydroxy)benzylimidazo[5,1-b]thiazolium-2-yl]-6-((1R)-1-hydroxyethyl)-1-methyl-1-carbapen-2-em-3-carboxylate (intramolecular salt) hydrochloride The procedure of Example 99d) was repeated, except that 172 mg of 4-nitrobenzyl (1S,6R,6S)-2-[7-(3-azidopropyl)thio-6-[3,5-bis(triethylsilyloxy)]benzylimidazo[5,1-b]thiazolium-2-yl]-6-((1R)-1-hydroxyethyl)-1-methyl-1-carbapen-2-em-3-carboxylate bromide was used as the starting compound. Thus, 7.8 mg of the title compound was prepared.

NMR (D$_2$O) δ (HOD=4.80 ppm): 1.26 (3H, d, J=7.2 Hz), 1.32 (3H, d, J=6.6 Hz), 1.7–1.85 (2H, m), 2.45–2.6 (2H, m), 2.9–3.0 (2H, m), 3.55–3.7 (2H, m), 4.25–4.4 (2H, m), 5.50 (2H, s), 6.35–6.45 (3H, m), 8.10 (1H, s), 9.52 (1H, s)

Example 168

(1S,6R,6S)-2-[6-(3-Aminomethylbenzyl)-7-methylthioimidazo[5,1-b]thiazolium-2-yl]-6-((1R)-1-hydroxyethyl)-1-methyl-1-carbapen-2-em-3-carboxylate (intramolecular salt) hydrobromide The procedure of Example 3a) was substantially repeated, except that 78 mg of 4-nitrobenzyl (1S,6R,6S)-2-[6-(3-bromomethylbenzyl)-7-methylthioimidazo[5,1-b]-thiazolium-2-yl]-6-((1R)-1-hydroxyethyl)-1-methyl-1-carbapen-2-em-3-carboxylate bromide and 39.4 µl of pyrimidine were used as the starting compounds. Thus, 67 mg of a corresponding quaternary salt was prepared. The procedure of Example 3b) was substantially repeated, except that this quaternary salt was used as the starting compound. Thus, 9.5 mg of the title compound was prepared.

NMR (DMSO-d$_6$) δ: 1.09 (3H, d, J=7.6 Hz), 1.11 (3H, d, J=6.6 Hz), 2.04 (3H, s), 3.14 (1H, m), 3.43 (1H, m), 3.93 (1H, m), 3.95 (2H, s), 4.10 (1H, dd, J$_1$=9.5 Hz, J$_2$=2.7 Hz), 5.00 (1H, d, J=5.1 Hz), 5.61 (2H, br s), 7.33 (1H, s), 7.38–7.44 (3H, m), 8.15 (2H, br s), 8.31 (1H, s), 9.58 (1H, s)

Example 169

(1S,6R,6S)-2-[6-(4-Aminomethylbenzyl)-7-methylthioimidazo[5,1-b]thiazolium-2-yl]-6-((1R)-1-hydroxyethyl)-1-methyl-1-carbapen-2-em-3-carboxylate (intramolecular salt) hydrobromide The procedure of Example 3a) was substantially repeated, except that 78 mg of 4-nitrobenzyl (1S,6R,6S)-2-[6-(4- bromomethylbenzyl)-7-methylthioimidazo[5,1-b]-thiazolium-2-yl]-6-((1R)-1-hydroxyethyl)-1-methyl-1-carbapen-2-em-3-carboxylate bromide and 39.4 µl of pyrimidine were used as the starting compounds. Thus, 79 mg of a corresponding quaternary salt was prepared. The procedure of Example 3b) was substantially repeated, except that this quaternary salt was used as the starting compound. Thus, 18.1 mg of the title compound was prepared.

NMR (DMSO-$d_6$) δ: 1.10 (3H, d, J=6.8 Hz), 1.11 (3H, d, J=6.1 Hz), 2.07 (3H, 9), 3.14 (1H, m), 3.44 (1H, m), 3.90 (1H, m), 3.97 (2H, s), 4.06 (1H, dd, $J_1$=9.5 Hz, $J_2$=2.7 Hz), 4.98 (1H, d, J=5.1 Hz), 5.62 (2H, s), 7.33 (2H, d, J=8.1 Hz), 7.41 (2H, d, J=8.3 Hz), 8.31 (1H, s), 9.64 (1H, s)

Example 170
(1S,6R,6S)-2-[6-[3-(3-Carbamoylpyridinium-1-yl)methylbenzyl]-7-methylthioimidazo[5,1-b]thiazolium-2-yl]-6-((1R)-1-hydroxyethyl)-1-methyl-1-carbapen-2-em-3-carboxylate bromide (intramolecular salt)

The procedure of Example 3a) was substantially repeated, except that 78 mg of 4-nitrobenzyl (1S,6R,6S)-2-[6-(3-bromomethylbenzyl)-7-methylthioimidazo[5,1-b]-thiazolium-2-yl]-6-((1R)-1-hydroxyethyl)-1-methyl-1-carbapen-2-em-3-carboxylate bromide and 92 mg of 3-carbamoylpyridine were used as the starting compounds. Thus, 114 mg of a corresponding quaternary salt was prepared. The procedure of Example 3b) was substantially repeated, except that this quaternary salt was used as the starting compound. Thus, 33.7 mg of the title compound was prepared.

NMR (DMSO-$d_6$) δ: 1.09 (3H, d, J=7.3 Hz), 1.11 (3H, d, J=6.3 Hz), 1.99 (3H, s), 3.12 (1H, m), 3.41 (1H, m), 3.89(1H, m), 4.06 (1H, dd, $J_1$=9.5 Hz, $J_2$=2.7 Hz) 4.97 (1H, d, J=5.3 Hz), 5.60 (2H, s), 5.85 (2H, s), 7.37–7.47 (4H, m), 8.13 (1H, br s), 8.25 (1H, m), 8.27 (1H, s), 8.58 (1H, br s), 8.90 (1H, d, J=8.1 Hz), 9.20 (1H, d, J=8.1 Hz), 9.53 (1H, s), 9.58 (1H, s)

Example 171
(1S,6R,6S)-2-[6-[2-[(3S,5S)-5-(Aminosulfonylaminomethyl)pyrrolidin-3-yl]thioethyl]-7-methylthioimidazo[5,1-b]thiazolium-2-yl]-6-((1R)-1-hydroxyethyl)-1-methyl-1-[carbapen-2-em-3-carboxylate (intramolecular salt) Hydrochloride The procedures of Examples 3a) and 70f) were repeated, except that 1.99 g of (3S,5S)-5-(N-aminosulfonyl-N-allyloxycarbonyl)aminomethyl-1-allyloxy-carbonyl-3-(2-methanesulfonyloxyethyl)thiopyrrolidine and 560 mg of allyl (1S,6R,6S)-6-((1R)-1-hydroxyethyl)-1-methyl-2-(7-methylthioimidazo[5,1-b]thiazol-2-yl)-1-carbapen-2-em-3-carboxylate were used as the starting compounds. Thus, 73 mg of the title compound was prepared.

NMR ($D_2O$) δ (HOD=4.65 ppm): 1.15 (3H, d, J=7.3 Hz), 1.21 (3H, d, J=6.3 Hz), 1.64 (1H, m), 2.31 (3H, s), 2.60 (1H, m), 3.16 (2H, m), 3.23–3.42 (3H, m), 3.47 (1H, dd, $J_1$=6.0 Hz, $J_2$=2.9 Hz), 3.55 (1H, m), 3.68 (2H, m), 3.81 (1H, m), 4.18 (1H, m), 4.25 (1H, dd, $J_1$=9.5 Hz, $J_2$=2.7 Hz), 4.60 (2H, m), 8.04 (1H, s), 9.30 (1H, s)

Example 172
(1S,6R,6S)-2-[6-Carbamoylmethyl-7-(2-fluoroethyl)thioimidazo[5,1-b]thiazolium-2-yl]-6-((1R)-1-hydroxyethyl)-1-methyl-1-carbapen-2-em-3-carboxylate (intramolecular salt)

a) 4-Nitrobenzyl (1S,6R,6S)-2-[7-(2-fluoroethyl)thioimidazo[5,1-b]thiazol-2-yl-6-((1R)-1-hydroxyethyl)-1-methyl]-carbapen-2-em-3-carboxylate The procedure of Example 1a) was repeated, except that 181 mg of 4-nitrobenzyl (1S,6R,6S)-6-((1R)-1-hydroxyethyl)-1-methyl-2-oxo-1-carbapenam-3-carboxylate and 232 mg of 7-(2-fluoroethyl)thio-2-(tri-n-butylstannyl)imidazo[-5,1-b]thiazole were used as the starting compounds. Thus, 69 mg of 4-nitrobenzyl (1S,6R,6S)-2-[7-(2-fluoroethyl)thioimidazo[5,1-b]-thiazol-2-yl]-6-((1R)-1-hydroxyethyl)-1-methyl-1-carbapen-2-em-3-carboxylate was prepared.

NMR (CDCl$_3$) δ: 1.32 (3H, d, J=7.3 Hz), 1.40 (3H, d, J=6.3 Hz), 3.04–3.13 (2H, m), 3.37 (1H, dd, $J_1$=6.6 Hz, $J_2$=2.9 Hz), 3.43–3.52 (1H, m), 4.29–4.36 (1H, m), 4.38 (1H, dd, $J_1$=9.5 Hz, $J_2$=2.7 Hz), 4.50 (1H, t, J=6.8 Hz), 4.62 (1H, t, J=6.8 Hz), 5.28 (1H, d, J=13.6 Hz), 5.53 (1H, d, J=13.6 Hz), 7.68 (2H, d, J=8.8 Hz), 8.02 (1H, s), 8.25 (2H, d, J=8.8 Hz), 8.31 (1H, s)

b) 4-Nitrobenzyl (1S,5R,6S)-2-[6-carbamoylmethyl-7-(2-fluoroethyl)thioimidazo[5,1-b]thiazolium-2-yl]-6-((1R)-1-hydroxyethyl)-1-methyl-1-carbapen-2em-3-carboxylate iodide The procedure of Example 3a) was repeated, except that 119 mg of 4-nitrobenzyl (1S,6R,6S)-2-[7-(2-fluoroethyl)thioimidazo[5,1-b]thiazol-2-yl]-6-((1R)-1-hydroxyethyl)-1-methyl-1-carbapen-2-em-3-carboxylate was used as the starting compound. Thus, 185 mg of 4-nitrobenzyl (1S,6R,6S)-2-[6-carbamoylmethyl-7-(2-fluoroethyl)thioimidazo[5,1-b]thiazolium-2-yl]-6-((1R)-1-hydroxyethyl)-1-methyl-1-carbapen-2-em-3-carboxylate iodide was prepared.

NMR (DMSO-$d_6$) δ: 1.19 (3H, d, J=6.3 Hz), 1.25 (3H, d, J=7.5 Hz), 3.05–3.2 (2H, m), 3.45–3.55 (1H, m), 3.7–3.8 (1H, m), 4.0–4.1 (1H, m), 4.35–4.45 (2H, m), 4.55–4.65 (1H, m), 5.21 (2H, s), 5.42 (1H, d, J=14.1 Hz), 5.55 (1H, d, J=14.1 Hz), 7.70 (1H, s), 7.75 (2H, d, J=8.7 Hz), 7.98 (1H, s), 8.24 (2H, d, J=8.7 Hz), 8.76 (1H, s), 9.76 (1H, s)

c) (1S,6R,6S)-2-[6-Carbamoylmethyl-7-(2-fluoroethyl)thioimidazo[5,1b-]thiazolium-2-yl]-6-((1R)-1-hydroxyethyl)-1-methyl-1-carbapen-2-em-3-carboxylate (intramolecular salt)

The procedure of Example 3b) was repeated, except that 185 mg of 4-nitrobenzyl (1S,6R,6S)-2-[6-carbamoylmethyl-7-(2-fluoroethyl)thioimidazo[5,1-b]thiazolium-2-yl]-6-((1R)-1-hydroxyethyl)-1-methyl-1-carbapen-2-em-3-carboxylate iodide was used as the starting compound. Thus, 78.1 mg of the title compound was prepared.

NMR ($D_2O$) δ (HOD=4.80 ppm): 1.32 (3H, d, J=6.3 Hz), 3.0–3.2 (2H, m), 3.57 (1H, dd, $J_1$=6.3 Hz, $J_2$=3.0 Hz), 3.6–3.7 (1H, m), 4.2–4.3 (1H, m), 4.36 (1H, dd, $J_1$=9.6 Hz, $J_2$=3.0 Hz), 4.5–4.7 (2H, m), 5.35 (2H, s), 8.21 (1H, s)

Example 173
(1S,6R,6S)-2-[6-[2-(2-Aminoethyl)thioethyl]-7-methylthioimidazo[5,1-b]thiazolium-2-yl]-6-((1R)-1-hydroxyethyl)-1-methyl-1-carbapen-2-em-3-carboxylate (intramolecular salt) methanesulfonate The procedures of Examples 3a) and 3b) were repeated, except that 204 mg of 4-nitrobenzyl (1S,6R,6S)-6-((1R)-1-hydroxyethyl)-1-methyl-2-(7-methyl-thioimidazo[5,1-b]thiazol-2-yl)-1-carbapen-2-em-3-carboxylate and [2-(2-azidoethyl)thioethyl]methanesulfonate were used as the starting compounds. Thus, 14 mg of the title compound was prepared.

NMR ($D_2O$) δ (HOD=4.65 ppm): 1.15 (3H, d, J=7.1 Hz), 1.21 (3H, d, J=6.3 Hz), 2.31 (3H, s), 2.70 (3H, s), 2.85 (2H, t, J=6.5 Hz), 3.05 (2H, t, J=6.5 Hz), 3.17 (2H, t, J=6.5 Hz), 3.47 (1H, m), 3.55 (1H, m), 4.14–4.28 (2H, m), 4.59 (2H, m), 8.04 (1H, s), 9.31 (1H, s)

Example 174
(1S,6R,6S)-2-[6-[2-(2-Aminoethyl)sulfonylethyl]-7-methylthioimidazo[5,1-b]thiazolium-2-yl]-6-(1R)-1- hydroxyethyl)-1-methyl-1-carbapen-2-em-3-carboxylate (intramolecular salt) hydrochloride The procedures of Examples 50a) and 50b) were repeated, except that 50 mg of 2-(2-azidoethyl)sulfonyl ethanol and 130 mg of 4-nitrobenzyl (1S,6R,6S)-6-((1R)-1-hydroxyethyl)-1-methyl-2-(7-methylthioimidazo[5,1-b]thiazol-2-yl)-1-carbapen-2-em-3-carboxylate were used at the starting compounds. Thus, 48 mg of the title compound was prepared.

NMR ($D_2O$) δ ($\underline{H}OD$=4.65 ppm): 1.16 (3H, d, J=7.0 Hz), 1.21 (3H, d, J=6.6 Hz), 2.34 (3H, s), 3.44–3.59 (4H, m), 3.67 (2H, t, J=6.5 Hz), 3.97 (2H, t, J=6.5 Hz), 4.18 (1H, m), 4.25 (1H, dd, $J_1$=9.5 Hz, $J_2$=2.9 Hz), 4.96 (2H, t, J=6.5 Hz), 8.06 (1H, s)

Example 175

(1S,6R,6S)-2-[6-[4-(4-Carbamoylpyridinium-1-yl)methylbenzyl]-7-methylthioimidazo[5,1-b]thiazolium-2-yl]-6-((1R)-1-hydroxyethyl)-1-methyl-1-carbapen-2-em-3-carboxylate bromide (intramolecular salt)

The procedure of Example 3a) was substantially repeated, except that 78 mg of 4-nitrobenzyl (1S,6R,6S)-2-(6-(4-bromomethylbenzyl)-7-methylthioimidazo[5,1-b]thiazolium-2-yl]-6-((1R)-1-hydroxyethyl)-1-methyl-1-carbapen-2-em-3-carboxylate bromide and 92 mg of 4-carbamoylpyridine were used as the starting compounds. Thus, 128 mg of a corresponding quaternary salt was prepared. The procedure of Example 3b) was substantially repeated, except that this quaternary salt was used as the starting compound. Thus, 14.4 mg of the title compound was prepared.

NMR (DMSO-$d_6$) δ: 1.08 (3H, d, J=7.1 Hz), 1.10 (3H, d, J=6.4 Hz), 2.07 (3H, s), 3.09 (1H, m), 3.40 (1H, m), 3.89 (1H, m), 4.03 (1H, dd, $J_1$=9.5 Hz, $J_2$=2.7 Hz), 4.98 (1H, d, J=5.1 Hz), 5.61 (2H, s), 5.82 (2H, s), 7.35 (2H, d, J=8.3 Hz), 7.51 (2H, d, J=8.3 Hz), 8.20 (1H, br s), 8.24 (1H, 2), 8.37 (2H, d, J=6.8 Hz), 8.37 (2H, d, J=6.8 Hz), 8.57 (1H, br s), 9.26 (2H, d, J=6.8 Hz), 9.58 (1H, s)

Example 176

(1S,6R,6S)-2-[6-((2R)-3-Amino-2-fluoromethoxypropyl)-7-methylthioimidazo[5,1-b]thiazolium-2-yl]-6-((1R)-1-hydroxyethyl)-1-methyl-1-carbapen-2-em-3-carboxylate (intramolecular salt) hydrochloride The procedures of Examples 50a) and 50b) were repeated, except that 75 mg of (2R)-3-azido-2-fluoromethoxypropanol and 234 mg of 4-nitrobenzyl (1S,6R,6S) 6-((1R)-1-hydroxyethyl)-1-methyl-2-(7-methylthioimidazo[5,1-b]thiazol-2-yl)-1-carbapen-2-em-3-carboxylate were used as the starting compounds. Thus, 86 mg of the title compound was prepared.

NMR ($D_2O$) δ ($\underline{H}OD$=4.65 ppm): 1.16 (3H, d, J=7.0 Hz), 1.21 (3H, d, J=6.3 Hz), 2.33 (3H, s), 3.06 (1H, dd, $J_1$=13.6 Hz, $J_2$=9.0 Hz), 3.38 (1H, dd, $J_1$=13.6 Hz, $J_2$=2.9 Hz), 3.47 (1H, dd, $J_1$=6.0 Hz, $J_2$=2.7 Hz), 3.55 (1H, m), 4.17 (1H, m), 4.25 (1H, dd, $J_1$=9.5 Hz, $J_2$=2.9 Hz), 4.45 (1H, m), 4.69 (2H, m), 5.12–5.35 (2H, m), 8.07 (1H, s), 9.32 (1H, s)

Example 177

(1S,5R,6S)-2-[6-(5-Aminopentyl)-7-methylthioimidazo[5,1-b]thiazolium-2-yl-6-((1R)-1-hydroxyethyl)-1-methyl-1-carbapen-2-em-3-carboxylate (intramolecular salt) hydrochloride The procedures of Examples 50a) and 50b) were repeated, except that 80 mg of 5-azido-1-pentanol and 296 mg of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate were used as the starting compounds. Thus, 53 mg of the title compound was prepared.

NMR ($D_2O$) δ ($\underline{H}OD$=4.65 ppm): 1.15 (3H, d, J=7.0 Hz), 1.21 (3H, d, J=6.6 Hz), 1.36 (2H, m), 1.65 (2H, m), 1.90 (2H, m), 2.30 (3H, s), 2.90 (2H, m), 3.46 (1H, dd, $J_1$=6.0 Hz, $J_2$=2.7 Hz), 3.54 (1H, m), 4.17 (1H, m), 4.25 (1H, dd, $J_1$=9.0 Hz, $J_2$=2.9 Hz), 4.36 (2H, m), 8.03 (1H, s), 9.22 (1H, s)

Example 178

(1S,5R,6S)-6-((1R)-1-Hydroxyethyl)-1-methyl-2-[6-[2-((3S)-pyrrolidin-3-yl)thioethyl]-7-methylthioimidazo[5,1-b]thiazolium-2-yl]-1-carbapen-2-em-3-carboxylate (intramolecular salt) hydrochloride The procedures of Examples 3a) and 50b) were repeated, except that 640 mg of (3S)-3-(2-methanesulfonyloxyethylthio)-1-(4-nitrobenzyloxy)carbonylpyrrolidine and 277 mg of 4-nitrobenzyl (1S,5R,6S)-6-((1R)-1-hydroxyethyl)-1-methyl-2-(7-methylthioimidazo-[5,1-b]thiazol-2-yl)-1-carbapen-2-em-3-carboxylate were used as the starting compounds. Thus, 61 mg of the title compound was prepared.

NMR ($D_2O$) δ ($\underline{H}OD$=4.65 ppm): 1.14 (3H, d, J=7.1 Hz), 1.21 (3H, d, J=6.3 Hz), 1.92 (1H, m), 2.29–2.41 (4H, m), 3.11 (2H, t, J=6.6 Hz), 3.20 (1H, dd, $J_1$=12.2 Hz, $J_2$=4.9 Hz), 3.26–3.62 (5H, m), 3.66 (1H, m), 4.17 (1H, m), 4.25 (1H, dd, $J_1$=9.5 Hz, $J_2$=2.9 Hz), 4.62 (2H, m), 8.03 (1H, s), 9.30 (1H, s)

Example 179

(1S,5R,6S)-2-[6-[2-(3,4-Dihydroxybenzyl)-sulfonylethyl]-7-methylthioimidazo[5,1-b]thiazolium-2-yl]-6-((1R)-1-hydroxyethyl)-1-methyl-1-carbapen-2-em-3-carboxylate (intramolecular salt)

The procedures of Examples 75a) and 70f) were repeated, except that 160 mg of 1-(2-hydroxyethanesulfonylmethyl)-3,4-diallylcatechol and 183 mg of allyl (1S,5R,6S)-6-((1R)-1-hydroxyethyl)-1-methyl-2-(7-methylthioimidazo[5,1-b]thiazol-2-yl)-1-carbapen-2-em-3-carboxylate were used as the starting compounds. Thus, 16 mg of the title compound was prepared.

NMR ($D_2O$) δ ($\underline{H}OD$=4.65 ppm): 1.16 (3H, d, J=7.1 Hz), 1.21 (3H, d, J=6.3 Hz), 2.24 (3H, s), 3.46 (1H, m), 3.54 (1H, m), 3.84 (2H, m), 4.17 (1H, m), 4.26 (1H, m), 4.32 (2H, s), 6.62 (3H, m), 6.71 (2H, s), 7.93 (1H, s)

Example 180

(1S,5R,6S)-2-[6-Carbamoylmethyl-7-(pyridin-2-yl)thioimidazo[5,1-b]thiazolium-2-yl]-6-((1R)-1-hydroxyethyl)-1-methyl-1-carbapen-2-em-3-carboxylate (intramolecular salt)

a) 4-Nitrobenzyl (1S,5R,6S)-6-((1R)-1-hydroxyethyl)-1-methyl-2-[7-(pyridin-2-yl)thioimidazo[5,1-b]-thiazol-2-yl]-1-carbapen-2-em-3-carboxylate The procedure of Example 1a) was repeated, except that 576 mg of 4-nitrobenzyl (1S,5R,6S)-6-((1R)-1-hydroxyethyl)-1-methyl-2-oxo-1-carbapenam-3-carboxylate and 872 mg of 7-(pyridin-2-yl)thio-2-(tri-n-butylstannyl)imidazo[5,1-b]thiazole were used as the starting compounds. Thus, 112 mg of 4-nitrobenzyl (1S,5R,6S)-6-((1R)-1-hydroxyethyl)-1-methyl-2-[7-(pyridin-2-yl)thioimidazo[5,1-b]thiazol-2-yl]-1-carbapen-2-em-3-carboxylate was prepared.

NMR (CDCl$_3$) δ: 1.30 (3H, d, J=7.5 Hz), 1.39 (3H, d, J=6.3 Hz), 3.37 (1H, dd, $J_1$=6.6 Hz, $J_2$=2.7 Hz), 3.4–3.5 (1H, m), 4.25–4.4 (2H, m), 5.28 (1H, d, J=13.5 Hz), 5.52 (1H, d, J=13.5 Hz), 6.9–7.05 (2H, m), 7.4–7.5 (1H, m), 7.67 (2H, d, J=8.7 Hz), 8.16 (1H, s), 8.23 (2H, d, J=8.7 Hz), 8.37 (1H, s), 8.4–8.45 (1H, m)

b) (1S,5R,6S)-2-[6-Carbamoylmethyl-7-(pyridin-2-yl)thioimidazo[5,1-b]thiazolium-2-yl]-6-((1R)-1- hydroxyethyl)-1-methyl-1-carbapen-2-em-3-carboxylate (intramolecular salt)

4-Nitrobenzyl (1S,5R,6S)-6-((1R)-1-hydroxyethyl)-1-methyl-2-[7-(pyridin-2-yl)thioimidazo[5,1-b]thiazol-2-yl]-1-carbapen-2-em-3-carboxylate (42.2 mg) was dissolved in 2 ml of acetone. 2-Iodoacetamide (140 mg) was added to the solution. The mixture was stirred at 40° C. for 4 days. Ethyl acetate (4 ml) was added to the reaction solution. The resultant precipitate was collected, and was allowed to react in the same manner as in Example 3b). Purification was then carried out by column chromatography on Cosmosil 40C$_{18}$-PREP (10 to 25% aqueous methanol solution). A main product eluted as the latter fraction was collected to prepare 7.38 mg of the title compound.

NMR (D$_2$O) δ (HOD=4.80 ppm): 1.28 (3H, d, J=7.2 Hz), 1.33 (3H, d, J=6.3 Hz), 3.58 (1H, dd, J$_1$=6.0 Hz, J$_2$=2.7 Hz), 3.6–3.75 (1H, m), 4.25–4.35 (1H, m), 4.37 (1H, dd, J$_1$=9.3 Hz, J$_2$=2.7 Hz), 5.21 (2H, s), 7.17 (1H, d, J=8.1 Hz), 7.2–7.3 (1H, m), 7.65–7.75 (1H, m), 8.2–8.3 (2H, m)

Example 181
(1S,5R,6S)-2-[6-[2-((3S,5S)-5-Carbamoylpyrrolidin-3-yl)thioethyl]-7-methylthioimidazo[5,1-b]thiazolium-2-yl]-6-((1R)-1-hydroxyethyl)-1-methyl-1-carbapen-2-em-carboxylate (intramolecular salt) hydrochloride The procedures of Examples 3a) and 50b) were repeated, except that 620 mg of (3S,5S)-5-carbamoyl-3-(2-methanesulfonyloxyethyl)thio-1-(4-nitrobenzyloxy)carbonylpyrrolidine and 180 mg of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate were used as the starting compounds. Thus, 21 mg of the title compound was prepared.

NMR (D$_2$O) δ (HOD=4.65 ppm): 1.15 (3H, d, J=7.3 Hz), 1.21 (3H, d, J=6.3 Hz), 1.99 (1H, m), 2.31 (3H, s), 2.81 (1H, m), 3.09 (2H, t, J=6.6 Hz), 3.32 (1H, m), 3.46 (1H, dd, J$_1$=6.0 Hz, J$_2$=2.9 Hz), 3.54 (1H, m), 3.69 (2H, m), 4.18 (1H, m), 4.25 (1H, dd, J$_1$=9.5 Hz, J$_2$=2.9 Hz), 4.40 (1H, m), 4.59 (2H, m), 8.04 (1H, s), 9.28 (1H, s)

Example 182
(1S,5R,6S)-6-((1R)-1-Hydroxyethyl)-2-[6-[2-((3S,5S)-5-hydroxymethylpyrrolidin-3-yl )thioethyl]-7-methylthioimidazo[5,1-b]thiazolium-2-yl]-1-methyl-1-carbapen-2-em-3-carboxylate (intramolecular salt) hydrochloride The procedures of Examples 3a) and 70f) were repeated, except that 1.63 g of (3S,5S)-1-allyloxycarbonyl-5-allyloxycarbonyloxymethyl-3-(2-methanesulfonyloxyethyl)thiopyrrolidine and 480 mg of allyl (1S,5R,6S)-6-((1R)-1-hydroxyethyl)-1-methyl-2-(7-methylthioimidazo[5,1-b]thiazol-2-yl)-1-carbapen-2-em-3-carboxylate were used as the starting compounds. Thus, 39 mg of the title compound was prepared.

NMR (D$_2$O) δ (HOD=4.65 ppm): 1.15 (3H, d, J=7.3 Hz), 1.21 (3H, d, J=6.3 Hz), 1.61 (1H, m), 2.31 (3H, s), 2.53 (1H, m), 3.10 (2H, m), 3.21 (1H, m), 3.55–3.81 (7H, m), 4.17 (1H, m), 4.25 (1H, dd, J$_1$=9.5 Hz, J$_2$=2.7 Hz), 4.60 (2H, m), 8.04 (1H, s), 9.29 (1H, s)

Example 183
(1S,5R,6S)-2-[6-[3-(3-Carbamoylpyridinium-1-1-yl)methyl-5-hydroxybenzyl]-7-methylthioimidazo[-5,1-b]-thiazolium-2-yl]-6-((1R)-1-hydroxyethyl)-1-methyl-1-carbapen-2-em-3-carboxylate bromide (intramolecular salt)

a) 4-Nitrobenzyl (1S,5R,6S)-2-[6-(3-bromomethyl-5-triethylsilyloxybenzyl)-7-methylthioimidazo[5,1-b]thiazolium-2-yl]-6-((1R)-1-hydroxyethyl)-1-methyl-1-carbapen-2-em-3-carboxylate bromide The procedure of Example 3a) was substantially repeated, except that 1.03 g of 4-nitrobenzyl (1S,5R,6S)-6-((1R)-1-hydroxyethyl)-1-methyl-2-(7-methylthioimidazo[5,1-b]thiazol-2-yl)-1-carbapen-2-em-3-carboxylate and 0.982 g of 1,3-bis(bromomethyl)-5-triethylsilyloxybenzene were used as the starting compounds. Thus, 453 mg of 4-nitrobenzyl (1S,5R,6S)-2-(6-(3-bromomethyl-5-triethylsilyloxybenzyl)-7-methylthioimidazo[5,1-b]thiazolium-2-yl]-6-((1R)-1-hydroxyethyl)-1-methyl-1-carbapen-2-em-3-carboxylate bromide was prepared.

NMR (CDCl$_3$) δ: 0.72 (6H, q, J=7.8 Hz), 0.96 (9H, t, J=8.0 Hz), 1.32 (3H, d, J=7.3 Hz), 1.38 (3H, d, J=6.4 Hz), 2.12 (3H, s), 3.44 (1H, m), 3.92 (1H, m), 4.21 (1H, m), 4.40–4.53 (3H, m), 5.36 (1H, d, J=13.7 Hz), 5.53 (1H, d, J=13.7 Hz), 5.60 (2H, s), 6.83 (1H, s), 6.89 (1H, s), 7.04 (1H, s), 7.65 (2H, d, J=8.8 Hz), 8.25 (2H, d, J=8.8 Hz), 9.18 (1H, s), 10.42 (1H, s)

b) (1S,5R,6S)-2-[6-3-(3-Carbamoylpyridinium-1-yl)-methyl-5-hydroxybenzyl]-7-methylthioimidazo[5,1-b] thiazolium-2-yl]-6-((1R)-1-hydroxyethyl)-1-methyl-1-carbapen-2-em-3-carboxylate bromide (intramolecular salt)

The procedure of Example 3a) was substantially repeated, except that 207 mg of 4-nitrobenzyl (1S,5R,6S)-2-[6-(3-bromomethyl-5-triethylsilyloxybenzyl)-7-methylthioimidazo[5,1-b]thiazolium-2-yl]-6-((1R)-1-hydroxyethyl)-1-methyl-1-carbapen-2-em-3-carboxylate bromide and 147 mg of 3-carbamoylpyridine were used as the starting compounds. Thus, 137 mg of a corresponding quaternary salt was prepared. The procedure of Example 99d) was substantially repeated, except that this quaternary salt was used as the starting compound. Thus, 41.4 mg of the title compound was prepared.

NMR (DMSO-d$_6$) δ: 1.09 (3H, d, J=7.6 Hz), 1.11 (3H, d, J=6.6 Hz), 2.03 (3H, s), 3.12 (1H, m), 3.40 (1H, m), 3.90 (1H, m), 4.05 (1H, dd, J$_1$=9.5 Hz, J$_2$=2.7 Hz), 4.98 (1H, d, J=5.3 Hz), 5.51 (2H, s), 5.75 (2H, s), 6.74 (1H, br s), 6.82 (1H, br s), 6.84 (1H, br s), 8.50 (1H, br s), 8.90 (1H, d, J=8.0 Hz), 9.17 (1H, d, J=6.1 Hz), 9.49 (1H, br 8), 9.55 (1H, s), 10.04 (1H, s)

Preparation Example 1
Preparation for Injections

Aseptical charging into vials was carried out so that each vial contained 1000 mg (potency) of the compound prepared in Example 3.

Preparation Example 2
Soft Capsules for Rectal Administration

Olive oil 160 parts (potency)
Polyoxyethylene lauryl ether 10 parts (potency)
Sodium hexametaphosphate 5 parts (potency)

The compound (250 parts (potency)) prepared in Example 3 was added to and homogeneously mixed with a homogeneous base comprising the above ingredients. The mixture was filled into soft capsules for rectal administration to provide 250 mg (potency) per capsule.

Test Example 1
Antimicrobial Activities

The minimum inhibiting concentrations (MIC, μg/ml) of representative compounds, among the novel carbapenem derivatives of the present invention, to various pathogenic bacteria were measured in accordance with the method described in CHEMOTHERAPY, vol. 16, No. 1, 99, 1968. The results are shown in Table 1. The culture medium for the measurement is Sensitivity Disk agar-N+5% Horse blood, and the amount of inoculants used is $10^6$ CFU/ml.

TABLE 1

| Test organisms | Compound of Ex. 2 | Compound of Ex. 3 | Compound of Ex. 14 | Compound of Ex. 99 | Compound A | Compound B |
|---|---|---|---|---|---|---|
| S. aureus 209P JC-1 | <0.025 | <0.025 | <0.025 | <0.025 | <0.025 | <0.025 |
| S. aureus M 126* | 1.56 | 1.56 | 0.39 | 0.78 | 25 | 3.13 |
| S. epidermidis ATCC 14990 | <0.025 | <0.025 | <0.025 | <0.025 | <0.025 | <0.025 |
| E. hirae ATCC 8043 | 0.78 | 0.39 | 0.39 | 0.39 | 0.78 | 0.78 |
| E. faecalis W-73 | 0.20 | 0.20 | 0.20 | 0.20 | 0.78 | 0.20 |
| S. pneumoniae PRC 9** | 0.025 | 0.025 | 0.025 | 0.05 | 0.20 | 0.05 |
| B. catarrhalis W-0500 | 0.025 | 0.025 | 0.025 | 0.05 | 0.05 | <0.025 |
| H. influenzae PRC 2 | 0.05 | 0.05 | 0.05 | 0.10 | 0.79 | 0.10 |
| H. influenzae PRC 44 | 0.20 | 0.20 | 0.78 | 0.78 | 12.5 | 0.39 |
| E. coli NIHJ JC-2 | 0.025 | 0.025 | 0.05 | 0.05 | 0.10 | <0.025 |
| K. pneumoniae PC 1602 | 0.10 | 0.10 | 0.10 | 0.10 | 0.20 | 0.10 |
| P. vulgaris GN 7919 | 0.20 | 0.20 | 0.39 | 0.39 | 0.10 | 0.20 |
| C. freundii GN 346 | 0.10 | 0.20 | 0.10 | 0.20 | 0.20 | 0.10 |

*Methicillin-hyperresistant strain
**Penicillin-hyperresistant strain
Compound A: Imipenem
Compound B: (1S,5R,6S)-6-((1R)-1-Hydroxyethyl)-1-methyl-2-(6-methylimidazo[5,1-b]thiazolium-2-yl)-1-carbapen-2-em-3-carboxylate (intramolecular salt)

The carbapenem derivatives represented by formula (I) according to the present invention have potent antimicrobial activities against MRSA, PRSP, and Influenzavirus, as well as various pathogenic bacteria including β-lactamase-producing bacteria.

Test Example 2

Acute Toxicity Test

The compound of Example 3 according to the present invention was intraveneously administered at a dose of 2000 mg/kg to mice (ICR, male) (one group consisting of three mice). As a result, all the mice survived.

What is claimed is:

1. A compound represented by formula (I) or a pharmaceutically acceptable salt thereof:

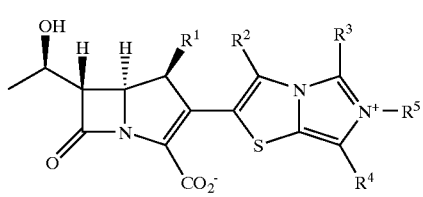

(I)

wherein $R^1$ represents a hydrogen atom or methyl;

$R^2$ and $R^3$, which may be the same or different, each independently represent a hydrogen atom, a halogen atom, lower alkyl on which one or more hydrogen atoms are optionally substituted by hydroxyl or amino, lower alkylcarbonyl, carbamoyl, aryl, or lower alkylthio;

$R^4$ represents lower alkylthio on which one or more hydrogen atoms are optionally substituted by a group selected from the group consisting of: a halogen atom; nitro; azido; cyano; lower cycloalkyl; lower alkylthio; hydroxyl; lower alkoxy; formyl; lower alkylcarbonyl; arylcarbonyl; carboxy; lower alkoxycarbonyl; carbamoyl; N-lower alkylcarbamoyl; N,N-di-lower alkylcarbamoyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; formimidoylamino; acetimidoylamino; guanidino; aminosulfonyl; (N-lower alkylamino)sulfonyl; (N,N-di-lower alkylamino)sulfonyl; aryl; a monocyclic heterocyclic ring selected from the group consisting of pyrrolidine, piperidine, pyridine, imidazole, thiazole, and thiophene, lower cycloalkylthio wherein one or more hydrogen atoms of the cycloalkyl portion are optionally substituted by a group selected from the group consisting of a halogen atom, nitro, cyano, hydroxyl, carbamoyl, and amino, $C_{2-4}$ alkenylthio, $C_{2-4}$ alkynylthio, arylthio, thio substituted by a heterocyclic ring selected from the group consisting of pyrrolidine, piperidine, pyridine, imidazole, thiazole, and thiophene, lower alkylsulfinyl wherein one or more hydrogen atoms of the alkyl portion are optionally substituted by a group selected from the group consisting of a halogen atom, hydroxyl, carbamoyl, and amino, lower alkylsulfonyl wherein one or more hydrogen atoms of the alkyl portion are optionally substituted by a group selected from the group consisting of a halogen atom, hydroxyl, carbamoyl, and amino, or arylcarbonyl or $R^4$ and $R^5$ together form —$R^4$—$R^5$— which represents —S—$(CH_2)_n$— wherein n is an integer of 2 to 4;

$R^5$ represents lower alkyl on which one or more hydrogen atoms are optionally substituted by a group selected from the group consisting of: a halogen atom; nitro; azido; cyano; lower cycloalkyl; lower alkylthio; hydroxyl; lower alkoxy; formyl; lower alkylcarbonyl; arylcarbonyl wherein one or more hydrogen atoms of the aryl portion are optionally substituted by a group selected from the group consisting of a halogen atom, nitro, cyano, lower alkyl on which one or more hydrogen atoms are optionally substituted by a halogen atom, hydroxyl, carbamoyl, or amino, hydroxyl, lower alkoxy, benzyloxy, carboxy, lower alkoxycarbonyl, carbamoyl, amino, and hydroxyamino; carboxy; lower alkoxycarbonyl; carbamoyl; N-lower alkylcarbamoyl wherein one or more hydrogen atoms of the alkyl portion are optionally substituted by amino, formimidoylamino, acetimidoylamino, or hydroxyl; N,N-di-lower alkylcarbamoyl wherein one or more hydrogen atoms of the alkyl portion are optionally substituted by amino, formimidoylamino, acetimidoylamino, or hydroxyl; heterocyclic carbonyl selected from the group consisting of morpholinylcarbonyl and piperazinylcarbonyl; N-arylcarbamoyl; N-hydroxycarbamoyl; N-benzyloxy-carbamoyl; N-lower alkyl-N-lower alkoxycarbamoyl; amino; N-lower alkylamino wherein one or more hydrogen atoms of the alkyl portion are optionally substituted by amino, formimidoylamino, acetimidoylamino, or hydroxyl; N,N-di-lower alkylamino wherein one or more hydrogen atoms of the alkyl portion are optionally substituted by amino, formimidoylamino, acetimidoylamino, or hydroxyl; formylamino; lower alkylcarbonylamino; aminosulfonylamino; (N-lower alkylamino)sulfonylamino; (N,N-di-lower alkylamino)sulfonylamino; piperazinyl-carbonylamino; N-lower alkylpiperazinylcarbonylamino; N-arylpiperazinylcarbonylamino; formimidoylamino; acetimidoylamino; guanidino; aminosulfonyl; (N-lower alkylamino)sulfonyl; (N,N-di-lower alkylamino) sulfonyl; aryl on which one or more hydrogen atoms are optionally substituted by a group selected from the group consisting of a halogen atom, nitro, cyano, lower alkyl on which one or more hydrogen atoms are optionally substituted by a halogen atom, hydroxyl, carbamoyl, amino, hydroxyl, lower alkoxy, benzyloxy, carboxy, lower alkoxycarbonyl, carbamoyl, amino, and hydroxyamino; and a heterocyclic ring selected from the group consisting of pyrrolidine, imidazole, thiazole, piperidine, pyridine, and thiophene, wherein one or more hydrogen atoms of the ring are optionally substituted by a halogen atom, hydroxyl, carbamoyl, or amino and, when the ring contains a nitrogen atom, lower alkyl optionally substituted by carbamoyl may be attached to the nitrogen atom, lower cycloalkyl, $C_{2-4}$ alkenyl, $C_{2-4}$ alkynyl, a heterocyclic ring selected from the group consisting of pyrrolidine, piperidine, and morpholine, wherein one or more hydrogen atoms on the carbon atoms in the heterocyclic ring are optionally substituted by a group selected from the group consisting of: lower alkyl on which one or more hydrogen atoms are optionally substituted by hydroxyl or amino; carboxy; lower alkoxycarbonyl; carbamoyl; N-lower alkylcarbamoyl; and N,N-di-lower alkylcarbamoyl, and wherein a hydrogen atom on the nitrogen atom in the heterocyclic ring is optionally substituted by lower alkyl, $C_{2-4}$ alkenyl, formimidoyl, acetimidoyl, or amidino.

2. The compound according to claim 1, wherein $R^4$ represents optionally substituted lower alkylthio, thio substituted by a heterocyclic ring selected from the group consisting of pyrrolidine, piperidine, pyridine, imidazole, thiazole, and thiophene, optionally substituted lower alkylsulfinyl, optionally substituted lower alkylsulfonyl, or arylcarbonyl or $R^4$ and $R^5$ together form —$R^4$—$R^5$— which represents —S—$(CH_2)_n$— wherein n is an integer of 2 to 4; and $R^5$ represents optionally substituted lower alkyl or optionally substituted heterocyclic ring selected from the group consisting of pyrrolidine, piperidine, and morpholine.

3. The compound according to claim 1, wherein $R^4$ represents optionally substituted lower alkylthio, optionally substituted lower cycloalkylthio, $C_{2-4}$ alkenylthio, $C_{2-4}$ alkynylthio, arylthio, thio substituted by a heterocyclic ring selected from the group consisting of pyrrolidine, piperidine, pyridine, imidazole, thiazole, and thiophene, optionally substituted lower alkylsulfinyl, optionally substituted lower alkylsulfonyl, or arylcarbonyl or $R^4$ and $R^5$ together form —$R^4$—$R^5$— which represents —S—$(CH_2)_n$— wherein n is an integer of 2 to 4; and $R^5$ represents lower alkyl on which one or more hydrogen atoms are optionally substituted by a substituent selected from the group consisting of: a halogen atom; nitro; azido; cyano; lower cycloalkyl; lower alkylthio; hydroxyl; lower alkoxy; formyl; lower alkylcarbonyl; optionally substituted arylcarbonyl; carboxy; lower alkoxycarbonyl; carbamoyl optionally substituted N-lower alkylcarbamoyl; optionally substituted N,N-di-lower alkylcarbamoyl; heterocyclic carbonyl selected from the group consisting of morpholinylcarbonyl and piperazinylcarbonyl; N-arylcarbamoyl; N-hydroxycarbamoyl; N-benzyloxy-carbamoyl; N-lower alkyl-N-lower alkoxycarbamoyl; amino; N-lower alkylamino wherein one or more hydrogen atoms of the alkyl portion are optionally substituted; N,N-di-lower alkylamino wherein one or more hydrogen atoms of the alkyl portion are optionally substituted; formylamino; lower alkylcarbonylamino; aminosulfonylamino; (N-lower alkylamino)sulfonylamino; (N,N-di-lower alkylamino) sulfonylamino; piperazinyl-carbonylamino; N-lower alkylpiperazinylcarbonylamino; N-arylpiperazinylcarbonylamino; formimidoylamino; acetimidoylamino; guanidino; aminosulfonyl; (N-lower alkylamino)sulfonyl; (N,N-di-lower alkylamino) sulfonyl; aryl on which one or more hydrogen atoms are optionally substituted by a group selected from the group consisting of a halogen atom, nitro, cyano, optionally substituted lower alkyl, hydroxyl, lower alkoxy, benzyloxy, carboxy, lower alkoxycarbonyl, carbamoyl, amino, and hydroxyamino; and an optionally substituted a heterocyclic ring selected from the group consisting of pyrrolidine, imidazole, thiazole, piperidine, pyridine, and thiophene, lower cycloalkyl, $C_{2-4}$ alkenyl, $C_{2-4}$ alkynyl, or an optionally substituted heterocyclic ring selected from the group consisting of pyrrolidine, piperidine, and morpholine.

4. The compound according to claim 1, wherein $R^1$ represents a hydrogen atom or methyl;

$R^2$ and $R^3$, which may be the same or different, represent a hydrogen atom, lower alkyl optionally substituted by hydroxyl, or lower alkylthio;

$R^4$ represents
lower alkylthio, one or more hydrogen atoms on which alkyl are optionally substituted by a group selected from the group consisting of a halogen atom, hydroxyl, carbamoyl, amino, formylamino, guanidino, aryl, pyridyl,
arylthio,
thio substituted by a heterocyclic ring selected from the group consisting of pyrrolidine, piperidine, and pyridine,
lower alkylsulfinyl,
lower alkylsulfonyl, or
arylcarbonyl or $R^4$ and $R^5$ together form —$R^4$—$R^5$— which represents —S—$(CH_2)_n$— wherein n is an integer of 2 to 4; and
$R^5$ represents
lower alkyl on which one or more hydrogen atoms are optionally substituted by a group selected from the group consisting of: a halogen atom; nitro; lower alkylthio; hydroxyl; lower alkoxy; arylcarbonyl optionally substituted by hydroxyamino; carboxy; lower alkoxycarbonyl; carbamoyl; N-lower alkylcarbamoyl wherein one or more hydrogen atoms of the alkyl portion are optionally substituted by amino, acetimidoylamino, or hydroxyl; N,N-di-lower alkylcarbamoyl; morpholinylcarbonyl; piperazinyl-carbonyl; N-arylcarbamoyl; N-hydroxycarbamoyl; N-benzyloxycarbamoyl; N-lower alkyl-N-lower alkoxycarbamoyl; amino; N-lower alkylamino optionally substituted by amino; lower alkylcarbonylamino; aminosulfonylamino;
N-arylpiperazinylcarbonylamino; formimidoylamino; acetimidoylamino; aminosulfonyl; aryl on which one or more hydrogen atoms are optionally substituted by a group selected from the group consisting of a halogen atom, cyano, lower alkyl on which one or more hydrogen atoms are optionally substituted by hydroxyl, hydroxyl, lower alkoxy, benzyloxy, carboxy, lower alkoxycarbonyl, carbamoyl, amino, and hydroxyamino; and a heterocyclic ring selected from the group consisting of pyrrolidine, imidazole, thiazole, piperidine, pyridine, and thiophene, wherein one or more hydrogen atoms of the ring are optionally substituted by amino and, when the ring contains a nitrogen atom, lower alkyl optionally substituted by carbamoyl may be attached to the nitrogen atom,
a pyrrolidine or piperidine ring wherein one or more hydrogen atoms on the carbon atoms of the heterocyclic ring are optionally substituted by a group selected from the group consisting of: lower alkyl optionally substituted by hydroxyl; carboxy; lower alkoxycarbonyl; and N,N-di-lower alkylcarbamoyl, and wherein one or more hydrogen atoms on the nitrogen atom of the heterocyclic ring are optionally substituted by acetimidoyl or amidino.

5. The compound according to claim 1, wherein $R^1$ represents methyl; $R^2$ and $R^3$ each represent a hydrogen atom; $R^4$ represents optionally substituted lower alkylthio; and $R^5$ represents optionally substituted lower alkyl.

6. The compound according to claim 1, wherein $R^1$ represents methyl; $R^2$ and $R^3$ each represent a hydrogen atom; $R^4$ represents optionally substituted lower alkylthio; and $R^5$ represents an optionally substituted heterocyclic ring selected from the group consisting of pyrrolidine, piperidine, and morpholine.

7. The compound according to claim 1, wherein $R^1$ represents methyl; $R^2$ and $R^3$ each represent a hydrogen atom; $R^4$ represents lower alkylthio; and $R^5$ represents lower alkyl substituted by carbamoyl, lower alkyl substituted by amino, pyrrolidinyl, lower alkyl substituted by amino and hydroxy, or lower alkyl substituted by aryl.

8. The compound according to claim 1, wherein $R^1$ represents methyl; $R^2$ and $R^3$ each represent a hydrogen atom; $R^4$ represents methylthio; and $R^5$ represents carbamoylmethyl, 3-aminopropyl, (3S)-pyrrolidin-3-yl, (2R)-3-amino-2-hydroxypropyl, or benzyl.

9. The compound according to claim 1, wherein $R^1$ represents methyl; $R^2$ and $R^3$ each represent a hydrogen atom; $R^4$ represents 3-aminopropylthio; and $R^5$ represents carbamoylmethyl.

10. A pharmaceutical composition comprising as active ingredient the compound according to any one of claims 1 to 9 or a pharmaceutically acceptable salt thereof, and a pharmaceutically acceptable additive.

11. A method for treating and/or preventing bacterial infectious diseases, comprising the step of administering an effective amount of the compound according to any one of claims 1 to 9 or a pharmaceutically acceptable salt thereof for the treatment and/or prevention of infectious diseases, to a mammal.

12. A compound selected from the group consisting of the following compounds:

(1S,5R,6S)-6-((1R)-1-hydroxyethyl)-1-methyl-2-[6-[2-(1-methylpyridinium-2-yl)ethyl]-7-methylthio-imidazo[5,1-b]thiazolium-2-yl]-1-carbapen-2-em-3-carboxylate chloride (intramolecular salt);

(1S,5R,6S)-6-((1R)-1-hydroxyethyl)-1-methyl-2-[6-methyl-7-[2-(4-methyl-1,4-diazoniabicyclo[2,2,2]oct-1-yl)ethyl]thioimidazo[5,1-b]thiazolium-2-yl]-1-carbapen-2-em-3-carboxylate dichloride (intramolecular salt);

(1S,5R,6S)-6-((1R)-1-hydroxyethyl)-1-methyl-2-[6-[2-(4-methylmorpholinium-4-yl)methylbenzyl]-7-methyl-thioimidazo[5,1-b]thiazolium-2-yl]-1-carbapen-2-em-3-carboxylate bromide (intramolecular salt);

(1S,5R,6S)-6-((1R)-1-hydroxyethyl)-1-methyl-2-[6-[3-(4-methylmorpholinium-4-yl)methylbenzyl]-7-methyl-thioimidazo[5,1-b]thiazolium-2-yl]-1-carbapen-2-em-3-carboxylate bromide (intramolecular salt);

(1S,5R,6S)-6-((1R)-1-hydroxyethyl)-1-methyl-2-[6-[4-(4-methylmorpholinium-4-yl)methylbenzyl]-7-methyl-thioimidazo[5,1-b]thiazolium-2-yl]-1-carbapen-2-em-3-carboxylate bromide (intramolecular salt);

(1S,5R,6S)-6-((1R)-1-hydroxyethyl)-1-methyl-2-[7-methylthio-6-[2-(pyridinium-1-yl)methylbenzyl]-imidazo[5,1-b]thiazolium-2-yl]-1-carbapen-2-em-3-carboxylate bromide (intramolecular salt);

(1S,5R,6S)-6-((1R)-1-hydroxyethyl)-1-methyl-2-[7-methylthio-6-[3-(pyridinium-1-yl)methylbenzyl]-imidazo[5,1-b]thiazolium-2-yl]-1-carbapen-2-em-3-carboxylate bromide (intramolecular salt);

(1S,5R,6S)-6-((1R)-1-hydroxyethyl)-1-methyl-2-[7-methylthio-6-[4-(pyridinium-1-yl)methylbenzyl]-imidazo[5,1-b]thiazolium-2-yl]-1-carbapen-2-em-3-carboxylate bromide (intramolecular salt);

(1S,5R,6S)-6-((1R)-1-hydroxyethyl)-1-methyl-2-[6-[3-(4-methyl-1,4-diazoniabicyclo[2,2,2]oct-1-yl)methylbenzyl]-7-methylthioimidazo[5,1-b]thiazolium-2-yl]-1-carbapen-2-em-3-carboxylate dichloride (intramolecular salt);

(1S,5R,6S)-6-((1R)-1-hydroxyethyl)-1-methyl-2-[6-[4-(4-methyl-1,4-diazoniabicyclo[2,2,2]oct-1-yl)methylbenzyl]-7-methylthioimidazo[5,1-b]thiazolium-2-yl]-1-carbapen-2-em-3-carboxylate dichloride (intramolecular salt);

(1S,5R,6S)-6-((1R)-1-hydroxyethyl)-1-methyl-2-[6-[3-(1-methylpyrrolidinium-1-yl)methyl-benzyl]-7-methylthioimidazo[5,1-b]thiazolium-2-yl]-1-carbapen-2-em-3-carboxylate bromide (intramolecular salt);

(1S,5R,6S)-6-((1R)-1-hydroxyethyl)-2-[6-[3-(3-hydroxymethylpyridinium-1-yl)methylbenzyl]-7-methyl-thioimidazo[5,1-b]thiazolium-2-yl]-1-methyl-1-carbapen-2-em-3-carboxylate bromide (intramolecular salt);

(1S,5R,6S)-6-((1R)-1-hydroxyethyl)-2-[6-[3-(4-hydroxymethylpyridinium-1-yl)methylbenzyl]-7-methyl-thioimidazo[5,1-b]thiazolium-2-yl]-1-methyl-1-carbapen-2-em-3-carboxylate bromide (intramolecular salt);

(1S,5R,6S)-2-[6-[3-[4-(3-aminopropyl)-1,4-diazoniabicyclo[2,2,2]oct-1-yl]methylbenzyl]-7-methyl-thioimidazo[5,1-b]thiazolium-2-yl]-6-((1R)-1-hydroxy-ethyl)-1-methyl-1-carbapen-2-em-3-carboxylate dichloride (intramolecular salt);

(1S,5R,6S)-2-[6-[3-(4-carbamoylmethyl-1,4-diazoniabicyclo[2,2,2]oct-1-yl)methylbenzyl]-7-methyl-thioimidazo[5,1-b]thiazolium-2-yl]-6-((1R)-1-hydroxyethyl)-1-methyl-1-carbapen-2-em-3-carboxylate dichloride (intramolecular salt);

(1S,5R,6S)-6-((1R)-1-hydroxyethyl)-1-methyl-2-[6-[4-(1-methylpyrrolidinium-1-yl)methylbenzyl]-7-methylthioimidazo[5,1-b]thiazolium-2-yl]-1-carbapen-2-em-3-carboxylate bromide (intramolecular salt);

(1S,5R,6S)-6-((1R)-1-hydroxyethyl)-2-[6-[3-(2-hydroxymethylpyridinium-1-yl)methylbenzyl]-7-methyl-thioimidazo[5,1-b]thiazolium-2-yl]-1-methyl-1-carbapen-2-em-3-carboxylate bromide (intramolecular salt);

(1S,5R,6S)-6-((1R)-1-hydroxyethyl)-2-[6-[3-(2-hydroxymethylimidazo[5,1-b]thiazolium-6-yl)methyl-benzyl]-7-methylthioimidazo[5,1-b]thiazolium-2-yl]-1-methyl-1-carbapen-2-em-3-carboxylate bromide (intramolecular salt);

(1S,5R,6S)-6-((1R)-1-hydroxyethyl)-2-[6-[3-(imidazo[5,1-b]thiazolium-6-yl)methylbenzyl]-7-methyl-thioimidazo[5,1-b]thiazolium-2-yl]-1-methyl-1-carbapen-2-em-3-carboxylate bromide (intramolecular salt);

(1S,5R,6S)-6-((1R)-1-hydroxyethyl)-2-[6-[4-(imidazo[5,1-b]thiazolium-6-yl)methylbenzyl]-7-methyl-thioimidazo[5,1-b]thiazolium-2-yl]-1-methyl-1-carbapen-2-em-3-carboxylate bromide (intramolecular salt);

(1S,5R,6S)-6-((1R)-1-hydroxyethyl)-2-[6-[3-[4-(2-hydroxyethyl)-1,4-diazoniabicyclo[2,2,2]oct-1-yl]-methylbenzyl]-7-methylthioimidazo[5,1-b]thiazolium-2-yl]-1-methyl-1-carbapen-2-em-3-carboxylate dichloride (intramolecular salt);

(1S,5R,6S)-6-((1R)-1-hydroxyethyl)-1-methyl-2-[7-methylthio-6-[3-(thiazolium-3-yl)methylbenzyl]-imidazo[5,1-b]thiazolium-2-yl]-1-carbapen-2-em-3-carboxylate bromide (intramolecular salt);

(1S,5R,6S)-6-((1R)-1-hydroxyethyl)-1-methyl-2-[7-methylthio-6-[4-(thiazolium-3-yl)methylbenzyl]-imidazo[5,1-b]thiazolium-2-yl]-1-carbapen-2-em-3-carboxylate bromide (intramolecular salt);

(1S,5R,6S)-6-((1R)-1-hydroxyethyl)-2-[6-[3-(isoquinolinium-2-yl)methylbenzyl]-7-methylthio-imidazo-[5,1-b]thiazolium-2-yl]-1-methyl-1-carbapen-2-em-3-carboxylate bromide (intramolecular salt);

(1S,5R,6S)-6-((1R)-1-hydroxyethyl)-1-methyl-2-[7-methylthio-6-[3-(3H-pyrimidinium-4-one-1-yl)methyl-benzyl]imidazo[5,1-b]thiazolium-2-yl]-1-carbapen-2-em-3-carboxylate bromide (intramolecular salt);

(1S,5R,6S)-6-((1R)-1-hydroxyethyl)-2-[6-[4-(isoquinolinium-2-yl)methylbenzyl]-7-methylthio-imidazo-[5,1-b]thiazolium-2-yl]-1-methyl-1-carbapen-2-em-3-carboxylate bromide (intramolecular salt);

(1S,5R,6S)-2-[6-[3-(3-carbamoylpyridinium-1-yl)methylbenzyl]-7-methylthioimidazo[5,1-b]thiazolium-2-yl]-6-((1R)-1-hydroxyethyl)-1-methyl-1-carbapen-2-em-3-carboxylate bromide (intramolecular salt);

1S,5R,6S)-2-[6-[4-(4-carbamoylpyridinium-1-yl)methylbenzyl]-7-methylthioimidazo[5,1-b]thiazolium-2-yl]-6-((1R)-1-hydroxyethyl)-1-methyl-1-carbapen-2-em-3-carboxylate bromide (intramolecular salt); and (1S,5R,6S)-2-[6-[3-(3-carbamoylpyridinium-1-yl)methyl-5-hydroxybenzyl]-7-methylthioimidazo[5,1-b]-thiazolium-2-yl]-6-((1R)-1-hydroxyethyl)-1-methyl-1-carbapen-2-em-3-carboxylate bromide (intramolecular salt)

a pharmaceutically acceptable salt thereof.

13. A method according to claim 11, wherein the mammal is a human.

* * * * *